(12) United States Patent
Chung et al.

(10) Patent No.: US 10,505,128 B2
(45) Date of Patent: Dec. 10, 2019

(54) CONDENSED CYCLIC COMPOUND AND ORGANIC LIGHT-EMITTING DEVICE INCLUDING THE SAME

(71) Applicants: Samsung Electronics Co., Ltd., Suwon-si, Gyeonggi-do (KR); Samsung SDI Co., Ltd., Yongin-si, Gyeonggi-do (KR)

(72) Inventors: Yeonsook Chung, Seoul (KR); Jhunmo Son, Yongin-si (KR); Sangmo Kim, Hwaseong-si (KR); Hyunjung Kim, Suwon-si (KR); Soonok Jeon, Seoul (KR); Dalho Huh, Suwon-si (KR); Yongsik Jung, Yongin-si (KR)

(73) Assignees: SAMSUNG ELECTRONICS CO., LTD., Gyeonggi-Do (KR); SAMSUNG SDI CO., LTD., Gyeonggi-Do (KR)

( * ) Notice: Subject to any disclaimer, the term of this patent is extended or adjusted under 35 U.S.C. 154(b) by 506 days.

(21) Appl. No.: 14/598,811

(22) Filed: Jan. 16, 2015

(65) Prior Publication Data

US 2016/0035986 A1 Feb. 4, 2016

(30) Foreign Application Priority Data

Aug. 1, 2014 (KR) ........................ 10-2014-0099240

(51) Int. Cl.
*H01L 51/00* (2006.01)
*C09K 11/06* (2006.01)
*H01L 51/50* (2006.01)
*C07D 493/10* (2006.01)
*C07D 519/00* (2006.01)
*C07D 495/10* (2006.01)

(52) U.S. Cl.
CPC ........ *H01L 51/0073* (2013.01); *C07D 493/10* (2013.01); *C07D 495/10* (2013.01); *C07D 519/00* (2013.01); *C09K 11/06* (2013.01); *H01L 51/0067* (2013.01); *H01L 51/0071* (2013.01); *H01L 51/0072* (2013.01); *H01L 51/0074* (2013.01); *C09K 2211/1007* (2013.01); *C09K 2211/1029* (2013.01); *C09K 2211/1088* (2013.01); *C09K 2211/1092* (2013.01); *H01L 51/0081* (2013.01); *H01L 51/0085* (2013.01); *H01L 51/5016* (2013.01)

(58) Field of Classification Search
CPC .. C07D 493/10; C07D 495/10; C07D 519/00; C09K 11/06; C09K 2211/1007; C09K 2211/1029; C09K 2211/1088; C09K 2211/1092; H01L 51/0067; H01L 51/0071; H01L 51/0072; H01L 51/0073; H01L 51/0074; H01L 51/0081; H01L 51/0085; H01L 51/5016

See application file for complete search history.

(56) References Cited

U.S. PATENT DOCUMENTS

| | | | |
|---|---|---|---|
| 2002/0048686 A1 | 4/2002 | Suzuki et al. | |
| 2002/0081454 A1 | 6/2002 | Suzuki et al. | |
| 2003/0064248 A1* | 4/2003 | Wolk | C09K 11/06 428/690 |
| 2004/0209115 A1 | 10/2004 | Thompson et al. | |
| 2006/0047128 A1* | 3/2006 | Zhang | C07C 231/18 548/409 |
| 2011/0227054 A1 | 9/2011 | Pampuch et al. | |
| 2015/0045529 A1* | 2/2015 | Stoessel | C07D 493/10 528/220 |

FOREIGN PATENT DOCUMENTS

| | | |
|---|---|---|
| EP | 1120839 A3 | 10/2005 |
| EP | 1120840 A3 | 10/2005 |
| JP | 2003096072 B2 | 4/2003 |
| WO | 0243449 A1 | 5/2002 |
| WO | 2010061315 A1 | 6/2010 |

OTHER PUBLICATIONS

Extended European Search Report issued by the European Patent Office dated Nov. 25, 2015 w/English Translation.

* cited by examiner

*Primary Examiner* — Dawn L Garrett
(74) *Attorney, Agent, or Firm* — Cantor Colburn LLP

(57) ABSTRACT

A condensed cyclic compound represented by Formula 1:

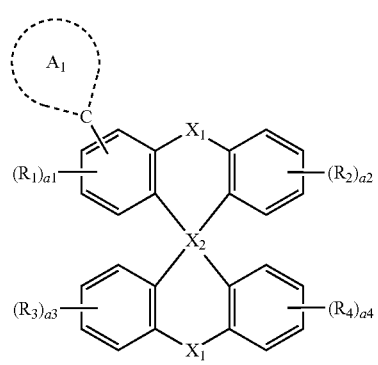

Formula 1 wherein, in Formula 1, $A_1$, $X_1$, $X_2$, $R_1$ to $R_4$, and a1 to a4 are described in the specification.

16 Claims, 1 Drawing Sheet

10

| 19 |
|----|
| 15 |
| 11 |

CONDENSED CYCLIC COMPOUND AND ORGANIC LIGHT-EMITTING DEVICE INCLUDING THE SAME

CROSS-REFERENCE TO RELATED APPLICATION

This application claims priority to Korean Patent Application No. 10-2014-0099240, filed on Aug. 1, 2014, in the Korean Intellectual Property Office, and all the benefits accruing therefrom under 35 U.S.C. § 119, the content of which is incorporated herein in its entirety by reference.

BACKGROUND

1. Field

The present disclosure relates to a condensed cyclic compound and an organic light-emitting device including the same.

2. Description of the Related Art

Organic light-emitting devices (OLEDs) are self-emission devices that have wide viewing angles, high contrast ratios, short response times, and excellent brightness, driving voltage, and response speed characteristics. They also produce full-color images.

A typical organic light-emitting device includes an anode, a cathode, and an organic layer that is disposed between the anode and the cathode and includes an emission layer. A hole transport region may be disposed between the anode and the emission layer, and an electron transport region may be disposed between the emission layer and the cathode. Holes provided from the anode may move toward the emission layer through the hole transport region, and electrons provided from the cathode may move toward the emission layer through the electron transport region. Carriers, such as the holes and the electrons, are recombined in the emission layer to produce excitons. These excitons change from an excited state to a ground state, thereby generating light.

Various types of organic light emitting devices are known. However, there still remains a need in OLEDs having low driving voltage, high efficiency, high brightness, and long lifespan.

SUMMARY

Provided are a novel condensed cyclic compound and an organic light-emitting device including the same.

Additional aspects will be set forth in part in the description which follows and, in part, will be apparent from the description, or may be learned by practice of the presented embodiments.

According to an aspect, a condensed cyclic compound is represented by Formula 1:

Formula 1

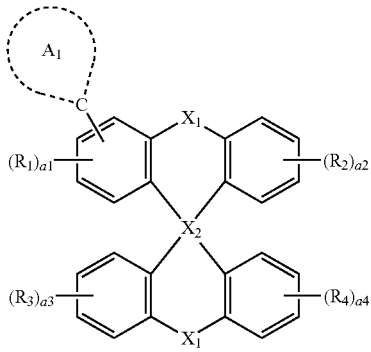

wherein, in Formula 1,
$X_1$ is O or S,
$X_2$ is C, Si, or Ge,
ring $A_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$), a1 is an integer selected from 0 to 3;
a2, a3, and a4 are each independently an integer selected from 0 to 4; and
when a1 is 2 or greater, groups $R_1$ are identical to or different from each other,
when a2 is 2 or greater, groups $R_2$ are identical to or different from each other,
when a3 is 2 or greater, groups $R_3$ are identical to or different from each other, and
when a4 is 2 or greater, groups $R_4$ are identical to or different from each other, at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{60}$ alkyl group, $C_2$-$C_{60}$ alkenyl group, $C_2$-$C_{60}$ alkynyl group and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric group acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), and $Q_1$ to $Q_7$, $Q_{11}$ to $Q_{17}$, $Q_{21}$ to $Q_{27}$, and $Q_{31}$ to $Q_{37}$ are each independently selected from a hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group According to another aspect, an organic light-emitting device includes:
 a first electrode;
 a second electrode; and
 an organic layer disposed between the first electrode and the second electrode, wherein the organic layer includes an emission layer, and further includes the condensed cyclic compound represented by Formula 1.

BRIEF DESCRIPTION OF THE DRAWINGS

These and/or other aspects will become apparent and more readily appreciated from the following description of the embodiments, taken in conjunction with the accompanying drawings in which:

The FIGURE is a cross-section view schematically illustrating an organic light-emitting device according to an exemplary embodiment.

DETAILED DESCRIPTION

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

It will be understood that when an element is referred to as being "on" another element, it can be directly in contact with the other element or intervening elements may be present therebetween. In contrast, when an element is referred to as being "directly on" another element, there are no intervening elements present.

It will be understood that, although the terms first, second, third etc. may be used herein to describe various elements, components, regions, layers, and/or sections, these elements, components, regions, layers, and/or sections should not be limited by these terms. These terms are only used to distinguish one element, component, region, layer, or section from another element, component, region, layer, or section. Thus, a first element, component, region, layer, or section discussed below could be termed a second element, component, region, layer, or section without departing from the teachings of the present embodiments.

The terminology used herein is for the purpose of describing particular embodiments only and is not intended to be limiting. As used herein, the singular forms "a," "an," and "the" are intended to include the plural forms as well, unless the context clearly indicates otherwise.

It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the FIGURES. For example, if the device in the FIGURES is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

"About" or "approximately" as used herein is inclusive of the stated value and means within an acceptable range of deviation for the particular value as determined by one of ordinary skill in the art, considering the measurement in question and the error associated with measurement of the particular quantity (i.e., the limitations of the measurement system). For example, "about" can mean within one or more standard deviations, or within ±30%, 20%, 10%, 5% of the stated value.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

Exemplary embodiments are described herein with reference to cross section illustrations that are schematic illustrations of idealized embodiments. As such, variations from the shapes of the illustrations as a result, for example, of manufacturing techniques and/or tolerances, are to be expected. Thus, embodiments described herein should not be construed as limited to the particular shapes of regions as illustrated herein but are to include deviations in shapes that result, for example, from manufacturing. For example, a region illustrated or described as flat may, typically, have rough and/or nonlinear features. Moreover, sharp angles that are illustrated may be rounded. Thus, the regions illustrated in the figures are schematic in nature and their shapes are not intended to illustrate the precise shape of a region and are not intended to limit the scope of the present claims.

A condensed cyclic compound is represented by Formula 1:

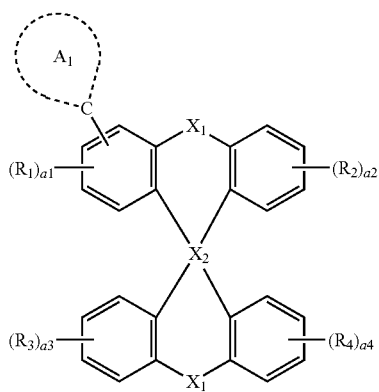

Formula 1

In Formula 1, $X_1$ may be O or S. For example, in Formula 1, $X_1$ may be O, but $X_1$ is not limited thereto.

In Formula 1, $X_2$ may be C, Si, or Ge. For example, in Formula 1, $X_2$ may be C, but $X_2$ is not limited thereto.

In Formula 1, ring $A_1$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formula 1, ring $A_1$ may be selected from a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, and a substituted or unsubstituted monovalent non-aromatic condensed heteropolycyclic group.

According to some embodiments, in Formula 1, ring $A_1$ may be selected from a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group; and a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —$N(Q_{31})(Q_{32})$, and —$Si(Q_{33})(Q_{34})(Q_{35})$, and $Q_{31}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group; and a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, but are not limited thereto.

According to an exemplary embodiment, in Formula 1, ring $A_1$ may be selected from a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group; and a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —$N(Q_{31})(Q_{32})$, and —$Si(Q_{33})(Q_{34})(Q_{35})$, and $Q_{31}$ to $Q_{35}$ are each independently selected from a hydrogen, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group; and a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group.

In Formula 1, $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$).

For example, in Formula 1, $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{20}$ alkyl group, a substituted or unsubstituted $C_1$-$C_{20}$ alkoxy group, a substituted or unsubstituted $C_6$-$C_{20}$ aryl group, a substituted or unsubstituted $C_1$-$C_{20}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), Si($Q_3$)($Q_4$)($Q_5$), and —B($Q_6$)($Q_7$).

According to some embodiments, in Formula 1, $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, and a triazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$); and —N($Q_1$)($Q_2$) and —Si($Q_3$)($Q_4$)($Q_5$), and $Q_1$ to $Q_5$ and $Q_{31}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group; and a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, but are not limited thereto.

According to an exemplary embodiment, in Formula 1, $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group;

a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$); and —N($Q_1$)($Q_2$) and —Si($Q_3$)($Q_4$)($Q_5$), and $Q_1$ to $Q_5$ and $Q_{31}$ to $Q_{35}$ are each independently selected from a hydrogen, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group; and a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group.

According to an exemplary embodiment, in Formula 1, ring $A_1$ may be selected from groups that are represented by Formulae 2-1 to 2-54, and $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —N($Q_1$)($Q_2$), —Si($Q_3$)($Q_4$)($Q_5$), and groups represented by Formula 2-1 to 2-59:

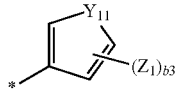

Formula 2-1

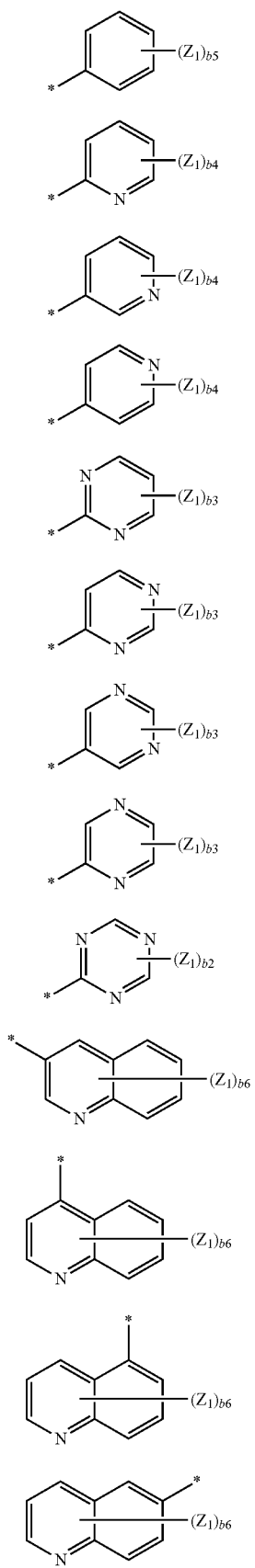
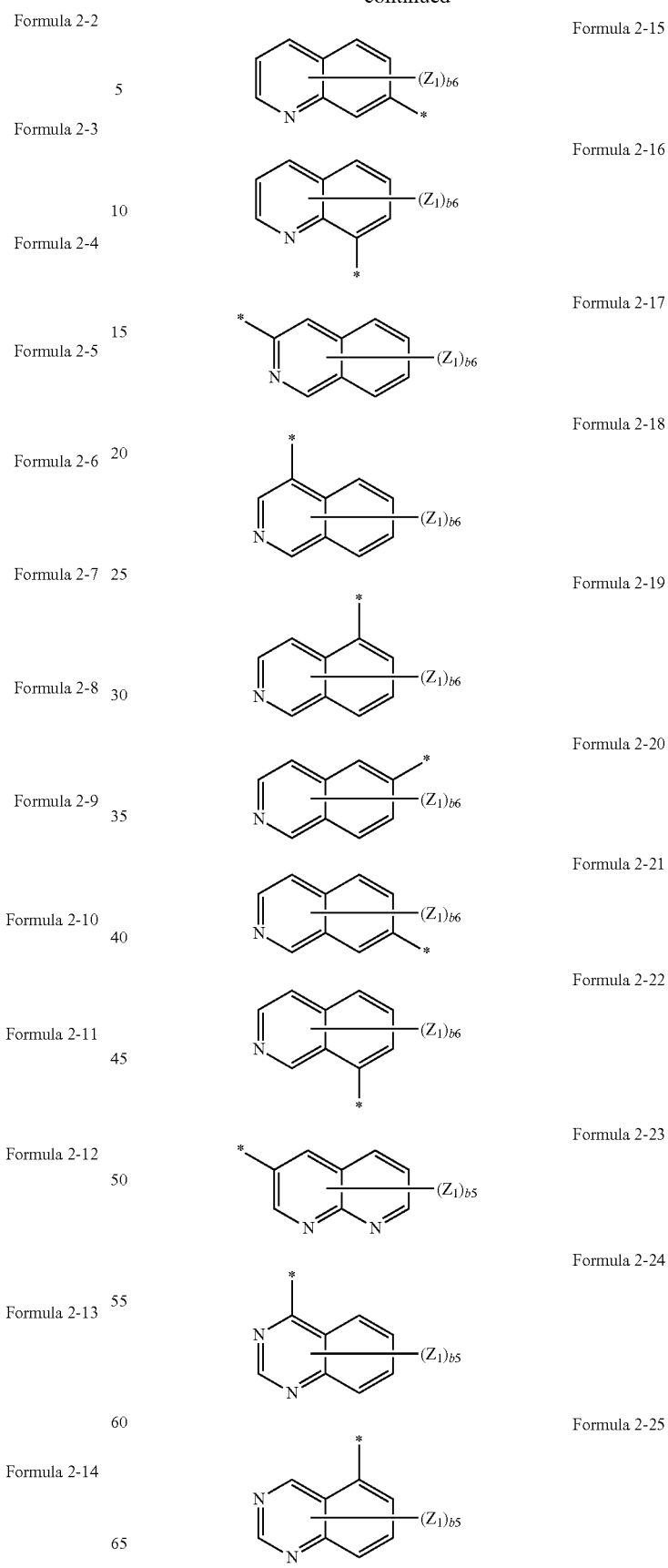
Formula 2-2
Formula 2-3
Formula 2-4
Formula 2-5
Formula 2-6
Formula 2-7
Formula 2-8
Formula 2-9
Formula 2-10
Formula 2-11
Formula 2-12
Formula 2-13
Formula 2-14
Formula 2-15
Formula 2-16
Formula 2-17
Formula 2-18
Formula 2-19
Formula 2-20
Formula 2-21
Formula 2-22
Formula 2-23
Formula 2-24
Formula 2-25

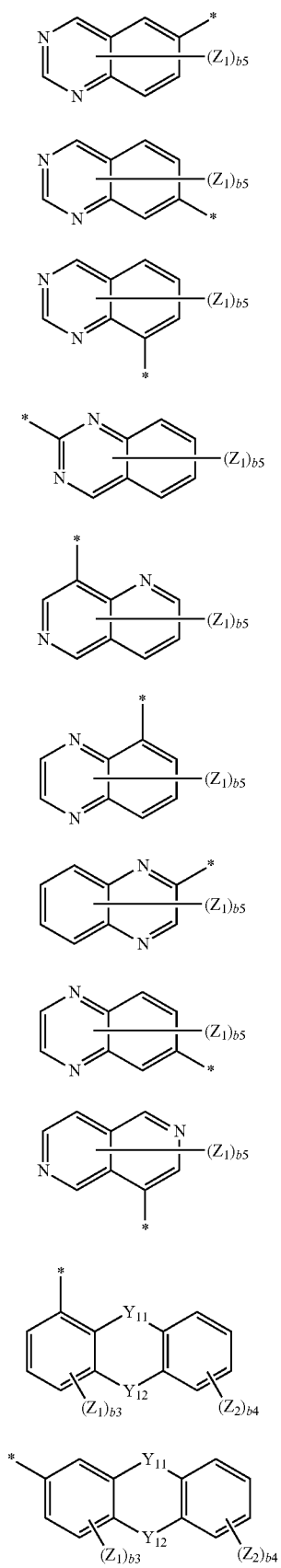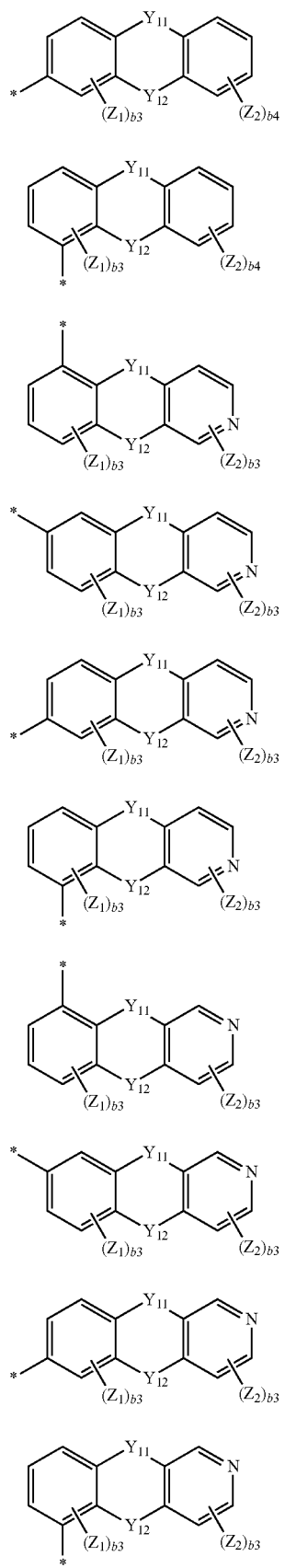

Formula 2-47 through Formula 2-59 (chemical structures)

In Formulae 2-1 to 2-59, $Y_{11}$ is O, S, N($Z_3$), or C($Z_3$)($Z_4$), $Y_{12}$ is a single bond, O, S, N($Z_5$), or C($Z_5$)($Z_6$), $Z_1$ to $Z_6$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{20}$ aryl group, a $C_6$-$C_{20}$ aryloxy group, a $C_6$-$C_{20}$ arylthio group, a $C_1$-$C_{20}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{20}$ aryl group, a $C_6$-$C_{20}$ aryloxy group, a $C_6$-$C_{20}$ arylthio group, a $C_1$-$C_{20}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkyl group, a $C_1$-$C_{10}$ heterocycloalkyl group, a $C_3$-$C_{10}$ cycloalkenyl group, a $C_2$-$C_{10}$ heterocycloalkenyl group, a $C_6$-$C_{20}$ aryl group, a $C_6$-$C_{20}$ aryloxy group, a $C_6$-$C_{20}$ arylthio group, a $C_1$-$C_{20}$ heteroaryl group, a monovalent non-aromatic condensed polycyclic group, and a monovalent non-aromatic condensed heteropolycyclic group; and —N($Q_{31}$)($Q_{32}$) and —Si($Q_{33}$)($Q_{34}$)($Q_{35}$), and $Q_{31}$ to $Q_{35}$ are each independently selected from a $C_6$-$C_{60}$ aryl group, a $C_1$-$C_{60}$ heteroaryl group, a monovalent non-aromatic condensed polycyclic group, and a monovalent non-aromatic condensed heteropolycyclic group, each substituted with at least one selected from a hydrogen, a $C_1$-$C_{20}$ alkyl group, a $C_1$-$C_{20}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, and a phenyl group, b2 is an integer of 1 or 2,
b3 is an integer selected from 1 to 3,
b4 is an integer selected from 1 to 4,
b5 is an integer selected from 1 to 5, and
b6 is an integer selected from 1 to 6, and
* is a binding site to a neighboring atom.

For example, in Formulae 2-1 to 2-59, —N($Q_1$)($Q_2$), and —Si($Q_3$)($Q_4$)($Q_5$), $Z_1$ to $Z_6$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$), and $Q_1$ to $Q_5$ and $Q_{31}$ to $Q_{35}$ are each independently selected from
a hydrogen, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group; and
a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, but are not limited thereto.

According to some embodiments, in Formulae 2-34 to 2-39, $Y_{11}$ may be 0, S, or N($Z_3$), and $Y_{12}$ may be a single bond or O.

According to an exemplary embodiment, in Formula 1,
ring $A_1$ may be selected from groups represented by Formula 2-1 to 2-10 and 2-35 to 2-54,
$R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, —N($Q_1$)($Q_2$), —Si($Q_3$)($Q_4$)($Q_5$), and groups represented by Formulae 2-1 to 2-10 and 2-35 to 2-54, wherein, in Formulae 2-1 to 2-10 and 2-35 to 2-54,
$Y_{11}$ may be O, S, or N($Z_3$),
$Y_{12}$ may be a single bond or O,
$Z_1$ to $Z_6$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, a pyrimidinyl group, a pyrazinyl group, a pyridazinyl group, and a triazinyl group, and
$Q_1$ to $Q_5$ are each independently selected from
a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group; and
a phenyl group, a naphthyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group,
b2 to b6 may be each independently an integer of 1 or 2, and
* may be a binding site to a neighboring atom, but they are not limited thereto.

According to some embodiments, in Formula 1,
ring $A_1$ may be selected from groups represented by Formulae 3-1 to 3-121, and
$R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_{20}$ alkyl group, a $C_1$-$C_{20}$ alkoxy group, —N($Q_1$)($Q_2$), —Si($Q_3$)($Q_4$)($Q_5$) (wherein, $Q_1$ to $Q_5$ are each independently selected from a phenyl group, a phenyl group substituted with a phenyl group, a naphthyl group, a pyridinyl group, a pyrimidinyl group, a pyrazinyl group, a pyridazinyl group, and a triazinyl group) and groups represented by Formulae 3-1 to 3-131, but they are not limited thereto:

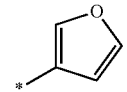

Formula 3-1

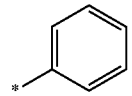

Formula 3-2

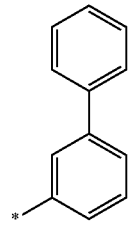

Formula 3-3

Formula 3-4
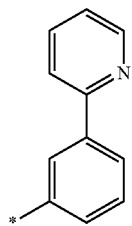
Formula 3-5
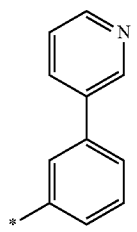
Formula 3-6
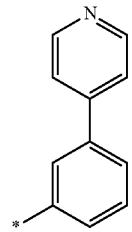
Formula 3-7
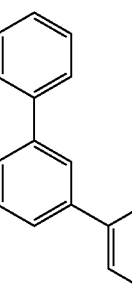
Formula 3-8
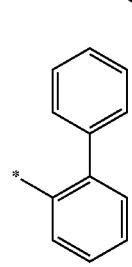
Formula 3-9
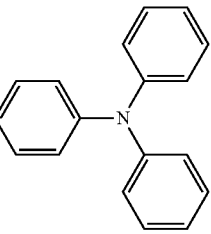
Formula 3-10
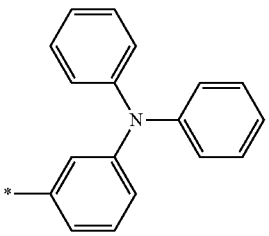
Formula 3-11
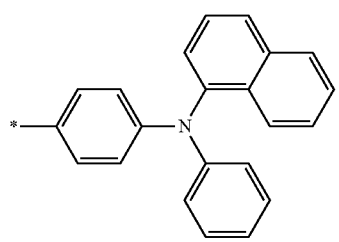
Formula 3-12
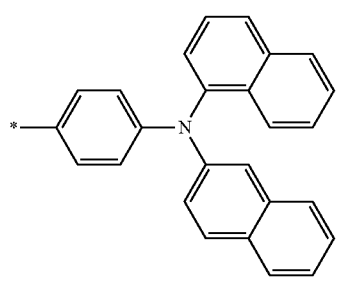
Formula 3-13
Formula 3-14
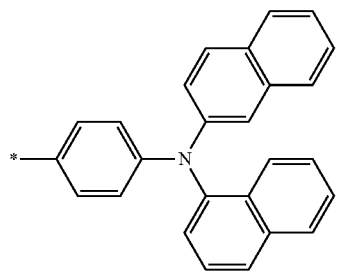

-continued
Formula 3-15
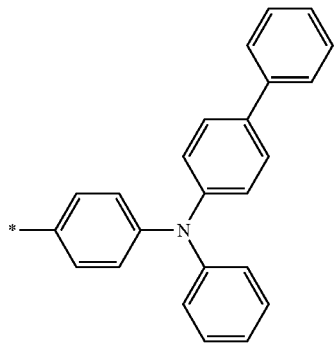
Formula 3-16
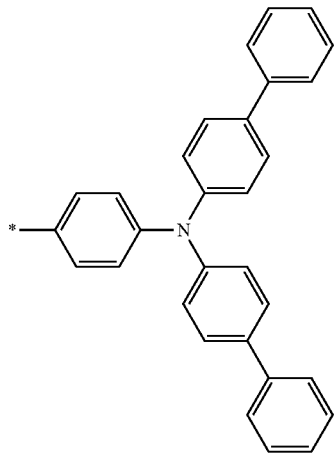
Formula 3-17
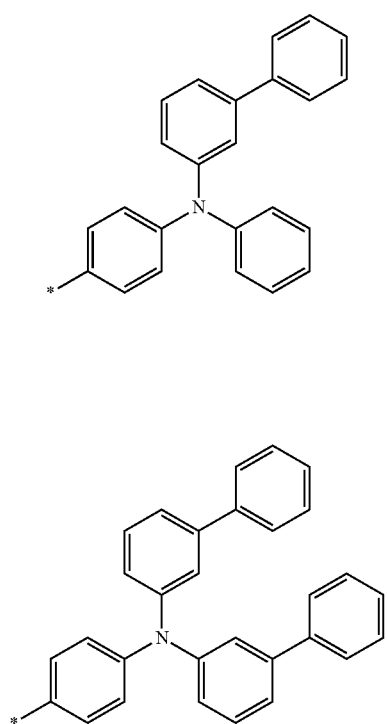
Formula 3-18
Formula 3-19
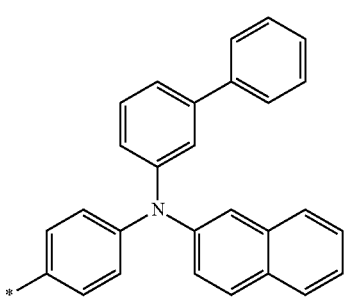
Formula 3-20
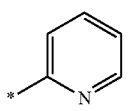
Formula 3-21
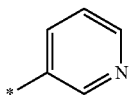
Formula 3-22
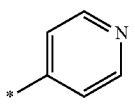
Formula 3-23
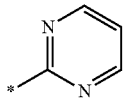
Formula 3-24
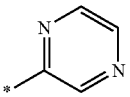
Formula 3-25
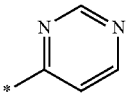
Formula 3-26
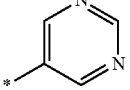
Formula 3-27
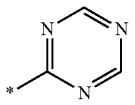
Formula 3-28
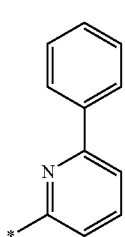

Formula 3-29

Formula 3-30

Formula 3-31

Formula 3-32

Formula 3-33

Formula 3-34

Formula 3-35

Formula 3-36

Formula 3-37

Formula 3-38

Formula 3-39

Formula 3-40

Formula 3-41
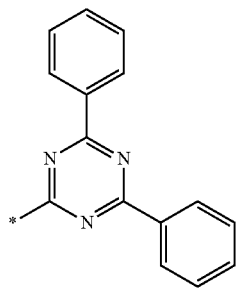
Formula 3-42
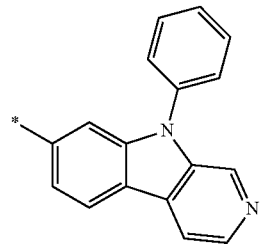
Formula 3-47
Formula 3-43
Formula 3-48
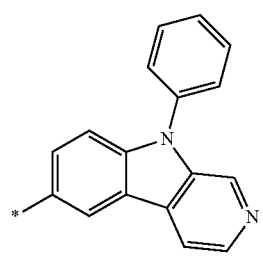
Formula 3-44
Formula 3-49
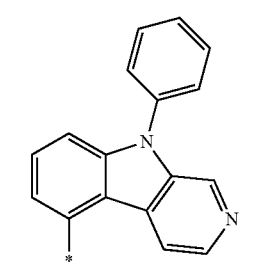
Formula 3-45
Formula 3-50
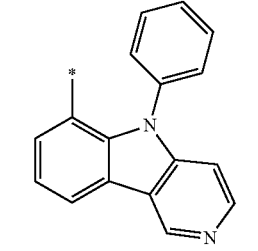
Formula 3-46
Formula 3-51
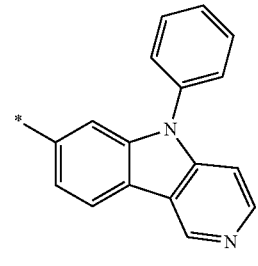
Formula 3-52
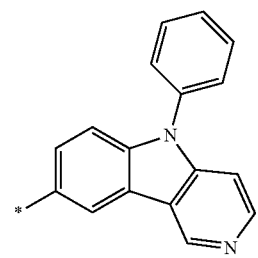

Formula 3-53
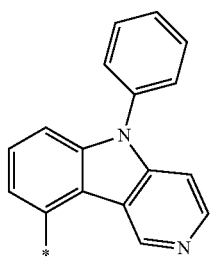
Formula 3-54
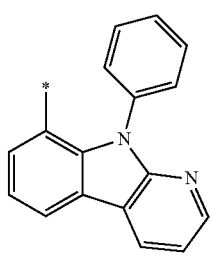
Formula 3-55
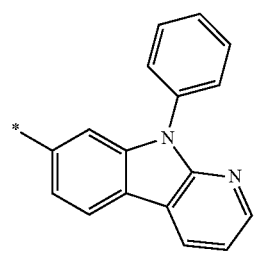
Formula 3-56
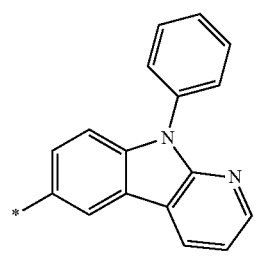
Formula 3-57
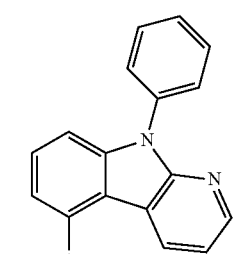
Formula 3-58
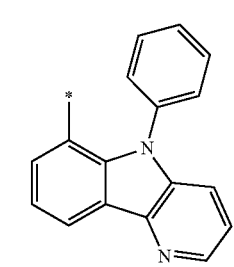
Formula 3-59
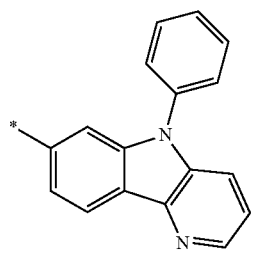
Formula 3-60
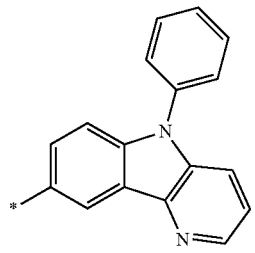
Formula 3-61
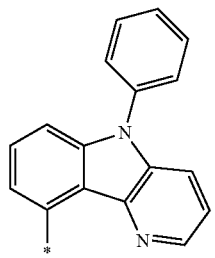
Formula 3-62
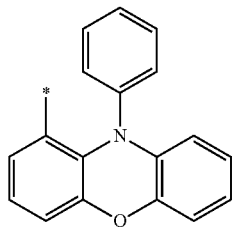
Formula 3-63
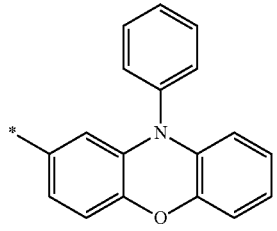
Formula 3-64
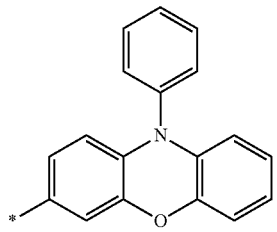

Formula 3-65
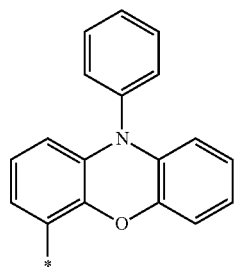
Formula 3-66
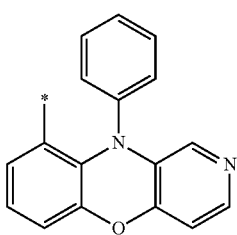
Formula 3-67
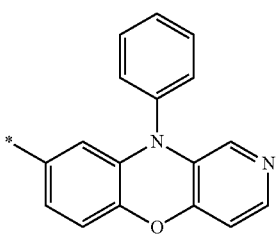
Formula 3-68
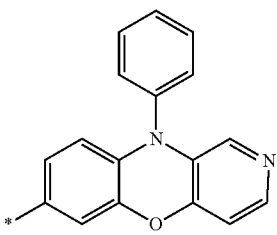
Formula 3-69
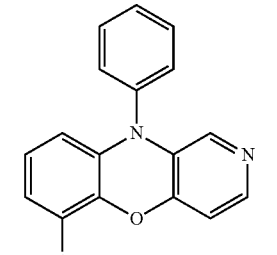
Formula 3-70
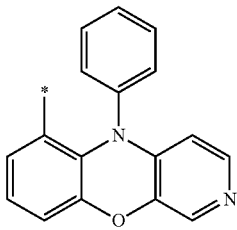
Formula 3-71
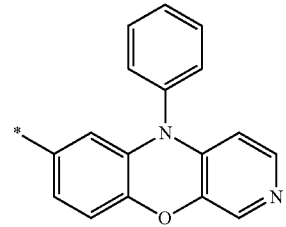
Formula 3-72
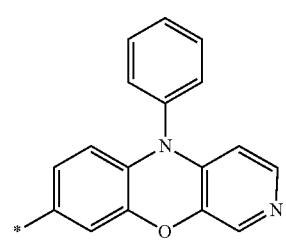
Formula 3-73
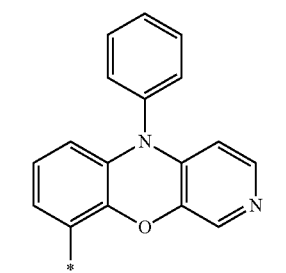
Formula 3-74
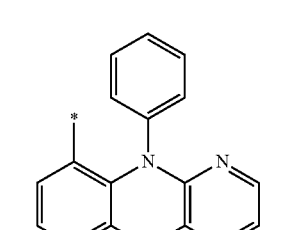
Formula 3-75
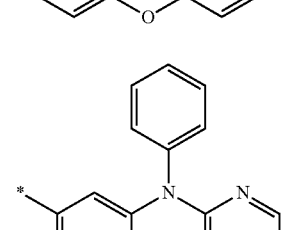
Formula 3-76
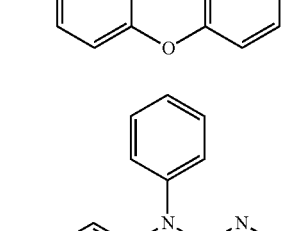

-continued

Formula 3-77

Formula 3-78

Formula 3-79

Formula 3-80

Formula 3-81

Formula 3-82

Formula 3-83

-continued

Formula 3-84

Formula 3-85

Formula 3-86

Formula 3-87

Formula 3-88

Formula 3-89

Formula 3-90

Formula 3-91

Formula 3-92

Formula 3-93

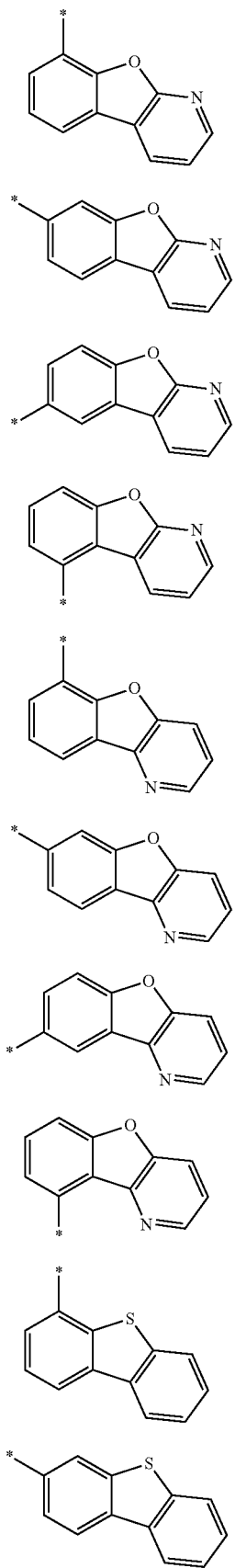
Formula 3-94
Formula 3-95
Formula 3-96
Formula 3-97
Formula 3-98
Formula 3-99
Formula 3-100
Formula 3-101
Formula 3-102
Formula 3-103
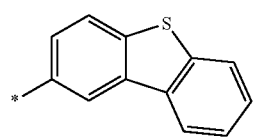
Formula 3-104
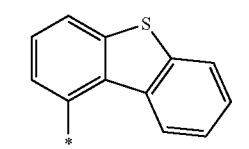
Formula 3-105
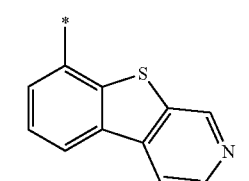
Formula 3-106
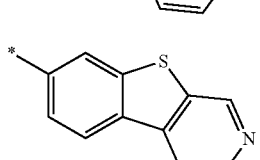
Formula 3-107
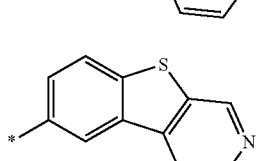
Formula 3-108
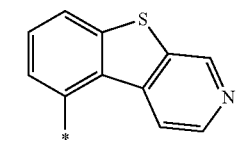
Formula 3-109
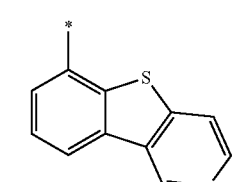
Formula 3-110
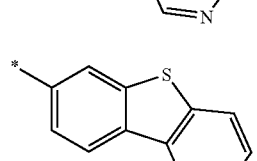
Formula 3-111
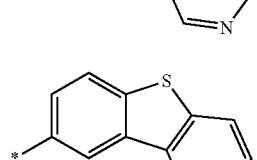
Formula 3-112
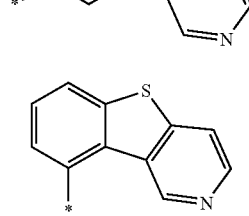
Formula 3-113

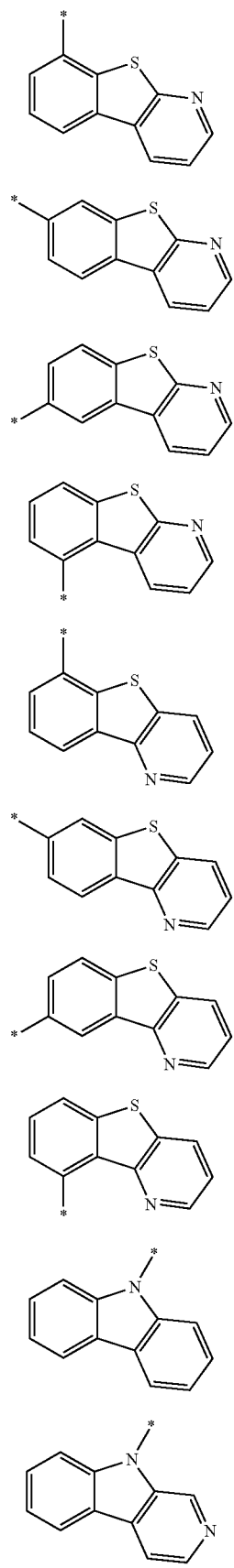

Formula 3-114
Formula 3-115
Formula 3-116
Formula 3-117
Formula 3-118
Formula 3-119
Formula 3-120
Formula 3-121
Formula 3-122
Formula 3-123

Formula 3-124
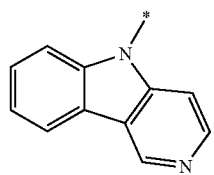

Formula 3-125
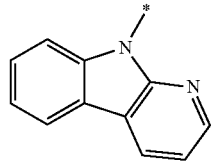

Formula 3-126
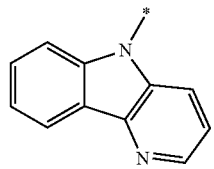

Formula 3-127
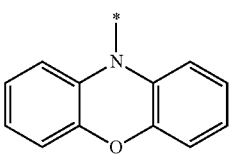

Formula 3-128
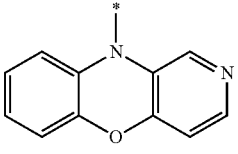

Formula 3-129
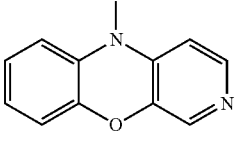

Formula 3-130
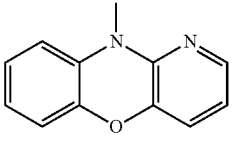

Formula 3-131

In Formula 1, a1 is an integer selected from 0 to 3, and a2, a3, and a4 are each independently an integer selected from 0 to 4.

For example, in Formula 1, a1 to a4 may be each independently an integer of 0, 1, or 2. For example, in Formula 1, a1 to a4 may be each independently an integer of 0 or 1.

In Formula 1, when a1 is 2 or greater, groups $R_1$ may be identical to or different from each other, when a2 is 2 or greater, groups $R_2$ may be identical to or different from each other, when a3 is 2 or greater, groups $R_3$ may be identical to or different from each other, and when a4 is 2 or greater, groups $R_4$ may be identical to or different from each other.

For example, in Formula 1, a1+a2+a3+a4 may be 2. According to some embodiments, in Formula 1, a1+a2+a3+a4 may be 1, but not limited thereto.

According to an exemplary embodiment, in Formula 1, a1 may be 0, a2 may be 1, $R_2$ may be selected from a substituted or unsubstituted cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and ring $A_1$ and $R_2$ may be different from each other.

According to some embodiments, in Formula 1, a1 may be 0, a3 may be 1, $R_3$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and ring $A_1$ and $R_3$ may be different from each other.

According to some embodiments, in Formula 1, a1 may be 0, a4 may be 1, $R_4$ may be selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, and ring $A_1$ and $R_4$ may be different from each other.

In some embodiments, a condensed cyclic compound represented by Formula 1 may be represented by one of Formulae 1-1 to 1-8:

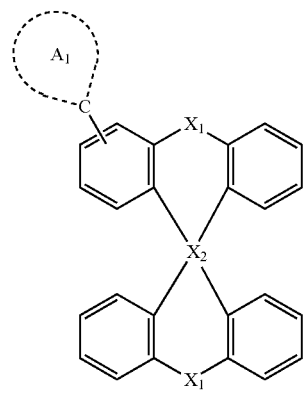

Formula 1-1

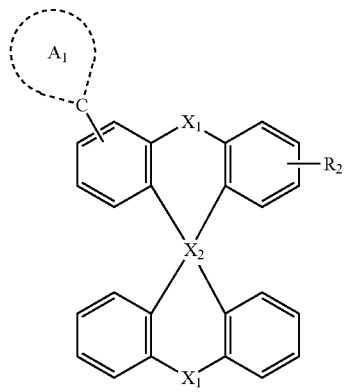

Formula 1-2

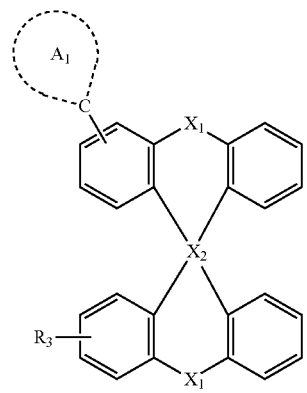

Formula 1-3

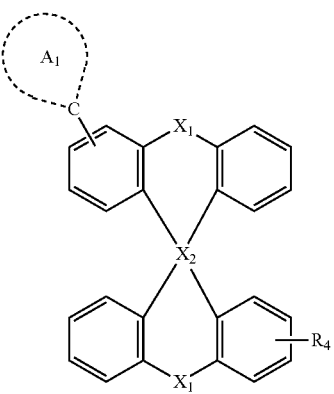

Formula 1-4

-continued

Formula 1-5

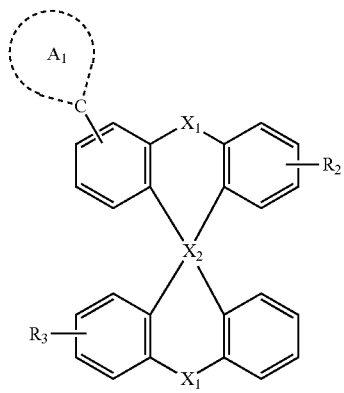

Formula 1-6

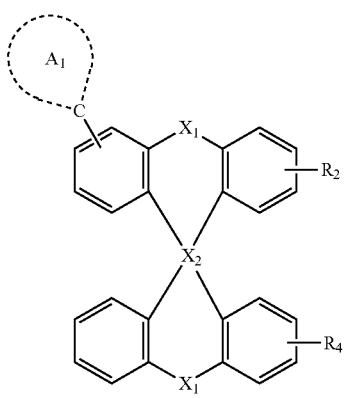

Formula 1-7

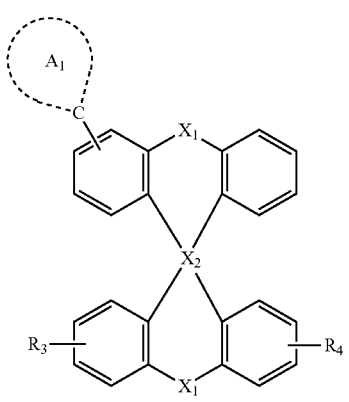

Formula 1-8

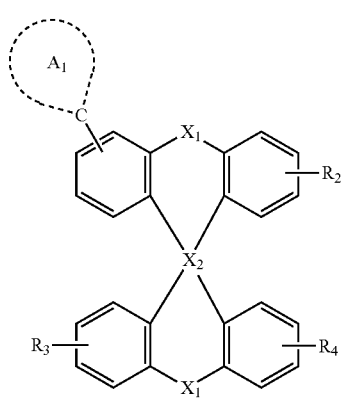

In Formulae 1-1 to 1-8, descriptions of $X_1$, $X_2$, ring $A_1$, $R_2$, and $R_4$ are the same as defined above in connection with those in Formula 1, but each of $R_1$ to $R_4$ is not a hydrogen.

According to an exemplary embodiment, in Formulae 1-1 to 1-8, $X_1$ may be O, and $X_2$ may be C.

According to some embodiments, in Formulae 1-1 to 1-8, ring $A_1$ may be selected from groups represented by Formulae 2-1 to 2-54, and $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —N($Q_1$)($Q_2$), —Si($Q_3$)($Q_4$)($Q_5$) (wherein, $Q_1$ to $Q_5$ are each independently selected from a phenyl group, a phenyl group substituted with a phenyl group, a naphthyl group, a pyridinyl group, a pyrimidinyl group, a pyrazinyl group, a pyridazinyl group, and a triazinyl group), and groups represented by Formulae 2-1 to 2-59.

According to some embodiments, in Formulae 1-1 to 1-8, ring $A_1$ may be selected from groups represented by Formulae 3-1 to 3-121, and $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —N($Q_1$)($Q_2$), —Si($Q_3$)($Q_4$)($Q_5$) (wherein, $Q_1$ to $Q_5$ are each independently selected from a phenyl group, a phenyl group substituted with a phenyl group, a naphthyl group, a pyridinyl group, a pyrimidinyl group, a pyrazinyl group, a pyridazinyl group, and a triazinyl group), and groups represented by Formulae 3-1 to 3-131.

According to some embodiments, in Formulae 1-1 to 1-8, $R_2$ to $R_4$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

In Formulae 1-2 to 1-4, ring $A_1$ and $R_2$ to $R_4$ may be different from one another. In this regard, charge transferring ability of a condensed cyclic compound represented by Formula 1 may be effectively controlled, and thus the condensed cyclic compound may have excellent electric characteristics.

According to some embodiments, in Formulae 1-1 to 1-8, $R_2$ to $R_4$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group; and in Formulae 1-2 to 1-4, ring $A_1$ and $R_2$ to $R_4$ may be identical to one another.

According to another embodiment, the condensed cyclic compound represented by Formula 1 may be represented by one of Formulae 1(1) to 1(4):

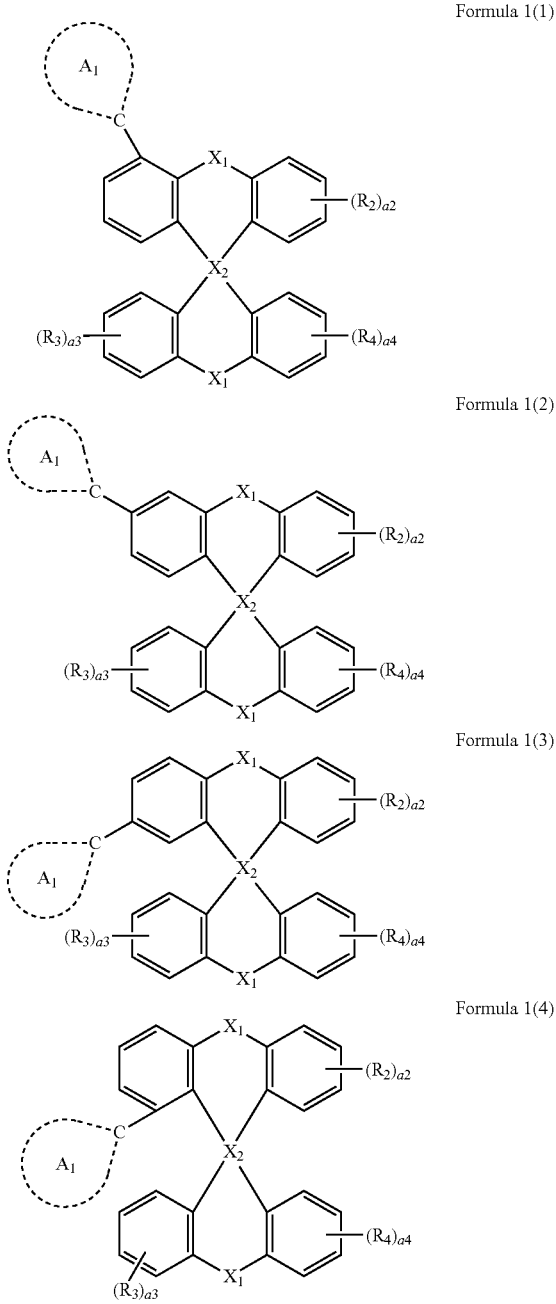

Formula 1(1)

Formula 1(2)

Formula 1(3)

Formula 1(4)

In Formulae 1(1) to 1(4), descriptions of $X_1$, $X_2$, ring $A_1$, $R_2$ to $R_4$, and a1 to a4 are the same as defined above in the present disclosures.

For example, in Formulae 1(1) to 1(4),
a2=0, a3=0, and a4=1;
a2=0, a3=1, and a4=0;
a2=1, a3=0, and a4=0;
a2=0, a3=1, and a4=1;
a2=1, a3=0, and a4=1;
a2=1, a3=1, and a4=0; or
a2=1, a3=1, and a4=1, but they are not limited thereto.

According to an exemplary embodiment, in Formulae 1(1) to 1(4), $X_1$ may be O and $X_2$ may be C.

According to another embodiment, in Formulae 1(1) to 1(4), ring $A_1$ may be selected from groups represented by Formulae 2-1 to 2-54;

$R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —N($Q_1$)($Q_2$), —Si($Q_3$)($Q_4$)($Q_5$) (wherein, $Q_1$ to $Q_5$ are each independently selected from a phenyl group, a phenyl group substituted with a phenyl group, a naphthyl group, a pyridinyl group, a pyrimidinyl group, a pyrazinyl group, a pyridazinyl group, and a triazinyl group), and groups represented by Formulae 2-1 to 2-59; and a2 to a4 may be each independently 0, 1, or 2.

According to some embodiments, in Formulae 1(1) to 1(4), ring A1 may be selected from groups represented by Formulae 3-1 to 3-121; and $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —N($Q_1$)($Q_2$), —Si($Q_3$)($Q_4$)($Q_5$) (wherein, $Q_1$ to $Q_5$ are each independently selected from a phenyl group, a phenyl group substituted with a phenyl group, a naphthyl group, a pyridinyl group, a pyrimidinyl group, a pyrazinyl group, a pyridazinyl group, and a triazinyl group), and groups represented by Formula 3-1 to 3-131.

According to some embodiments, in Formulae 1(1) to 1(4), $R_2$ to $R_4$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, but they are not limited thereto.

A molecular weight of the condensed cyclic compound represented by Formula 1 may be, for example, in a range of about 300 to about 2,000. In some embodiments, a molecular weight of the condensed cyclic compound represented by Formula 1 may be, for example, in a range of about 348 to about 1,500. When a molecular weight of the condensed cyclic compound represented by Formula 1 is within these ranges, the condensed cyclic compound may be easily purified by using a sublimation purification method.

For example, the condensed cyclic compound represented by Formula 1 may be one of Compounds 1 to 532, but it is not limited thereto:

1
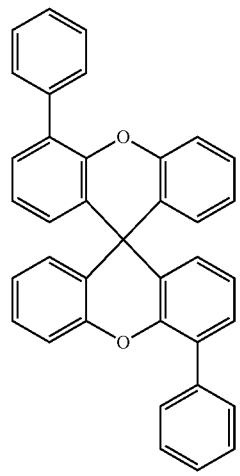
2
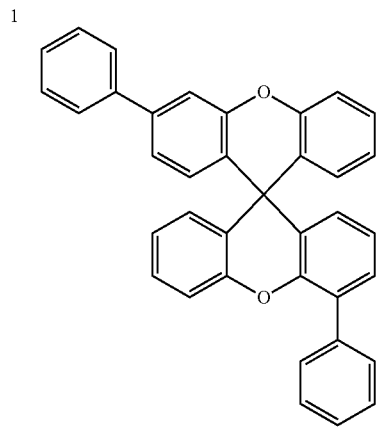
3
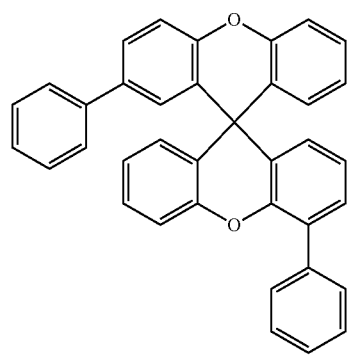
4
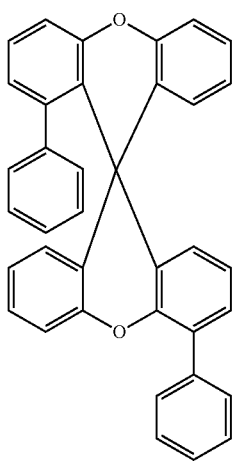
5
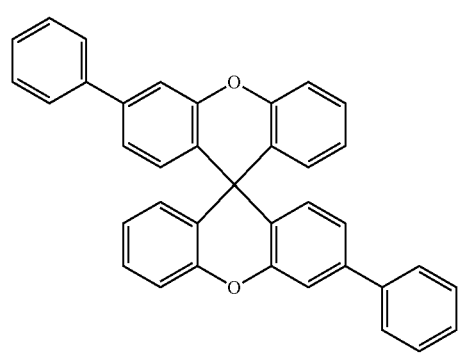
6
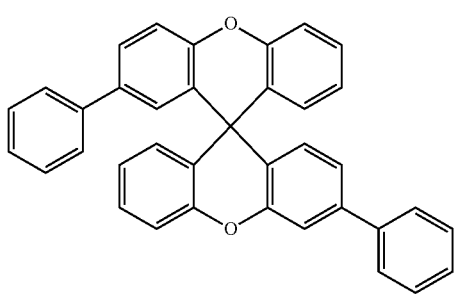

-continued
7
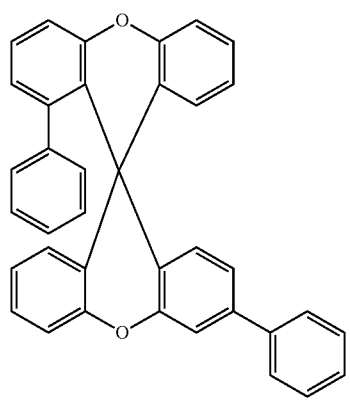
8
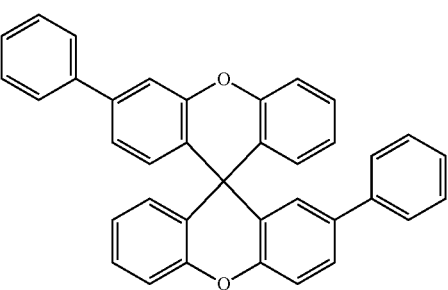
9
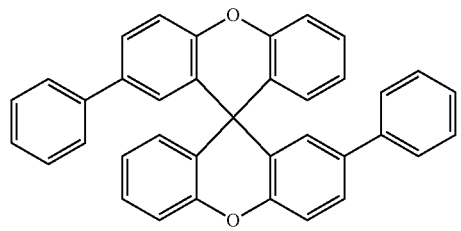
10
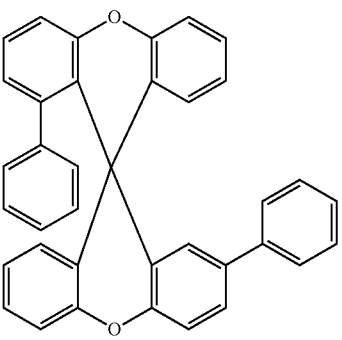
11
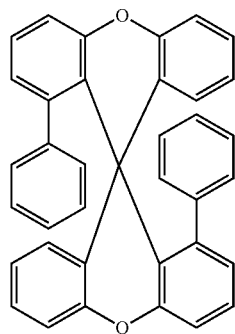
12
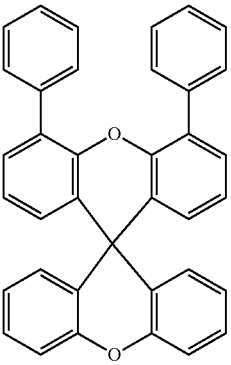
13
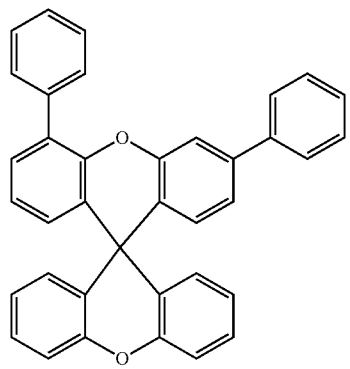
14
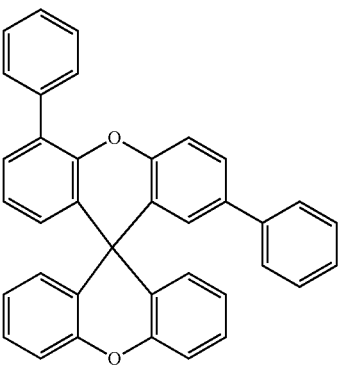

-continued
15
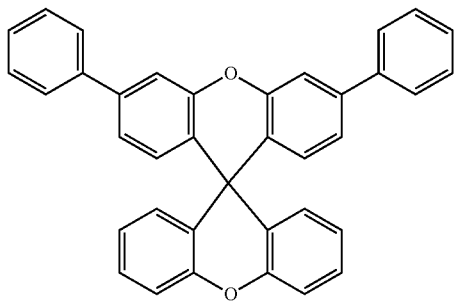
16
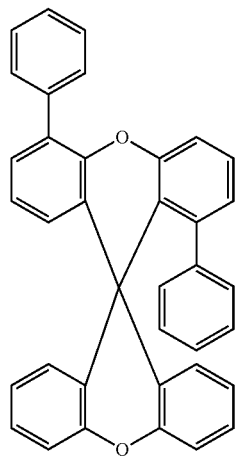
17
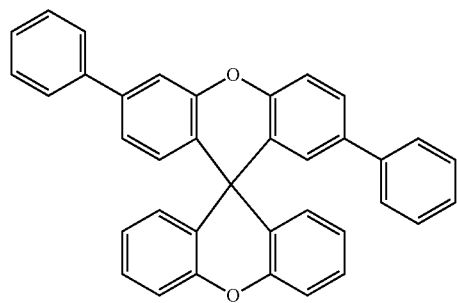
18
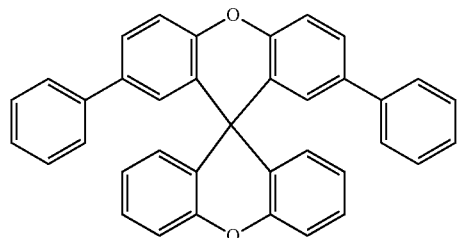
19
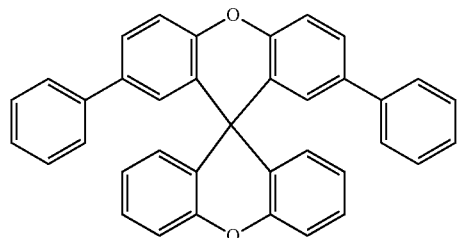
20
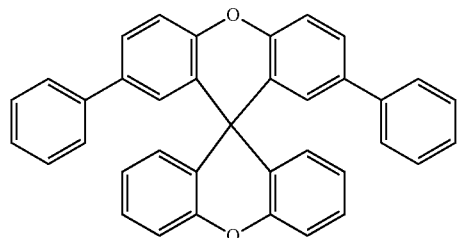
21
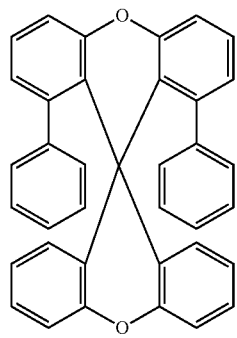
22
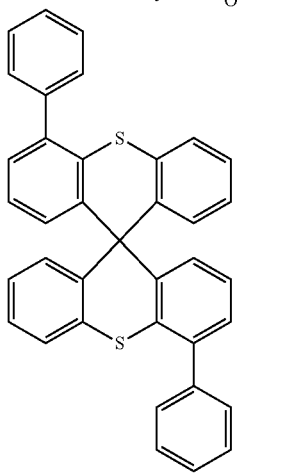

-continued
23
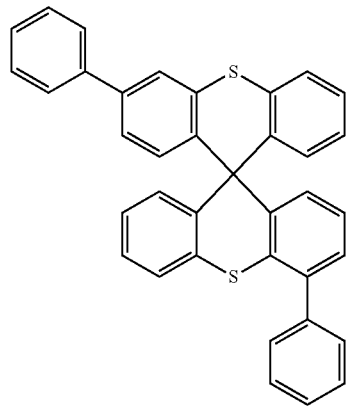
24
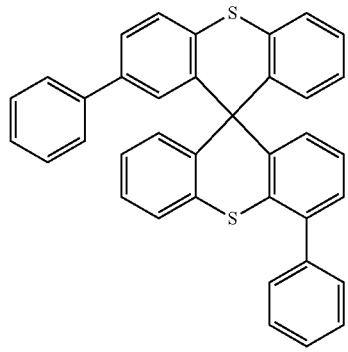
25
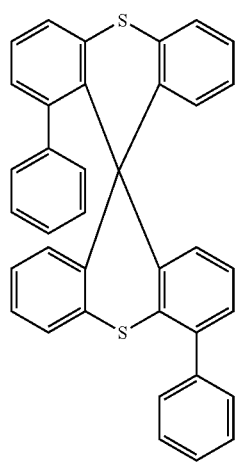
26
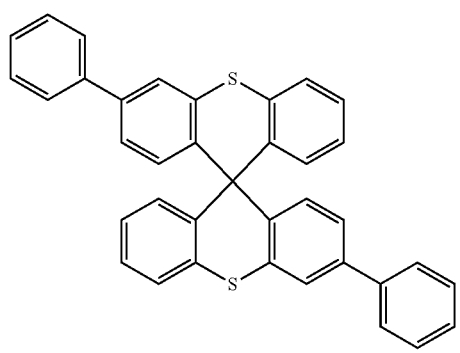
27
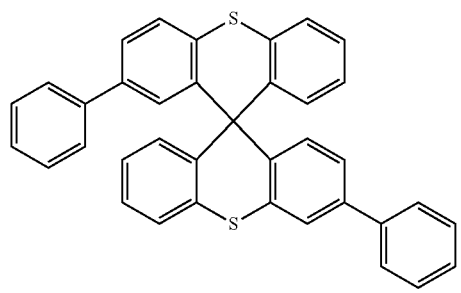
28
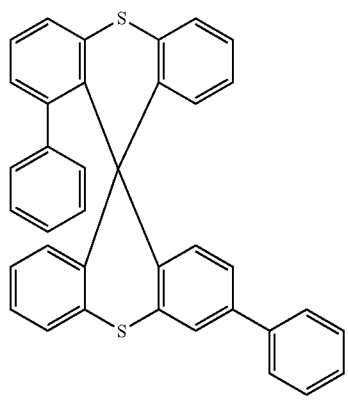
29
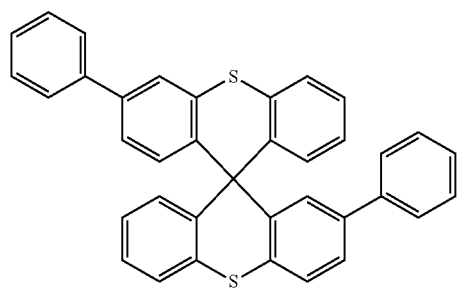
30
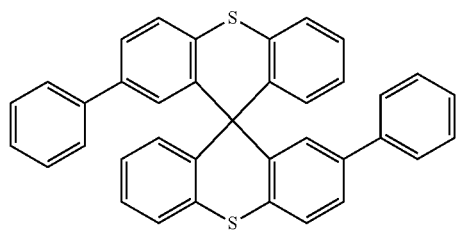

-continued
31
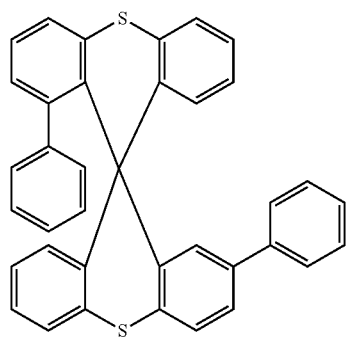
32
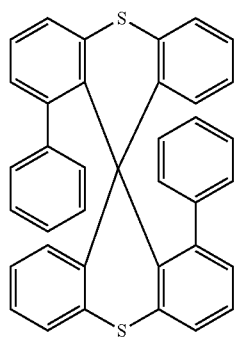
33
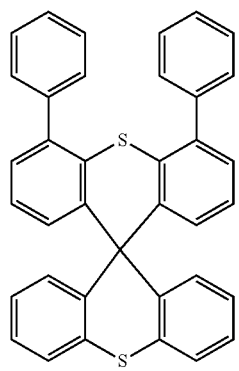
34
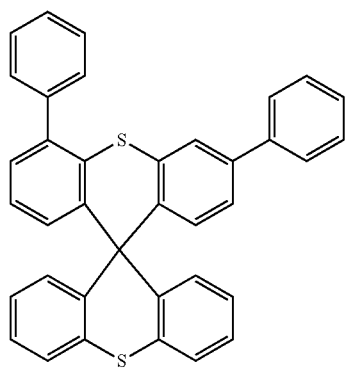
35
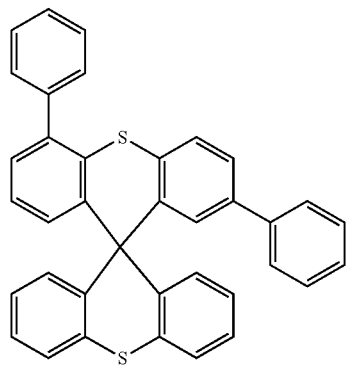
36
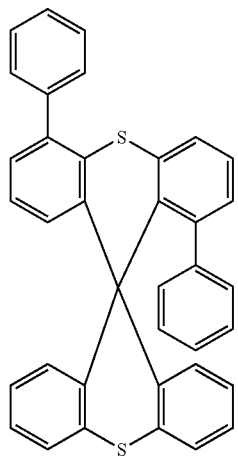
37
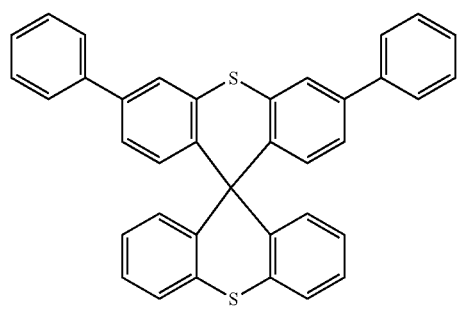
38
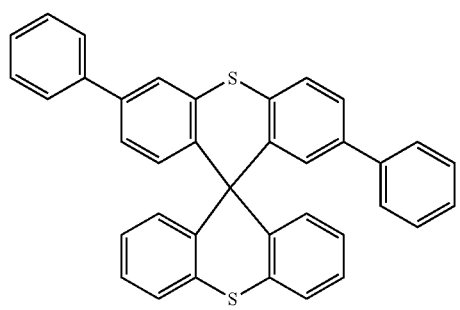

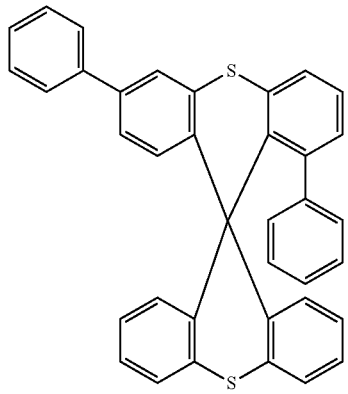
39
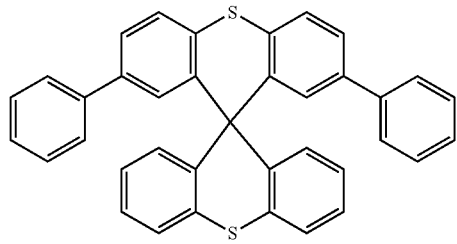
40
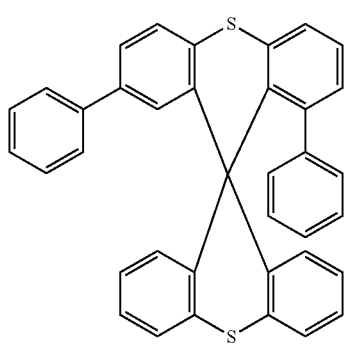
41
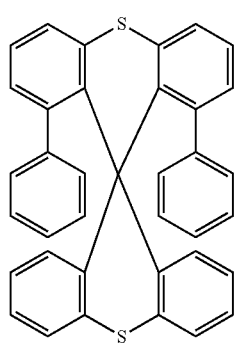
42
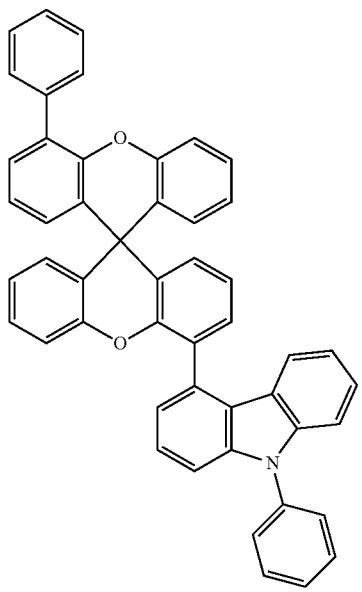
43
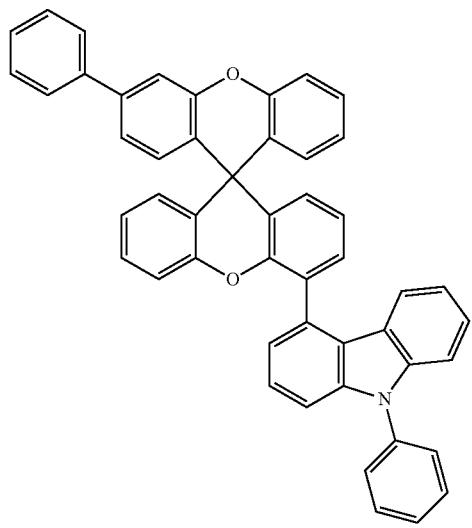
44

-continued
45
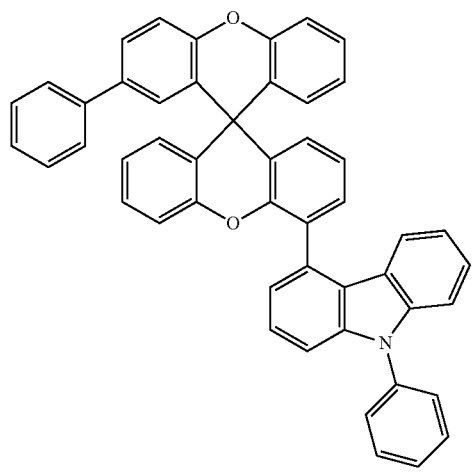
46
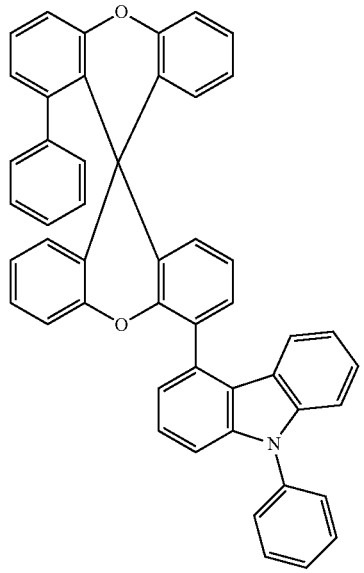
47
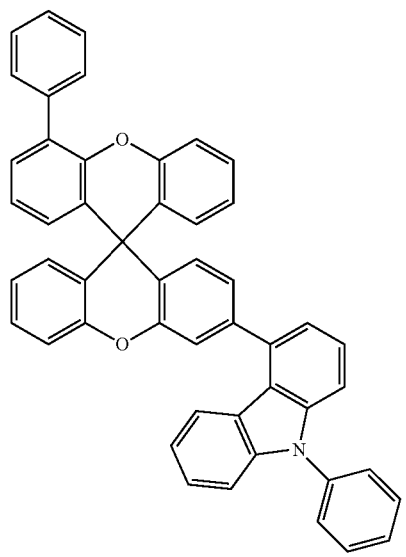
48
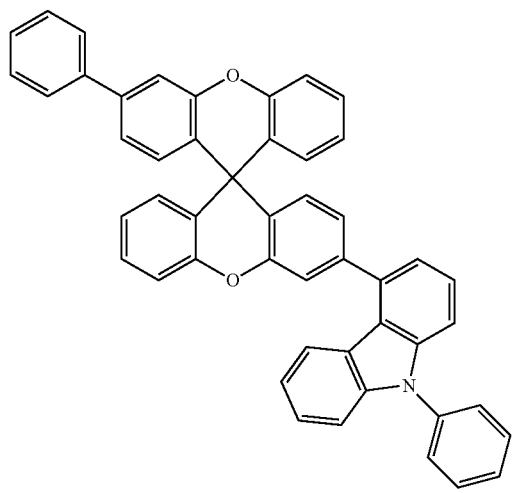
49
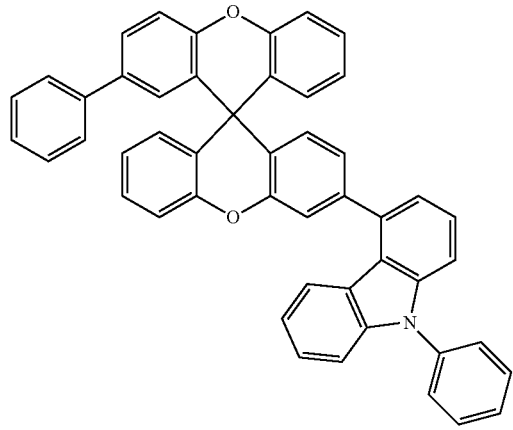
50
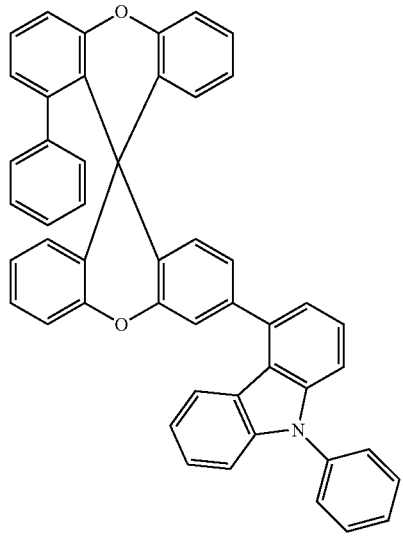

-continued
51
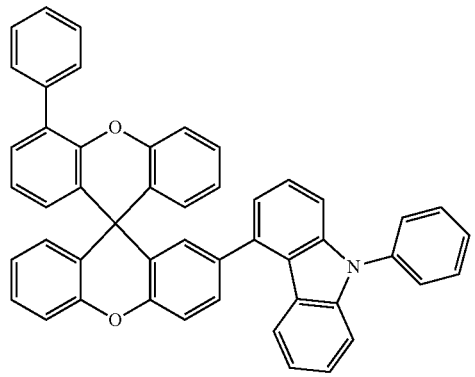
52
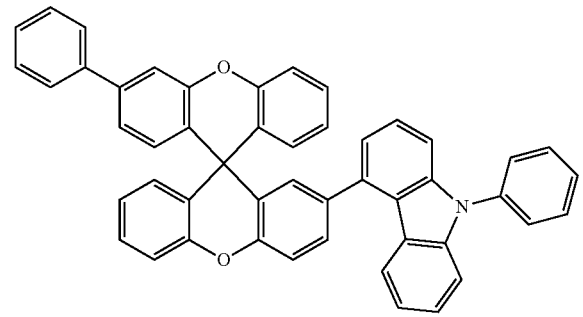
53
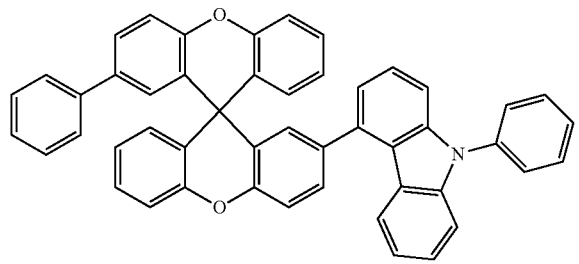
54
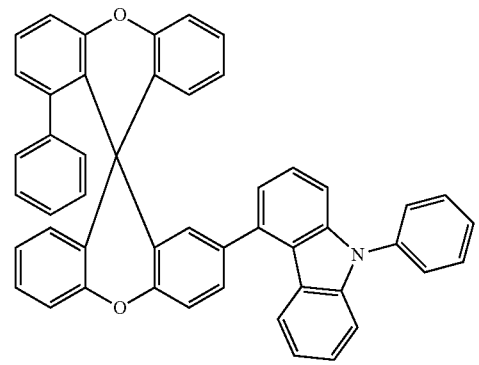
55
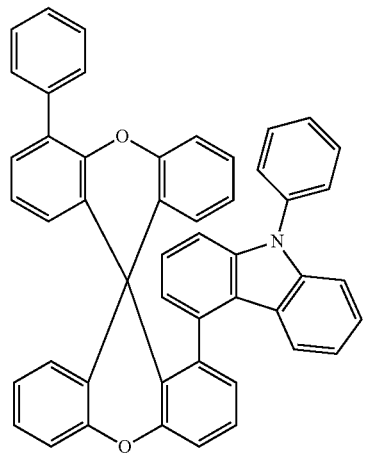
56
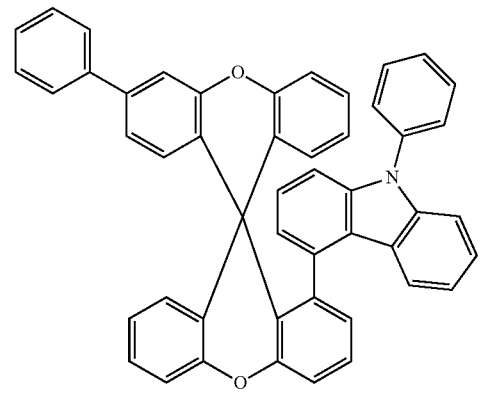
57
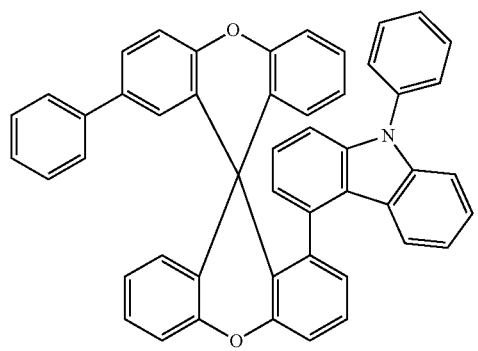
58
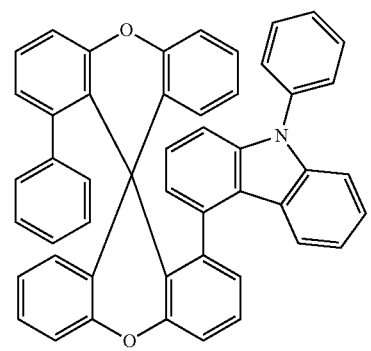

-continued
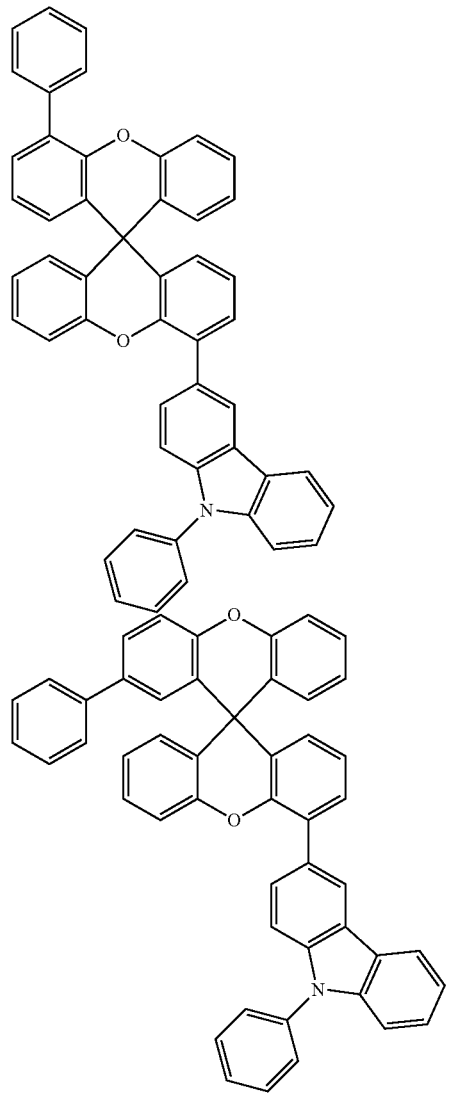
59
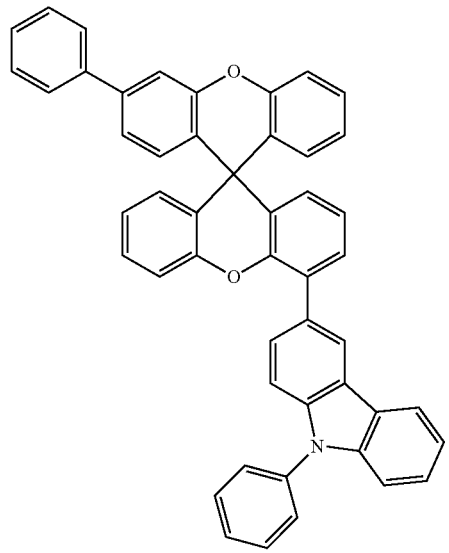
60
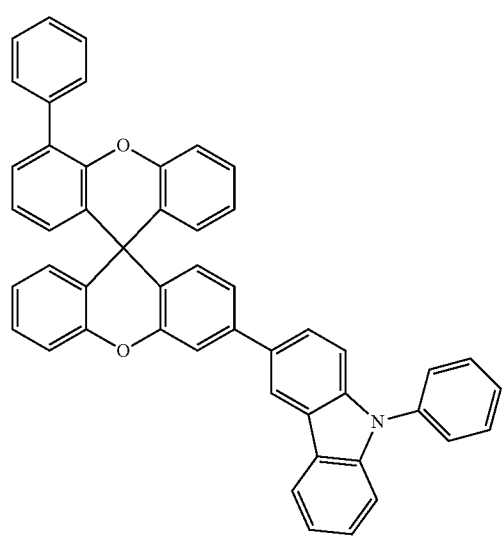
63
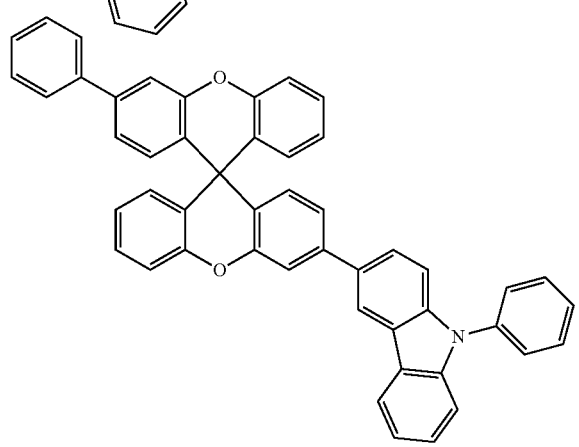
64

-continued
65
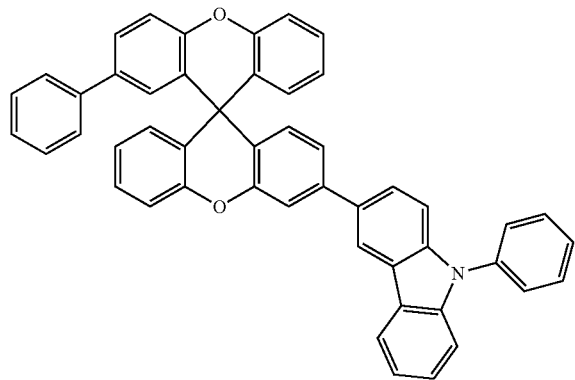
66
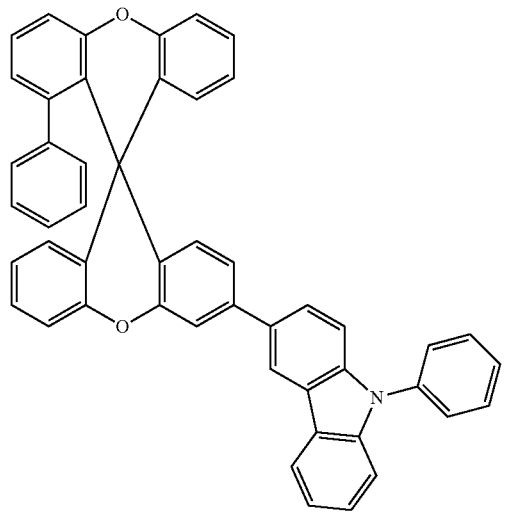
67
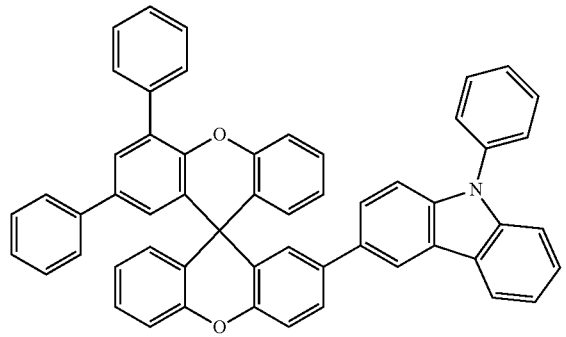
68
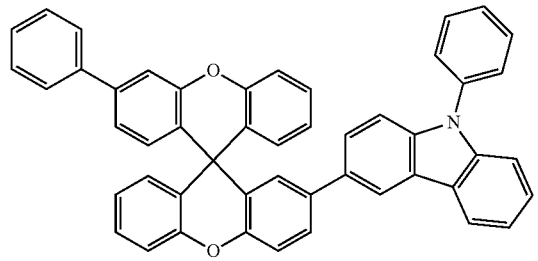
69
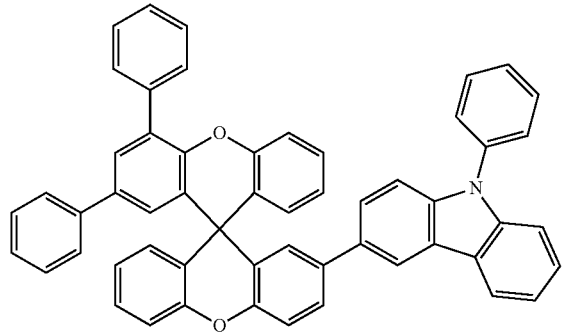
70
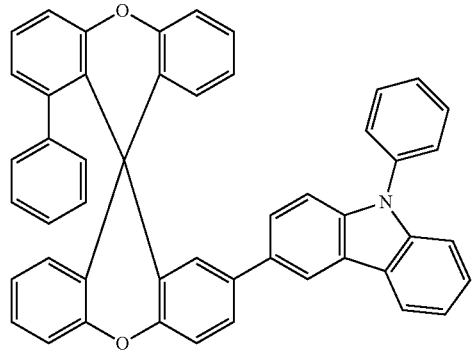
71
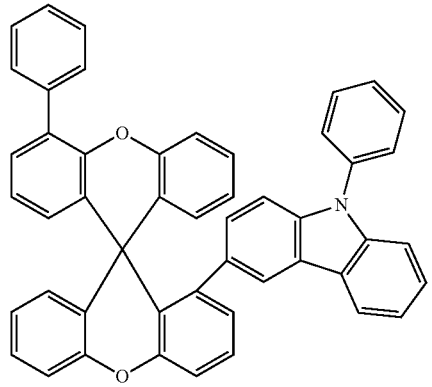
72
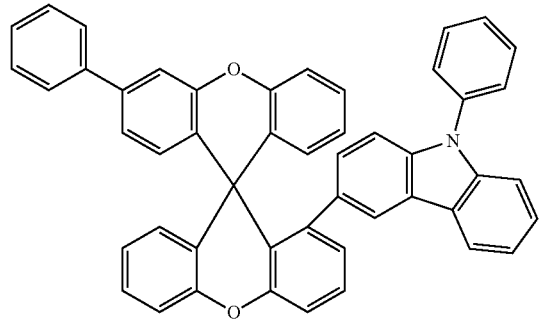

-continued
73
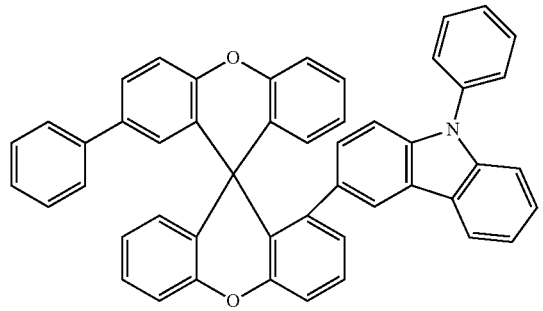
74
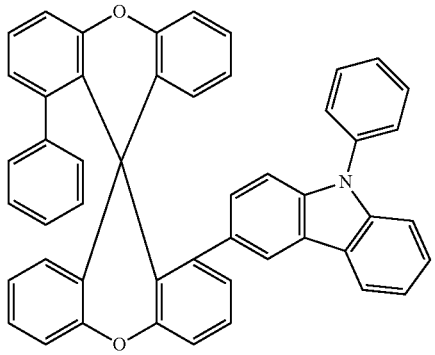
75
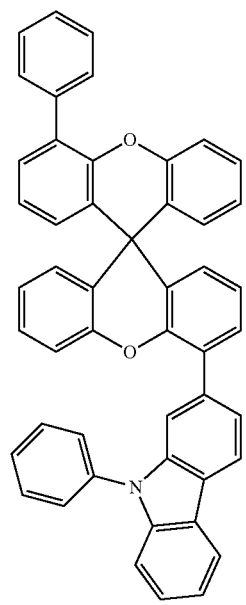
76
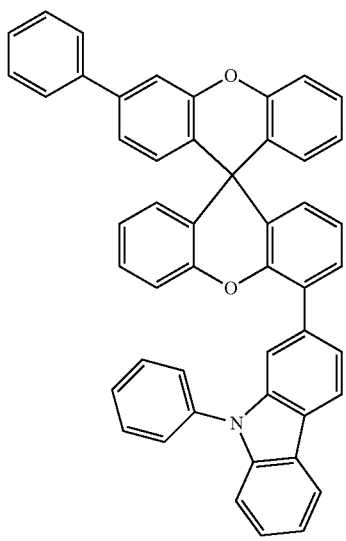
77
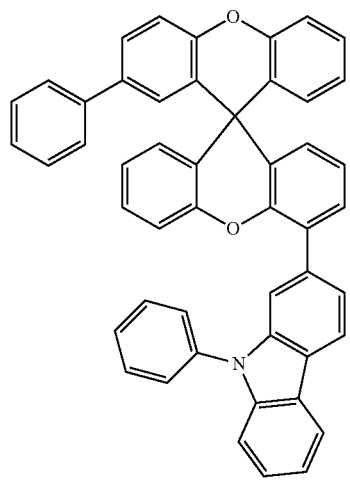
78
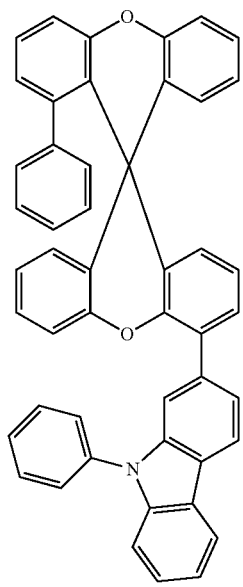

-continued
79
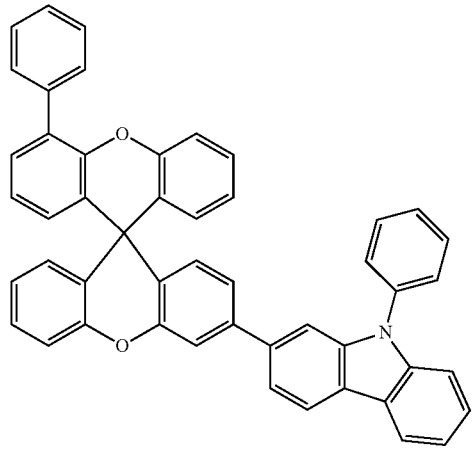
80
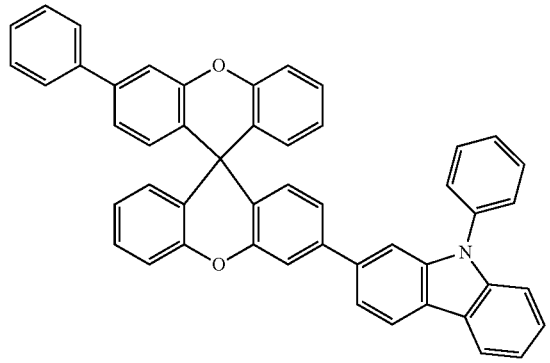
81
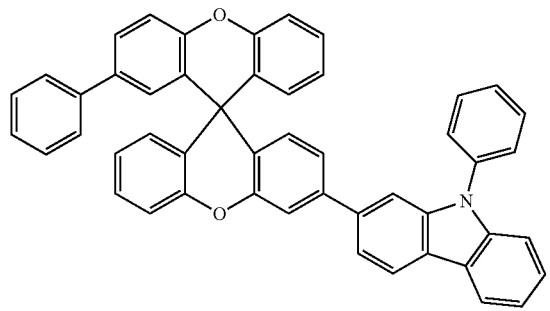
82
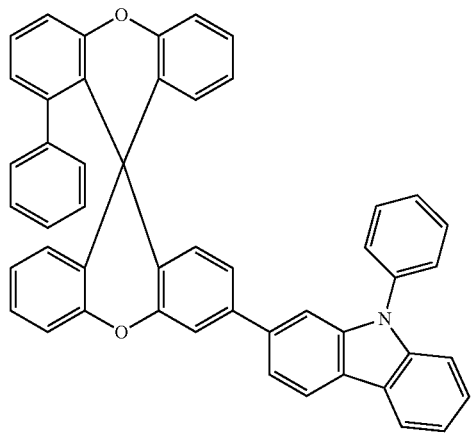
83
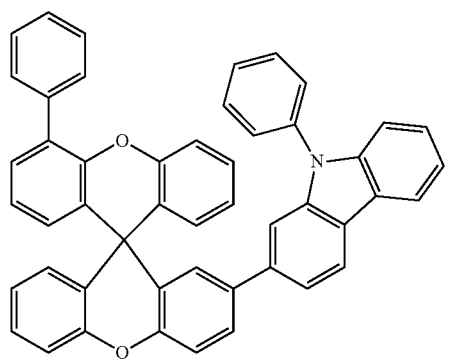
84
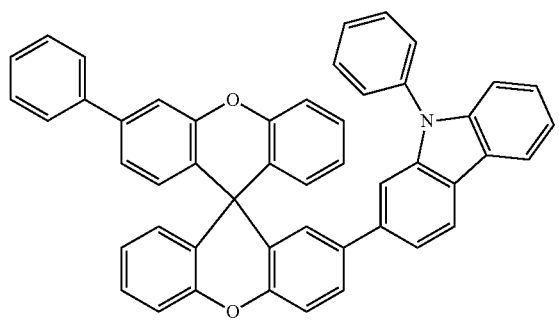
85
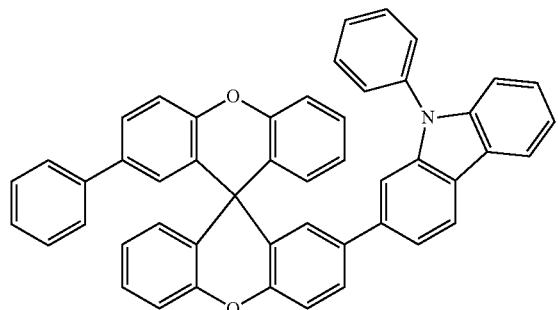
86
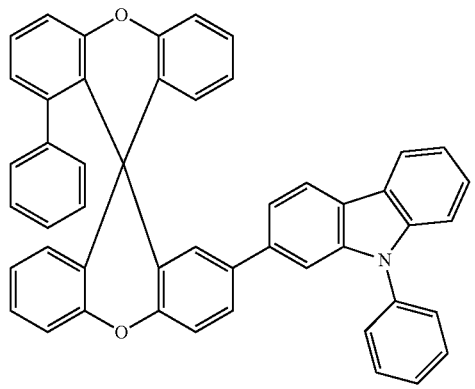

87
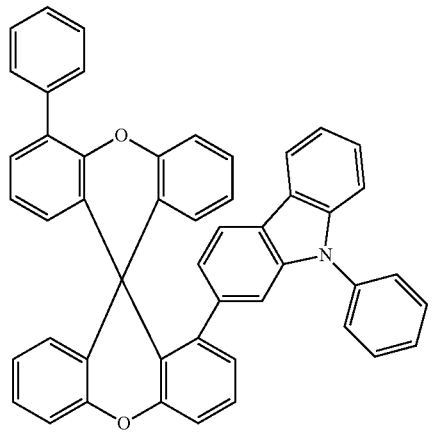
88
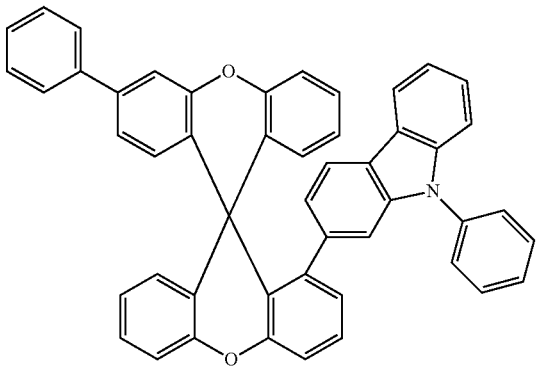
89
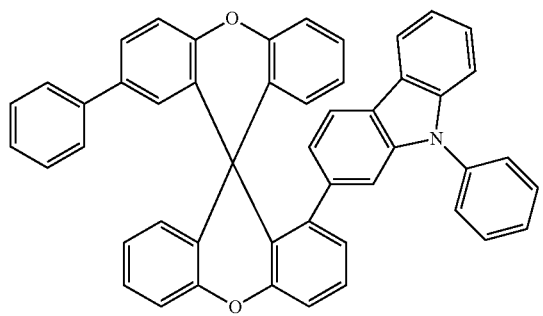
90
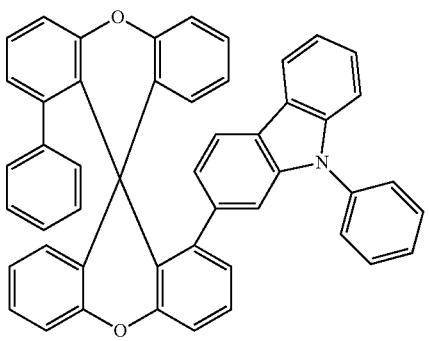
91
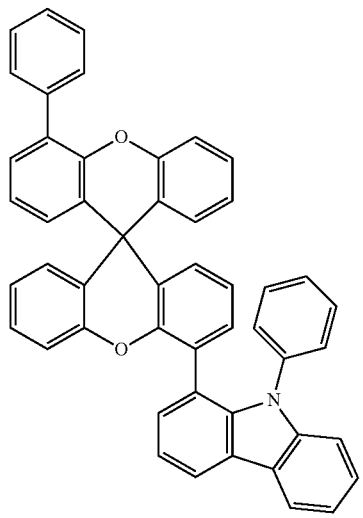
92
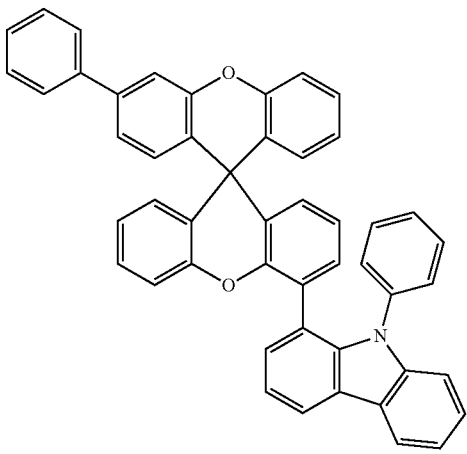

-continued
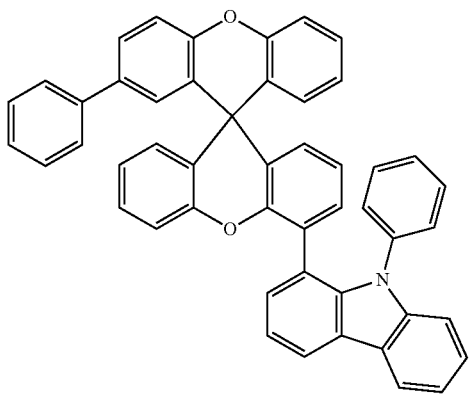
93
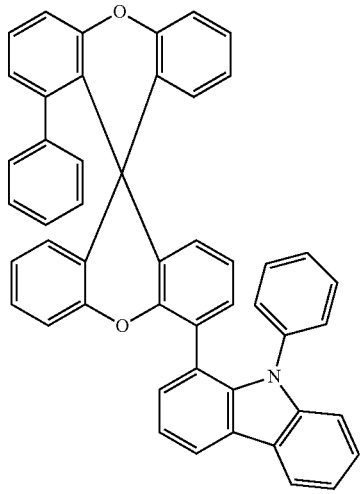
94
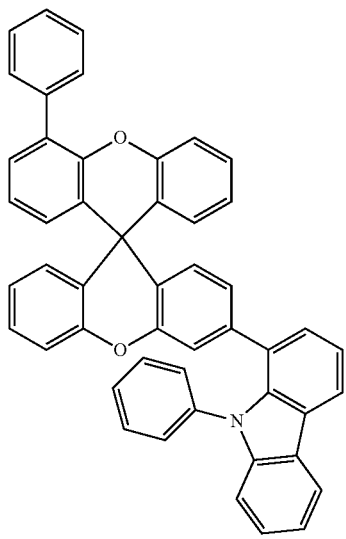
95
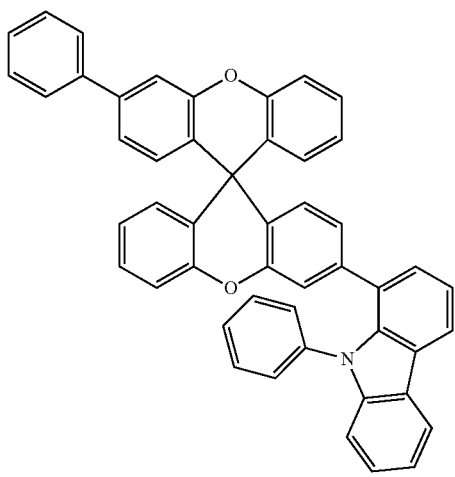
96
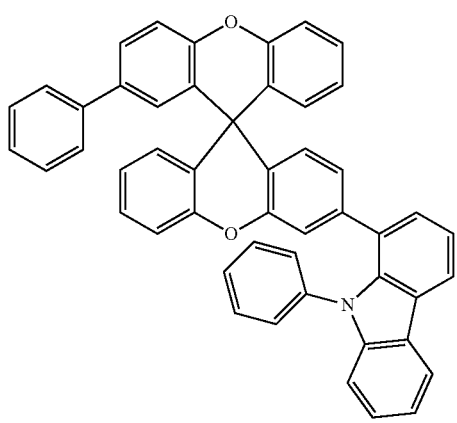
97
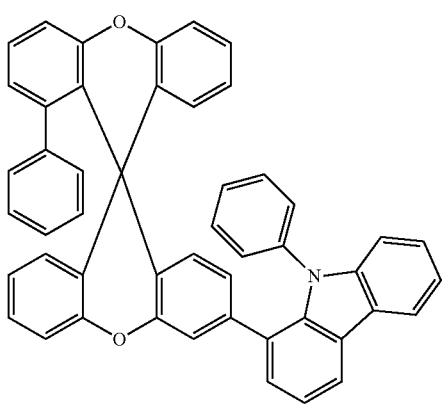
98

-continued
99
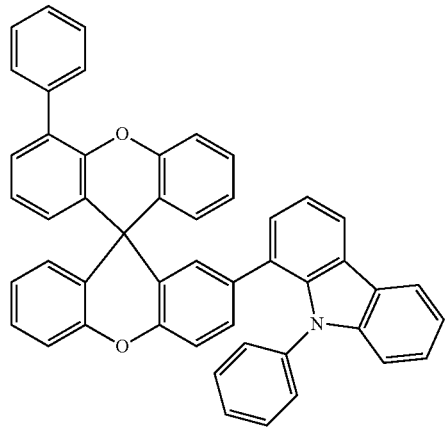
100
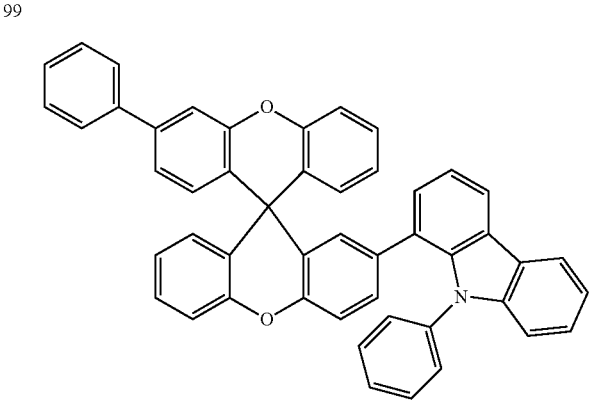
101
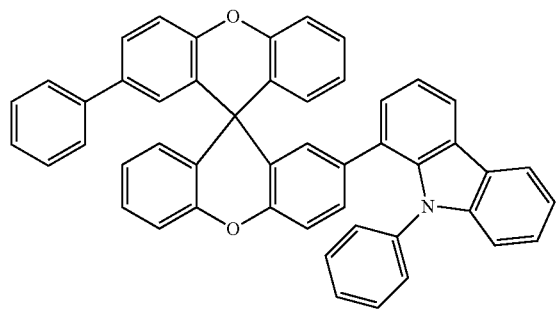
102
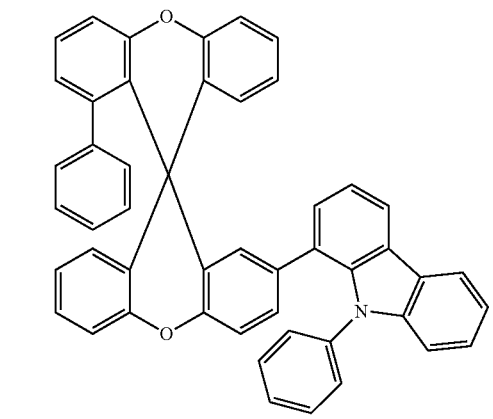
103
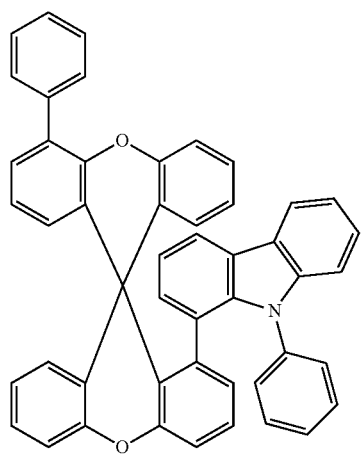
104
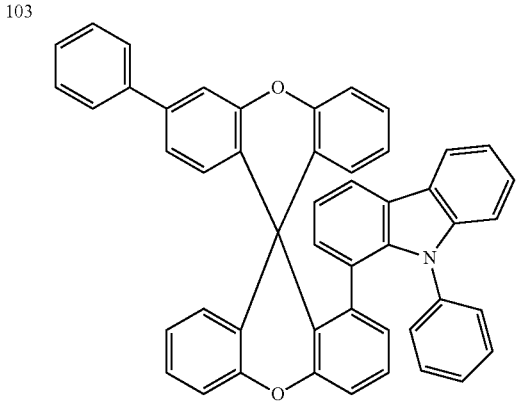

-continued
105 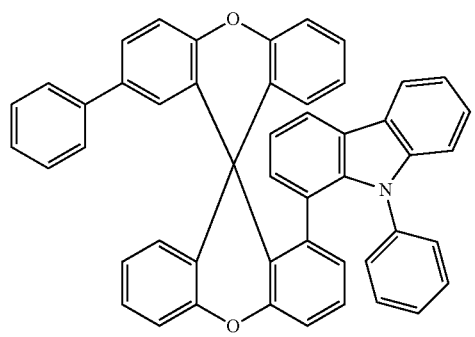 106 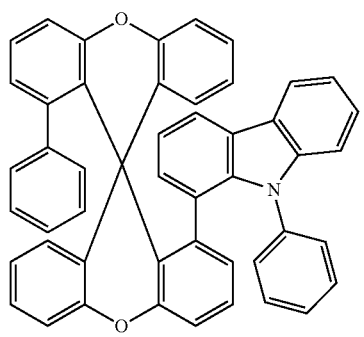
107 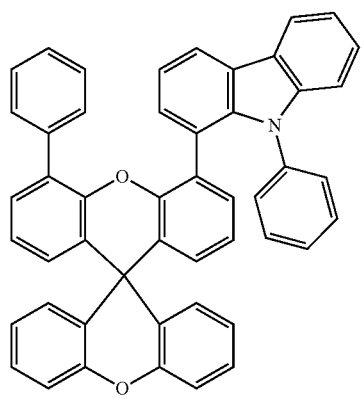 108 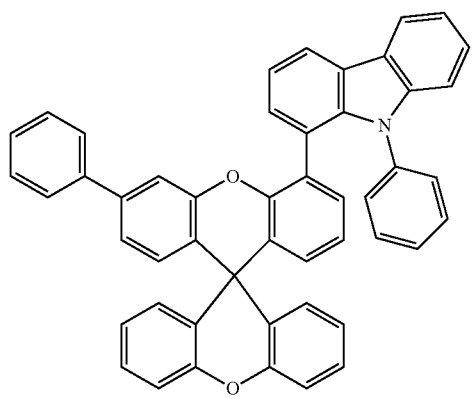
109 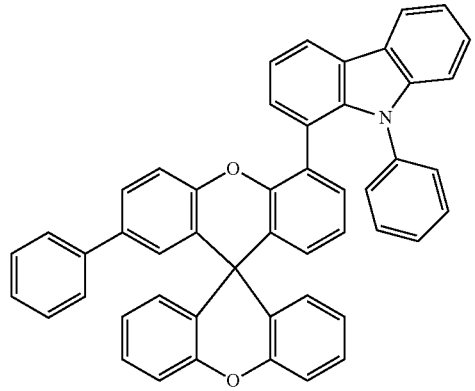 110 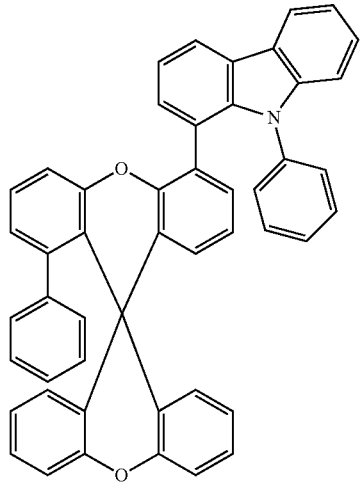
111 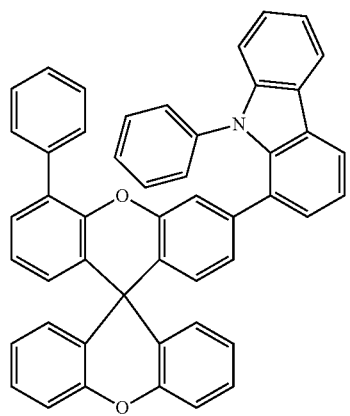 112 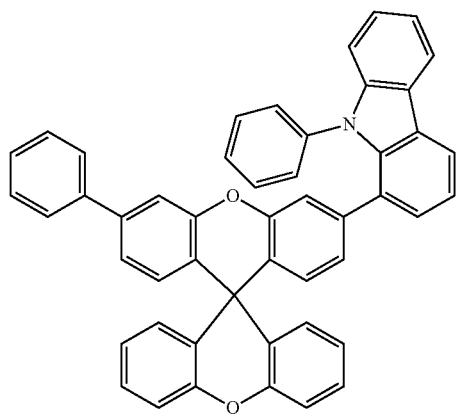

-continued
113
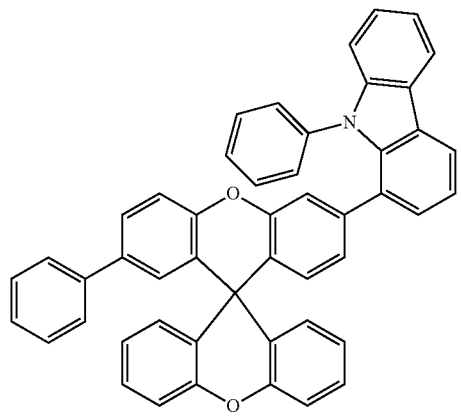
114
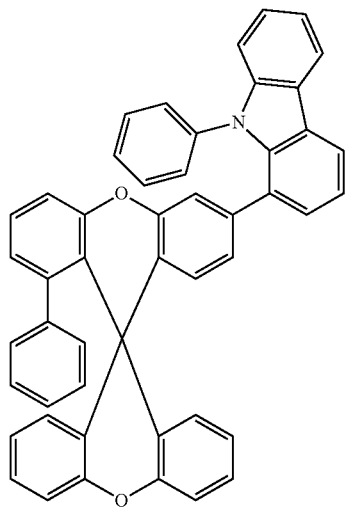
115
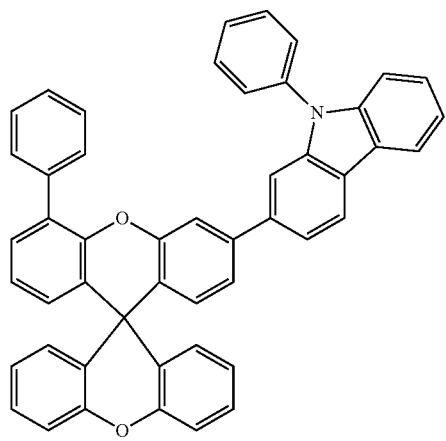
116
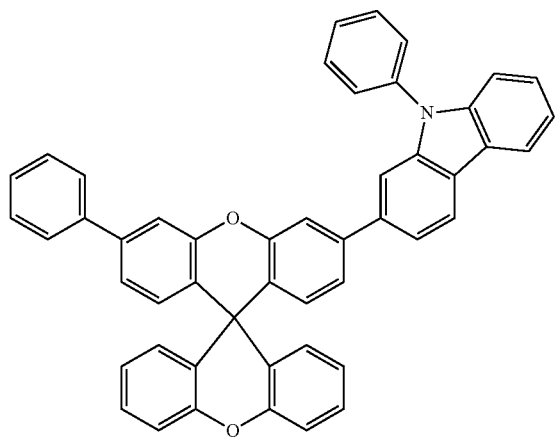
117
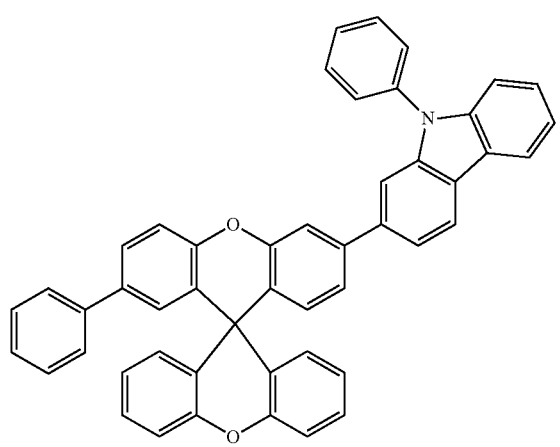
118
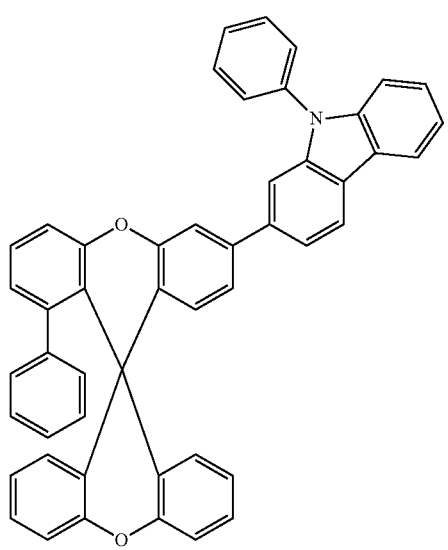

-continued
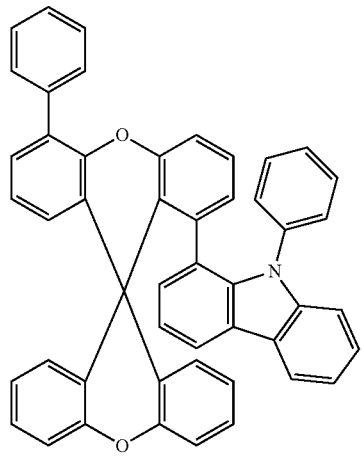
119
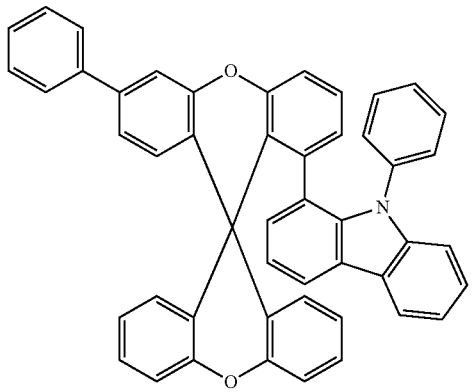
120
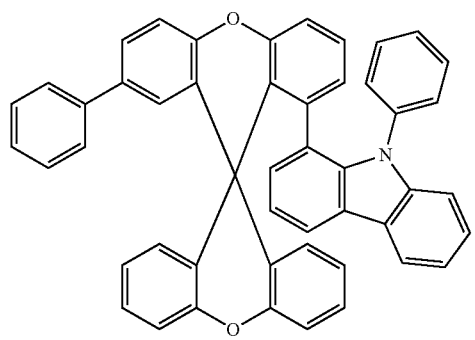
121
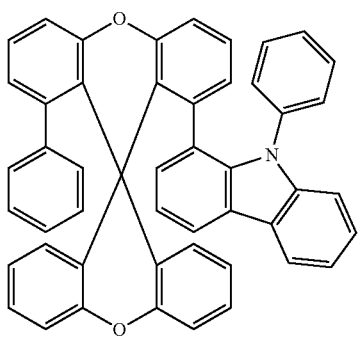
122
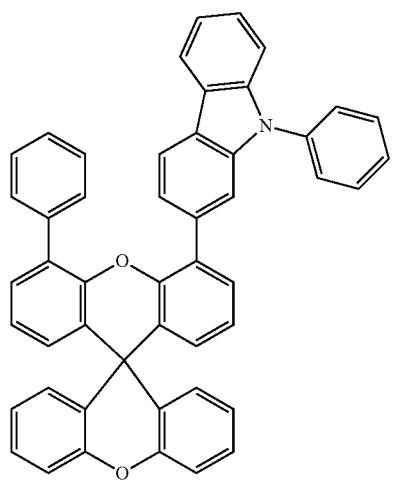
123
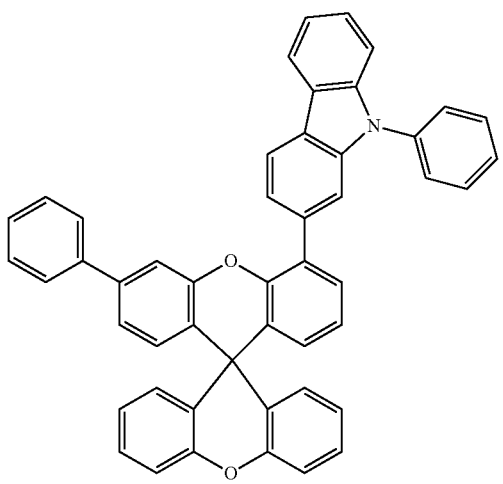
124

-continued
125
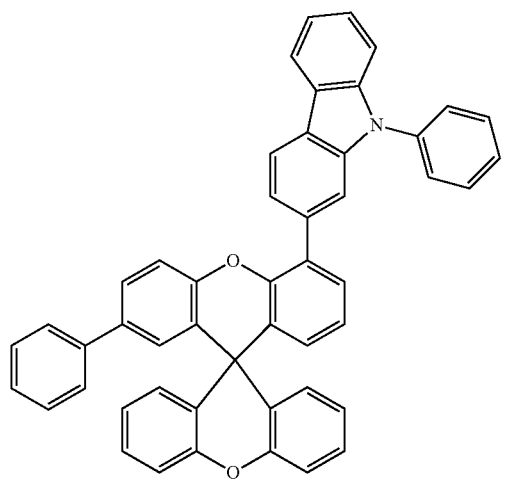
126
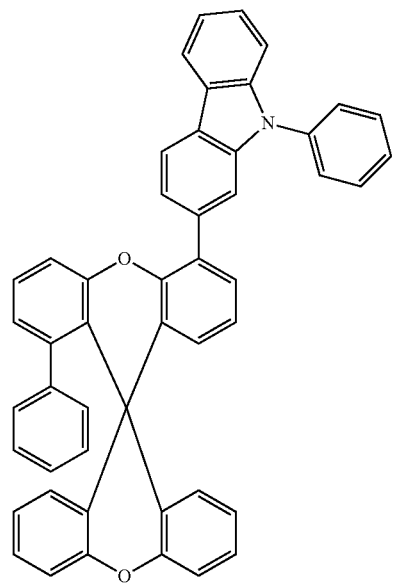
127
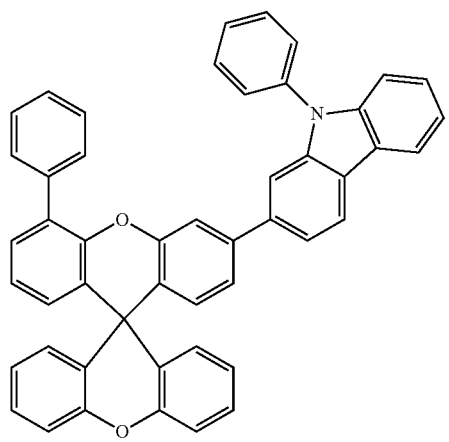
128
129
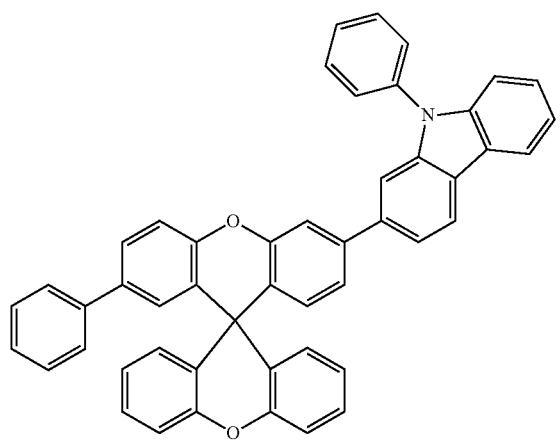
130
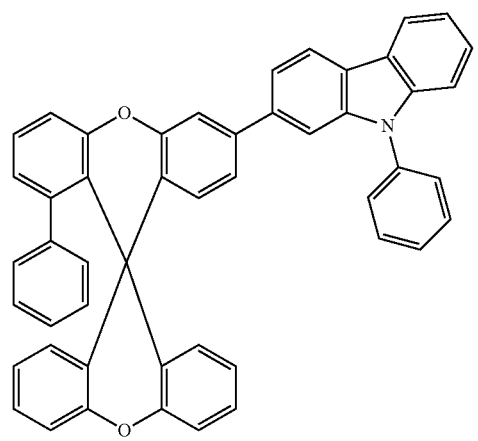

-continued
131
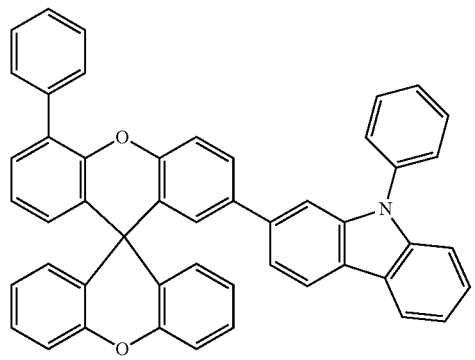
132
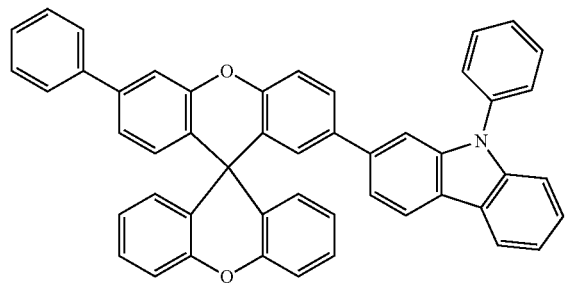
133
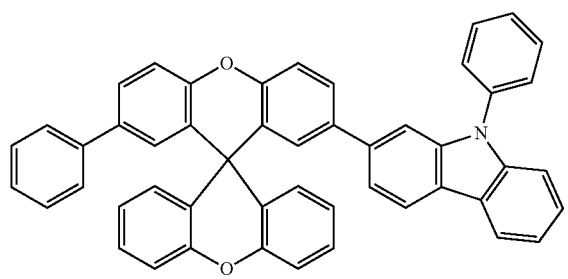
134
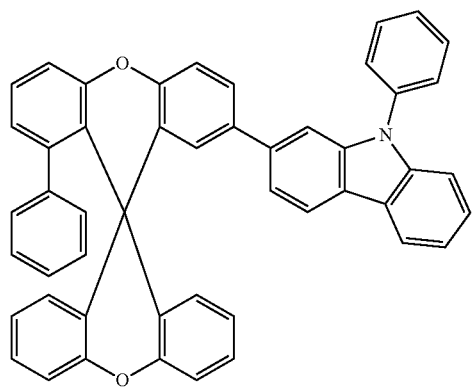
135
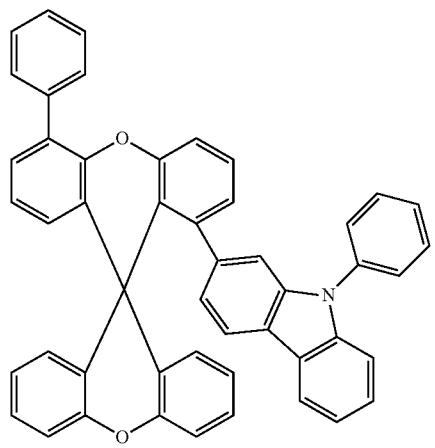
136
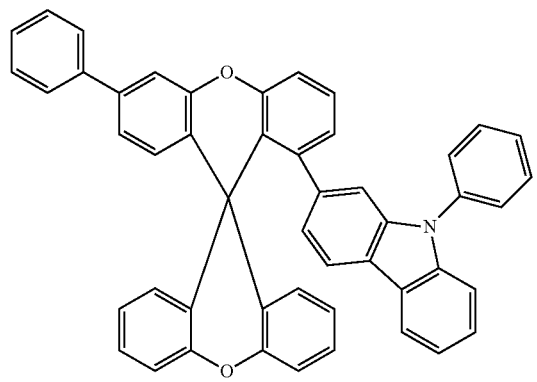
137
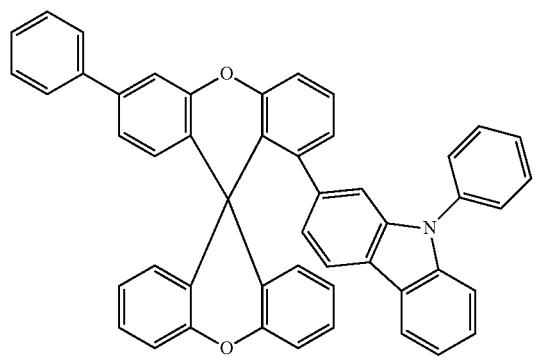
138
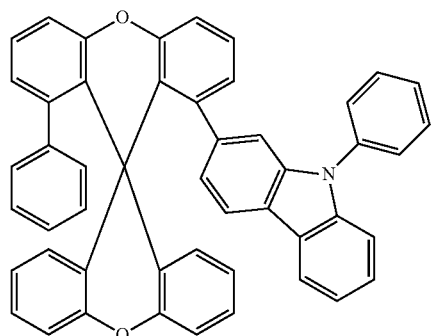

-continued
139
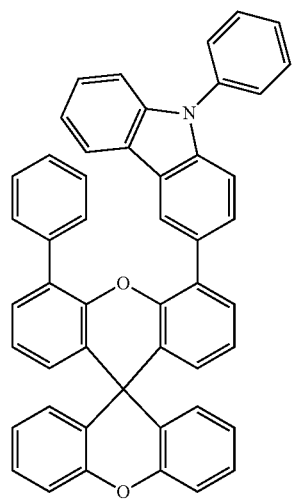
140
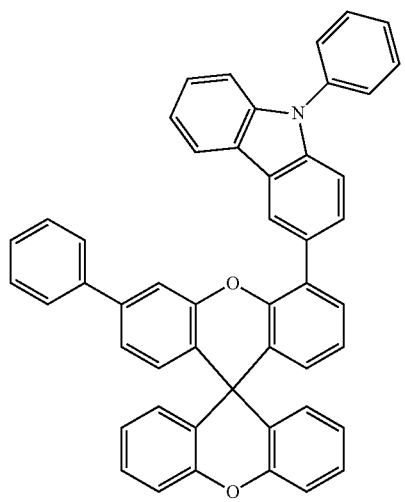
141
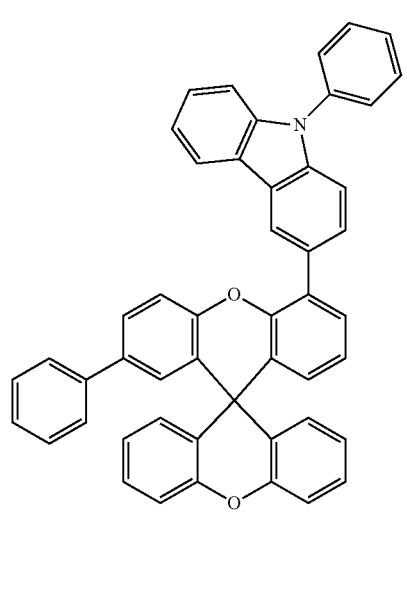
142
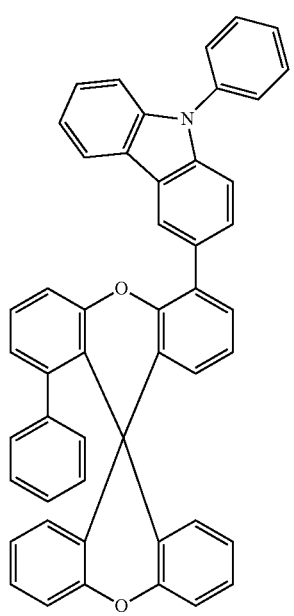
143
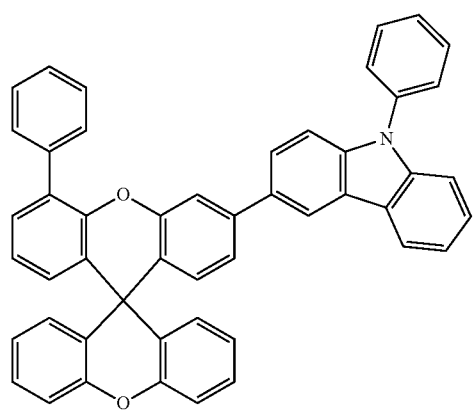
144
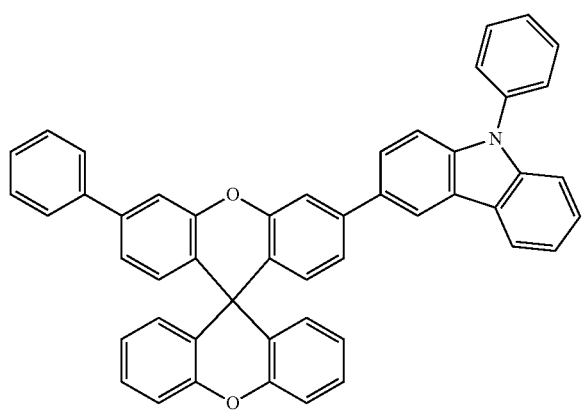

-continued
145
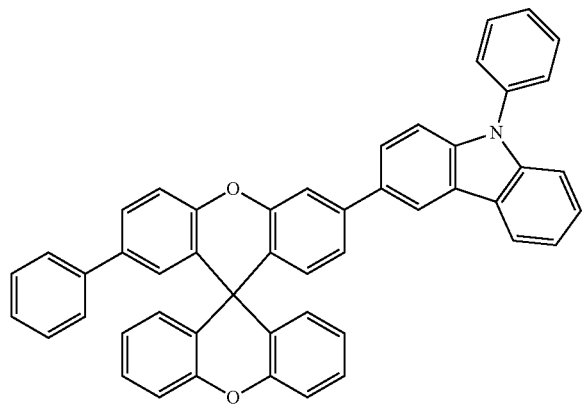
146
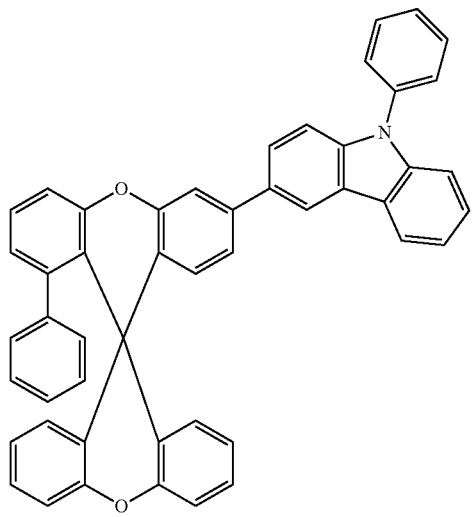
147
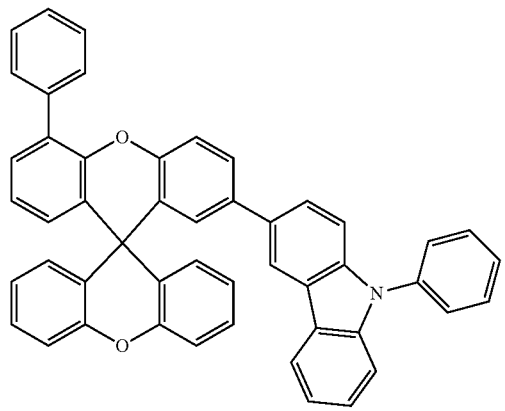
148
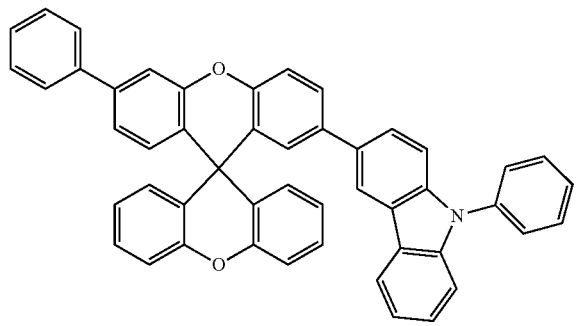
149
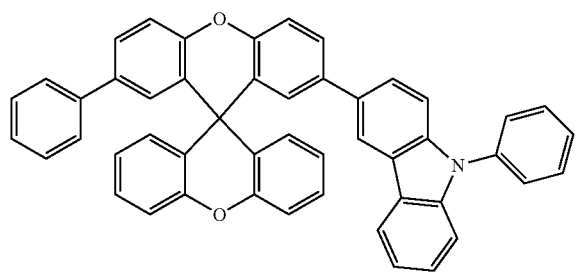
150
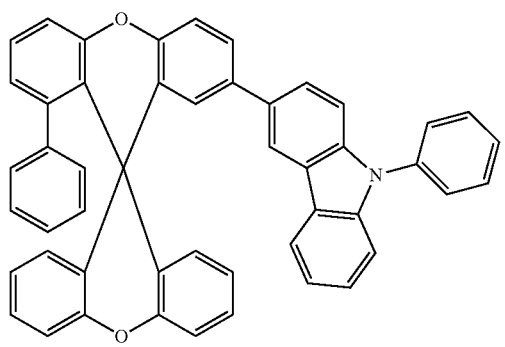

151
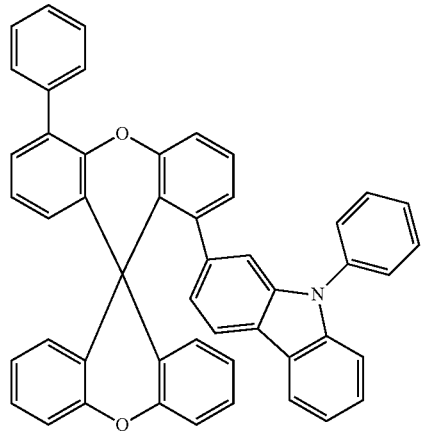
152
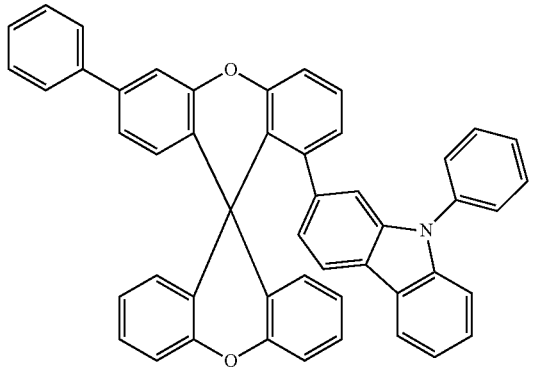
153
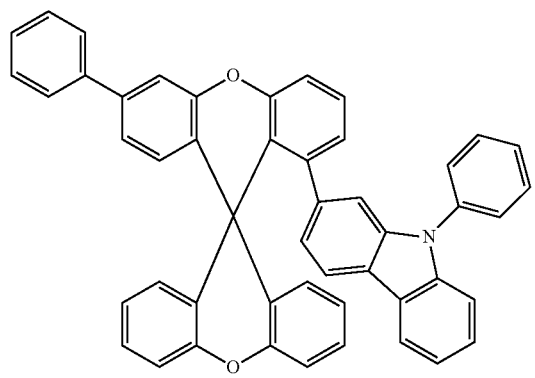
154
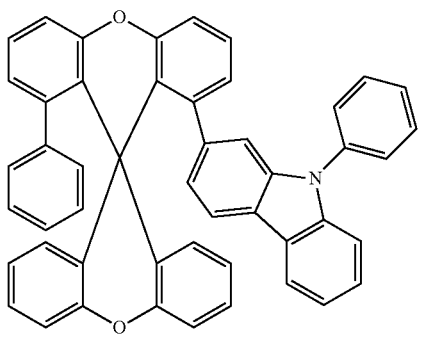
155
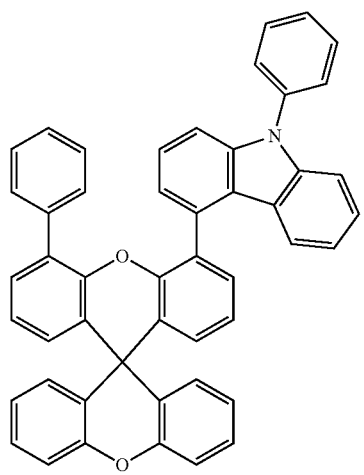
156
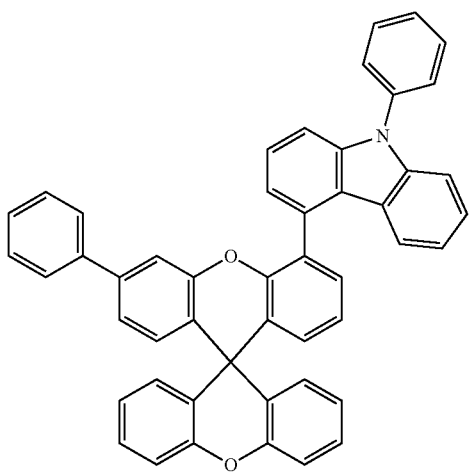

-continued
157
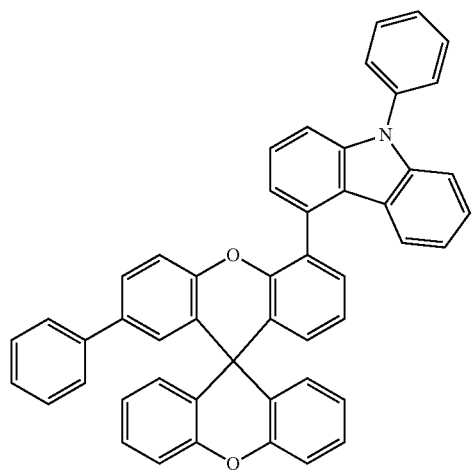
158
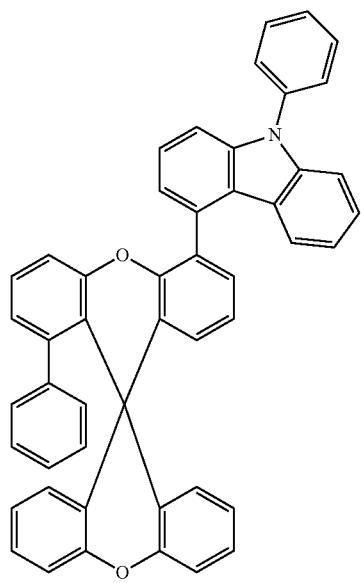
159
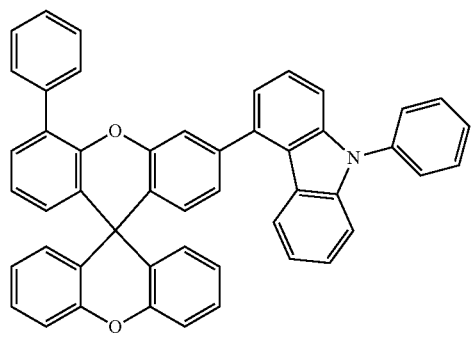
160
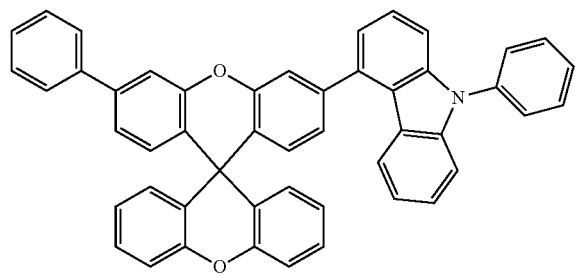
161
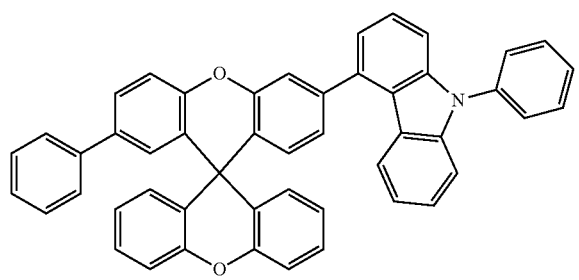
162
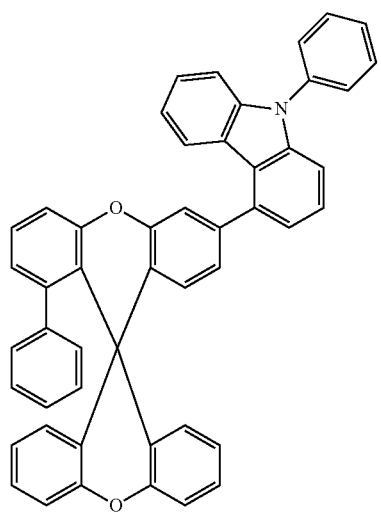

-continued
163
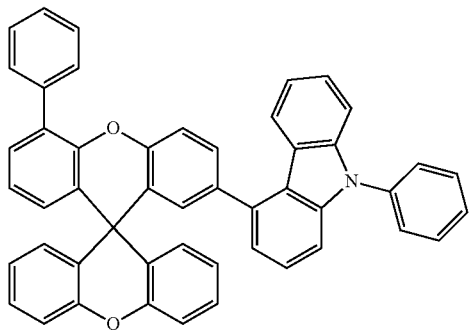
164
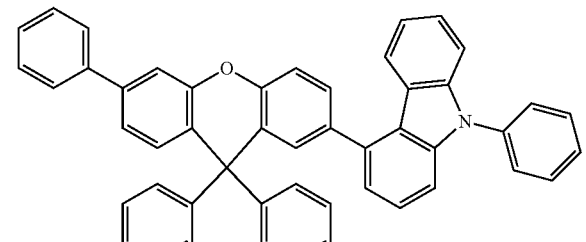
165
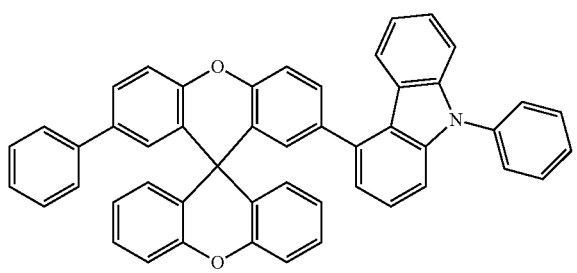
166
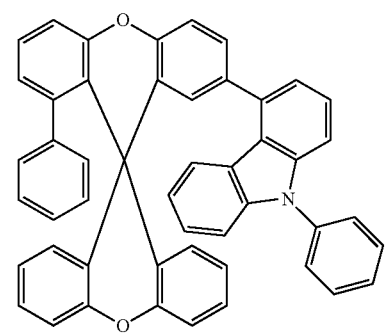
167
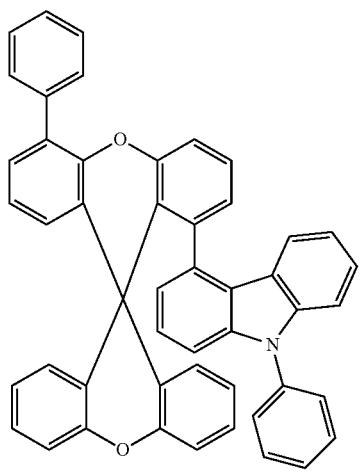
168
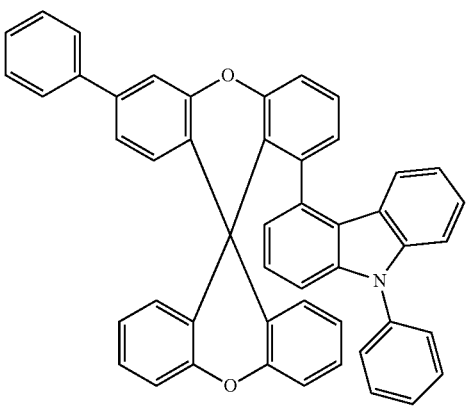
169
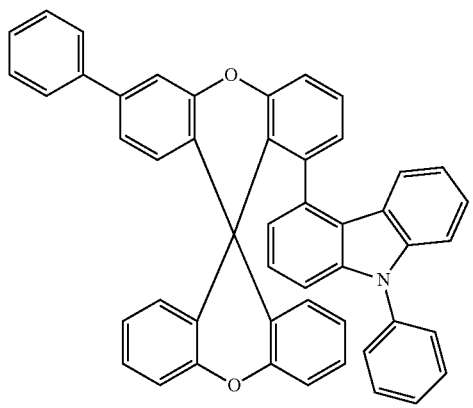
170
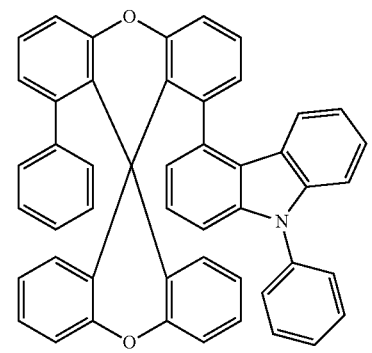

-continued
| 171 | 172 |
|---|---|
| 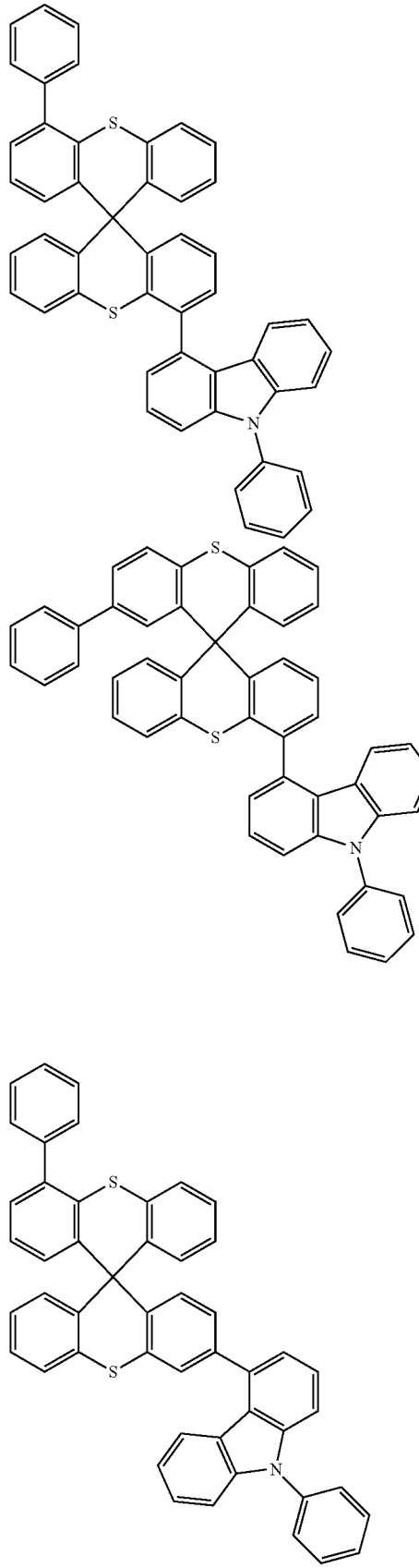 | 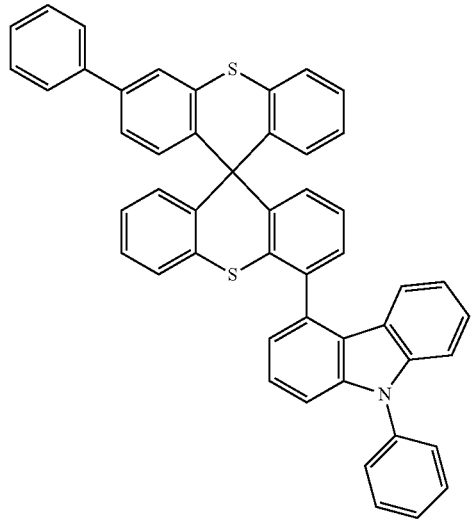 |
| 173 | 174 |
| 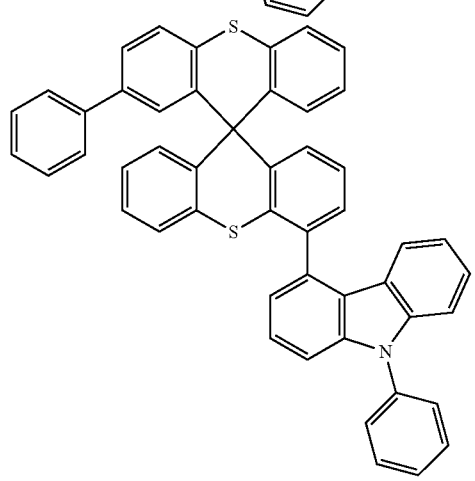 | 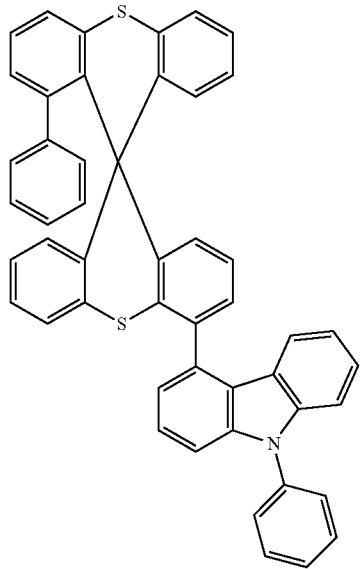 |
| 175 | 176 |
| 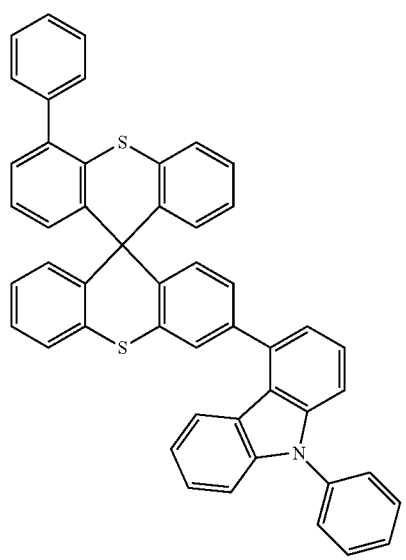 | 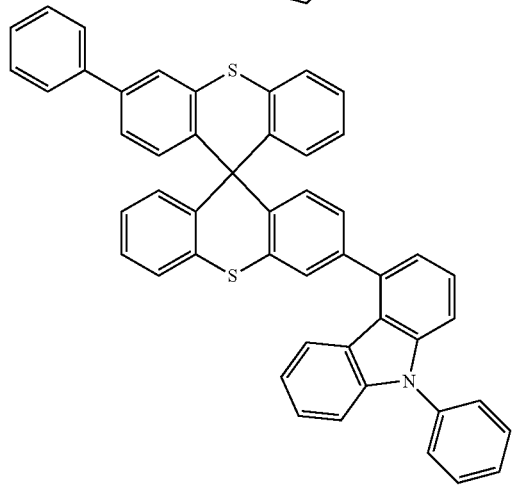 |

-continued
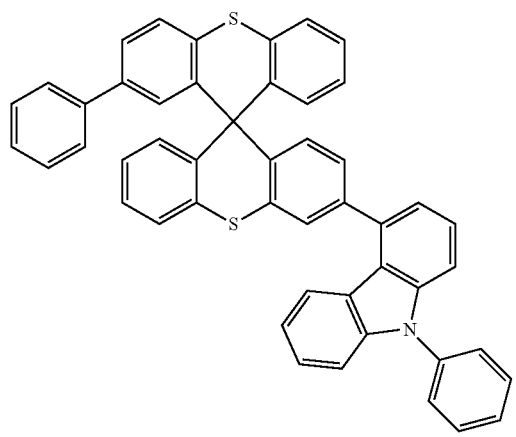
177
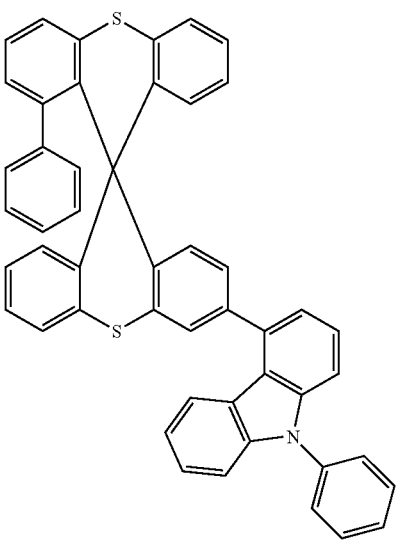
178
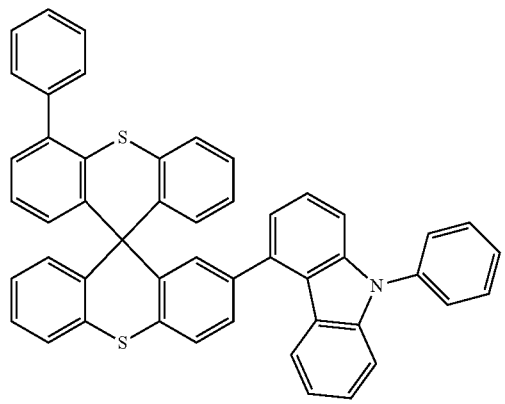
179
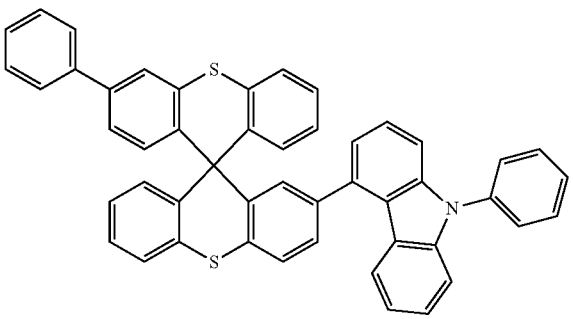
180
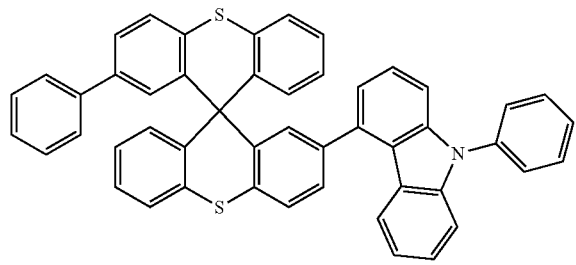
181
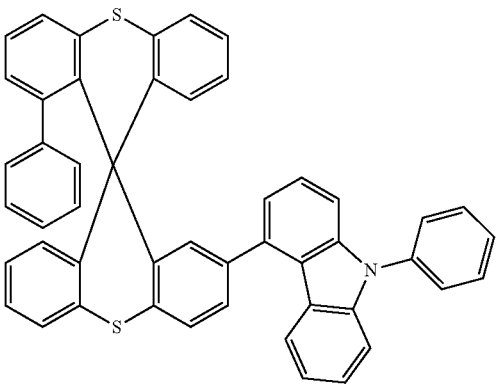
182

-continued
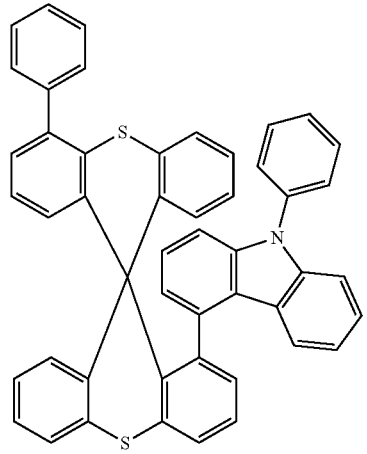
183
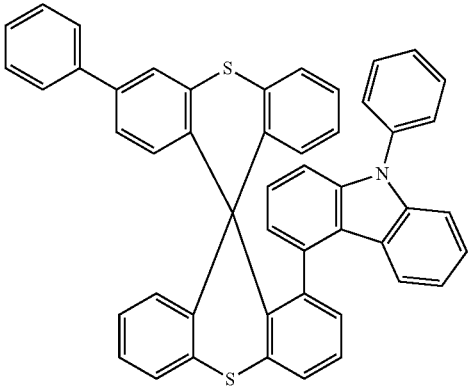
184
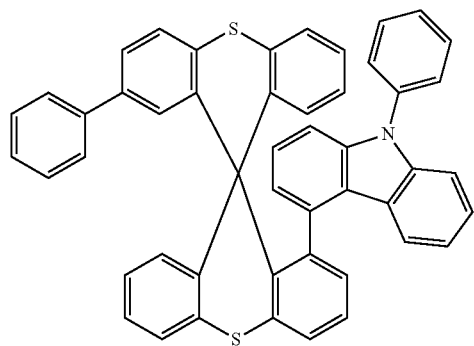
185
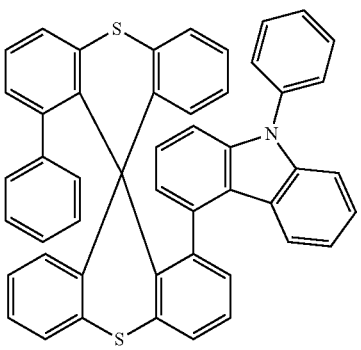
186
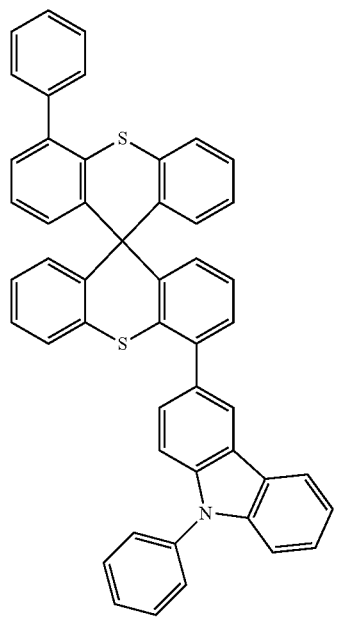
187
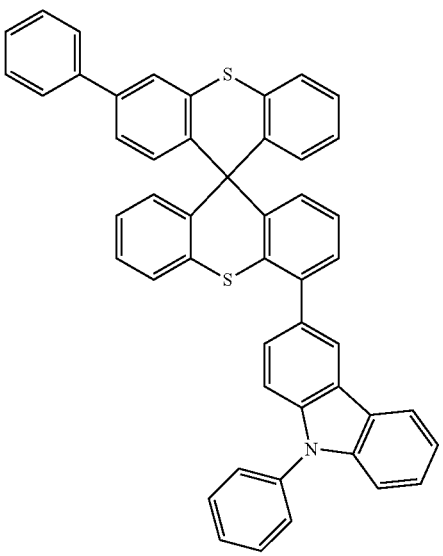
188

-continued
189
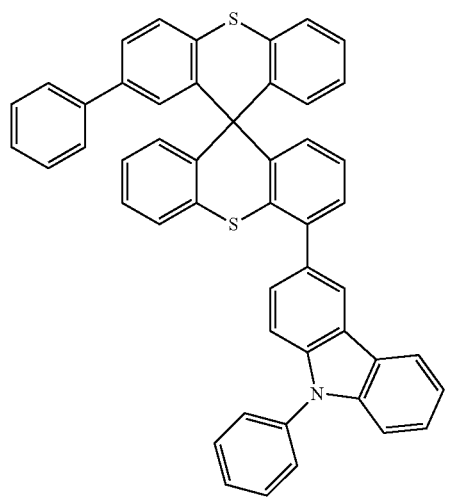
190
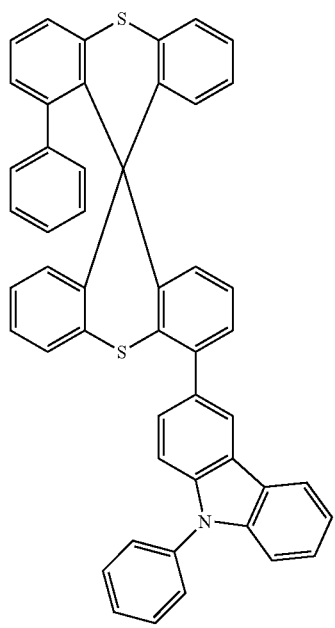
191
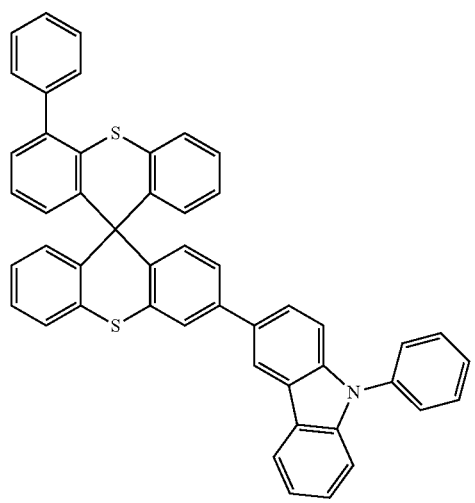
192
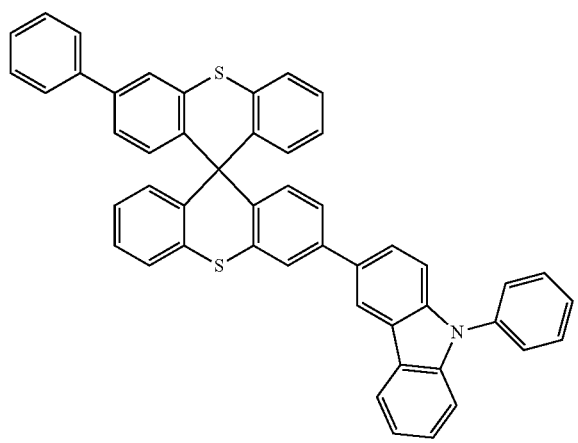
193
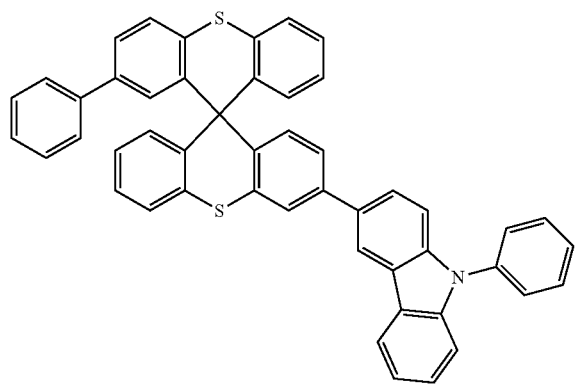
194
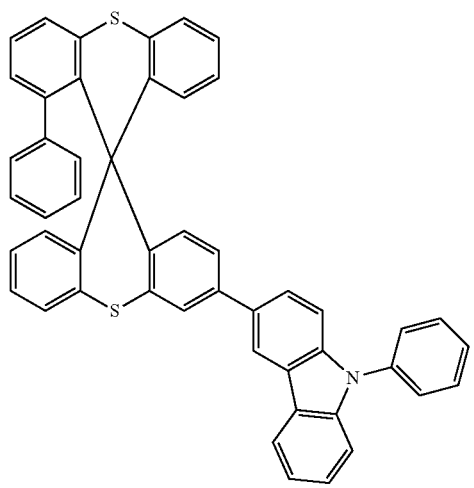

-continued
195
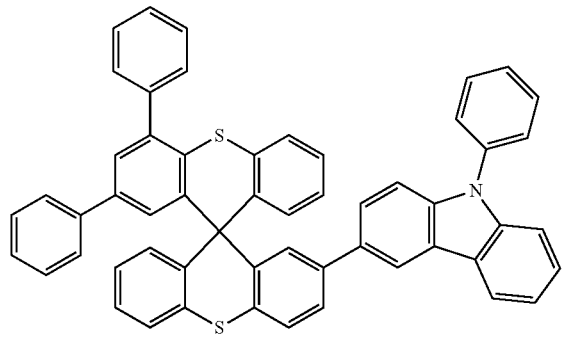
196
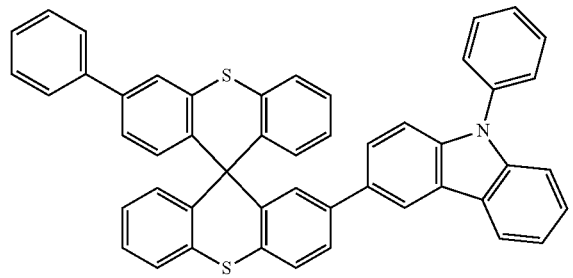
197
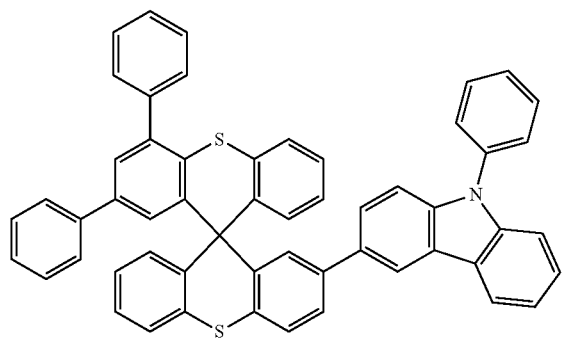
198
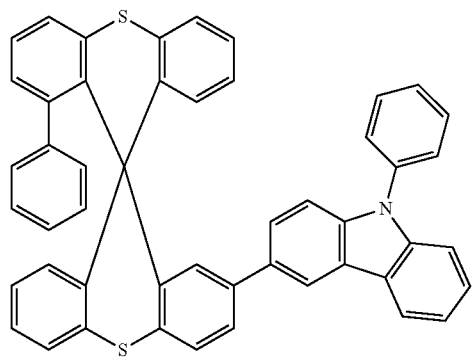
199
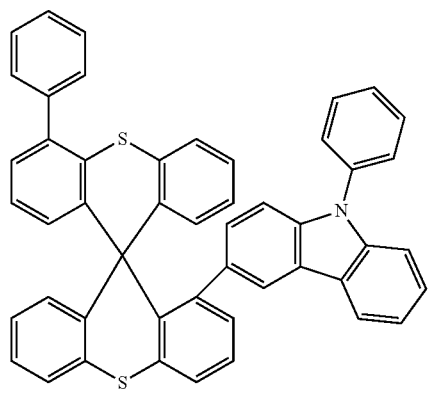
200
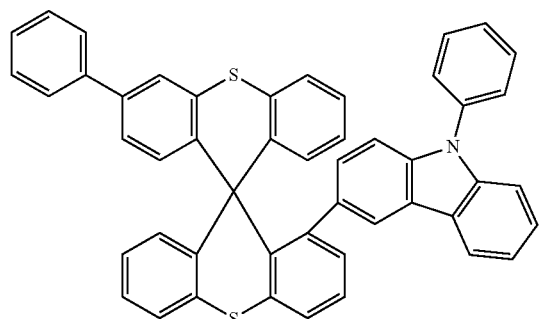
201
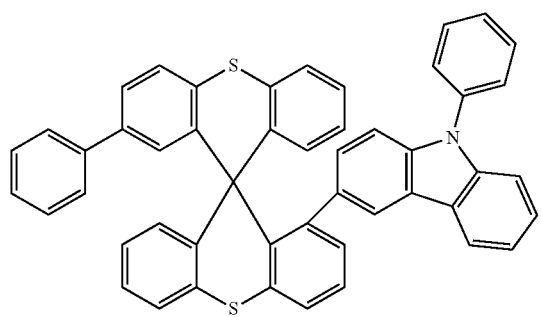
202
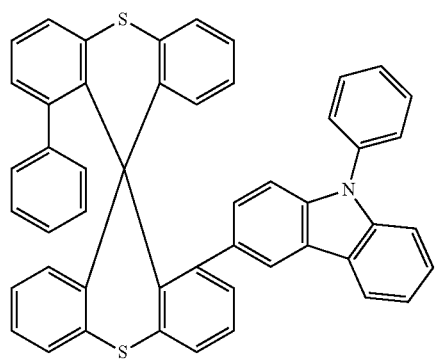

-continued
203
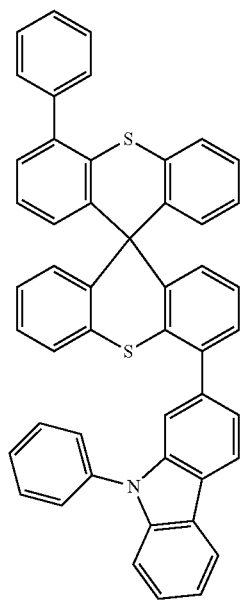
204
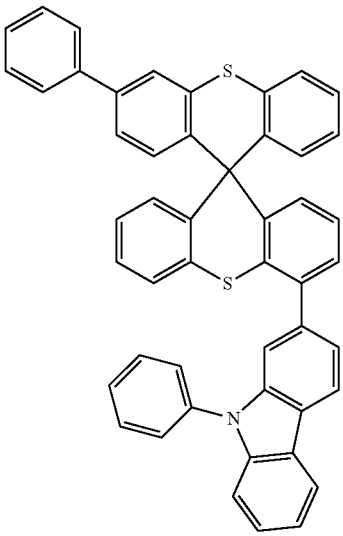
205
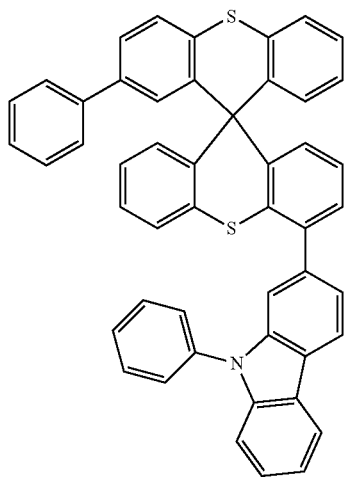
206
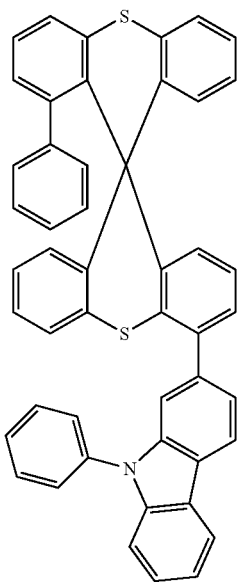
207
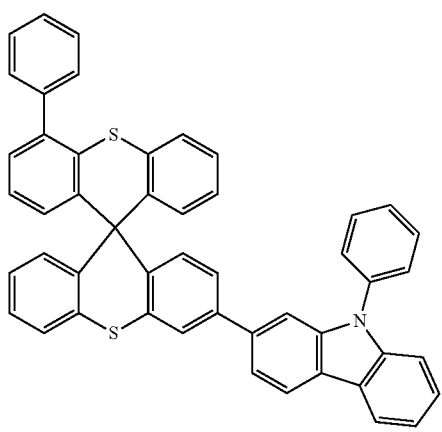
208
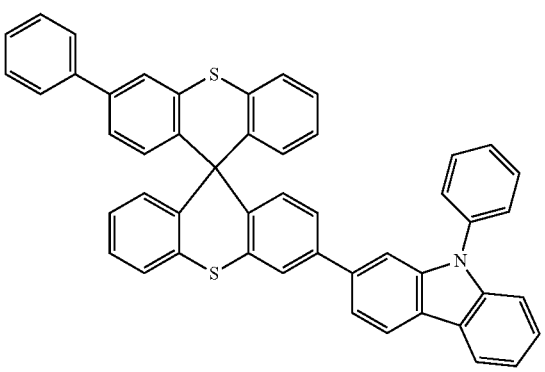

-continued
209
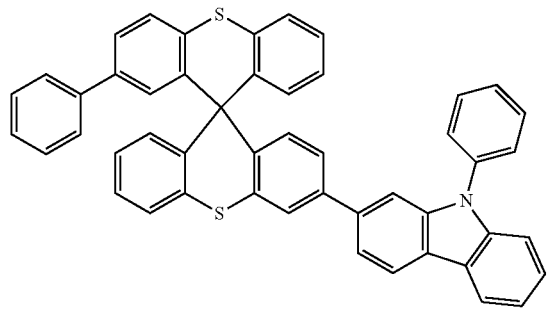
210
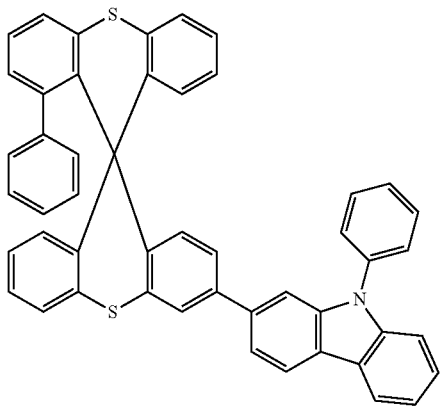
211
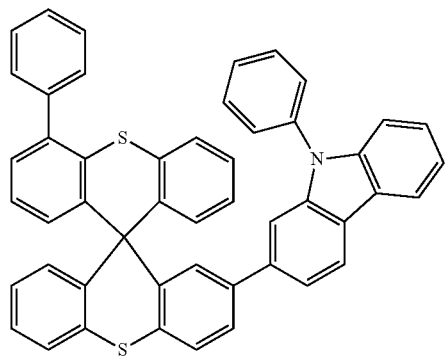
212
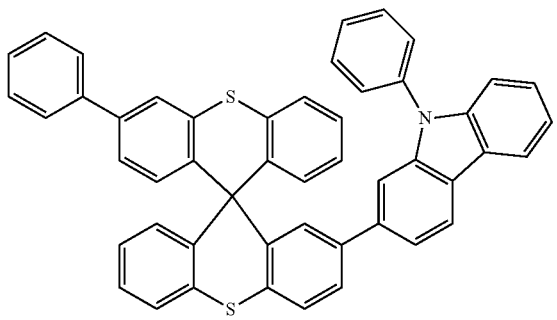
213
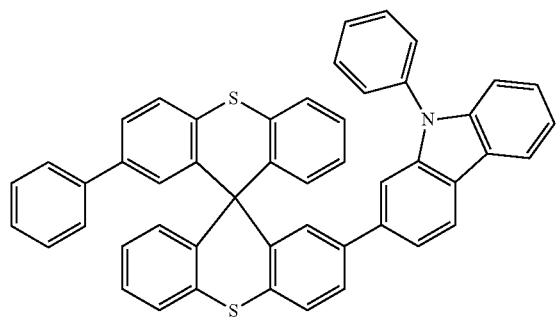
214
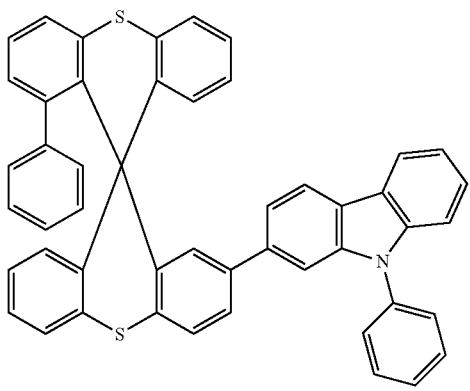
215
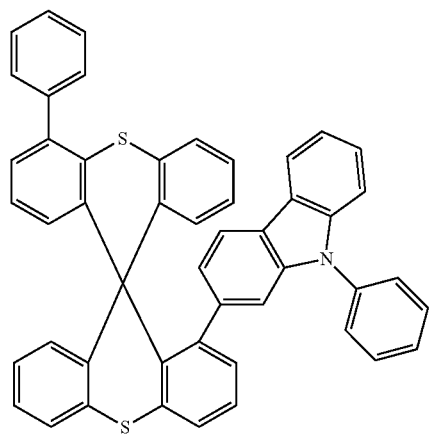
216
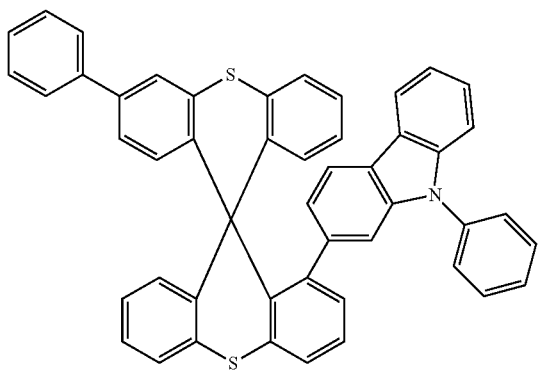

-continued
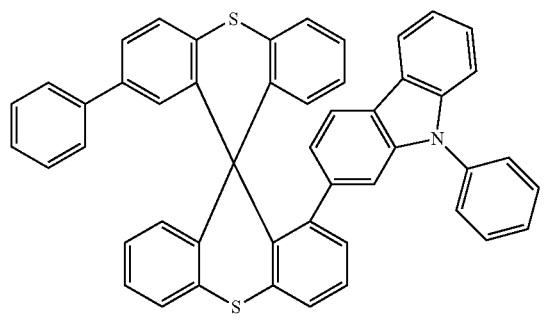
217
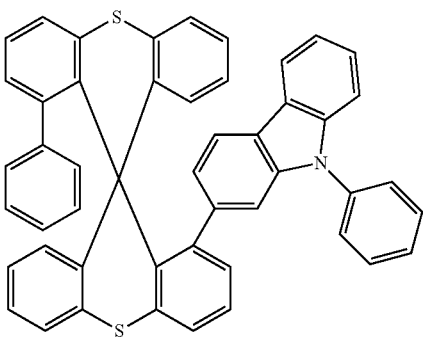
218
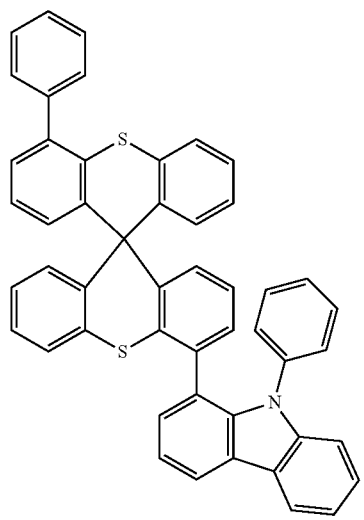
219
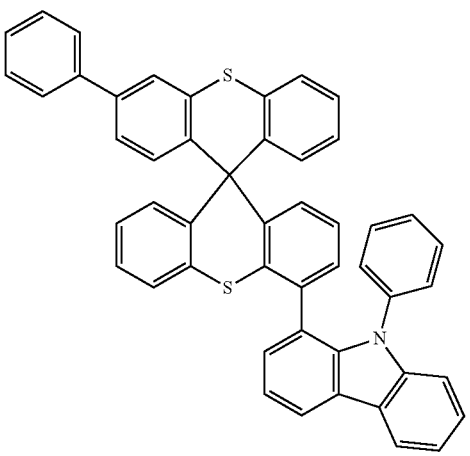
220
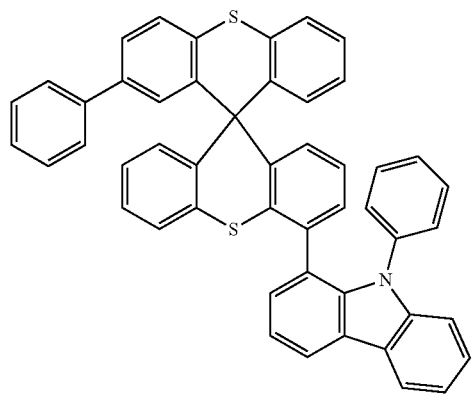
221
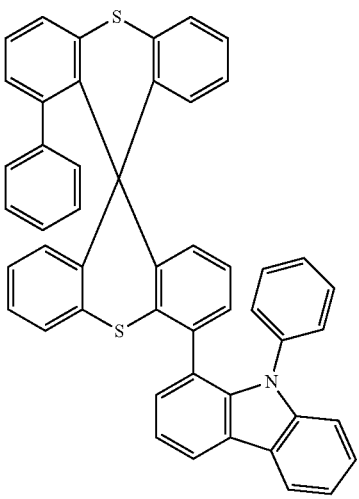
222

-continued
| 223 | 224 |
|---|---|
| 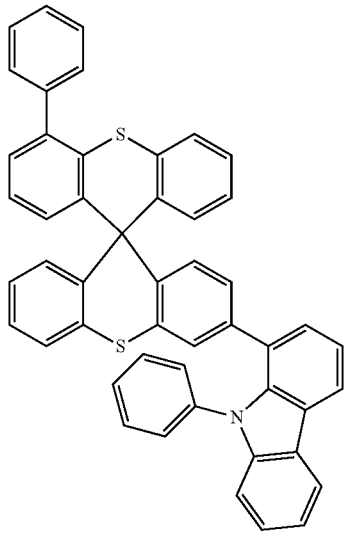 | 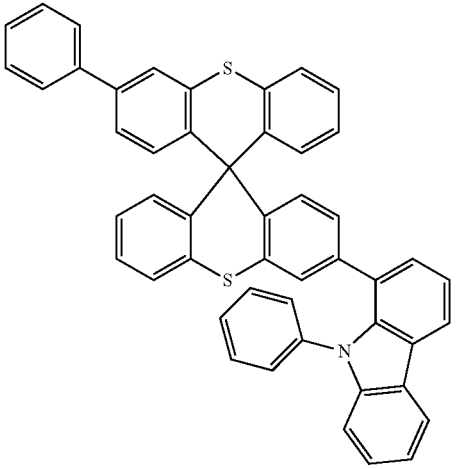 |
| 225 | 226 |
| 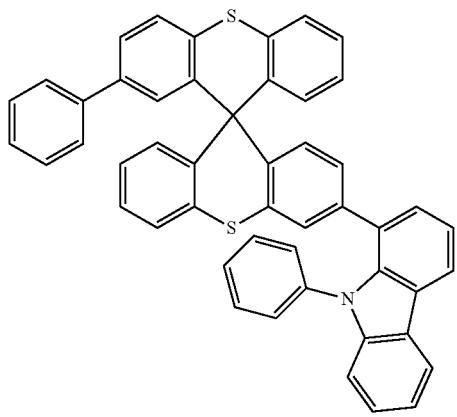 | 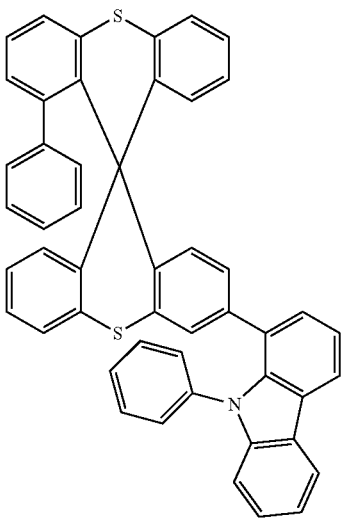 |
| 227 | 228 |
| 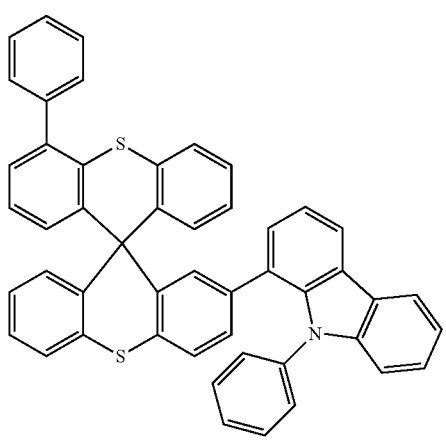 | 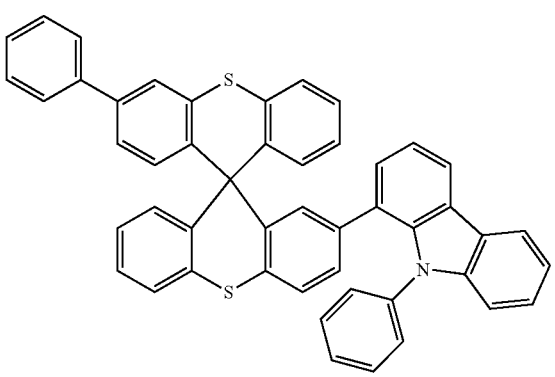 |

229
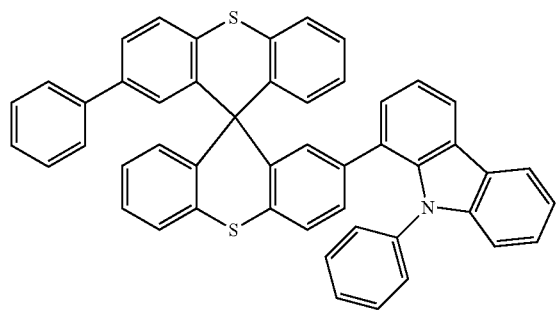
230
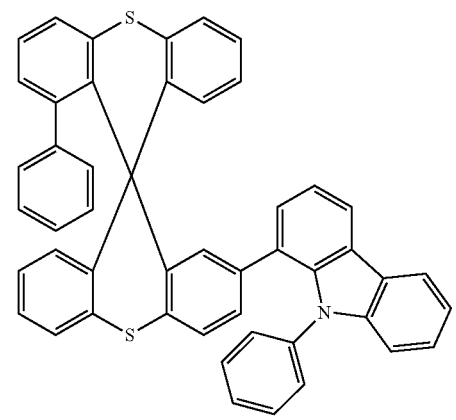
231
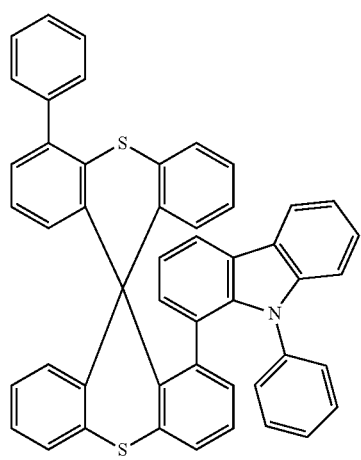
232
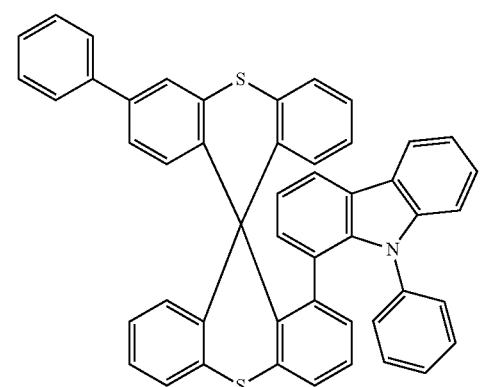
233
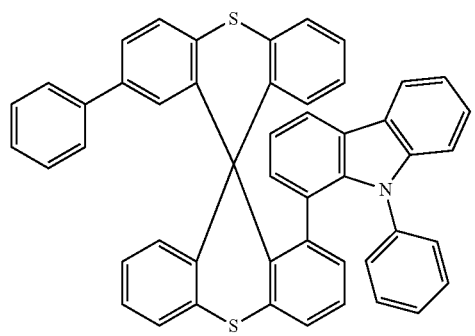
234
235
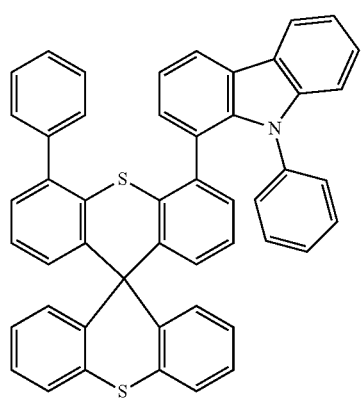
236
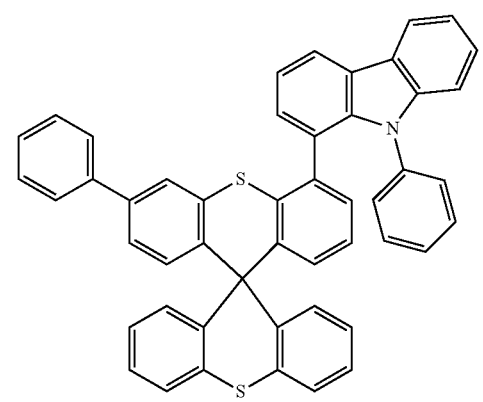

237
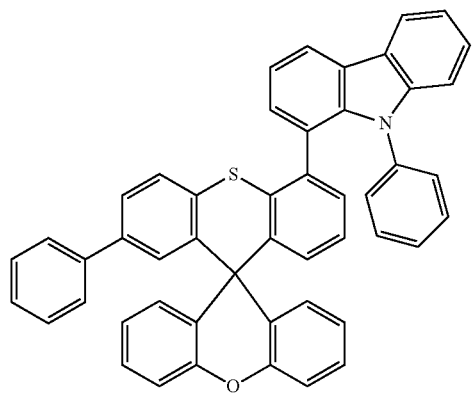
238
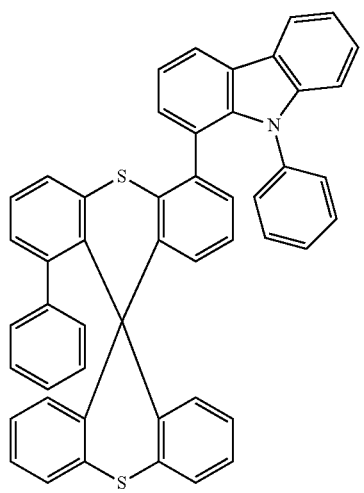
239
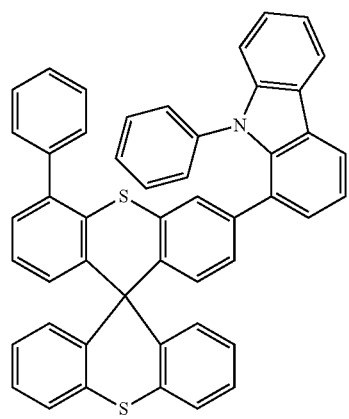
240
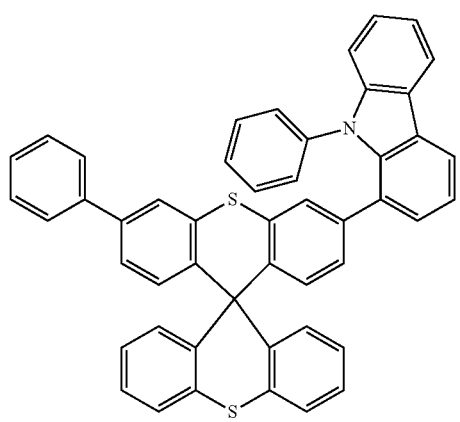
241
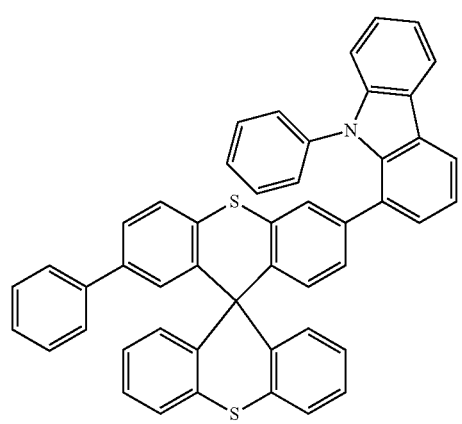
242
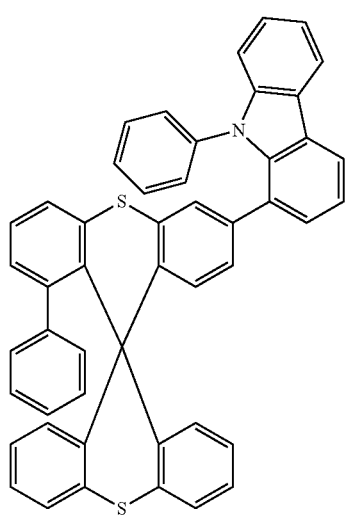

-continued
243
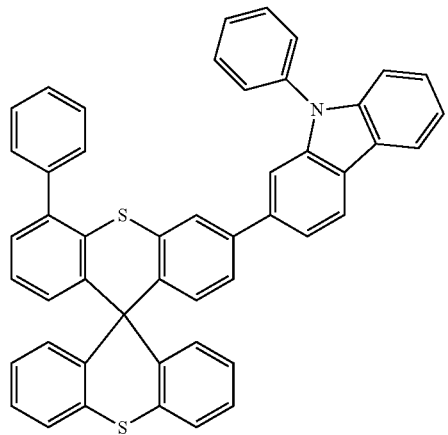
244
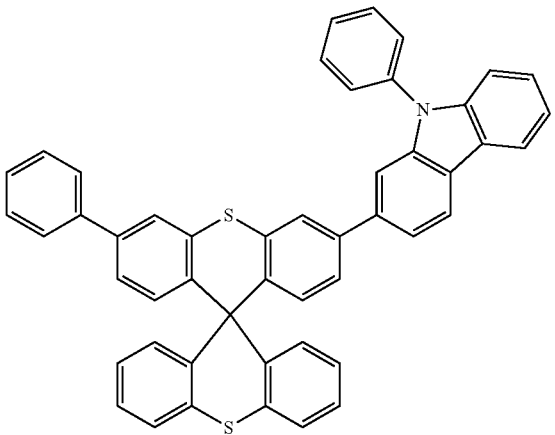
245
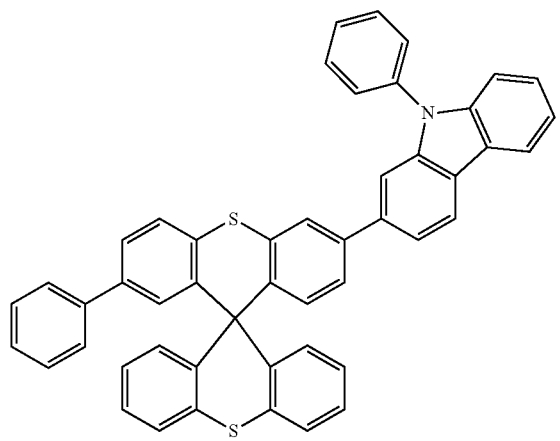
246
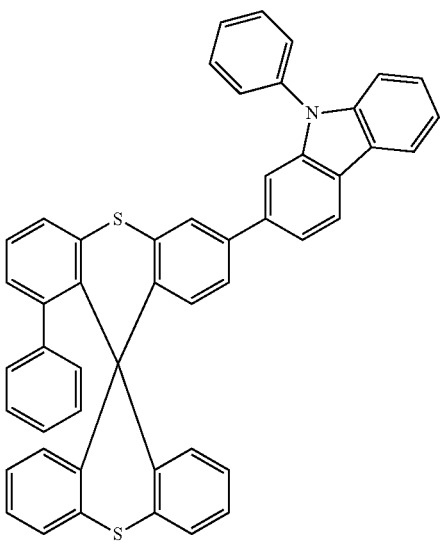
247
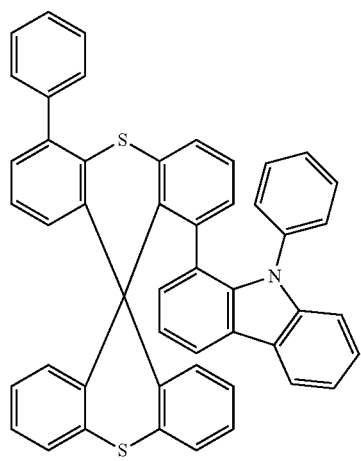
248
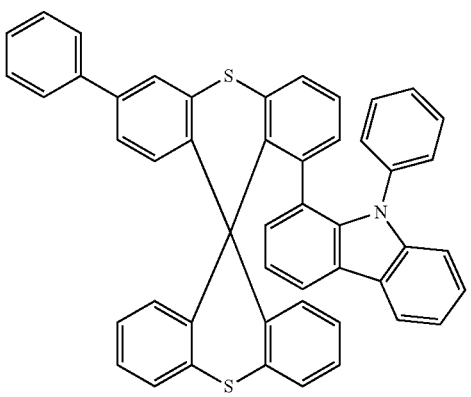

249
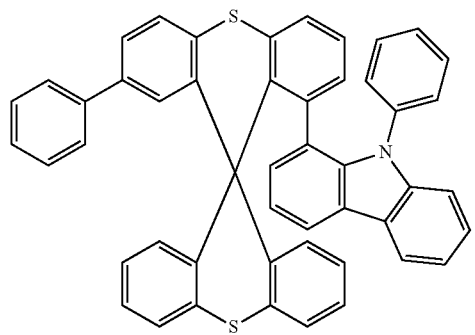
250
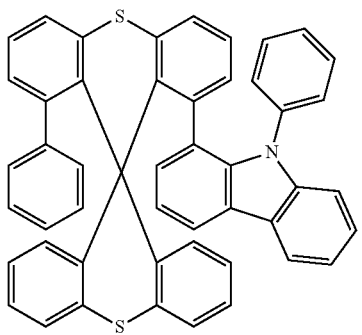
251
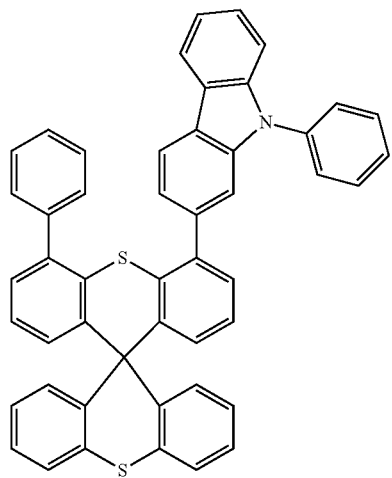
252
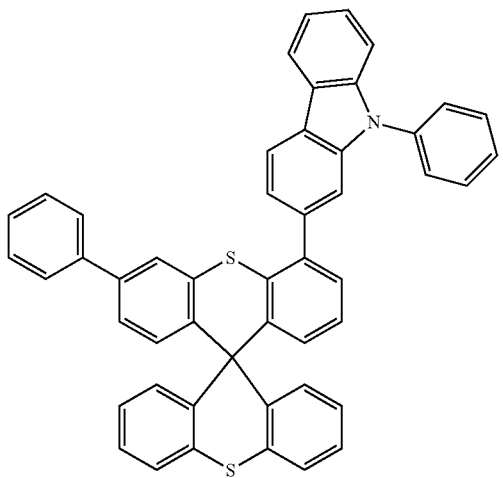
253
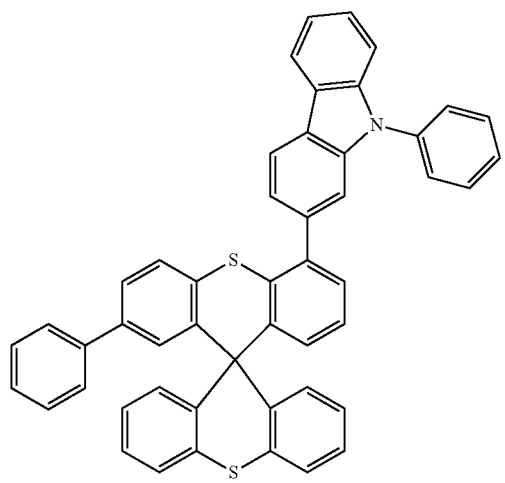
254
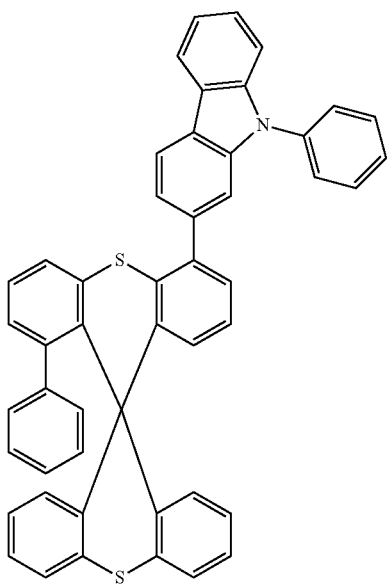

-continued
255
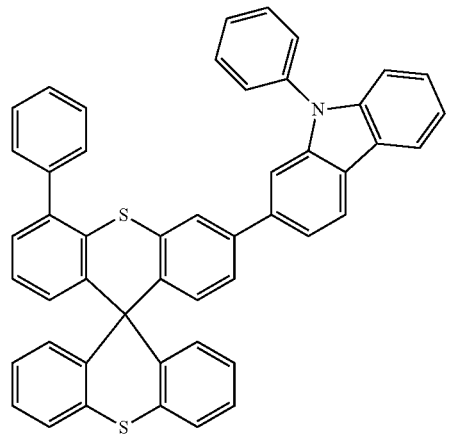
256
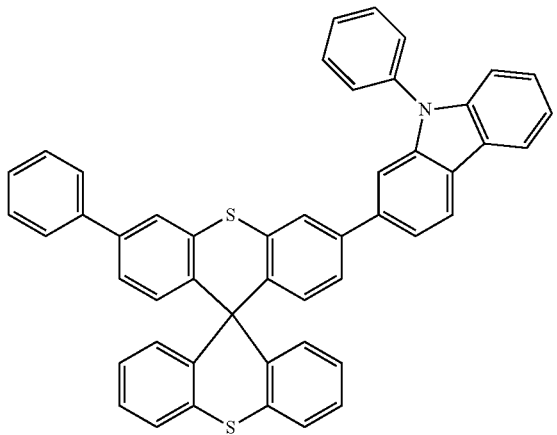
257
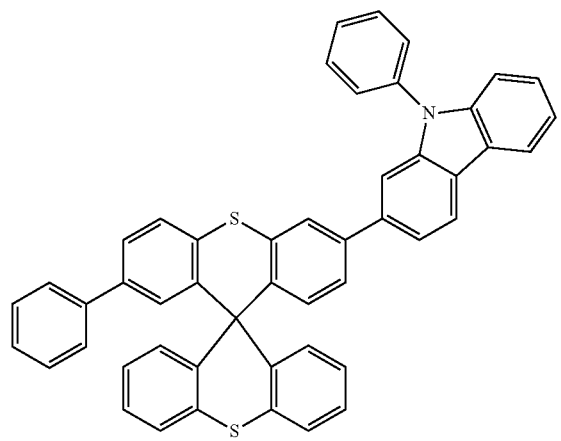
258
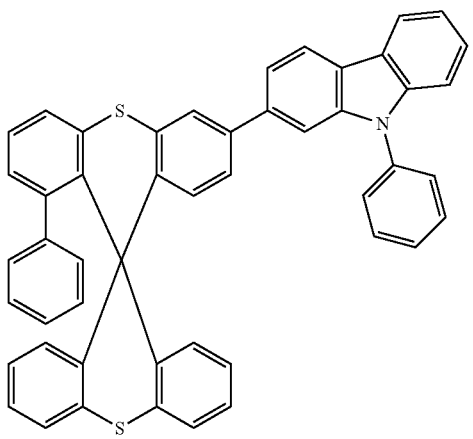
259
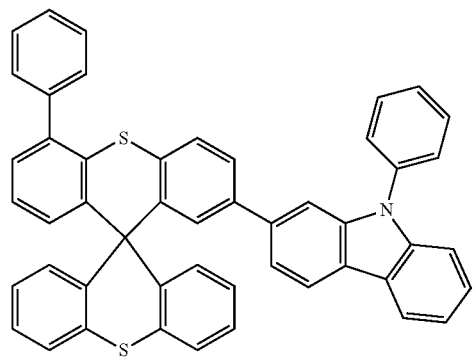
260
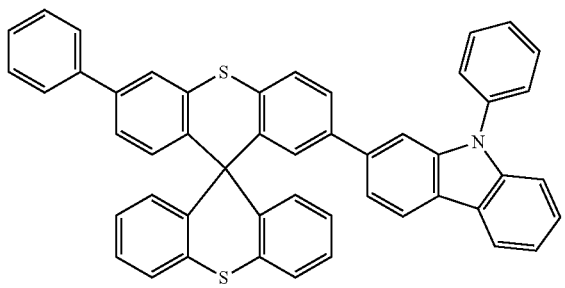

-continued
261
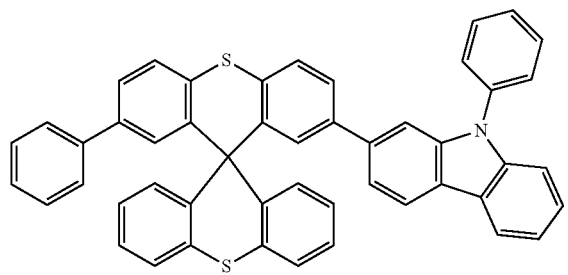
262
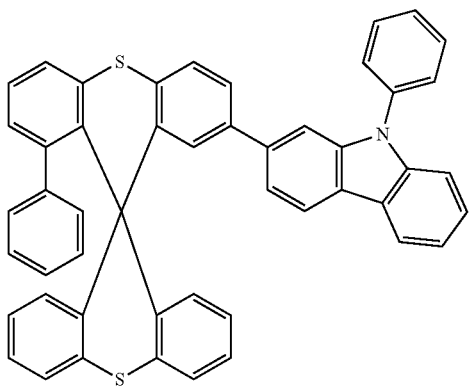
263
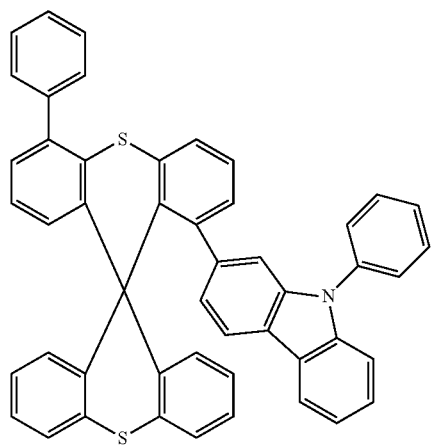
264
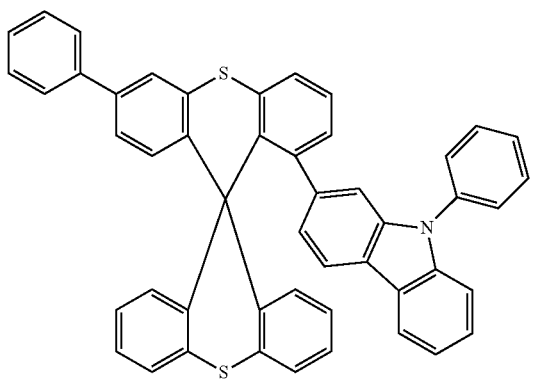
265
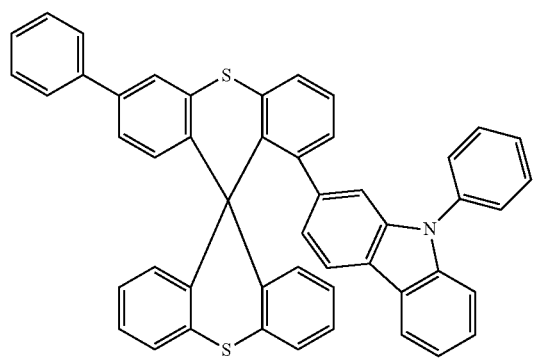
266
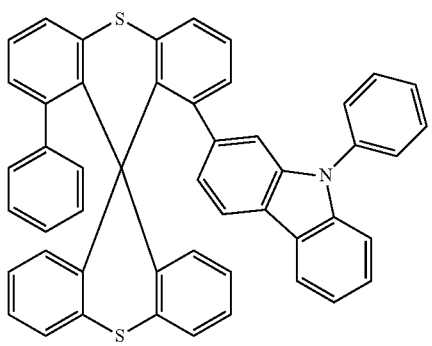

-continued
267
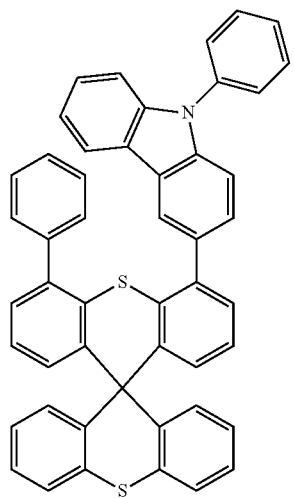
268
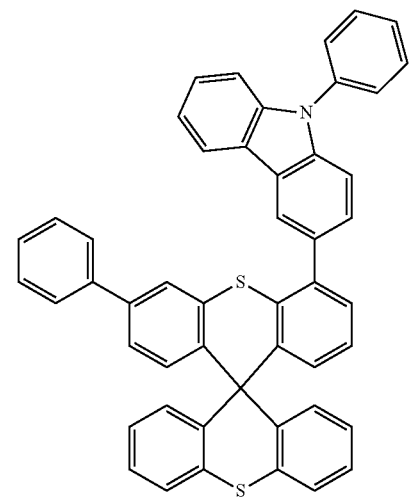
269
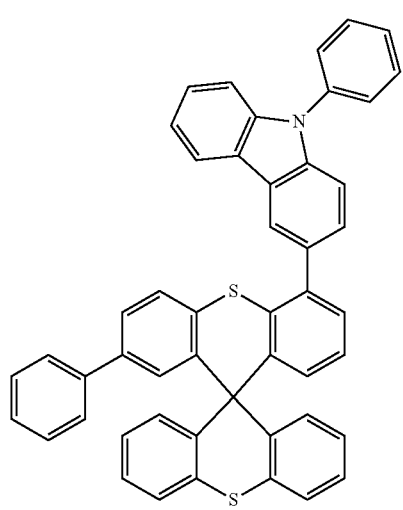
270
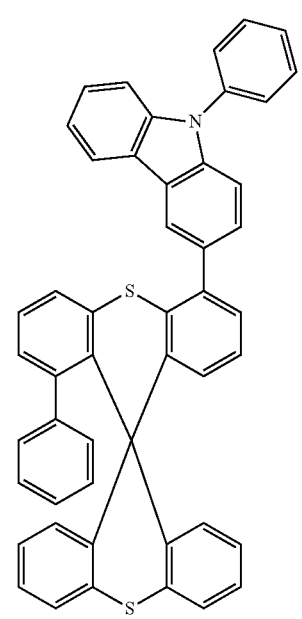
271
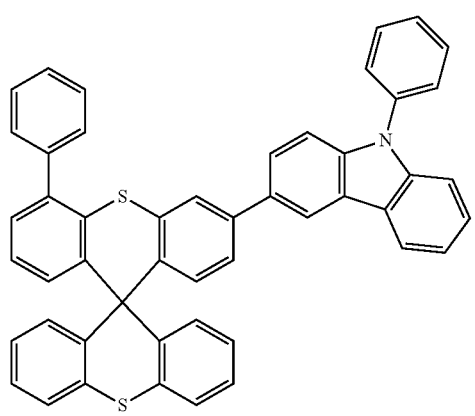
272
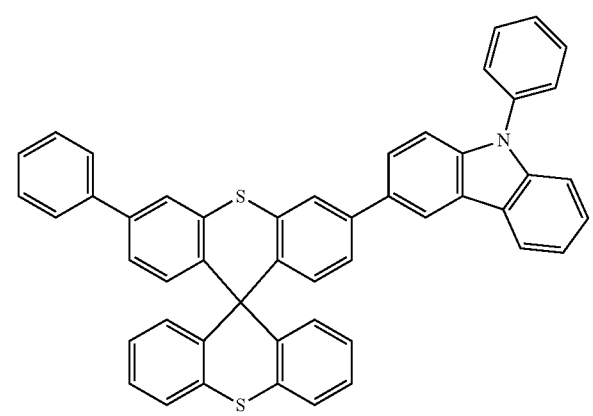

273
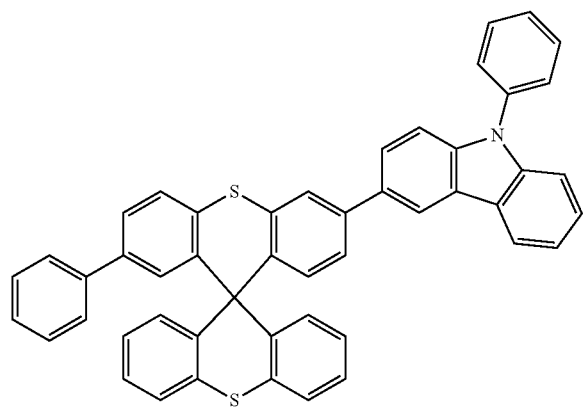
274
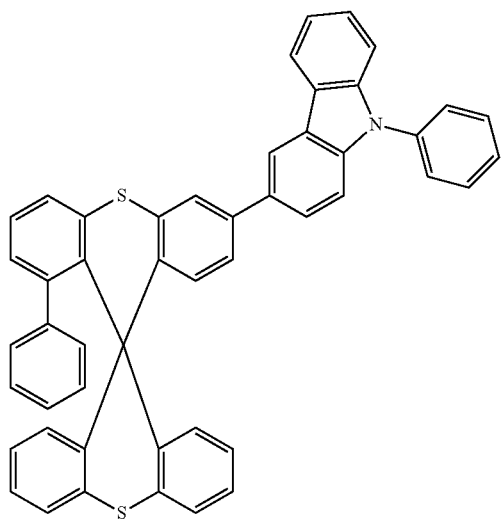
275
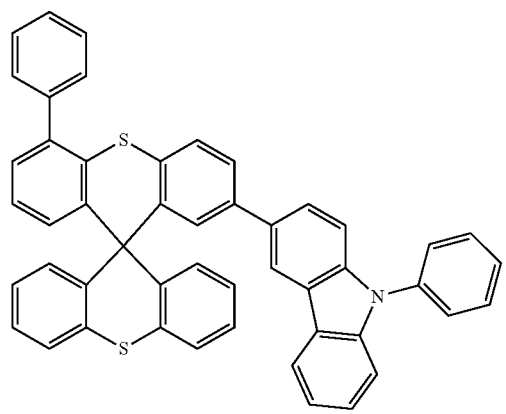
276
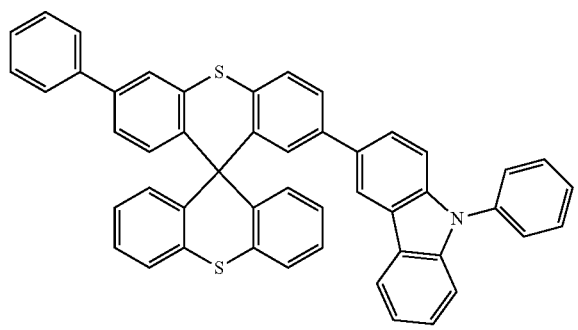
277
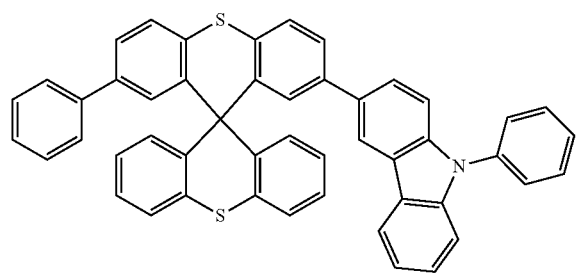
278
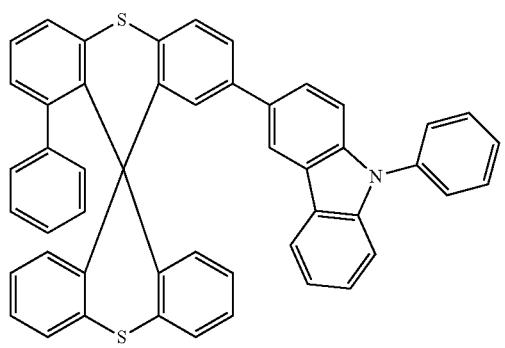

279
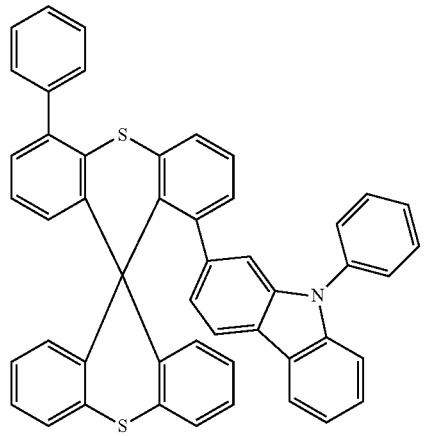
280
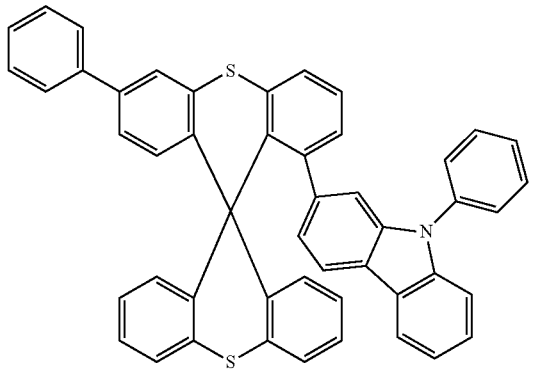
281
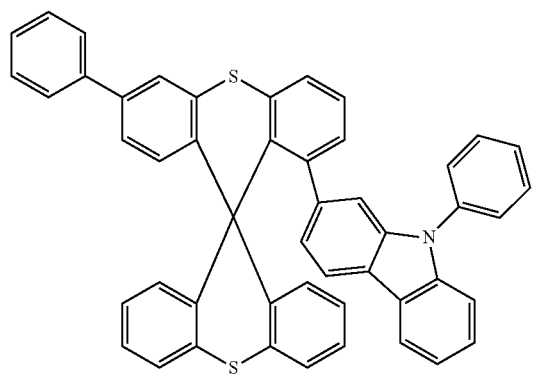
282
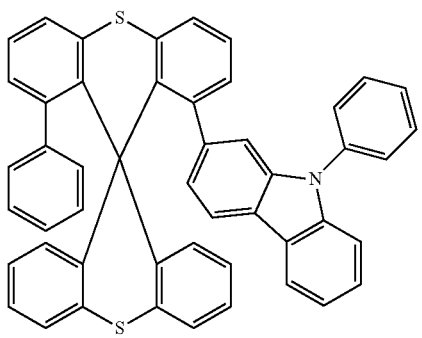
283
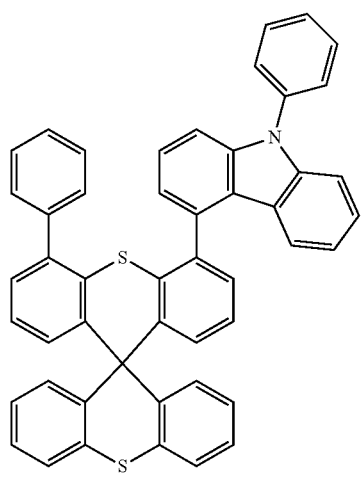
284
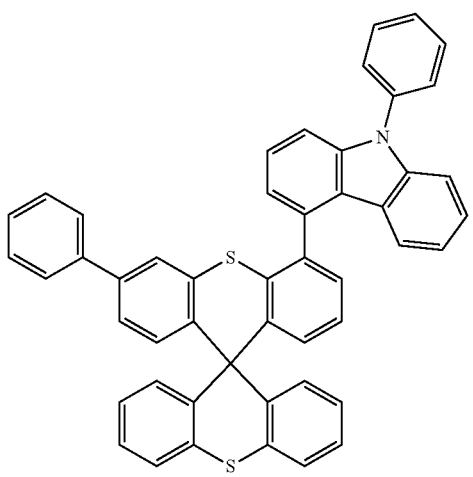

-continued
285
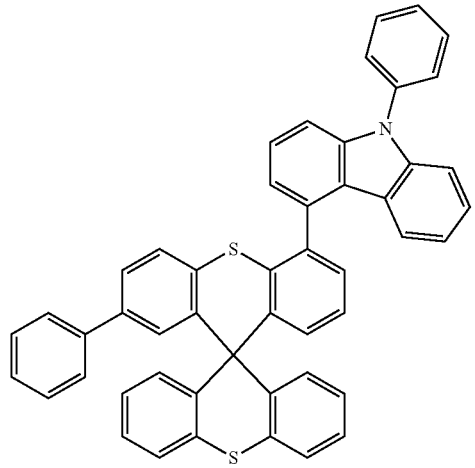
286
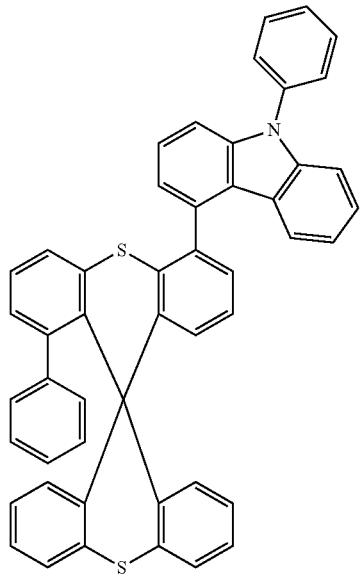
287
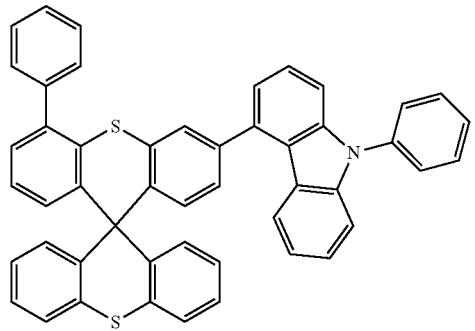
288
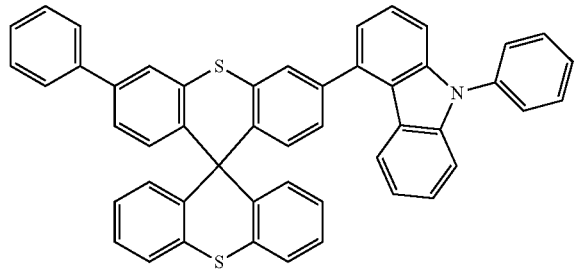
289
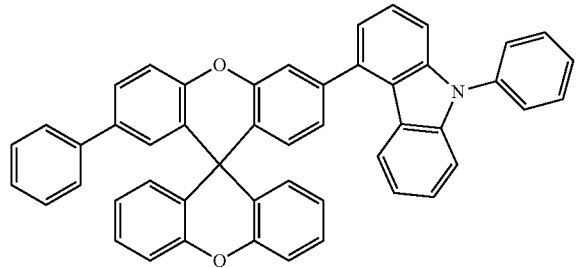
290
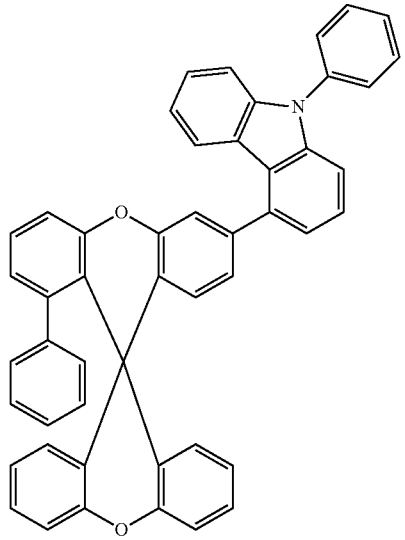

291 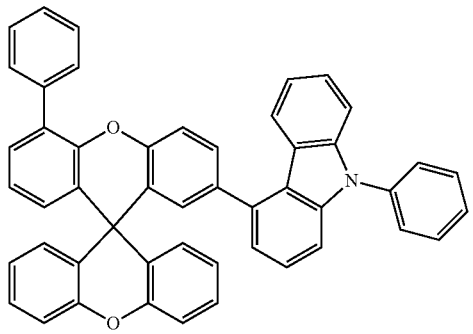
292 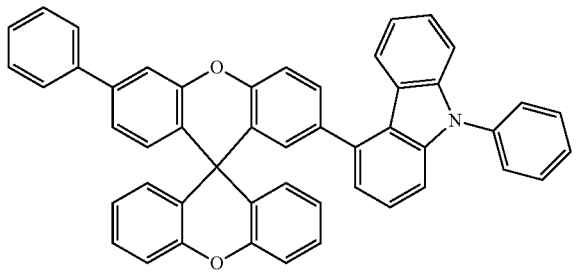
293 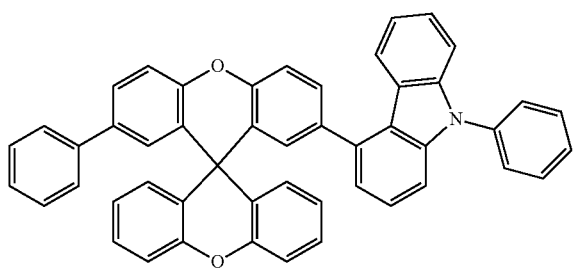
294 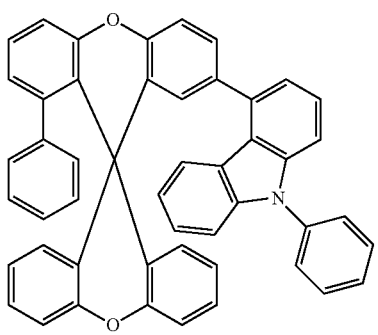
295 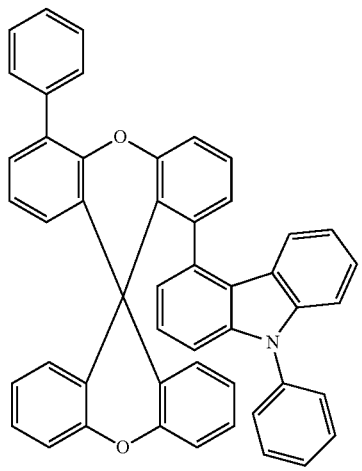
296 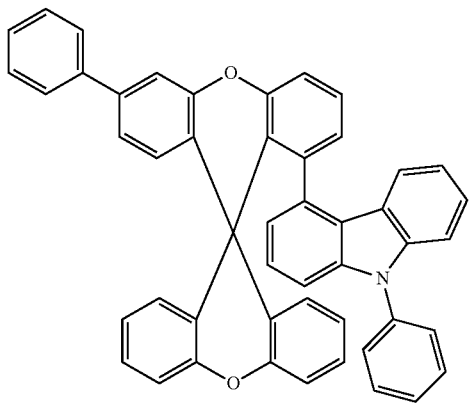
297 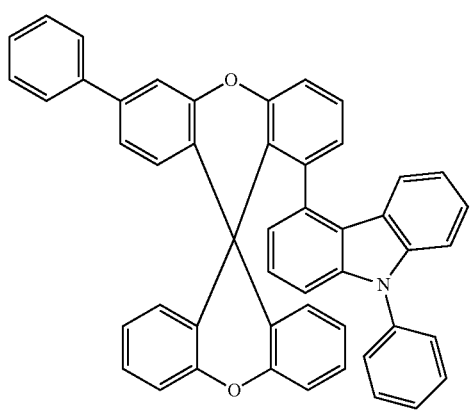
298 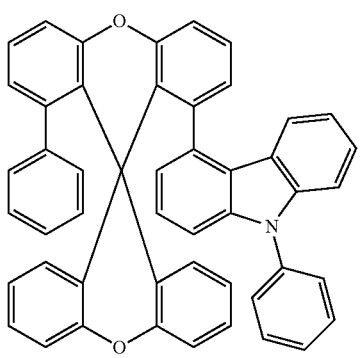

-continued
299
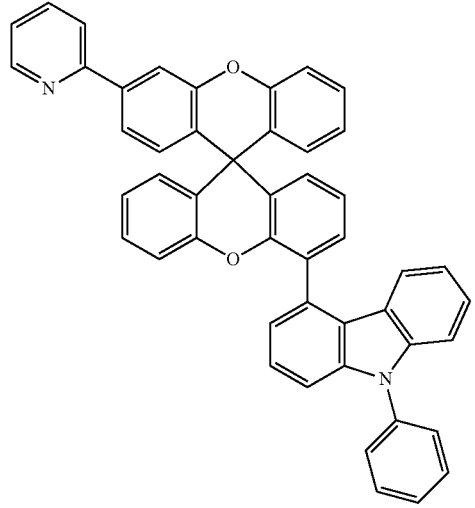
300
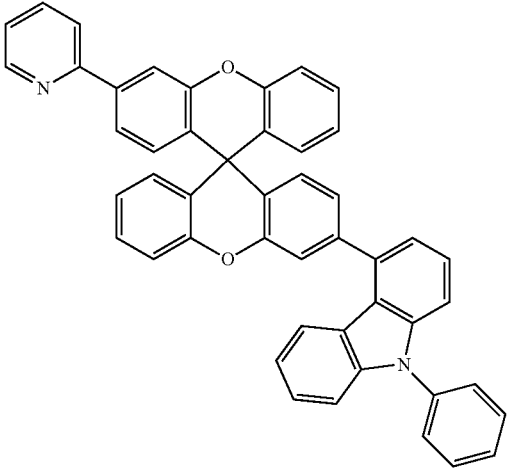
301
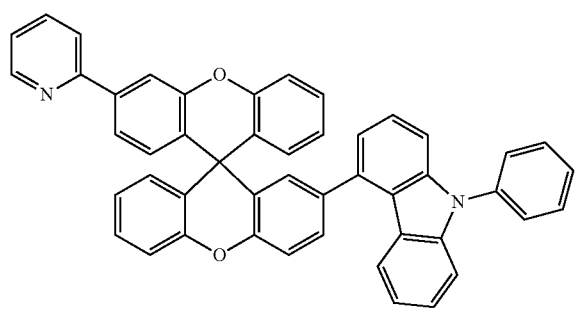
302
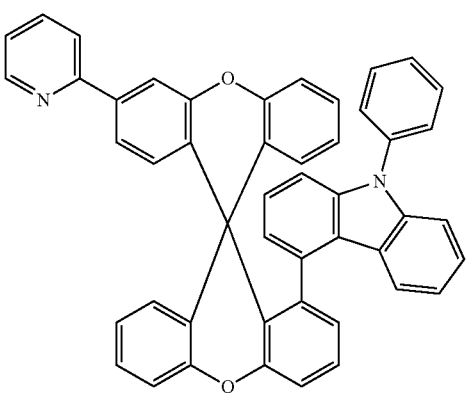
303
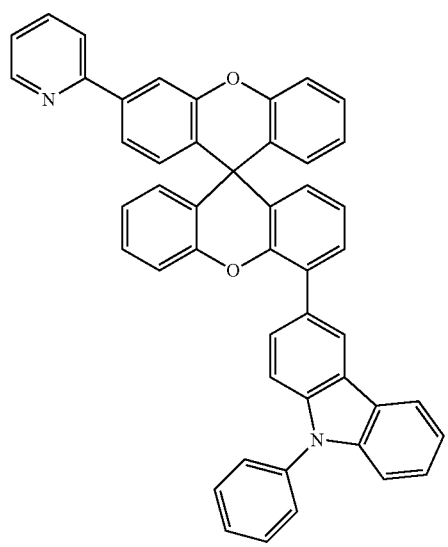
304
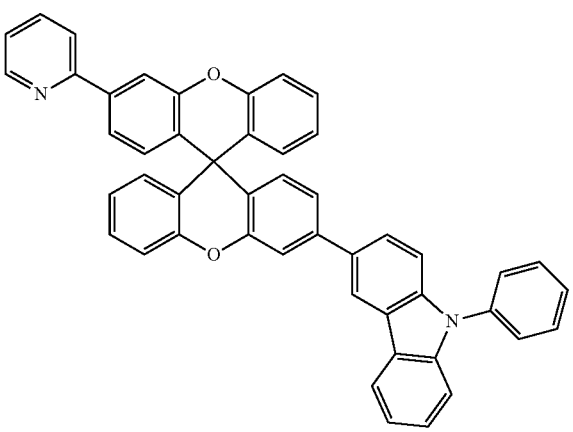

-continued
305
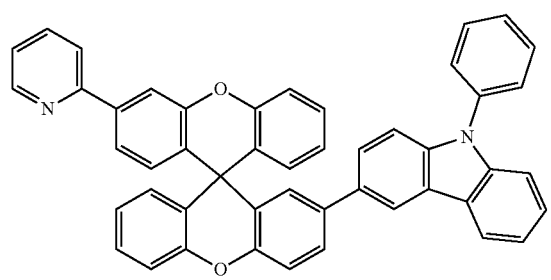
306
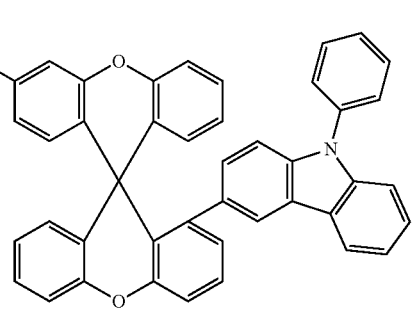
307
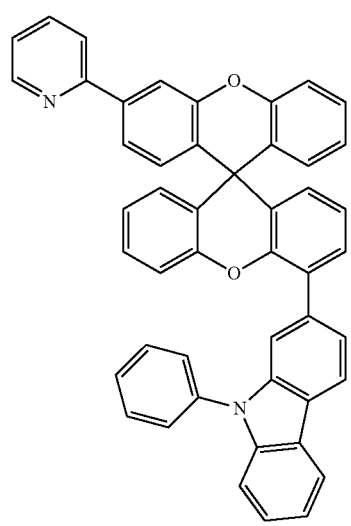
308
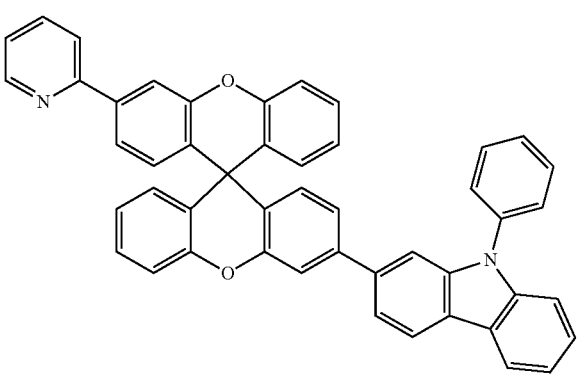
309
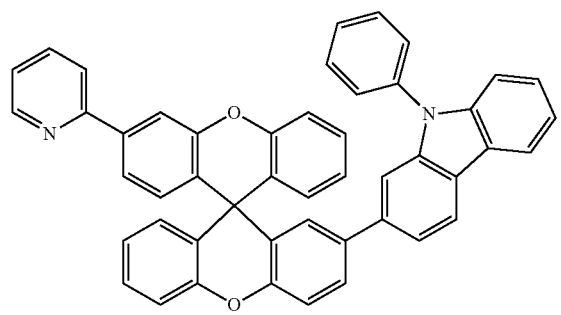
310
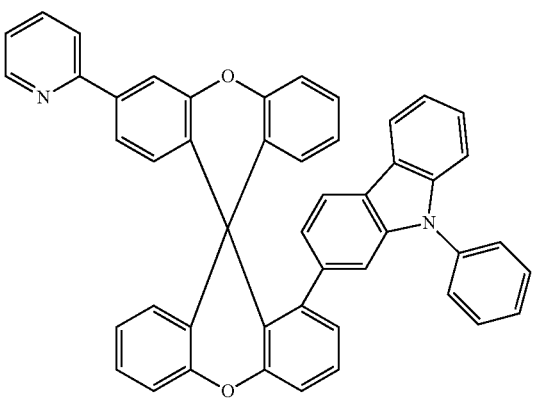

311
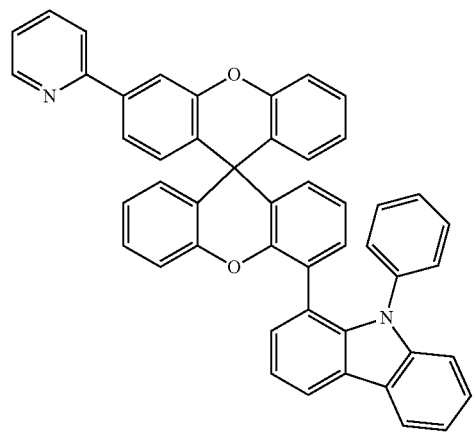
312
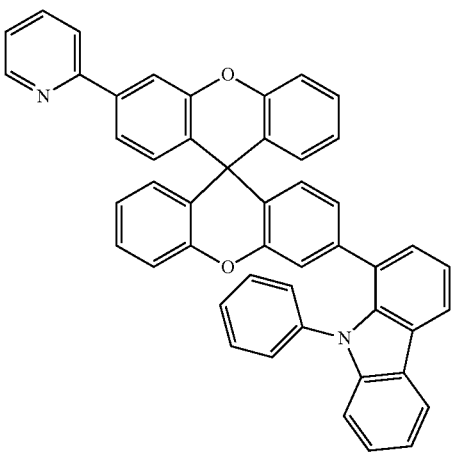
313
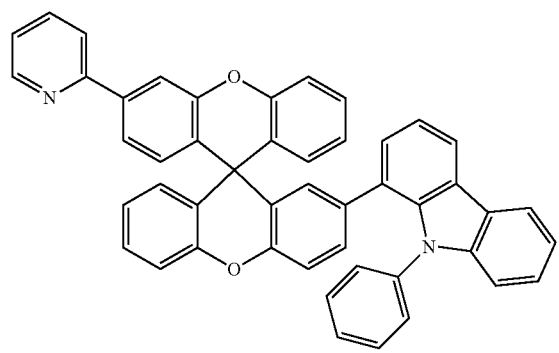
314
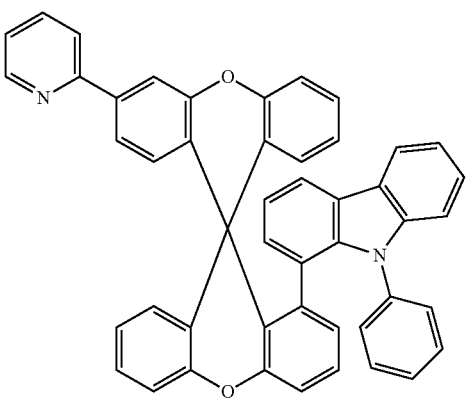
315
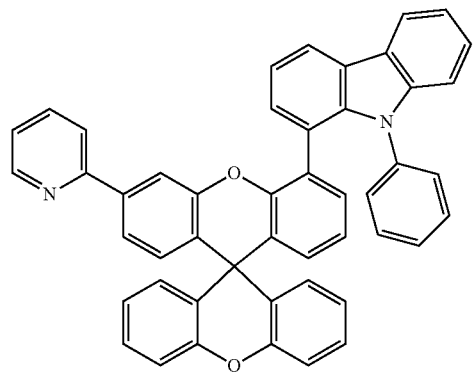
316
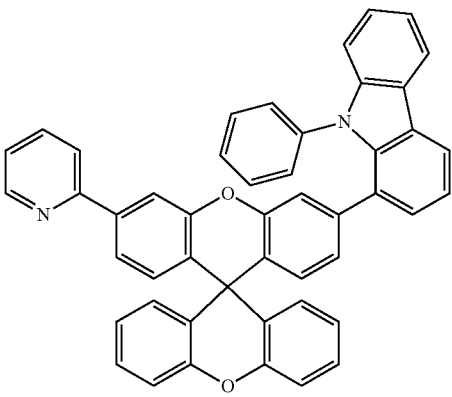

-continued
317
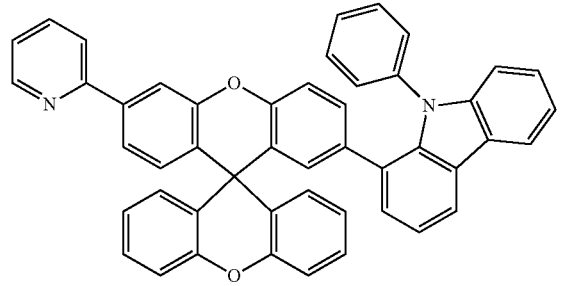
318
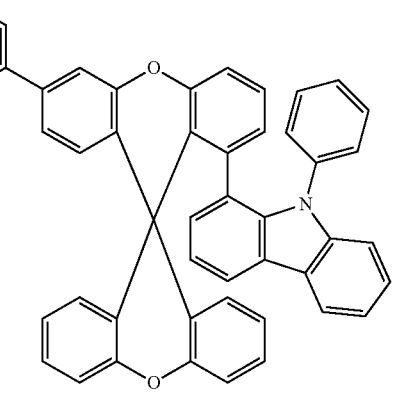
319
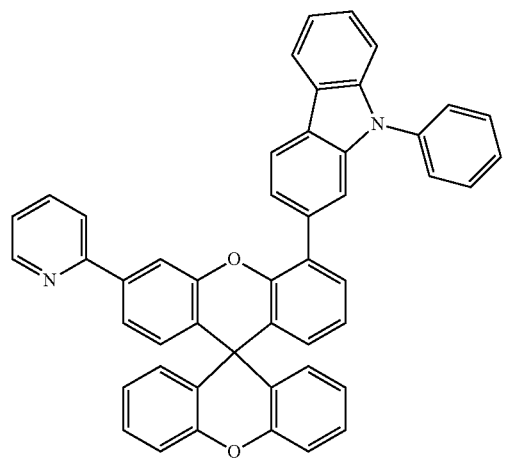
320
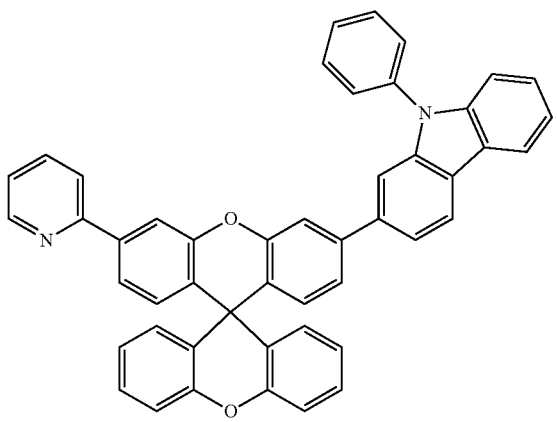
321
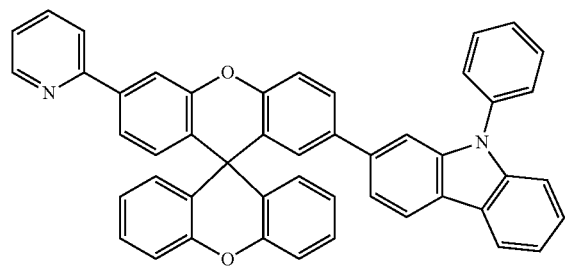
322
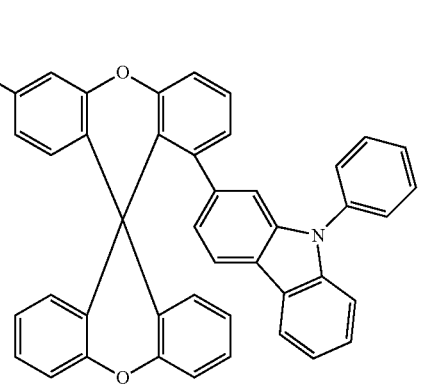

-continued
323
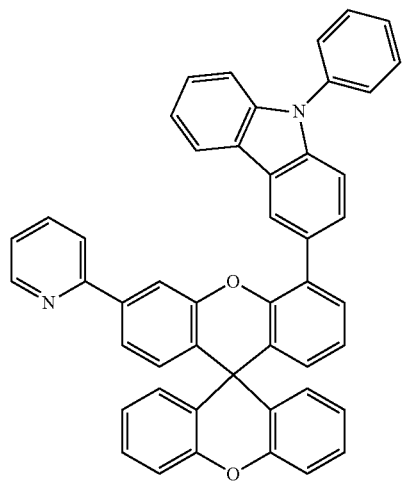
324
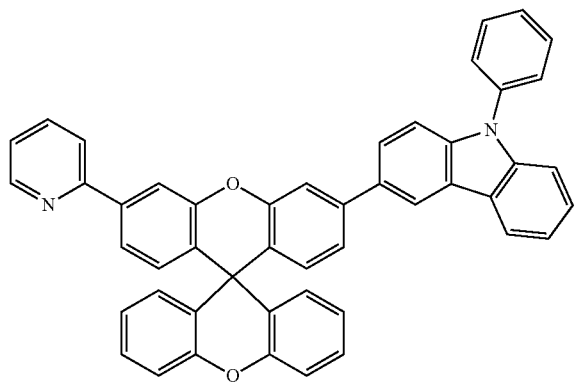
325
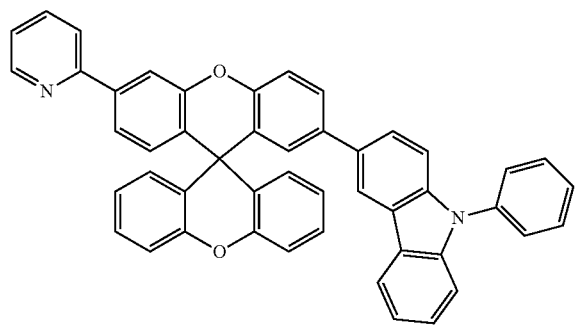
326
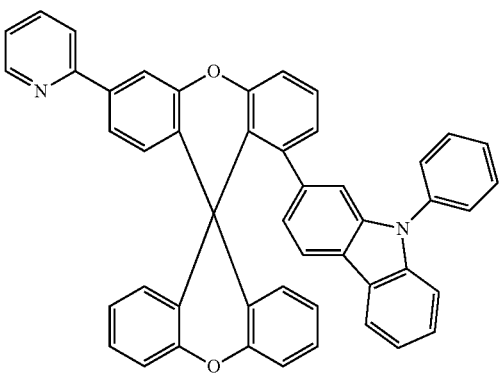
327
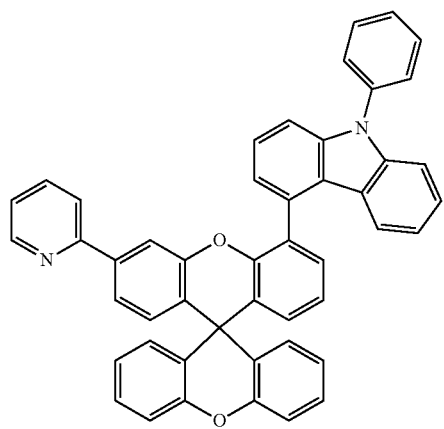
328
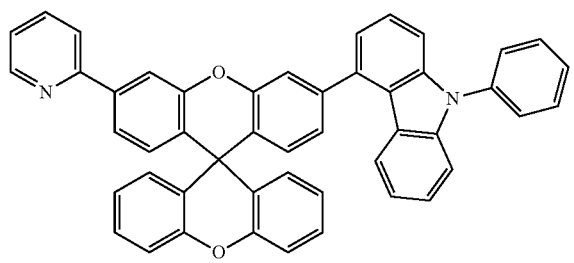

329
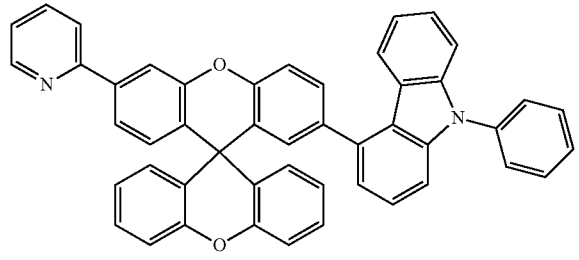
330
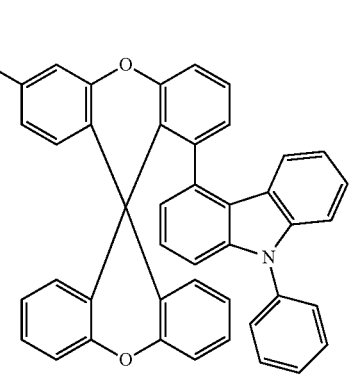
331
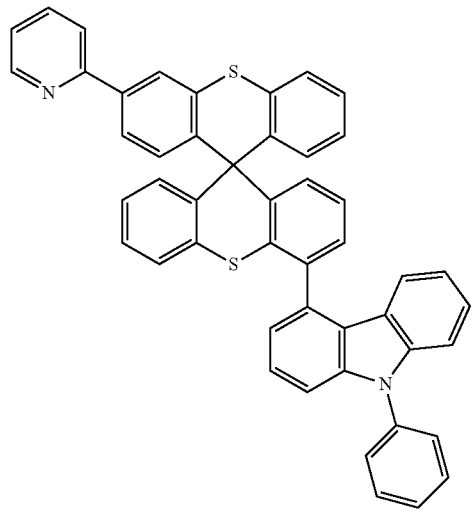
332
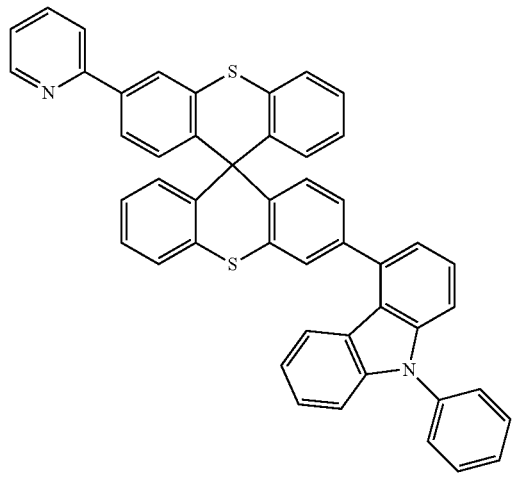
333
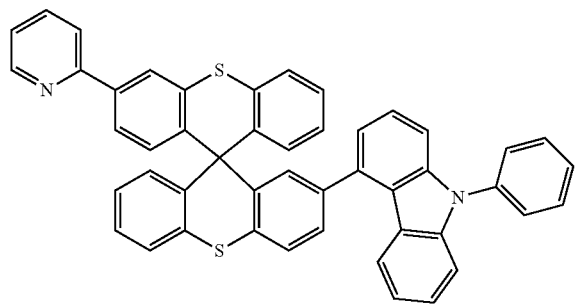
334
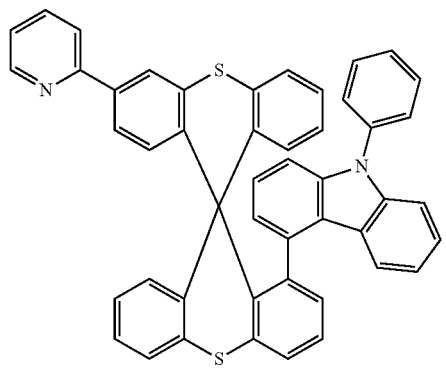

-continued
335
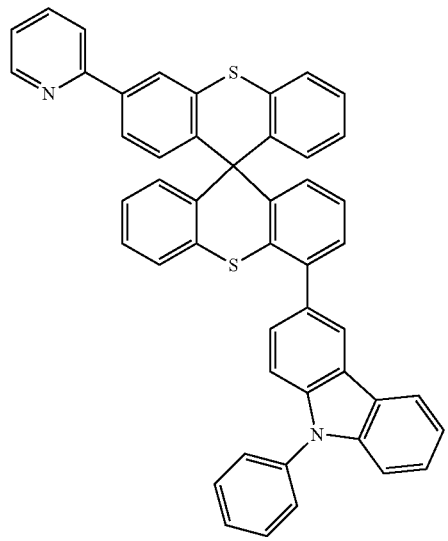
336
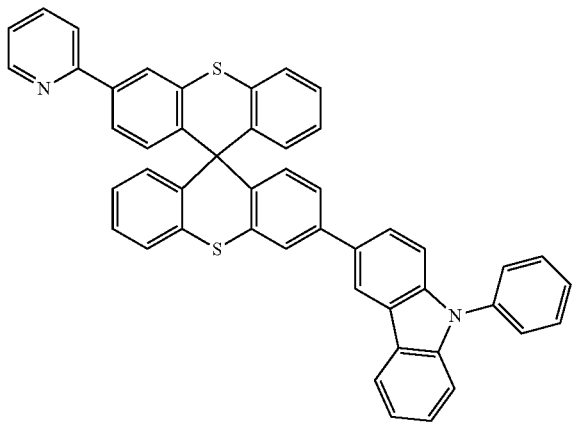
337
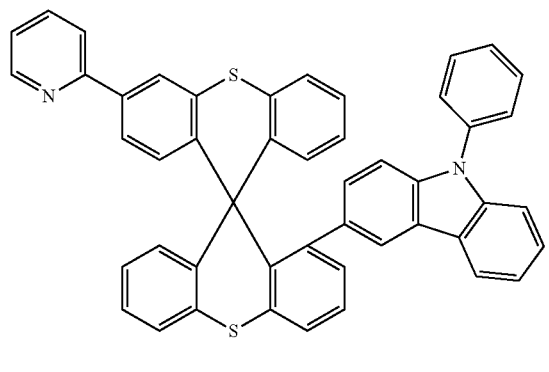
338
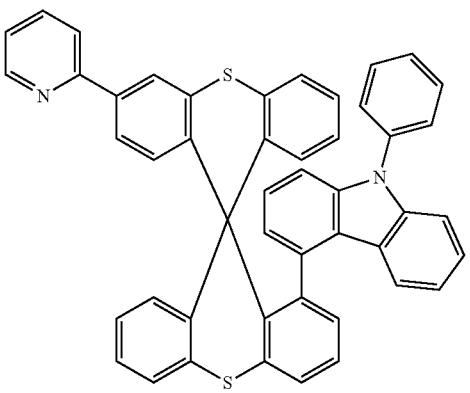
339
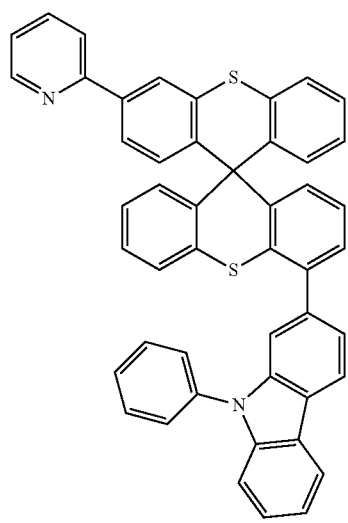
340
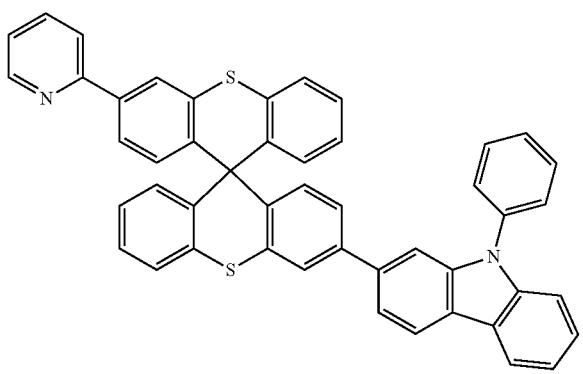

341
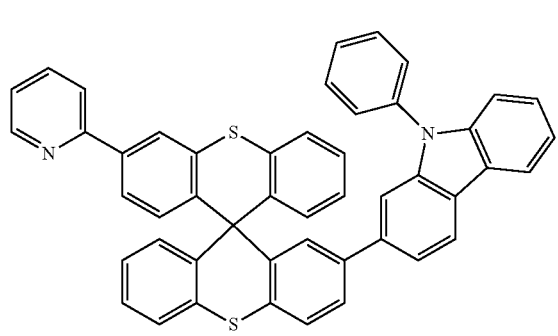
342
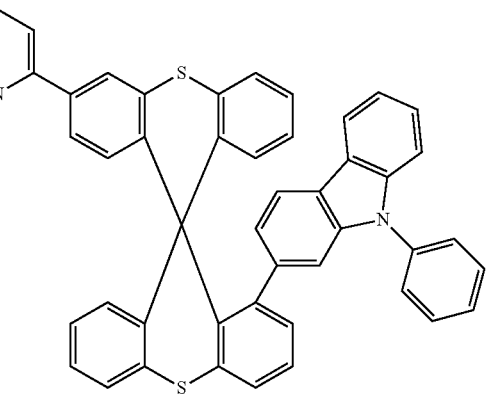
343
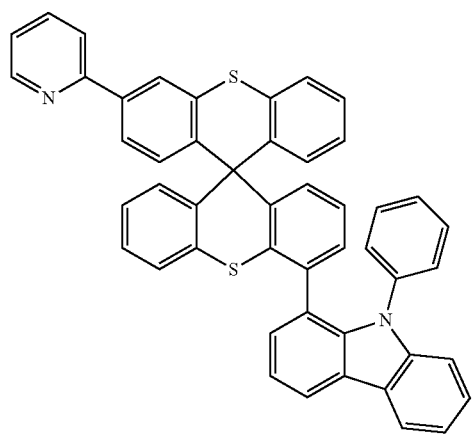
344
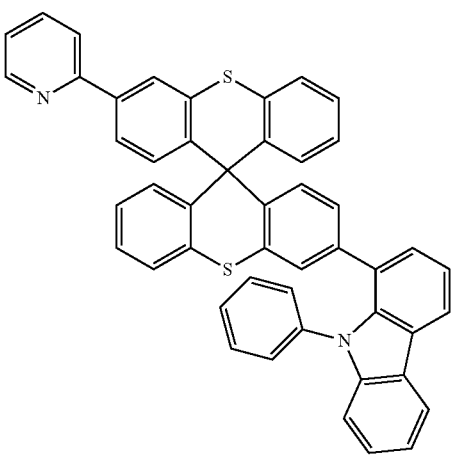
345
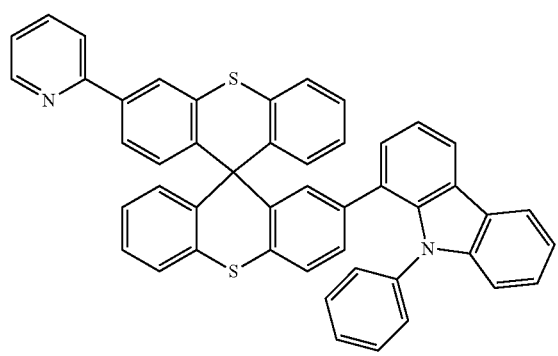
346
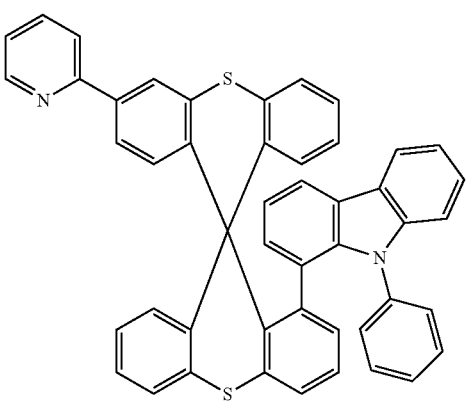

-continued
347
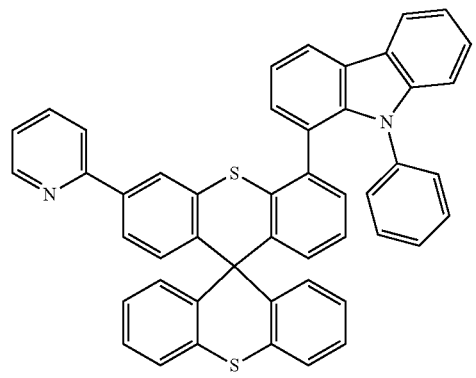
348
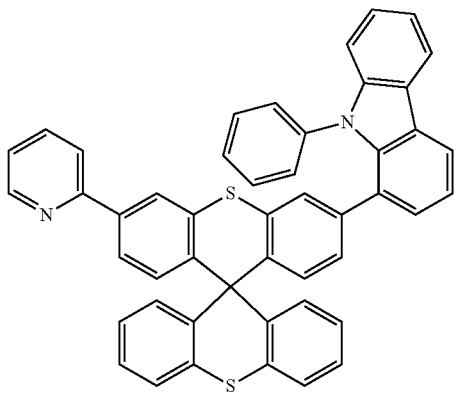
349
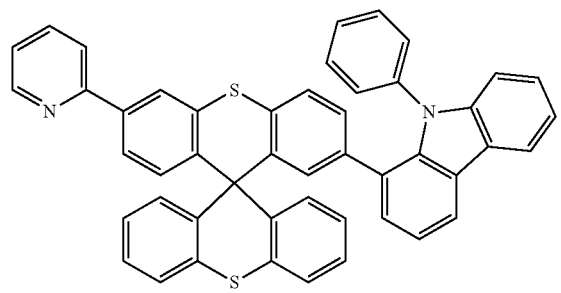
350
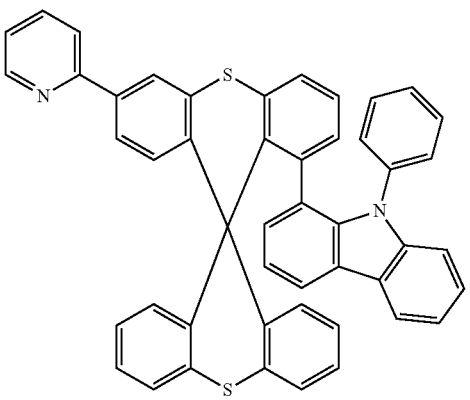
351
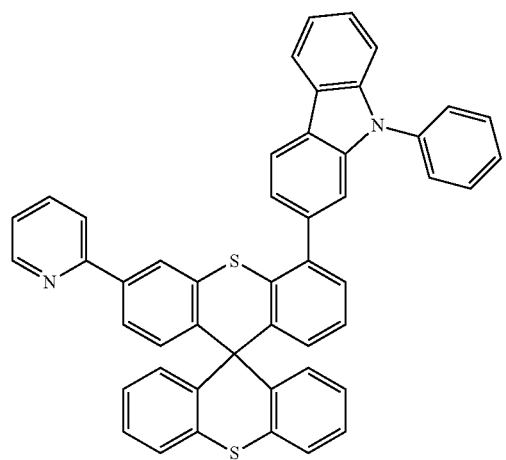
352
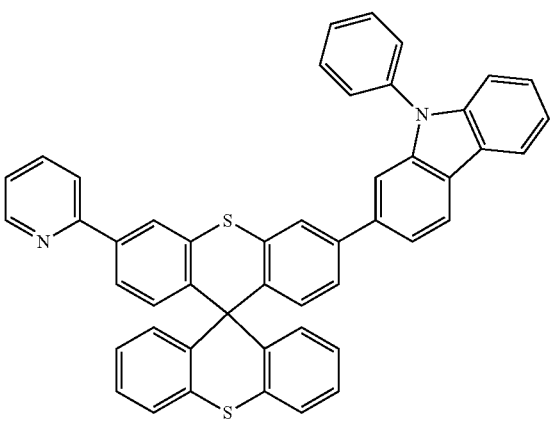

-continued
353
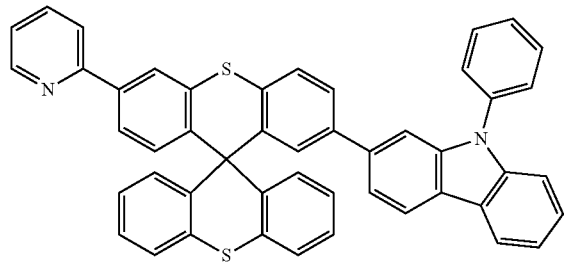
354
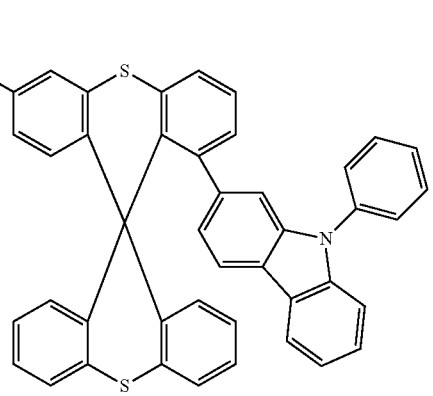
355
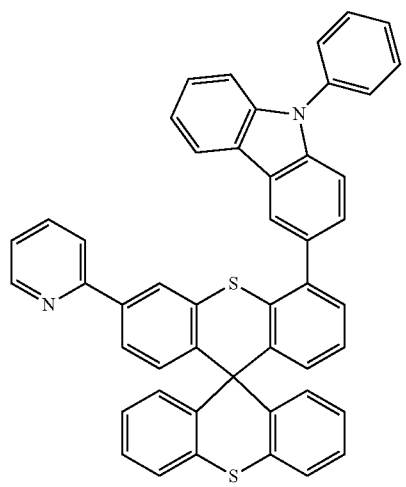
356
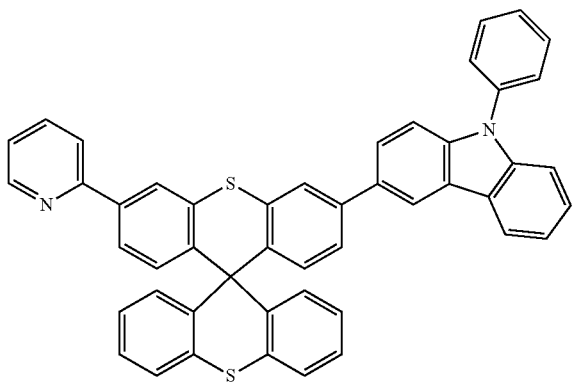
357
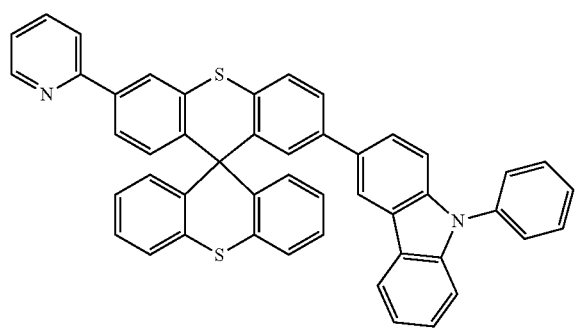
358
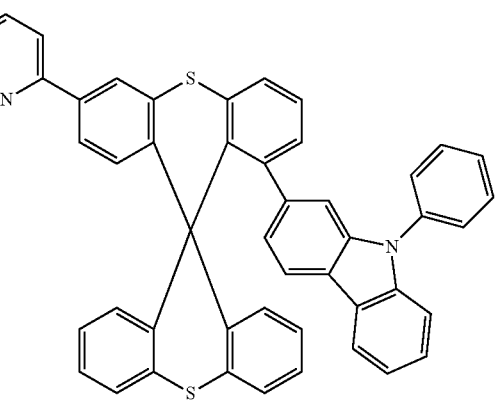

-continued
359
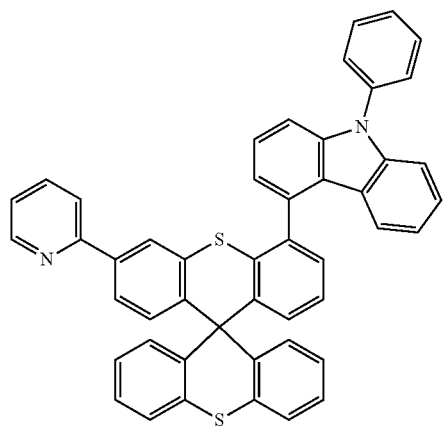
360
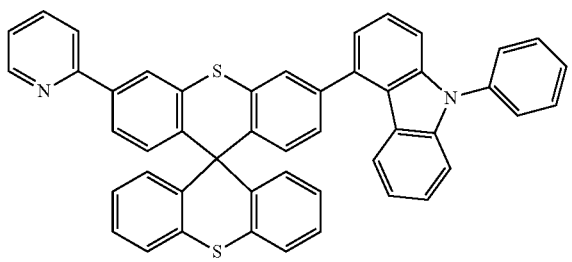
361
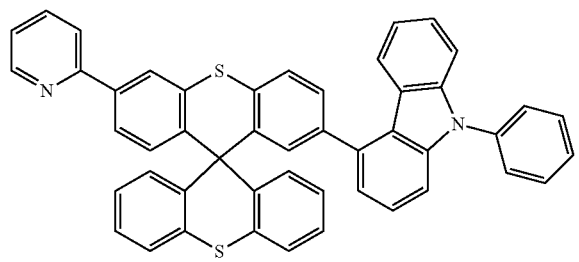
362
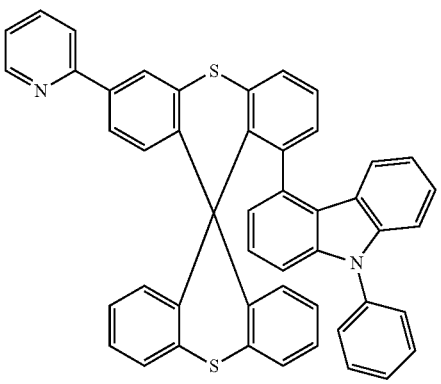
363
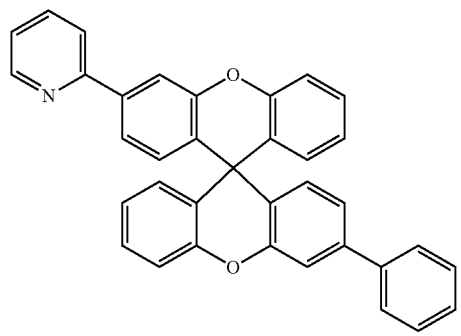
364
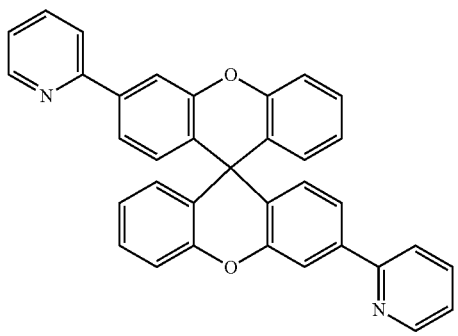
365
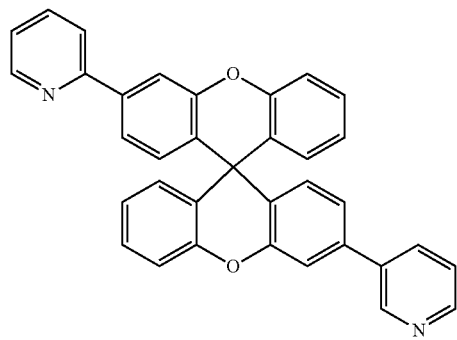
366
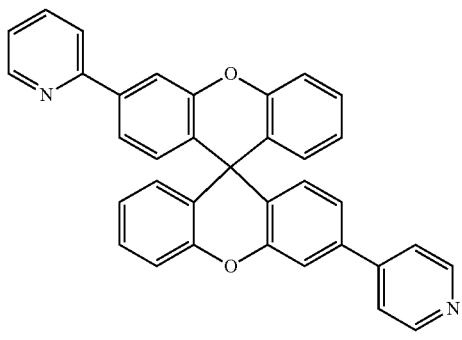

-continued
| 367 | 368 |
|---|---|
| 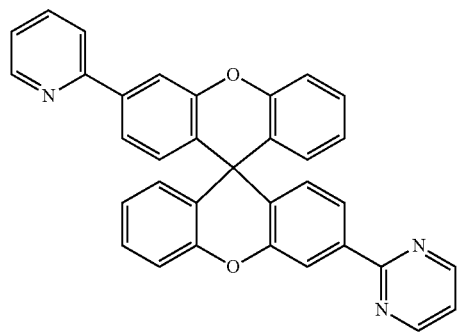 | 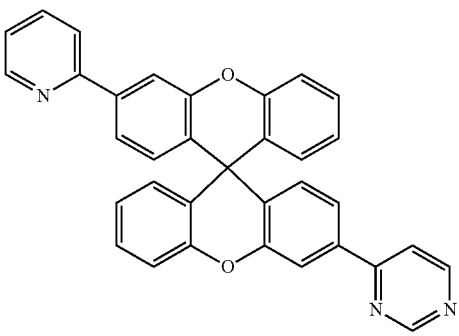 |
| 369 | 370 |
| 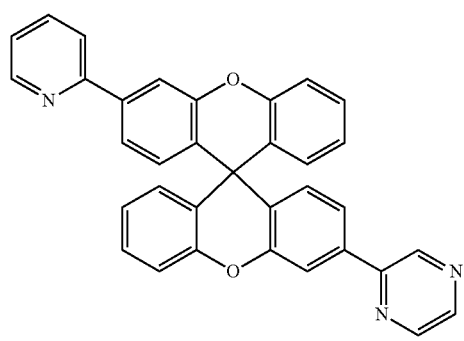 | 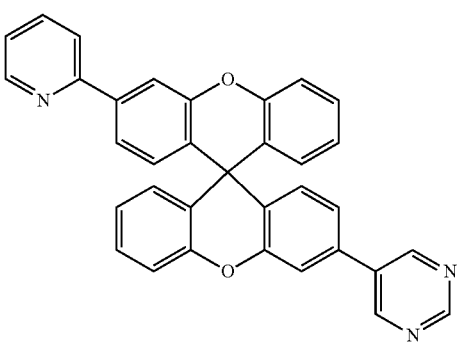 |
| 371 | 372 |
| 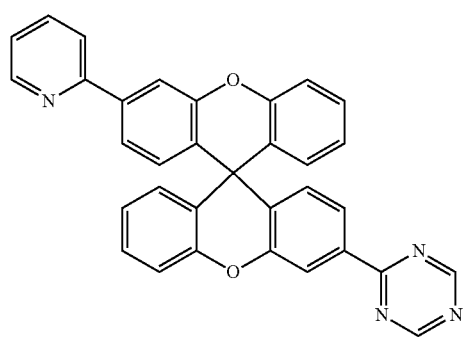 | 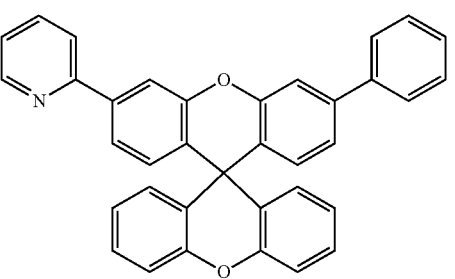 |
| 373 | 374 |
| 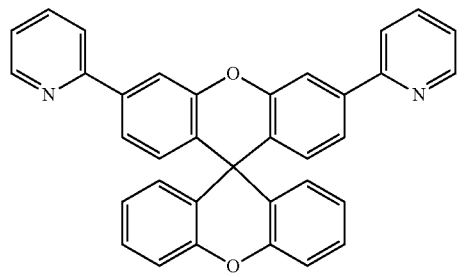 | 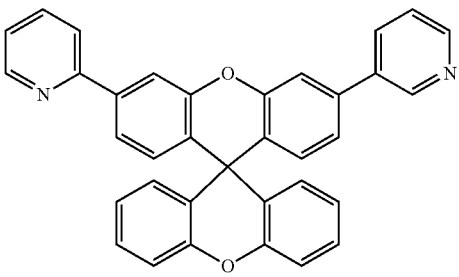 |
| 375 | 376 |
| 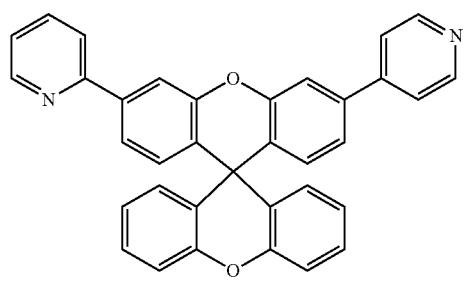 | 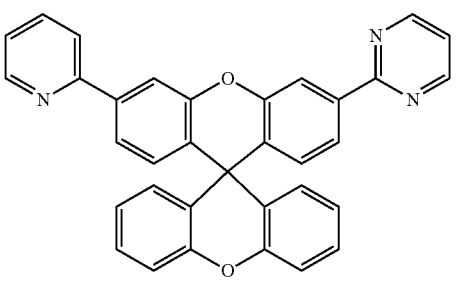 |

-continued
| | |
|---|---|
| 377 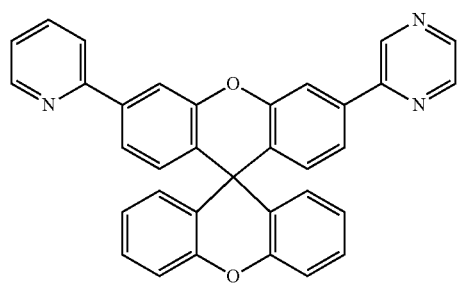 | 378 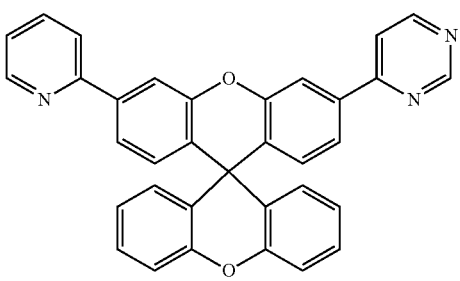 |
| 379 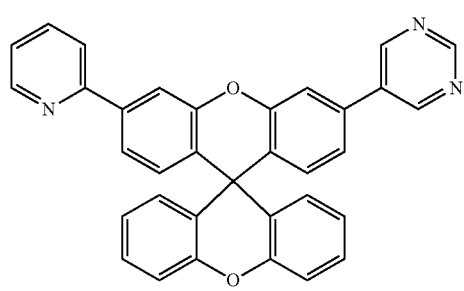 | 380 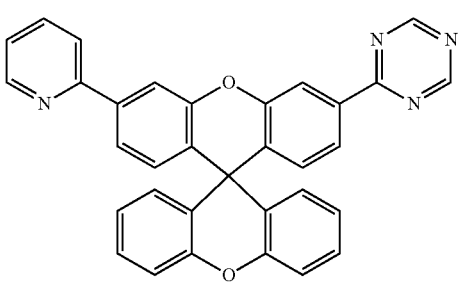 |
| 381 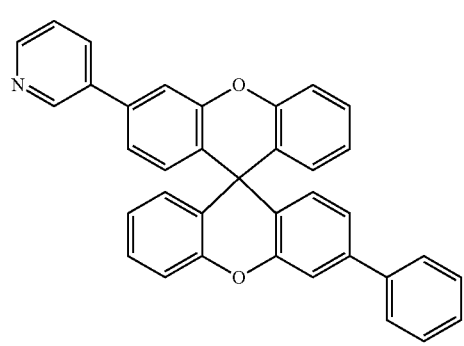 | 382 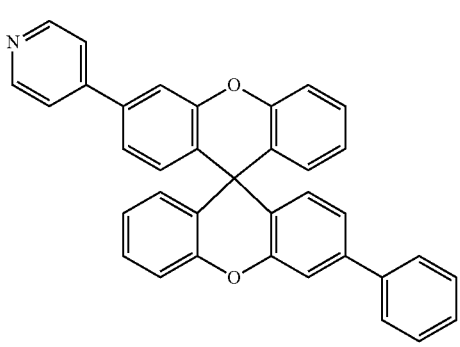 |
| 383 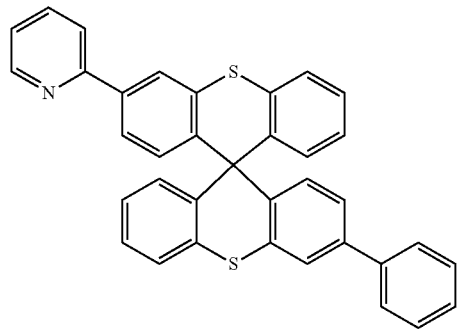 | 384 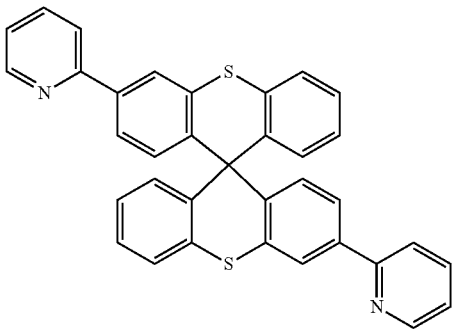 |
| 385 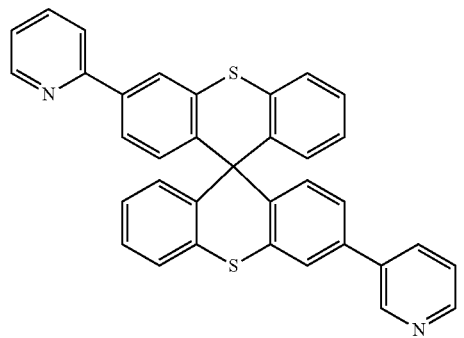 | 386 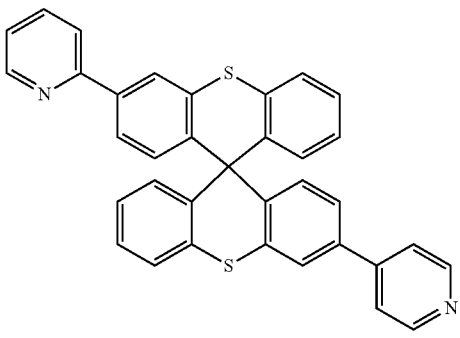 |

-continued
387
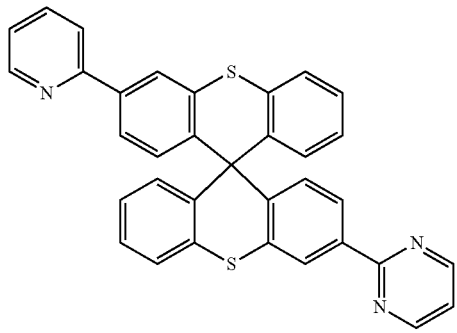
388
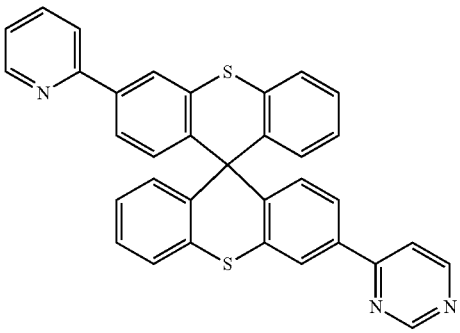
389
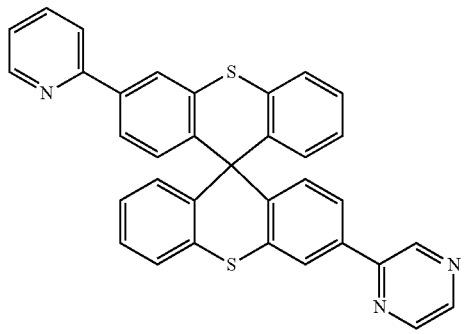
390
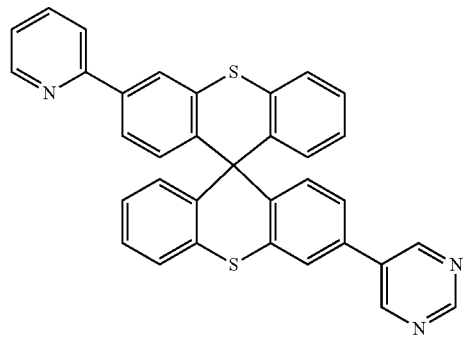
391
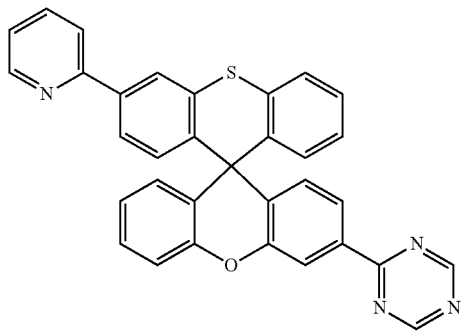
392
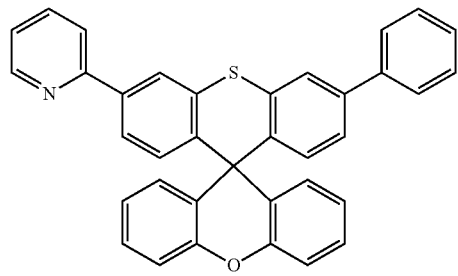
393
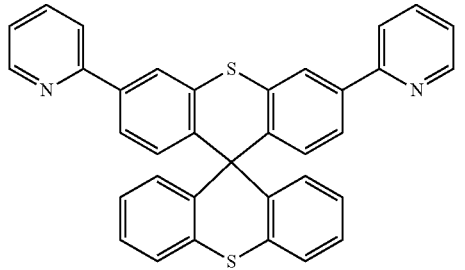
394
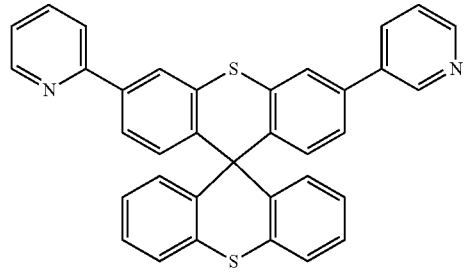
395
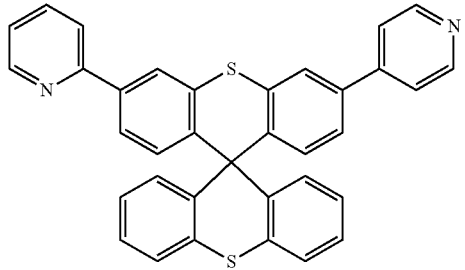
396
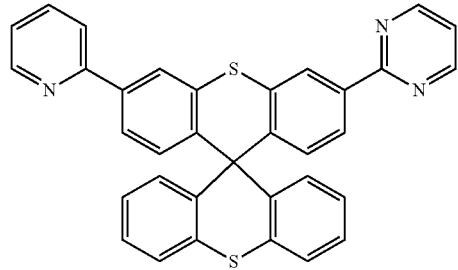

-continued
397
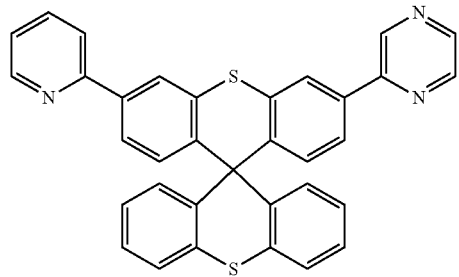
398
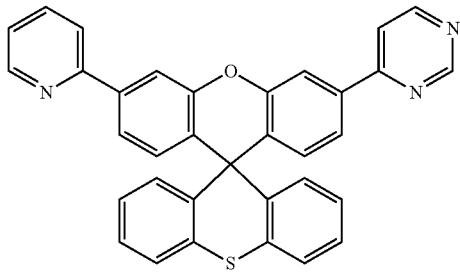
399
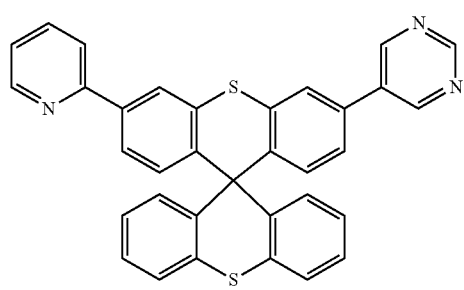
400
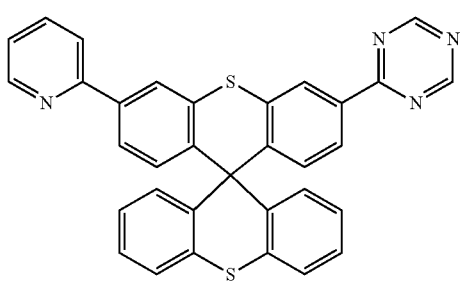
401
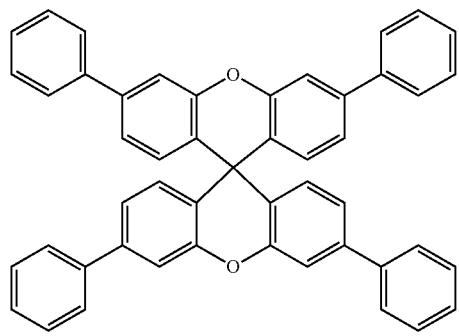
402
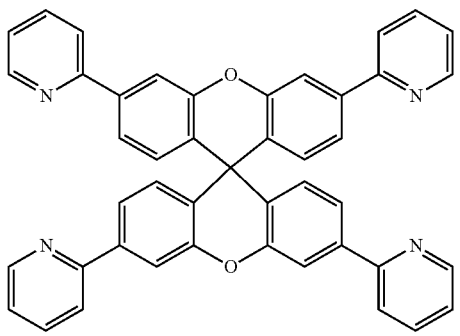
403
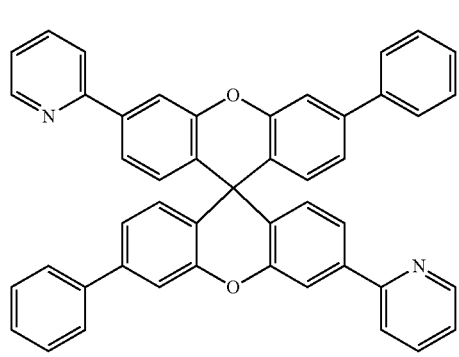
404
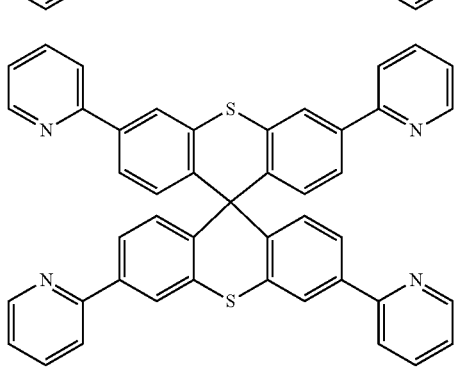
405
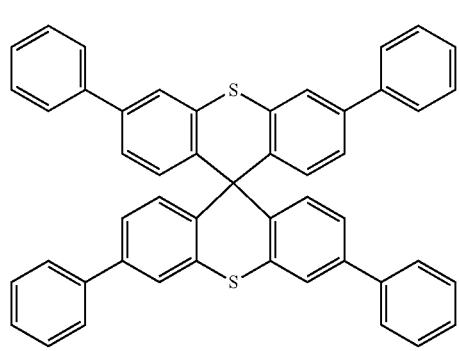
406
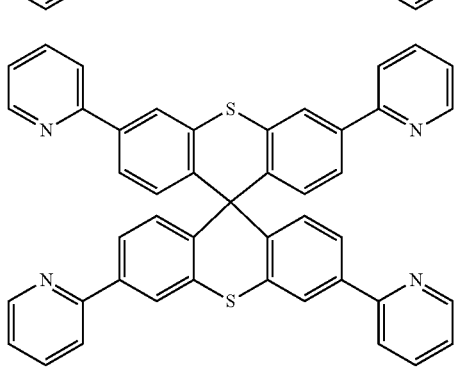

-continued
407
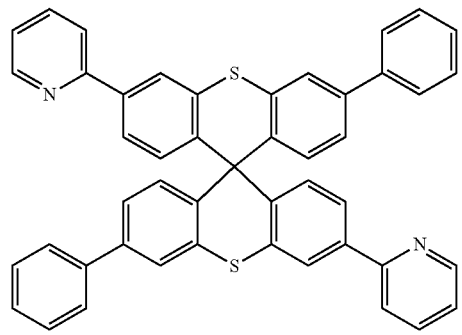
408
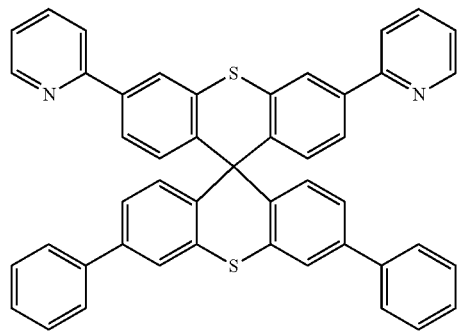
409
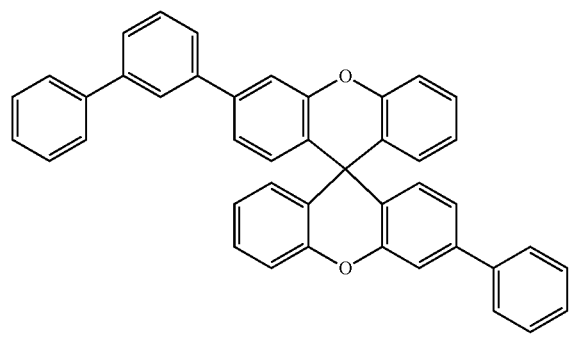
410
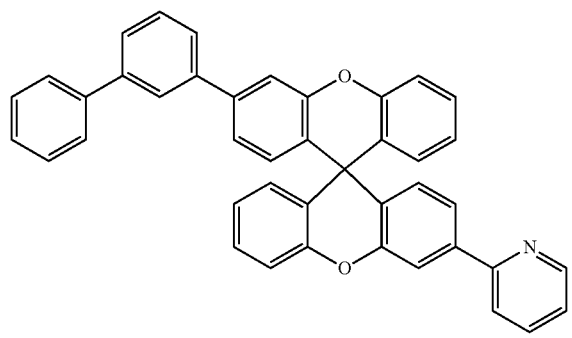
411
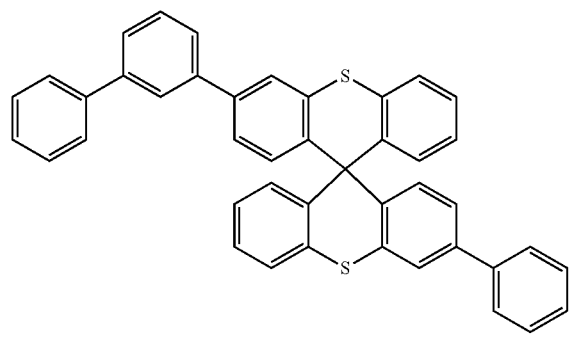
412
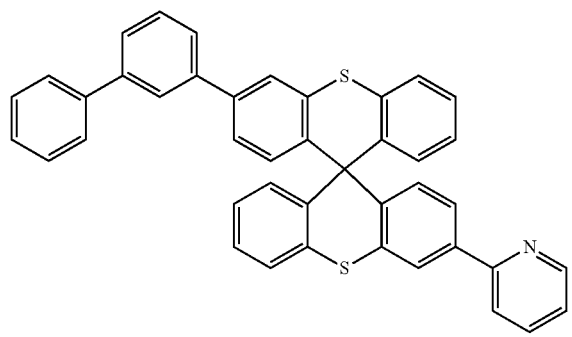
413
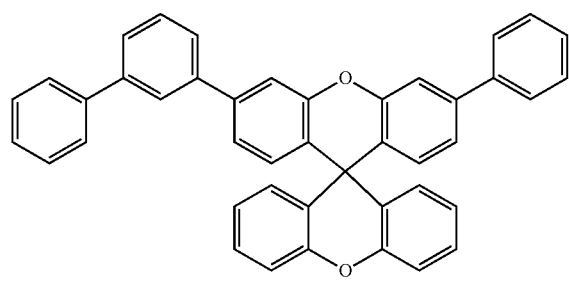
414
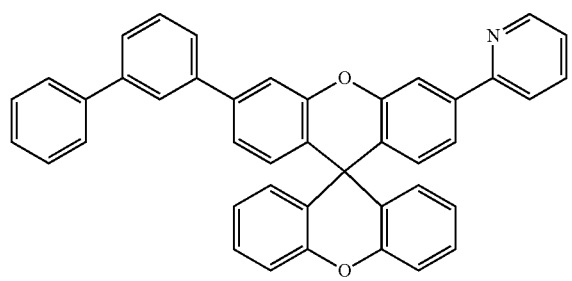
415
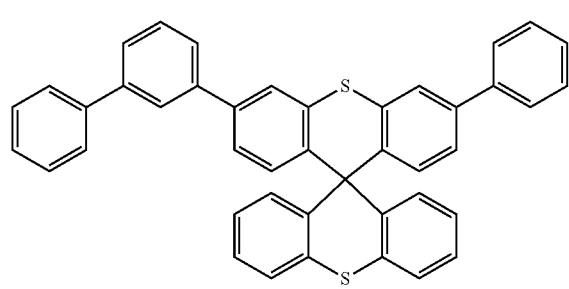
416
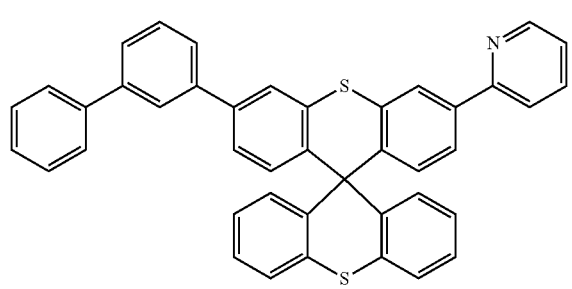

417
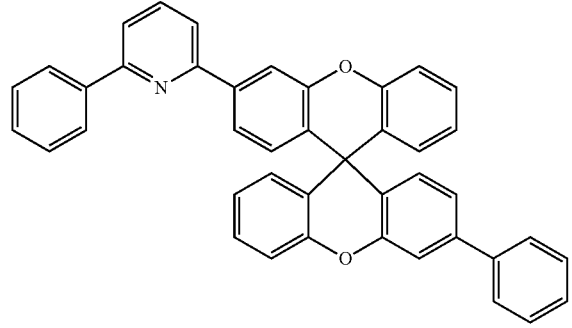
418
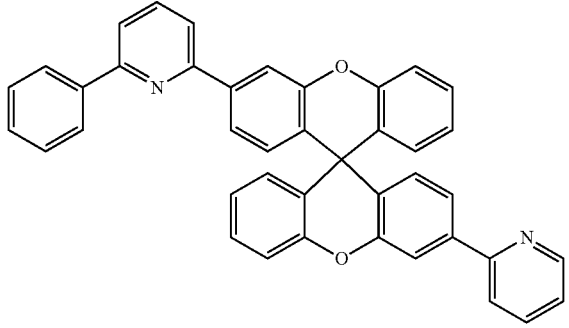
419
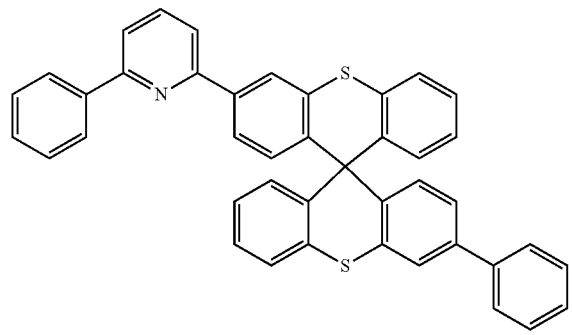
420
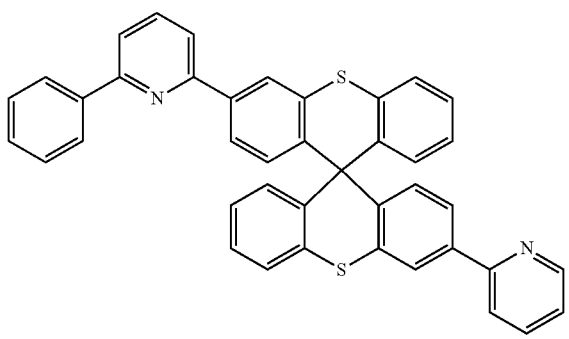
421
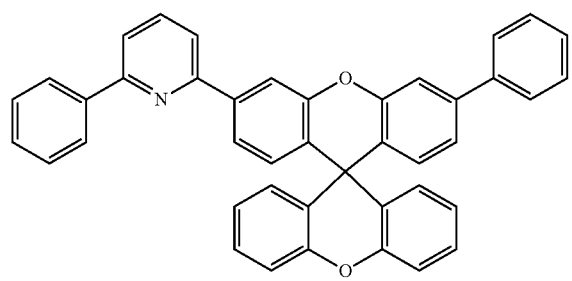
422
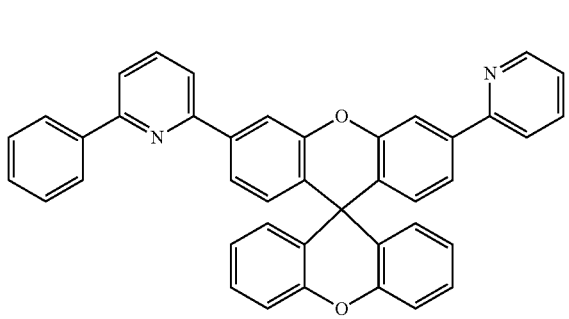
423
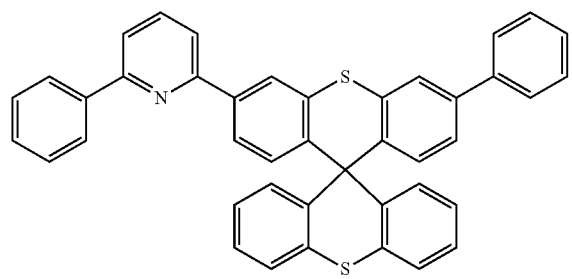
424
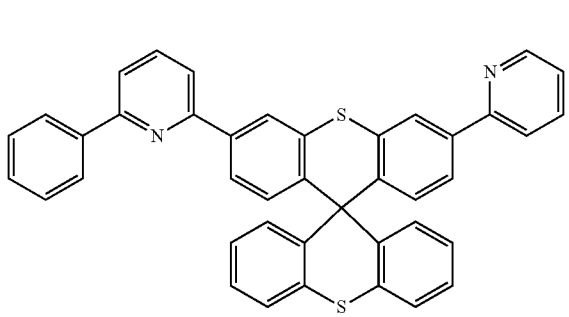

425
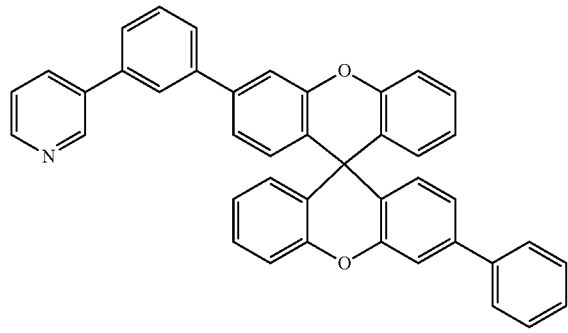
426
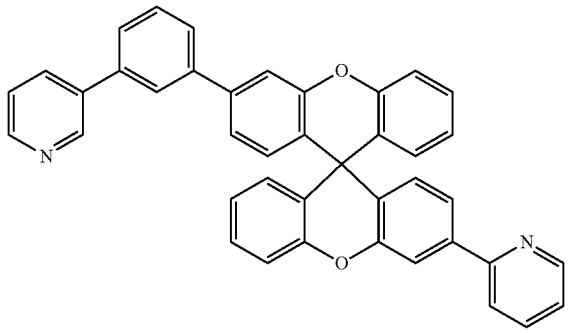
427
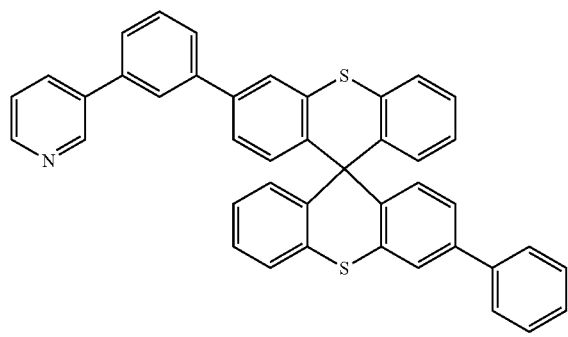
428
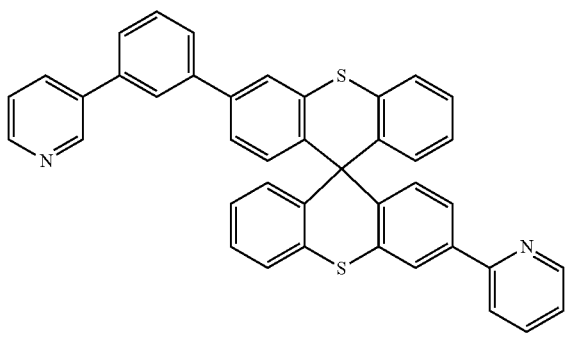
429
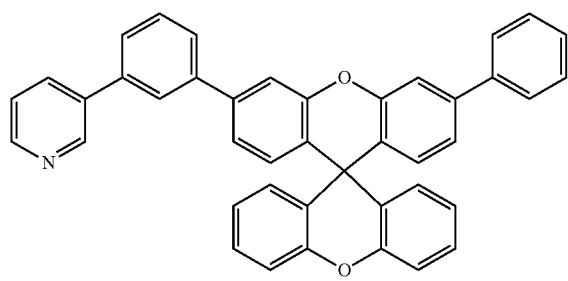
430
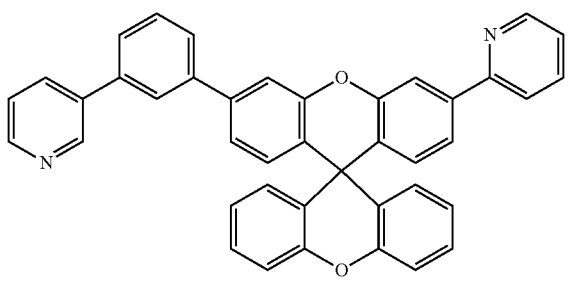
431
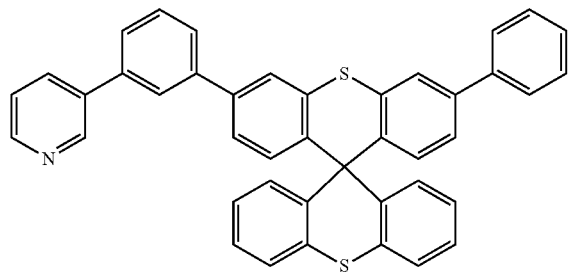
432
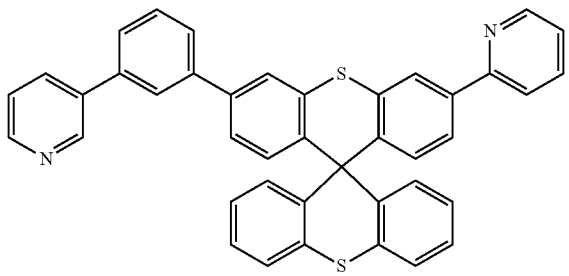

-continued
433
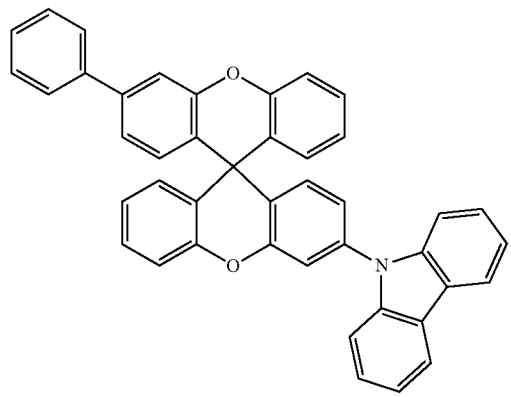
434
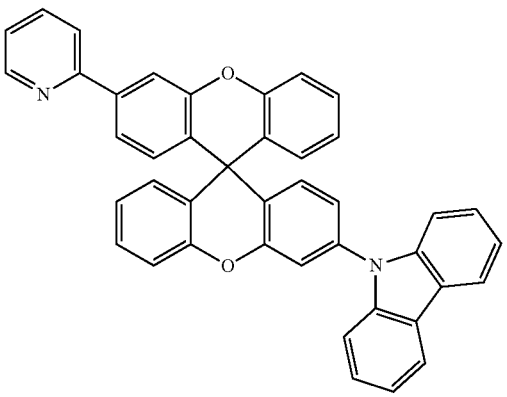
435
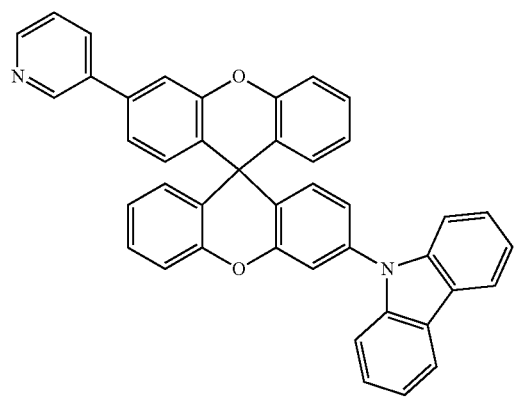
436
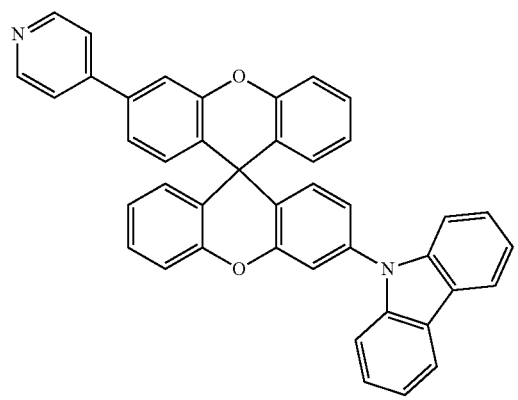
437
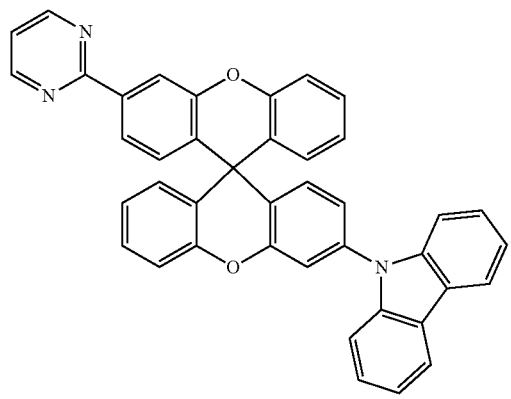
438
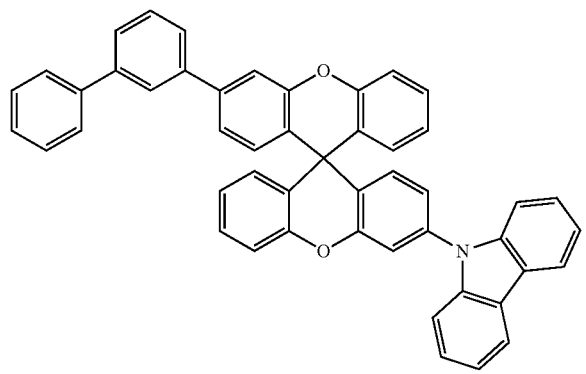
439
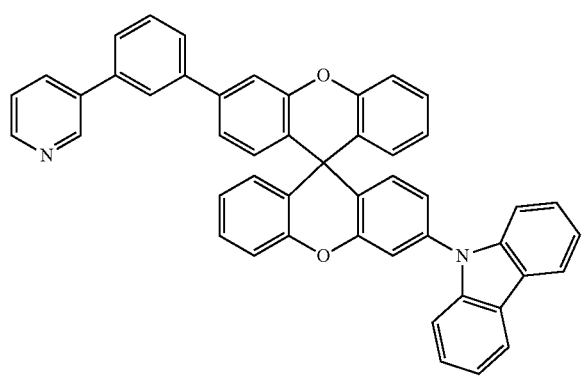
440
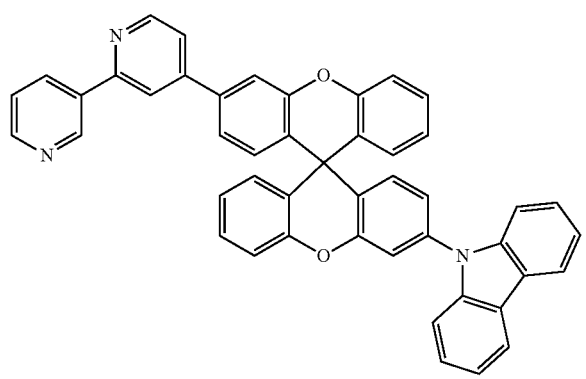

441 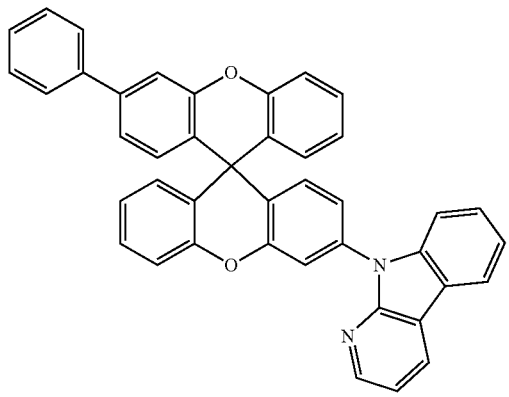
442 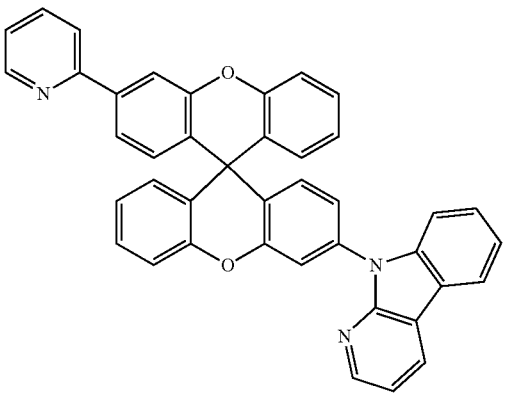
443 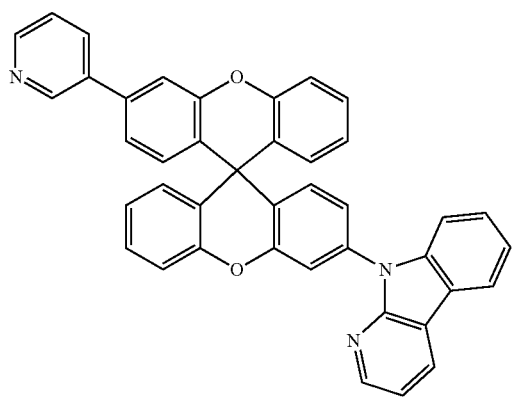
444 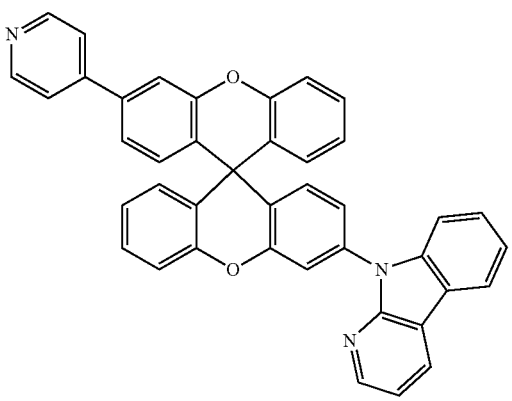
445 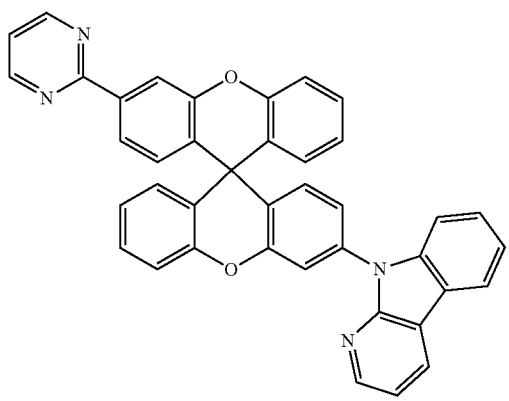
446 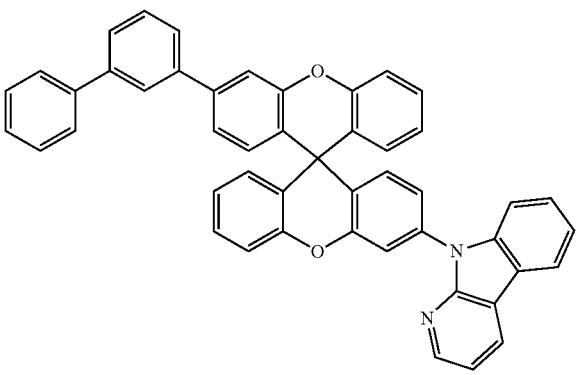
447 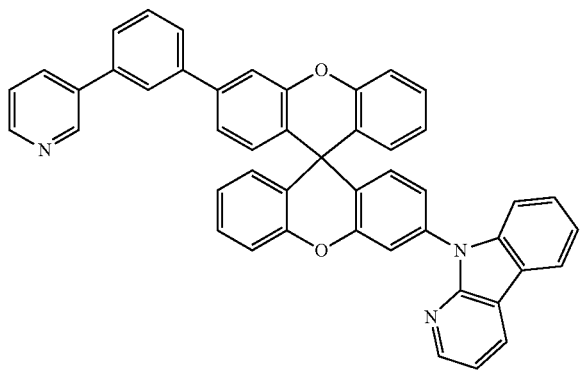
448 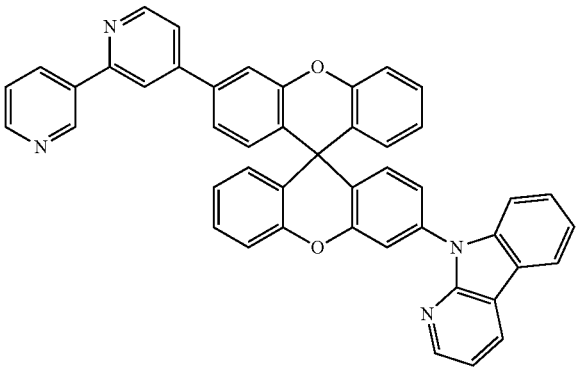

-continued
449
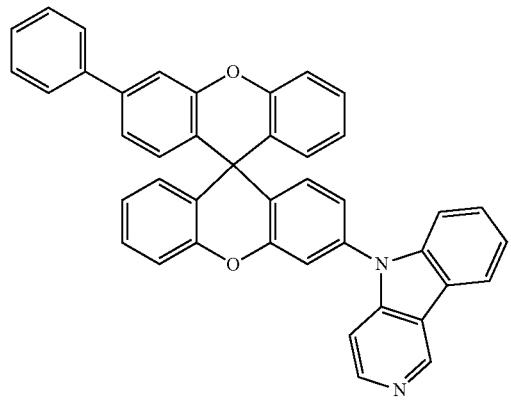
450
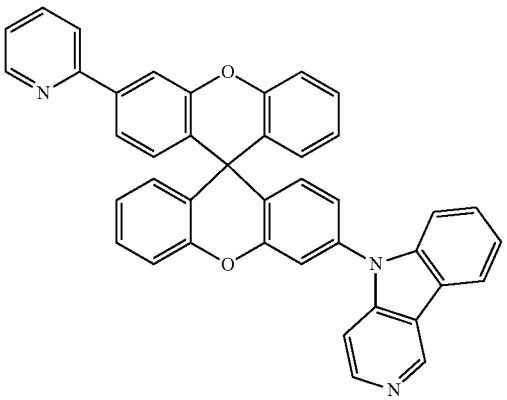
451
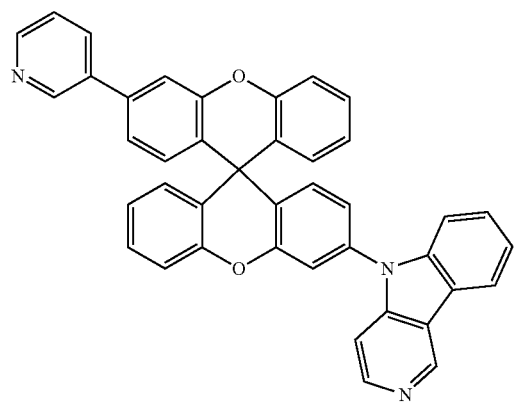
452
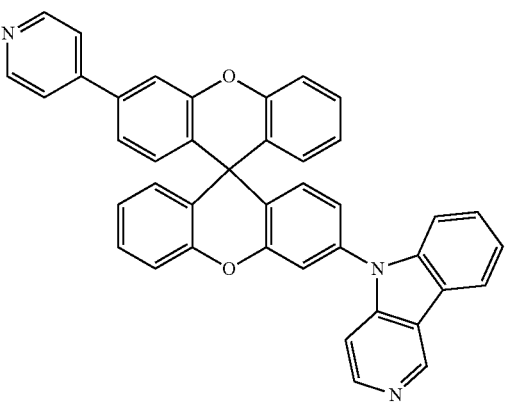
453
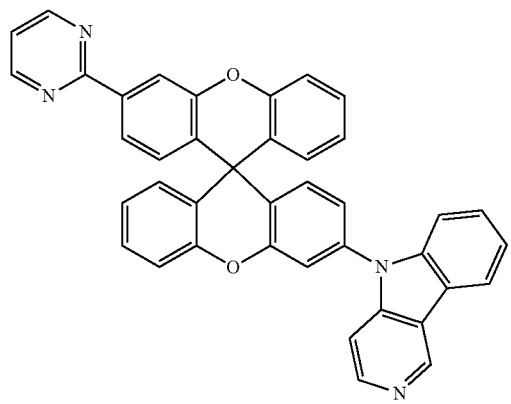
454
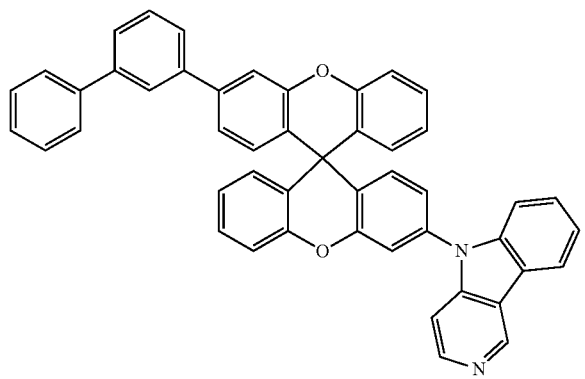
455
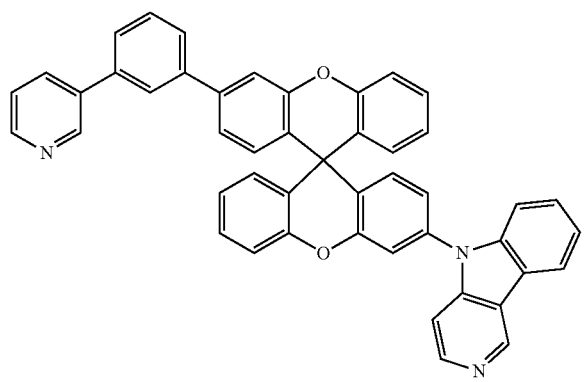
456
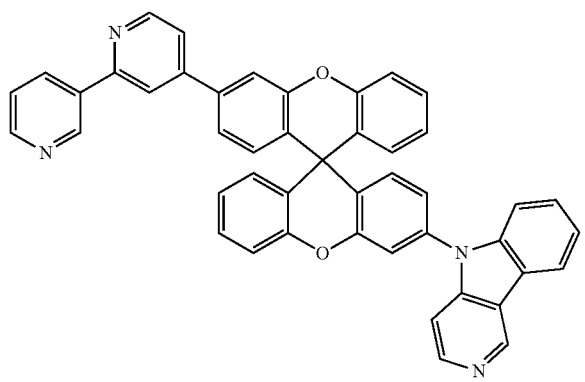

-continued
457
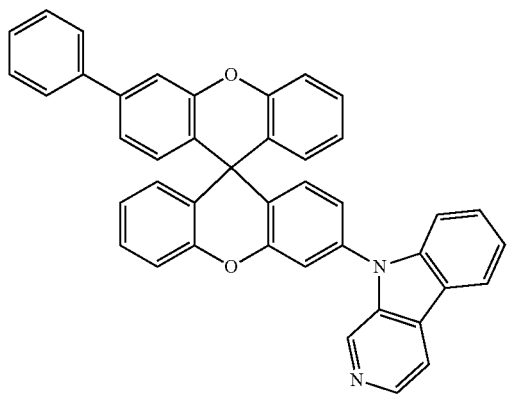
458
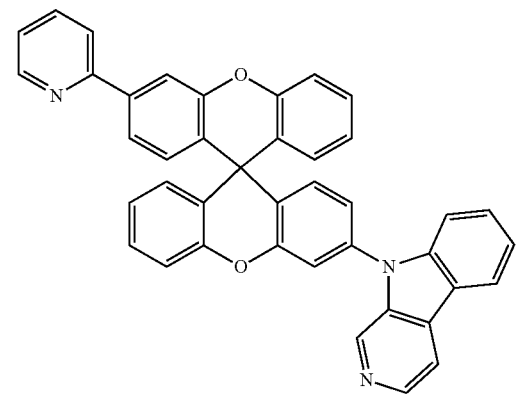
459
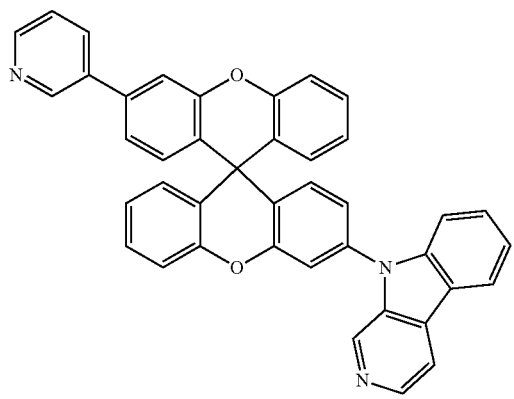
460
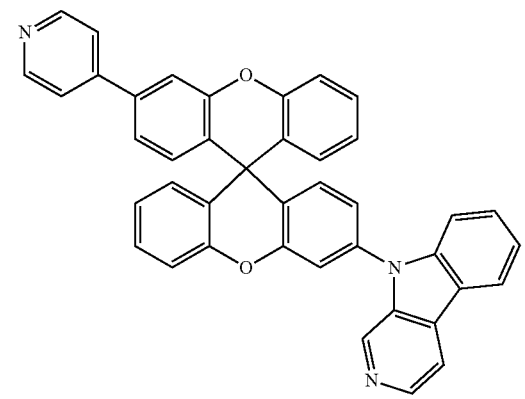
461
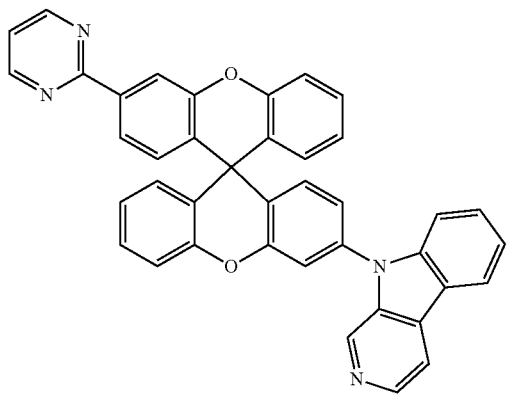
462
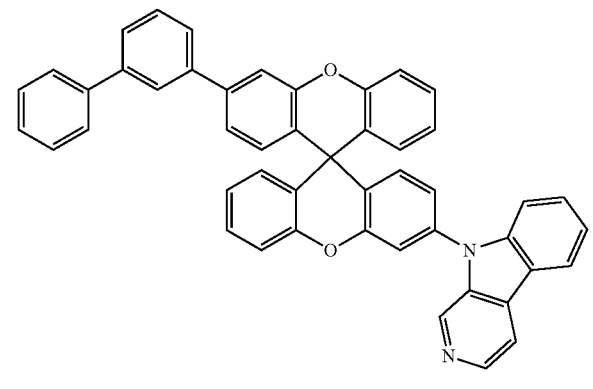
463
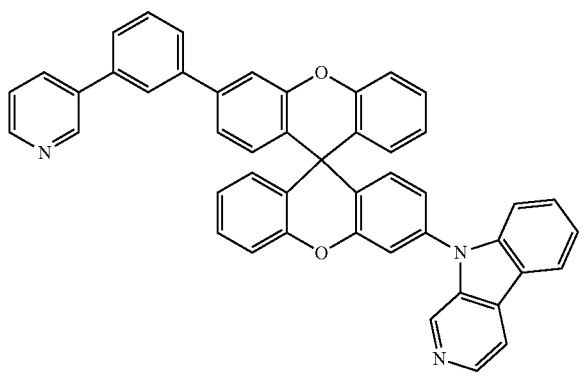
464
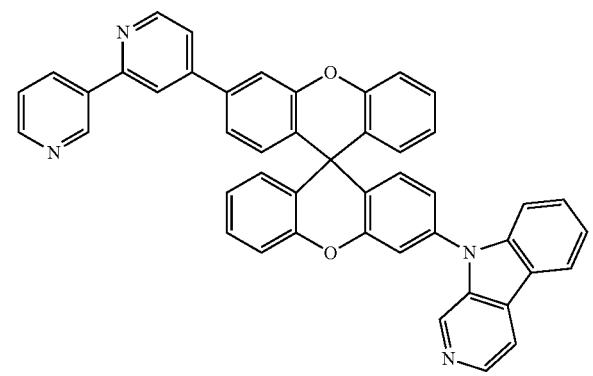

465 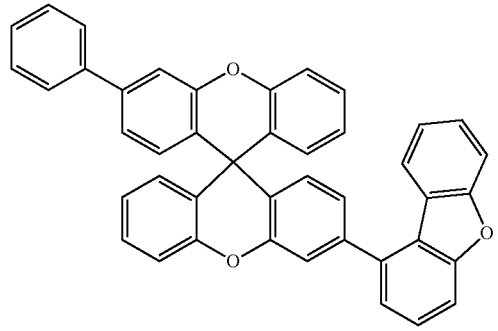
466 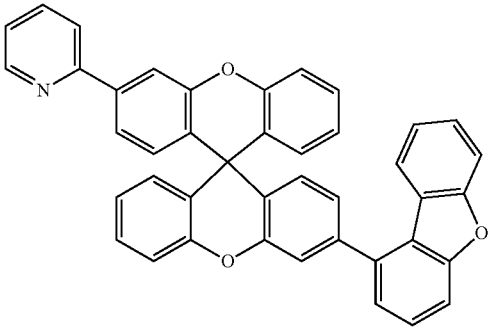
467 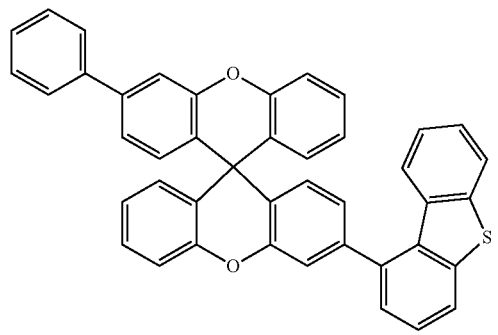
468 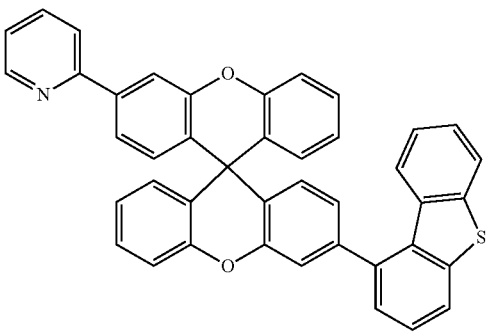
469 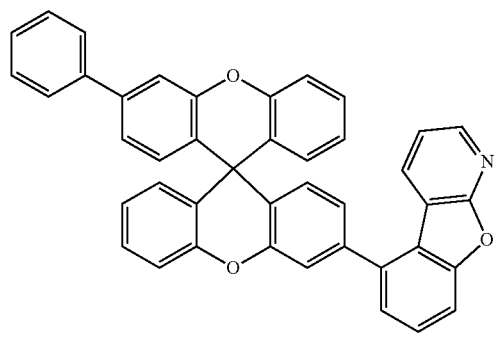
470 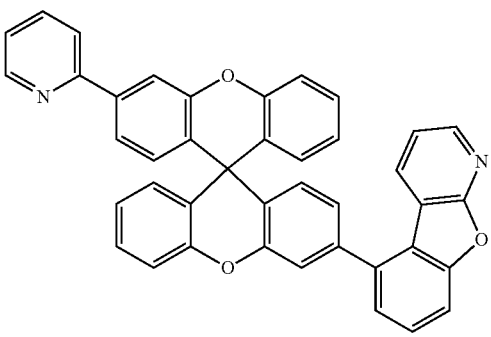
471 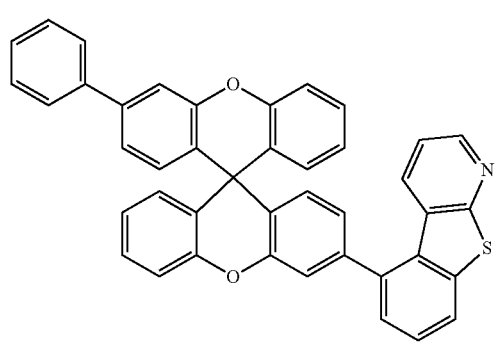
472 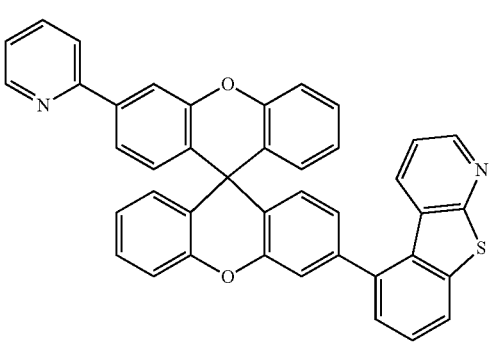

-continued
473
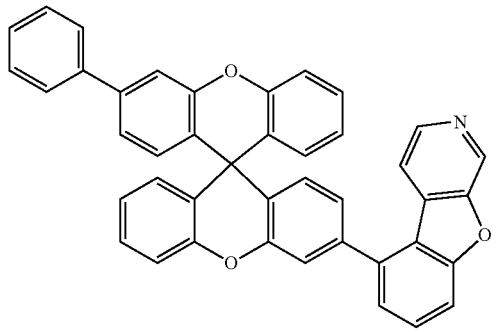
474
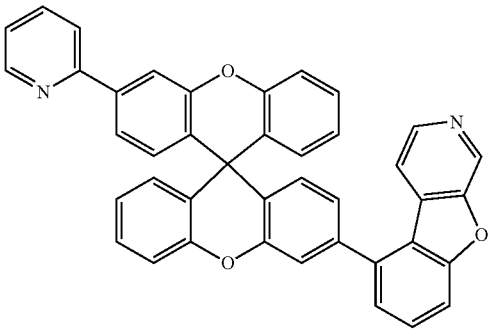
475
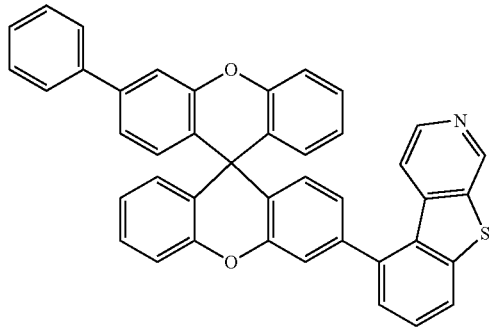
476
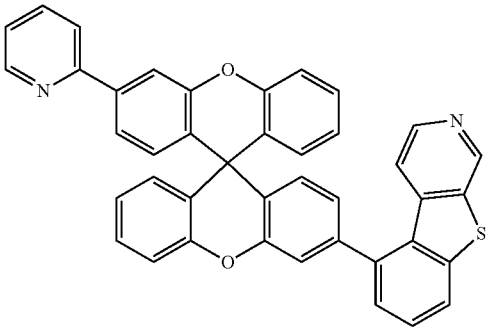
477
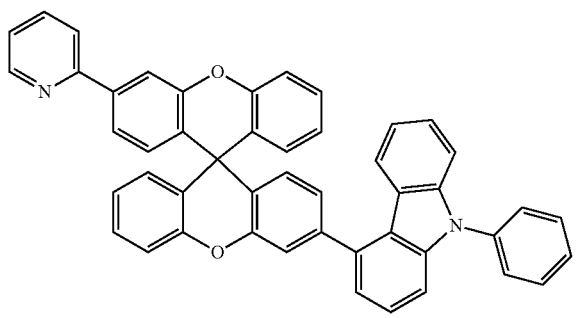
478
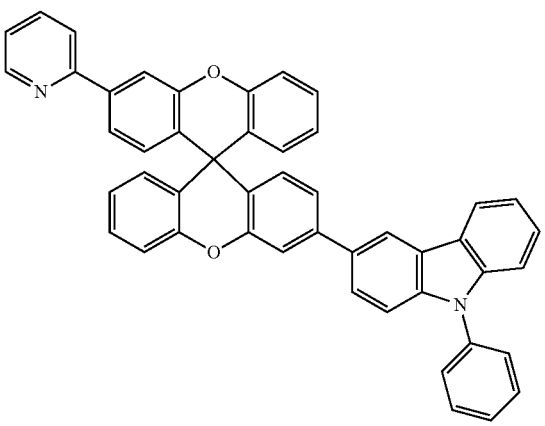
479
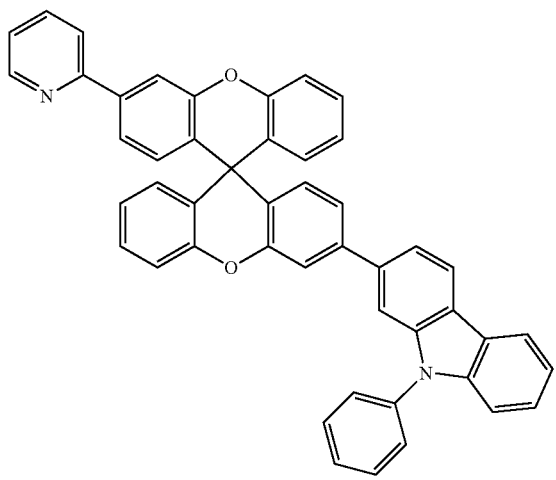
480
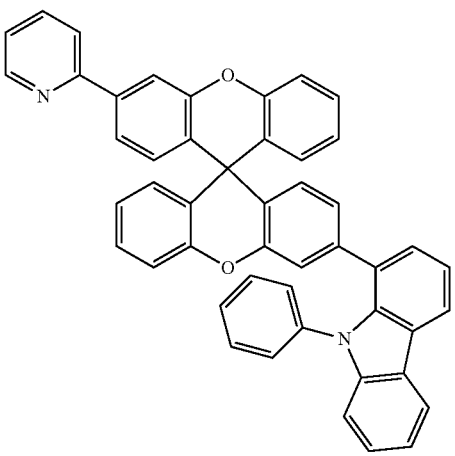

481
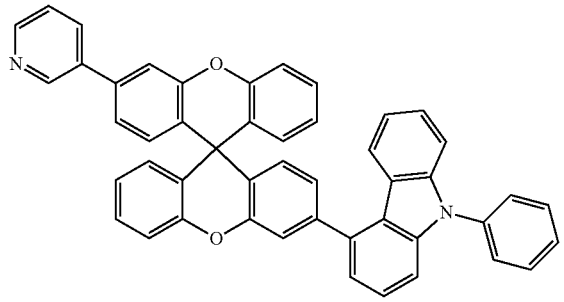
482
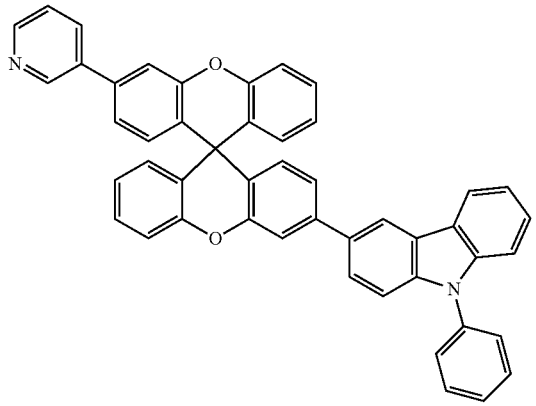
483
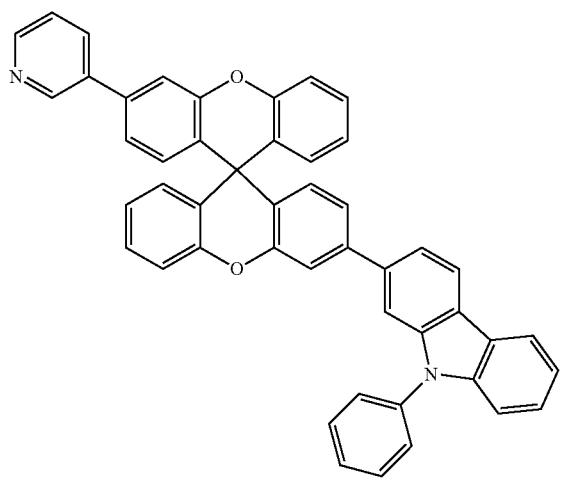
484
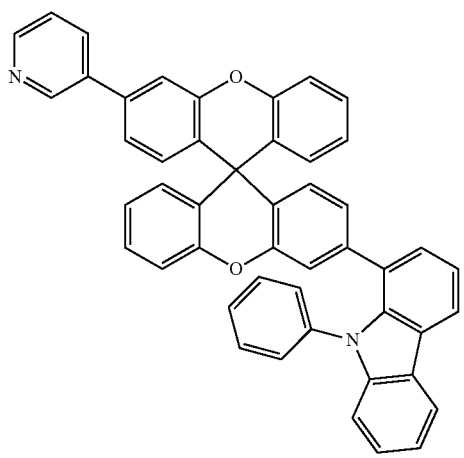
485
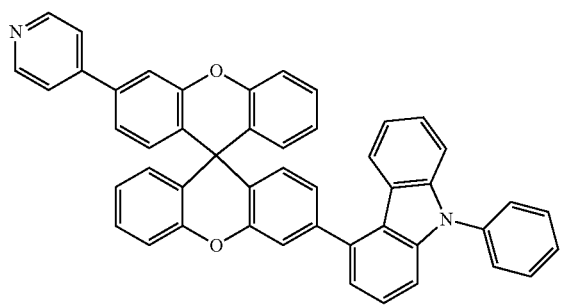
486
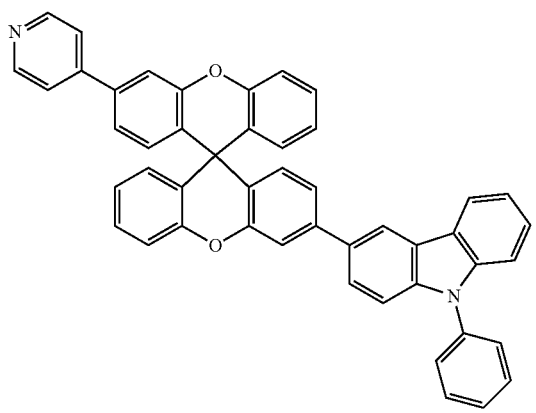

-continued
487
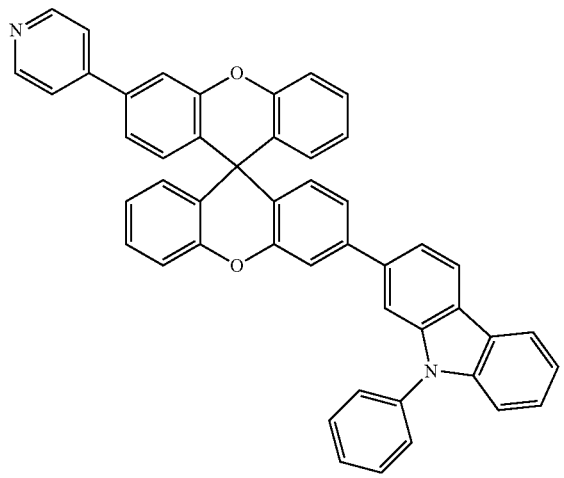
488
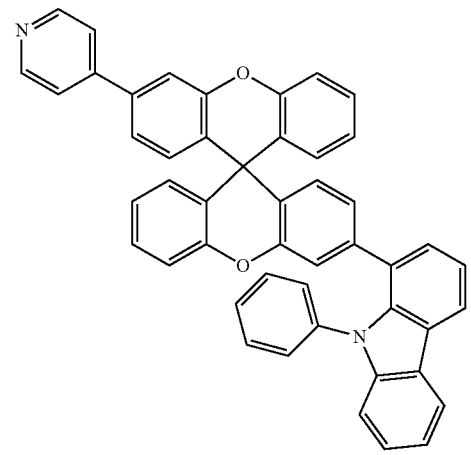
489
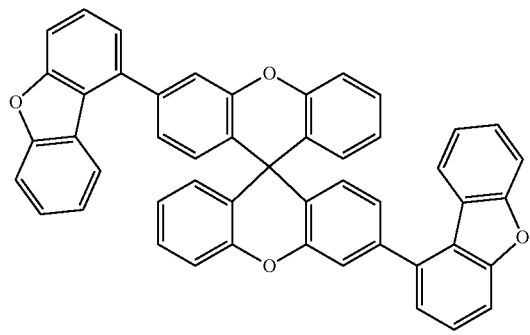
490
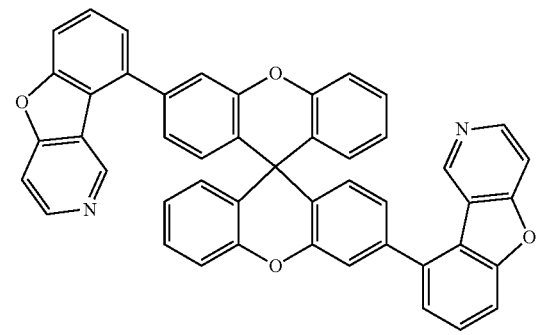
491
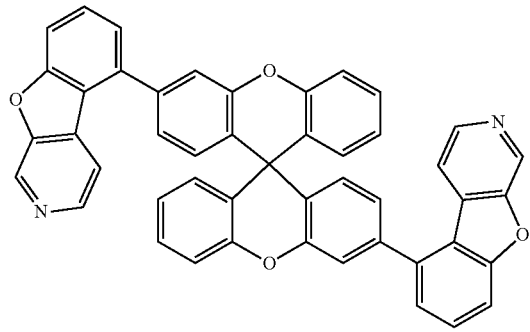
492
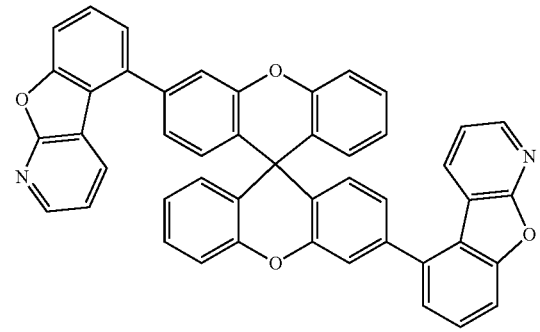
493
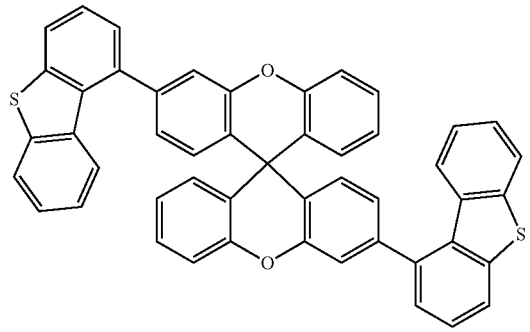
494
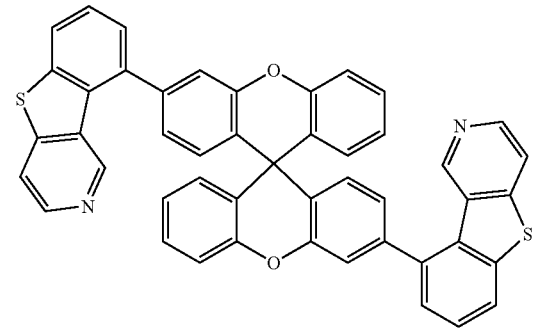

-continued
495
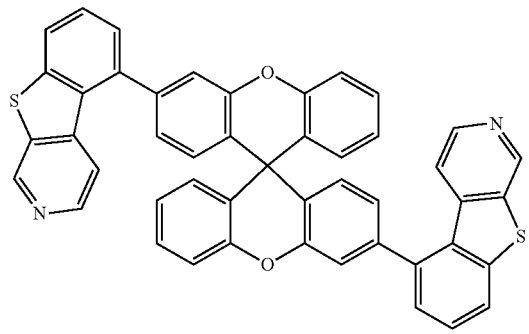
496
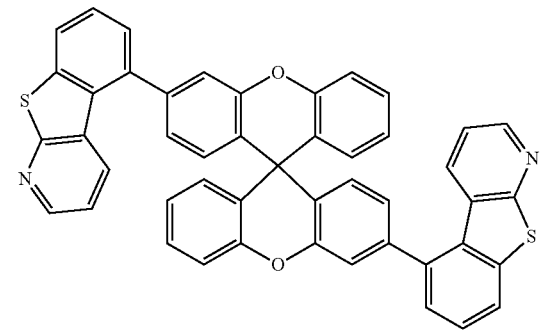
497
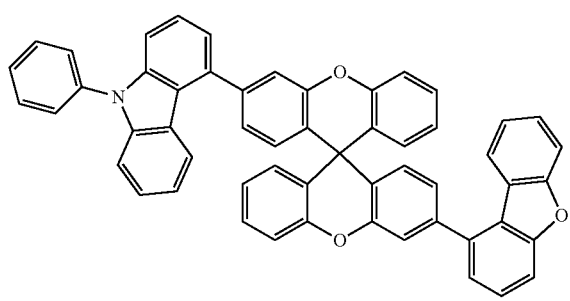
498
499
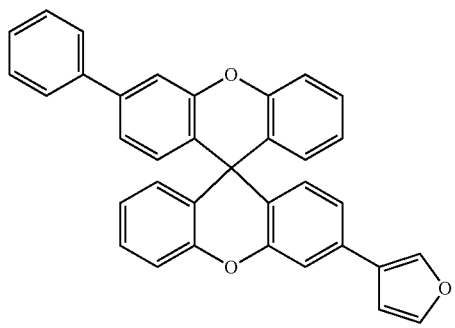
500
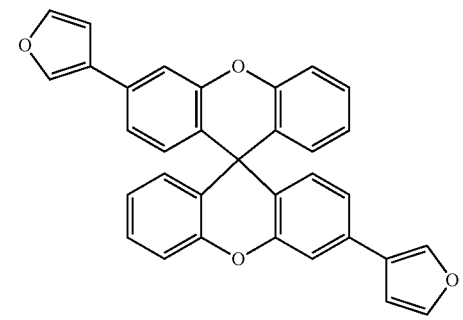
501
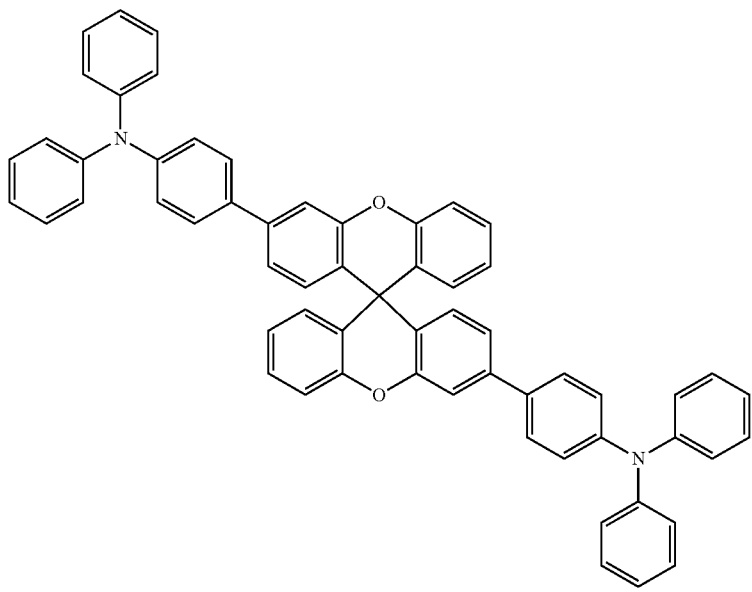

-continued
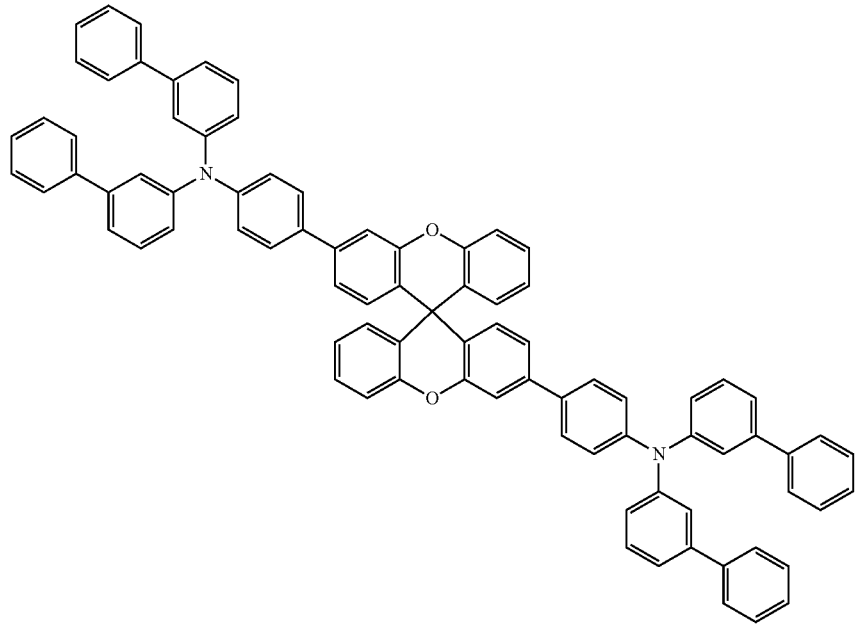
502
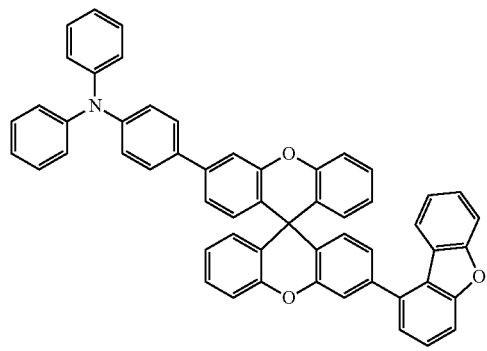
503
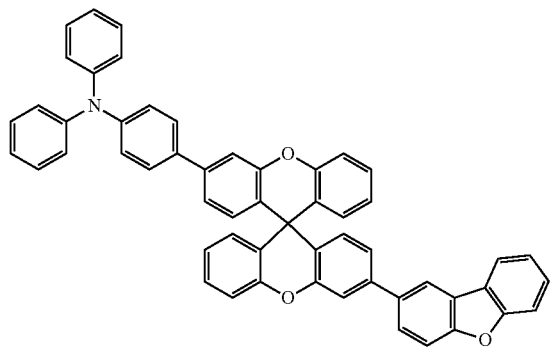
504
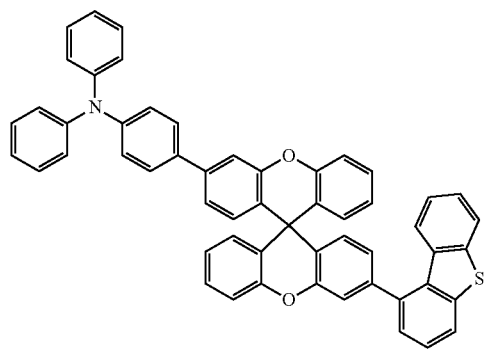
505
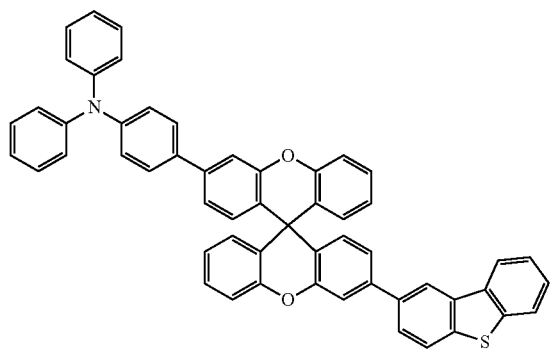
506
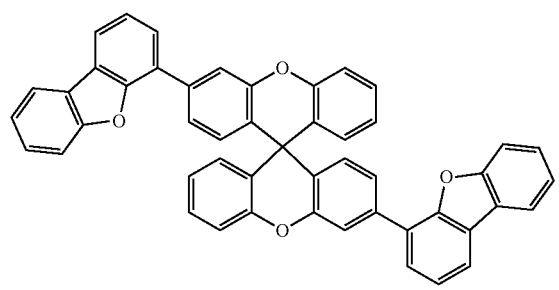
507
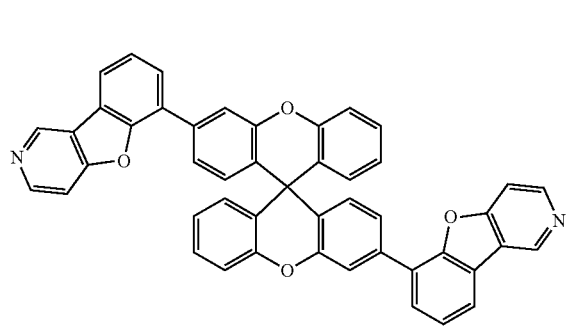
508

-continued
509
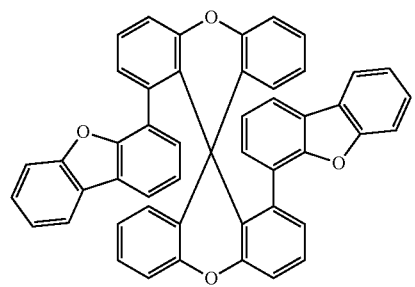
510
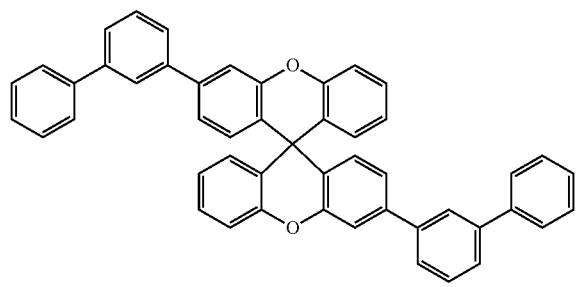
511
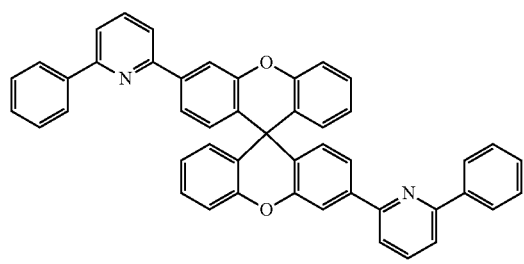
512
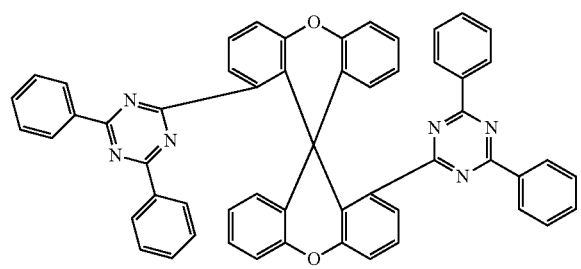
513
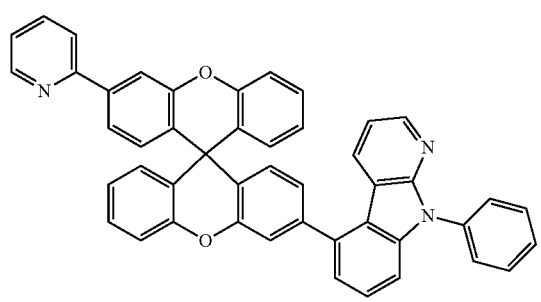
514
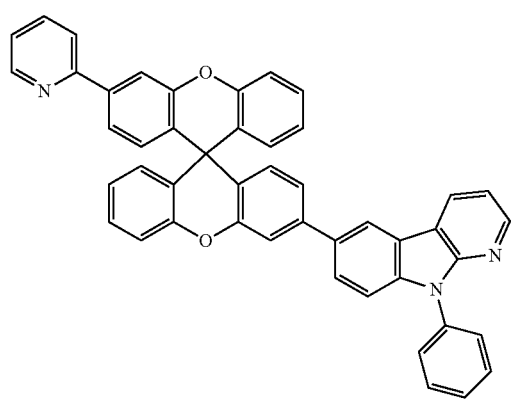
515
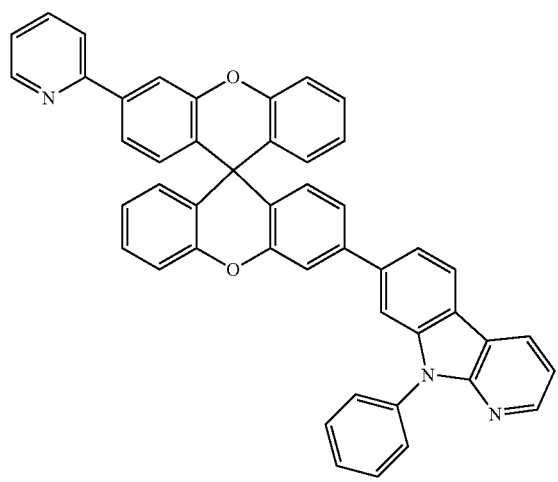
516
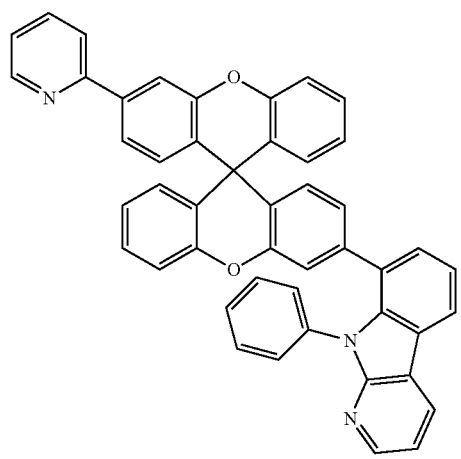

-continued
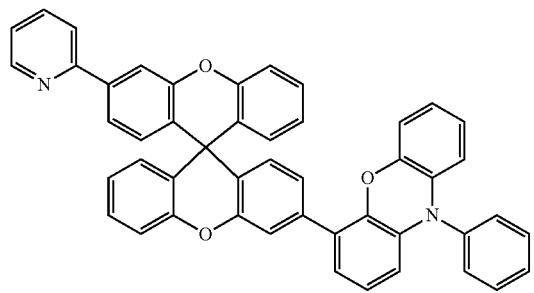
517
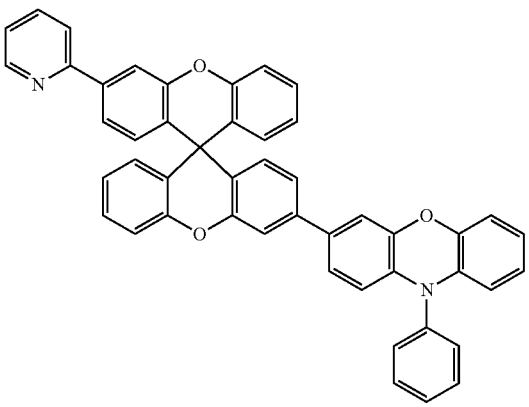
518
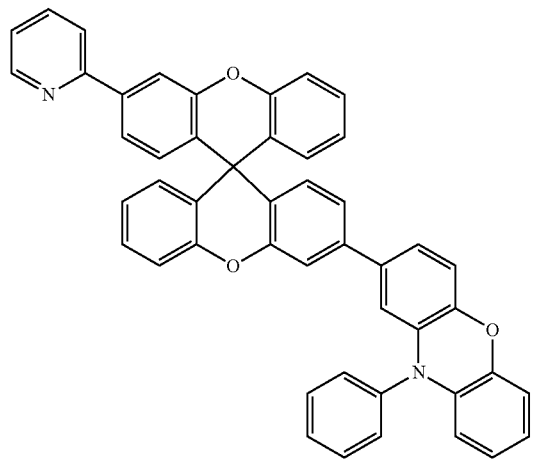
519
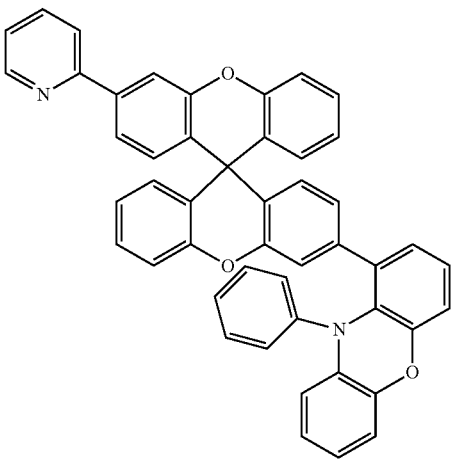
520
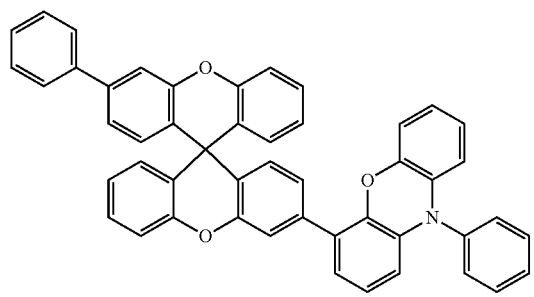
521
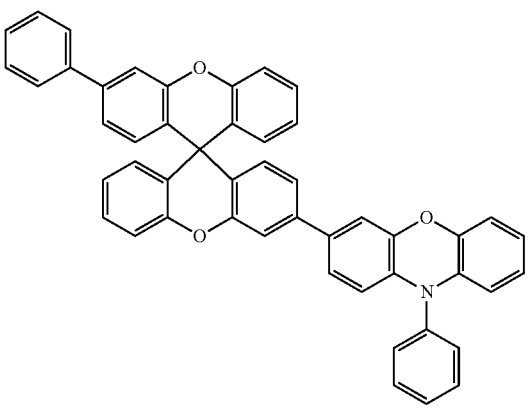
522

-continued
523
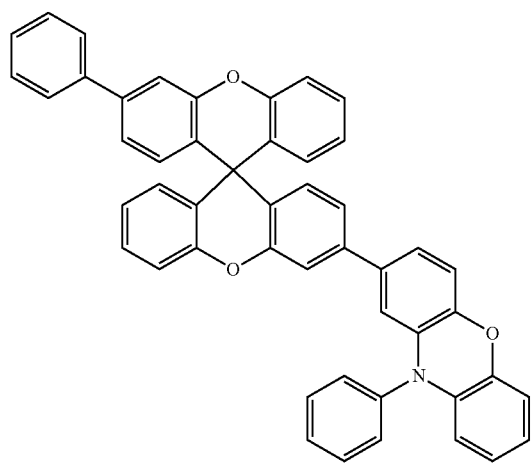
524
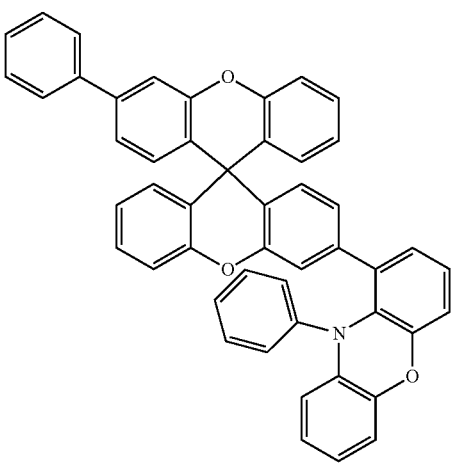
525
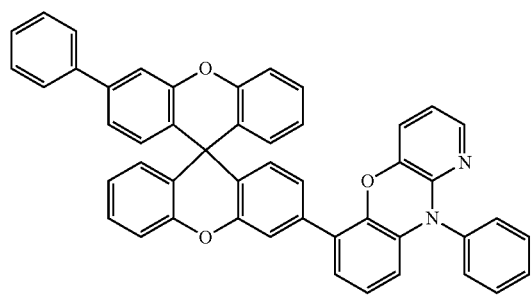
526
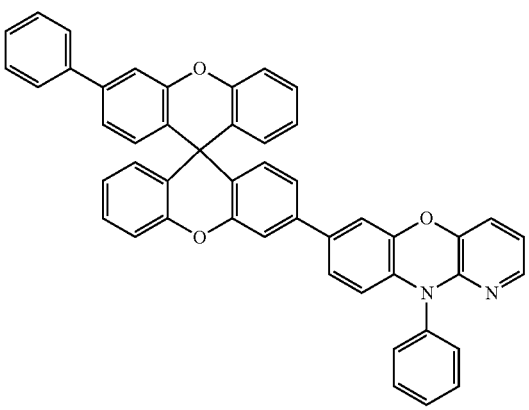
527
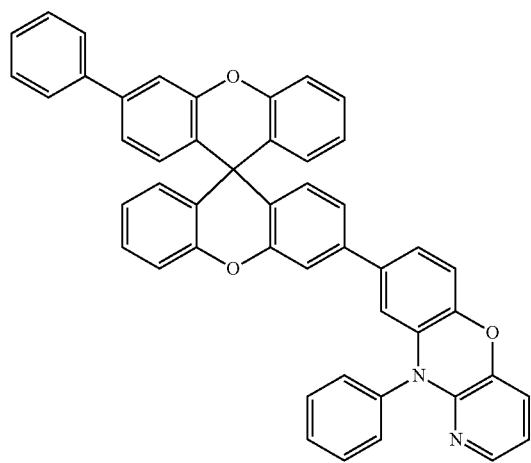
528
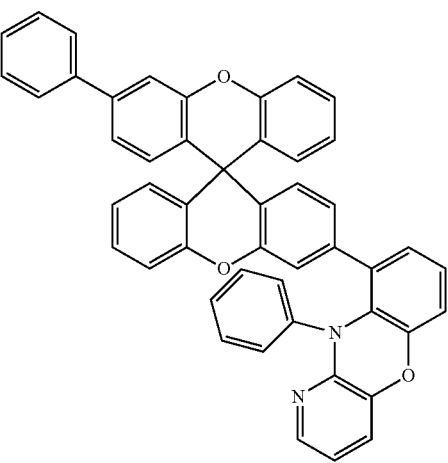

-continued

529

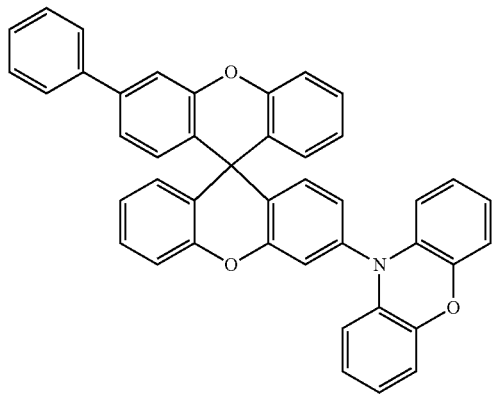

530

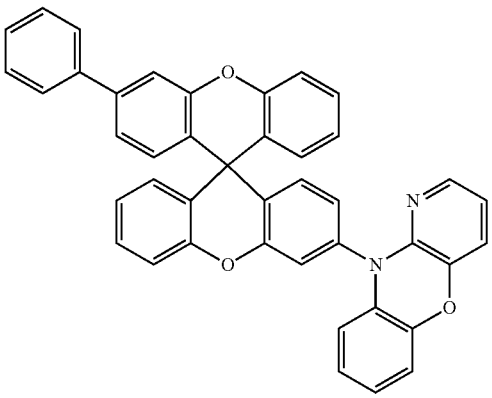

531

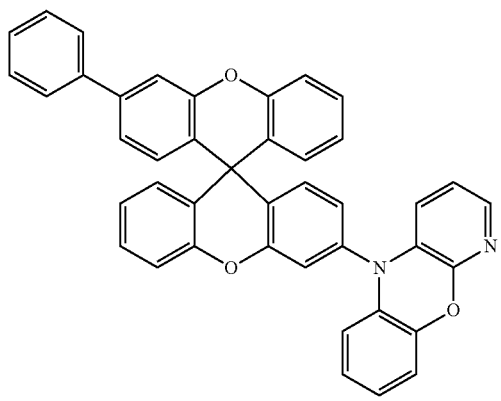

532

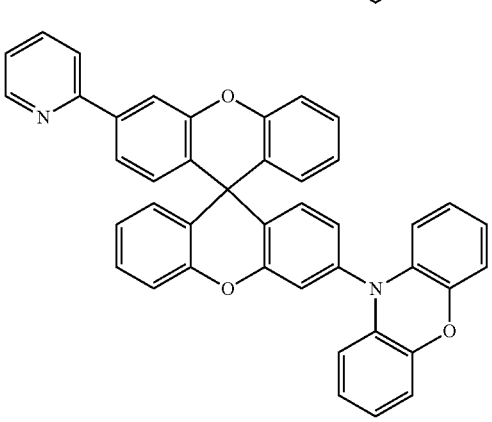

A core of the compound represented by Formula 1 has two groups "$X_1$", These groups $X_1$ are either O or S at the same time. Accordingly, the core of the compound represented by Formula 1 has a symmetrical shape with respect to an X-axis (see Formula 1'), and thus, the core creates the same environment effect to a substituent introduced to a molecule. Therefore, since property change may be easily controlled through the substituent introduction and interaction between molecules may be effectively generated, the condensed cyclic compound may have excellent thermal stability and charge mobility.

Formula 1'

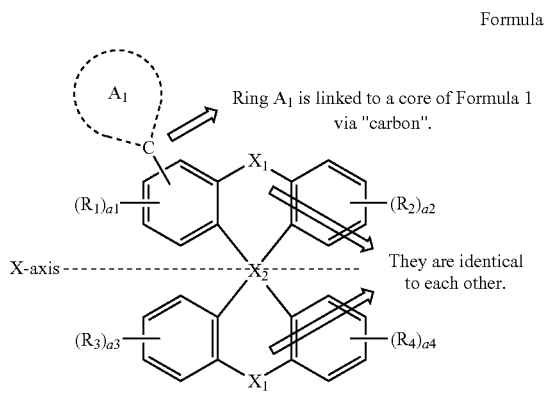

Ring $A_1$ is linked to a core of Formula 1 via "carbon".

They are identical to each other.

Also, the condensed cyclic compound represented by Formula 1 essentially includes ring $A_1$, which is described above in the present specification. However, as it may be confirmed from Formula 1, ring $A_1$ is linked to a core of the compound represented by Formula 1 via "carbon". In this regard, since ring $A_1$ is linked to the core of the compound represented by Formula 1 via "a carbon-carbon bond", decomposition (detachment) of ring $A_1$ from the molecule of Formula 1 may be prevented when the condensed cyclic compound is purified and/or deposited, and thus, the condensed cyclic compound may have excellent thermal stability. Therefore, in some embodiments, the condensed cyclic compound may have a decomposition temperature that is higher than a sublimation temperature of the compound in vacuum of about $10^{-8}$ torr to about $10^{-3}$ torr. As a result, even when the number of substituent groups introduced to the molecule of the condensed cyclic compound is reduced or a substituent group of a simple structure is introduced to the molecule, the condensed cyclic compound represented by Formula 1 may have an excellent process property. Therefore, when an organic light-emitting device includes the condensed cyclic compound represented by Formula 1, device stability improves when driving the organic light-emitting device, and thus the organic light-emitting device may have long lifespan.

A method of synthesizing the condensed cyclic compound represented by Formula 1 may be understood by one of ordinary skill in the art by referring to Synthesis Examples used herein.

The condensed cyclic compound represented by Formula 1 may be appropriate to serve as a material for an organic layer, for example, a host of an emission layer of an organic light-emitting device. According to another aspect of an exemplary embodiment, an organic light-emitting device includes a first electrode; a second electrode; and an organic layer including at least one of the condensed cyclic compounds represented by Formula 1, wherein the organic layer is disposed between the first electrode and the second electrode and includes an emission layer.

When the organic light-emitting device includes an organic layer including the condensed cyclic compound represented by Formula 1, the organic light-emitting device may have a low driving voltage, high efficiency, high brightness, and long lifespan.

The condensed cyclic compound represented by Formula 1 may be included between a pair of electrodes of the organic light-emitting device. For example, the condensed cyclic compound may be included in at least one of the emission layer, a hole transport region (for example, including at least one of a hole injection layer, a hole transport layer, and an electron blocking layer) between the first electrode and the emission layer, and an electron transport region (for example, including at least one of a hole blocking layer, an electron transport layer, and an electron injection layer) between the emission layer and the second electrode. In some embodiments, the condensed cyclic compound represented by Formula 1 may be included in the emission layer. Here, the emission layer may further include a dopant, and the condensed cyclic compound in the emission layer may serve as a host. The emission layer may be a green emission layer or a blue emission layer emitting green light or blue light, and the dopant may be a phosphorescent dopant.

As used herein, the expression "the (organic layer) includes at least one condensed cyclic compounds" may be construed as "the (organic layer) may include one condensed cyclic compound represented by Formula 1 or two or more different condensed cyclic compounds represented by Formula 1".

In an embodiment, the organic layer may include only Compound 1 as the condensed cyclic compound. In this regard, Compound 1 may be included in the emission layer of the organic light-emitting device. In another embodiment, the organic layer may include Compound 1 and Compound 2 as the condensed cyclic compound. In this regard, Compound 1 and Compound 2 may be included in the same layer (for example, Compound 1 and Compound 2 may all be included in the emission layer), or different layers.

The first electrode may be an anode, which is a hole injection electrode, and the second electrode may be a cathode, which is an electron injection electrode. Alternatively, the first electrode may be a cathode, which is an electron injection electrode, and the second electrode may be an anode, which is a hole injection electrode.

For example, the first electrode may be an anode, the second electrode may be a cathode, and the organic layer may include:

i) a hole transport region that is disposed between the first electrode and the emission layer, wherein the hole transport region includes at least one selected from a hole injection layer, a hole transport layer, and an electron blocking layer; and ii) an electron transport region that is disposed between the emission layer and the second electrode, wherein the electron transport region includes at least one selected from a hole blocking layer, an electron transport layer, and an electron injection layer.

As used herein, the term the "organic layer" refers to a single layer and/or a plurality of layers disposed between the first electrode and the second electrode in an organic light-emitting device. The "organic layer" may include an organometallic complex including a metal in addition to an organic compound.

The FIGURE is a schematic view of an organic light-emitting device 10 according to an exemplary embodiment. Hereinafter, a structure of the organic light-emitting device 10 and a method of manufacturing the organic light-emitting device 10 will be described with reference to FIG. 1. The organic light-emitting device 10 includes a first electrode 11, an organic layer 15, and a second electrode 19, which are sequentially stacked in the stated order.

A substrate may be additionally disposed under the first electrode 11 or on the second electrode 19. The substrate may be a conventional substrate that is used in an organic light-emitting device, such as a glass substrate or a transparent plastic substrate, each having excellent mechanical strength, thermal stability, transparency, surface smoothness, ease of handling, and water repellency.

The first electrode 11 may be formed by depositing or sputtering a material for forming the first electrode 11 on the substrate. The first electrode 11 may be an anode. The material for the first electrode 11 may be selected from materials with a high work function for an easy hole injection. The first electrode 11 may be a reflective electrode, a semi-transmissive electrode, or a transmissive electrode. The material for the first electrode 11 may be an indium tin oxide (ITO), indium zinc oxide (IZO), tin oxide ($SnO_2$), or zinc oxide (ZnO). In some embodiments, the material for the first electrode 11 may be a metal such as magnesium (Mg), aluminum (Al), aluminum-lithium (Al—Li), calcium (Ca), magnesium-indium (Mg—In), or magnesium-silver (Mg—Ag).

The first electrode 11 may have a single-layer structure or a multi-layer structure including two or more layers. For example, the first electrode 11 may have a triple-layer structure of ITO/Ag/ITO, but it is not limited thereto.

The organic layer 15 is disposed on the first electrode 11.

The organic layer 15 may include a hole transport region, an emission layer, and an electron transport region.

The hole transport region may be disposed between the first electrode 11 and the emission layer.

The hole transport region may include at least one selected from a hole injection layer, a hole transport layer, an electron blocking layer, and a buffer layer.

The hole transport region may include only either a hole injection layer or a hole transport layer. In some embodiments, the hole transport region may include a structure in which a hole injection layer/a hole transport layer or a hole injection layer/a hole transport layer/an electron blocking layer are sequentially stacked on the first electrode 11.

When the hole transport region includes a hole injection layer, the hole injection layer (HIL) may be formed on the first electrode 11 by using one of various methods such as vacuum deposition, spin coating, casting, or Langmuir-Blodgett (LB) method.

When a hole injection layer is formed by vacuum deposition, the vacuum deposition may be performed at a deposition temperature in a range of about 100° C. to about 500° C., at a vacuum degree in a range of about $10^{-8}$ torr to about $10^{-3}$ torr, and at a deposition rate in a range of about 0.01 Angstroms per second (A/sec) to about 100 Å/sec. However, these conditions may vary depending on a compound that is used as a hole injection material and a structure and thermal properties of a desired hole injection layer, but the conditions are not limited thereto.

When a hole injection layer is formed by spin coating, the spin coating may be performed at a coating rate in a range of about 2,000 revolutions per minute (rpm) to about 5,000 rpm, and at a temperature in a range of about 80° C. to about 200° C. to remove the solvent after the spin coating. However, these conditions may vary depending on a compound that is used as a hole injection material and a structure and thermal properties of a desired hole injection layer, but the conditions are not limited thereto.

The conditions for forming a hole transport layer and an electron blocking layer may be inferred based on the conditions for forming the hole injection layer.

The hole transport region may include, for example, at least one selected from m-MTDATA, TDATA, 2-TNATA, NPB, β-NPB, TPD, Spiro-TPD, Spiro-NPB, methylated NPB, TAPC, HMTPD, 4,4',4"-tris(N-carbazolyl)triphenylamine) (TCTA), polyaniline/dodecyl benzenesulfonic acid (Pani/DBSA), poly(3,4-ethylenedioxythiophene)/poly (4-styrenesulfonate) (PEDOT/PSS), polyaniline/camphor sulfonic acid (Pani/CSA), (polyaniline)/poly(4-styrenesulfonate) (PANI/PSS), a compound represented by Formula 201, and a compound represented by Formula 202:

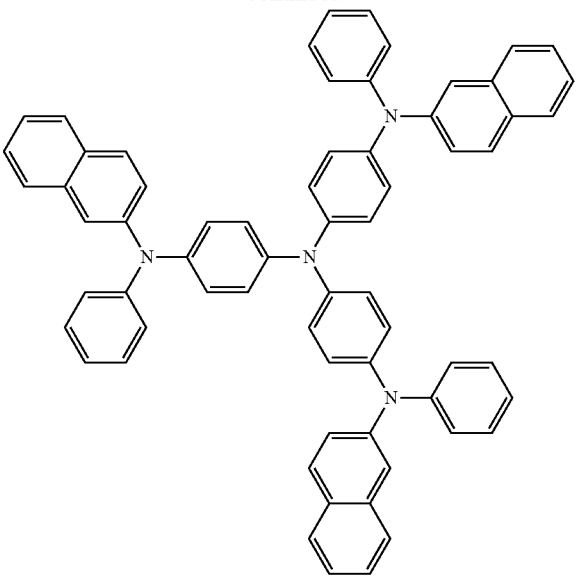

2-TNATA

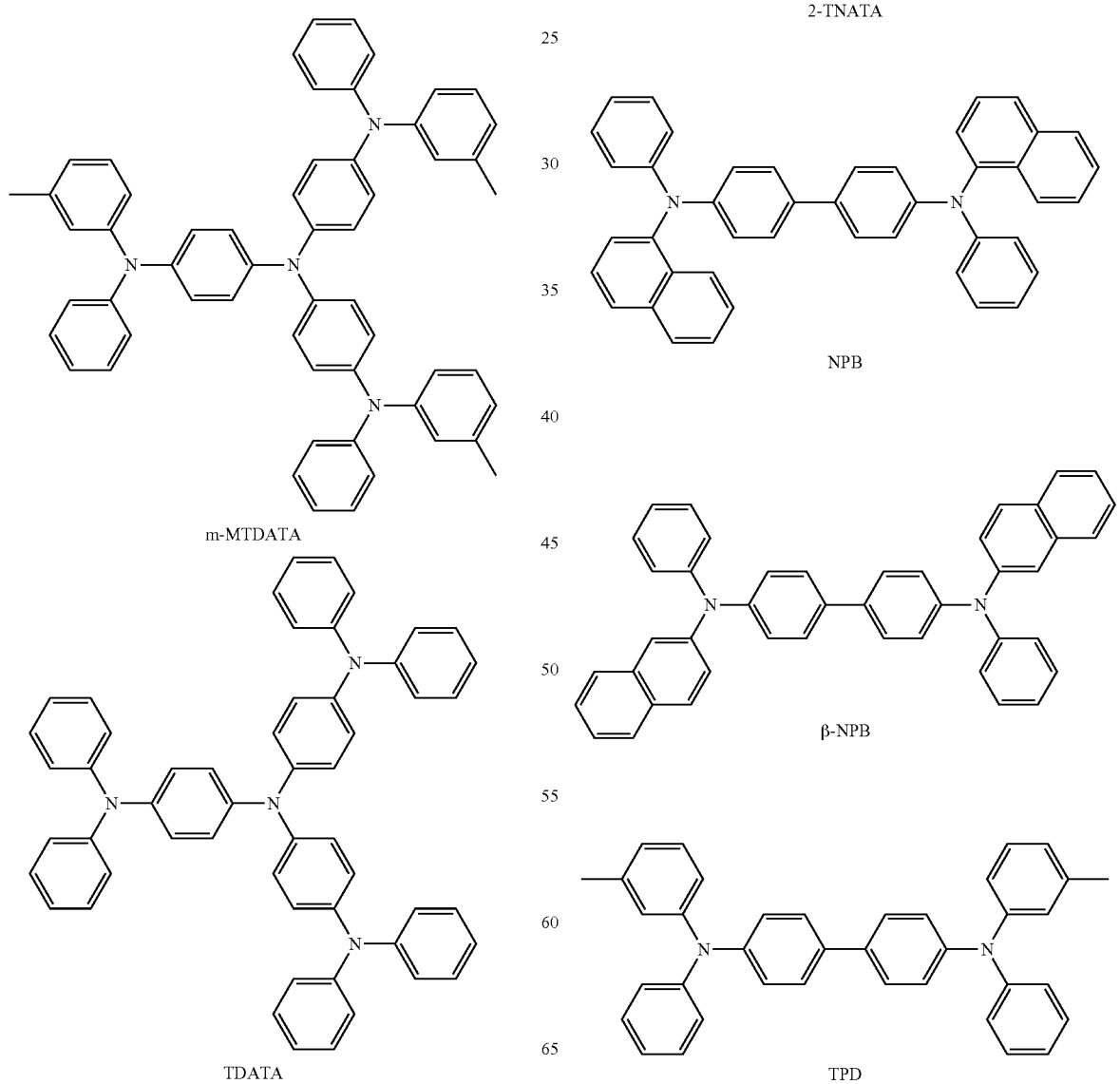

m-MTDATA

NPB

β-NPB

TDATA

TPD

-continued

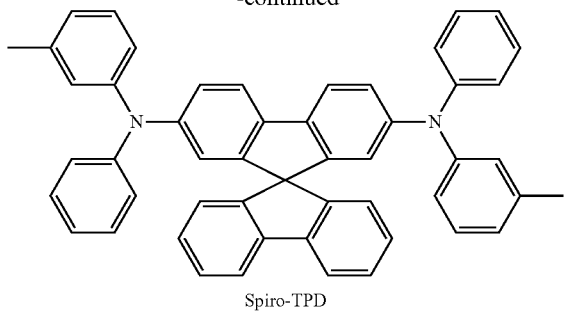
Spiro-TPD

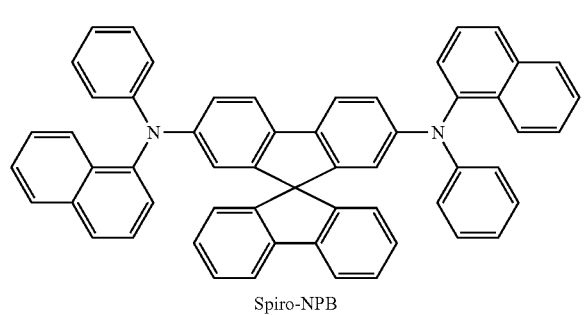
Spiro-NPB

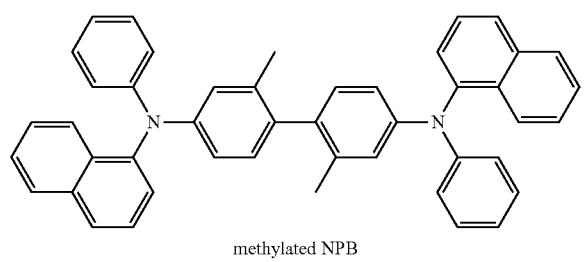
methylated NPB

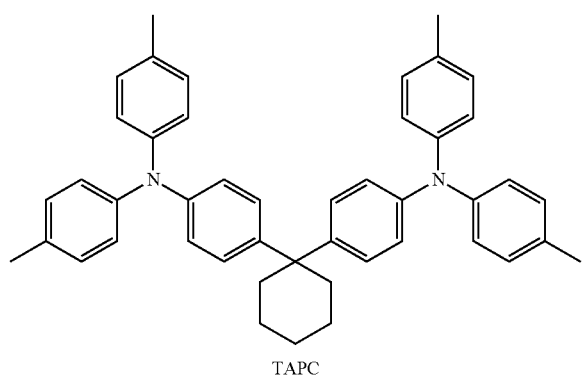
TAPC

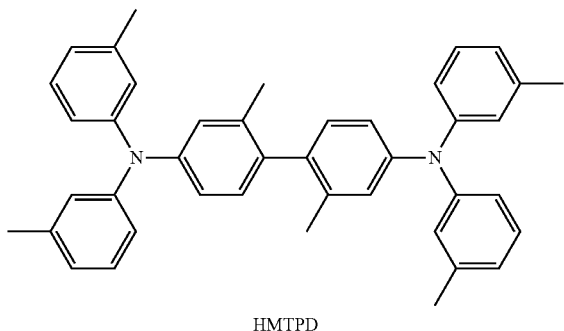
HMTPD

-continued

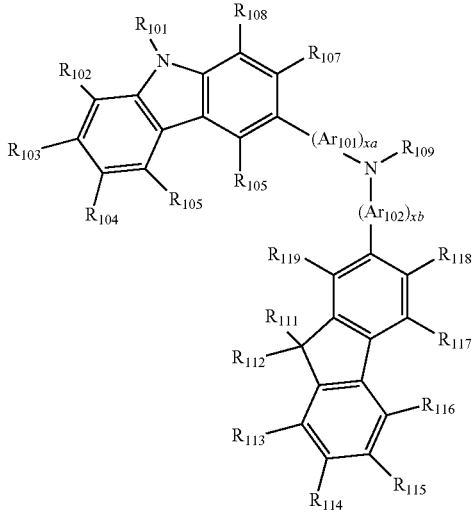

Formula 201 / Formula 202

In Formula 201, $Ar_{101}$ and $Ar_{102}$ may be each independently selected from a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group; and a phenylene group, a pentalenylene group, an indenylene group, a naphthylene group, an azulenylene group, a heptalenylene group, an acenaphthylene group, a fluorenylene group, a phenalenylene group, a phenanthrenylene group, an anthracenylene group, a fluoranthenylene group, a triphenylenylene group, a pyrenylene group, a chrysenylenylene group, a naphthacenylene group, a picenylene group, a perylenylene group, and a pentacenylene group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ cycloalkenyl group, a $C_1$-$C_{10}$ heterocycloalkyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

In Formula 201, xa and xb may be, each independently, an integer of 0 to 5, for example, 0, 1, or 2. For example, xa may be 1, and xb may be 0, but xa and xb are not limited thereto.

In Formulae 201 and 202, $R_{101}$ to $R_{108}$, $R_{111}$ to $R_{119}$, and $R_{121}$ to $R_{124}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group (e.g., a methyl group, an ethyl group, a propyl group, a butyl group, a pentyl group, or a hexyl group) and a $C_1$-$C_{10}$ alkoxy group (e.g., a methoxy group, an ethoxy group, a propoxy group, a butoxy group, or a pentoxy group);

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, an anthracenyl group, a fluorenyl group, and a pyrenyl group; and a phenyl group, a naphthyl group, an anthracenyl group, a fluorenyl group, and a pyrenyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, and a $C_1$-$C_{10}$ alkoxy group, but they are not limited thereto.

In Formula 201, $R_{109}$ may be selected from a phenyl group, a naphthyl group, an anthracenyl group, and a pyridinyl group; and a phenyl group, a naphthyl group, an anthracenyl group, and a pyridinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, and a $C_1$-$C_{20}$ alkoxy group.

In some embodiments, the compound represented by Formula 201 may be represented by Formula 201A, but it is not limited thereto:

Formula 201A

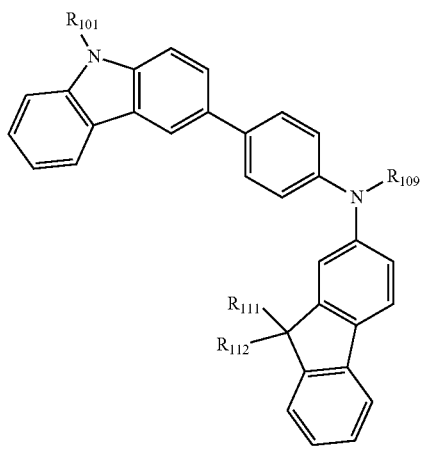

In Formula 201A, descriptions of $R_{101}$, $R_{111}$, $R_{112}$, and $R_{109}$ are the same as defined above in the present specification.

For example, the compound represented by Formula 201 and the compound represented by Formula 202 may include Compounds HT1 to HT20, but they are not limited thereto:

-continued
HT4
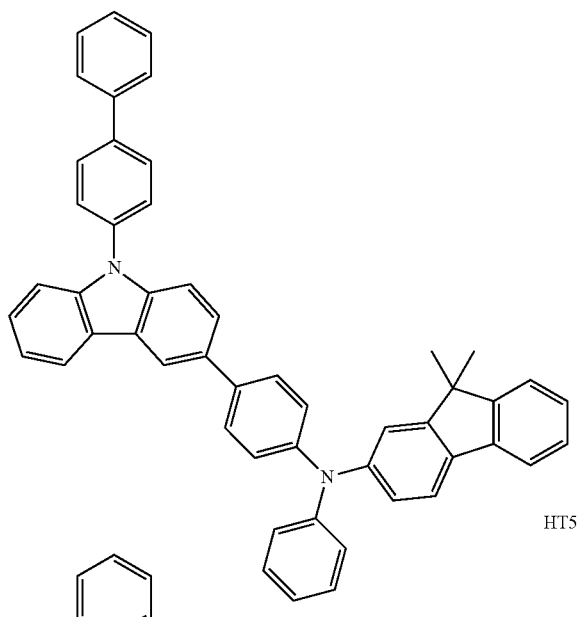
HT5
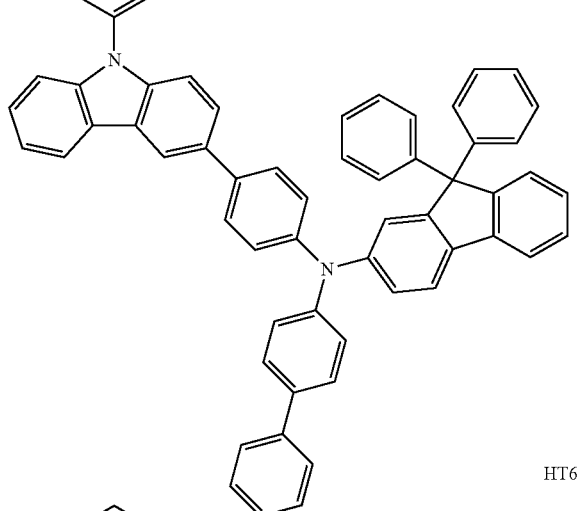
HT6
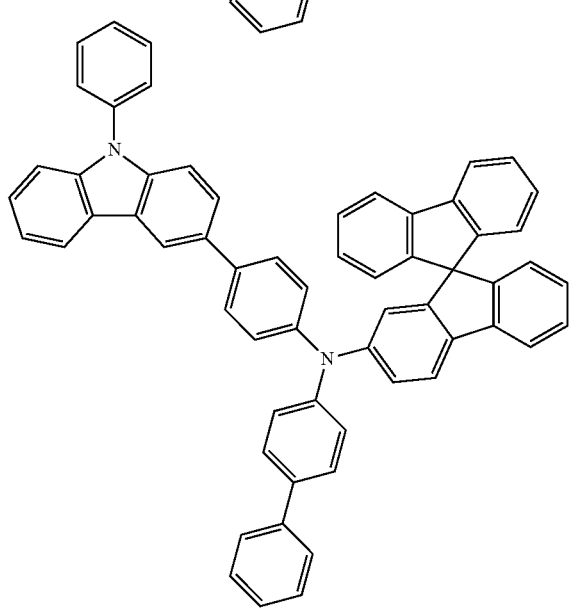
-continued
HT7
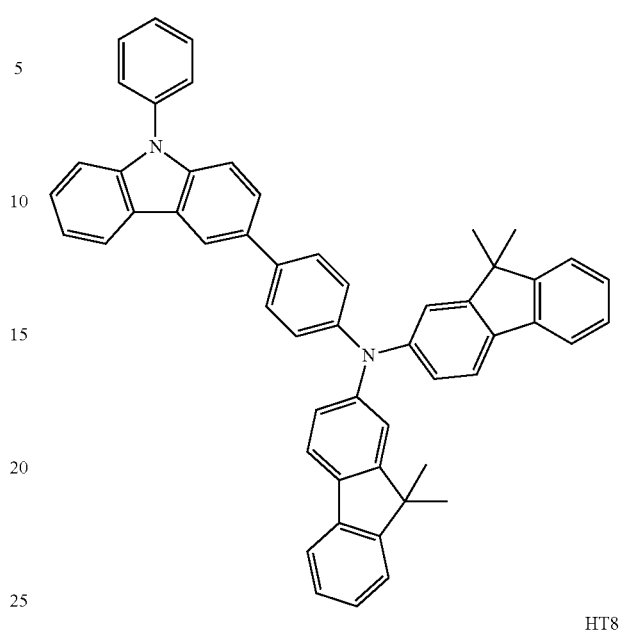
HT8
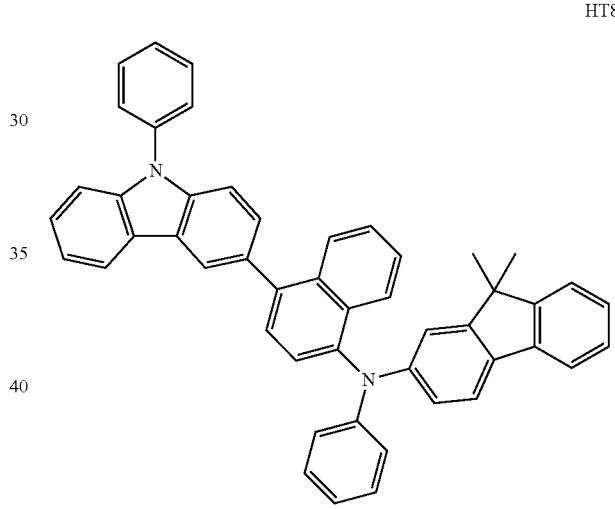
HT9
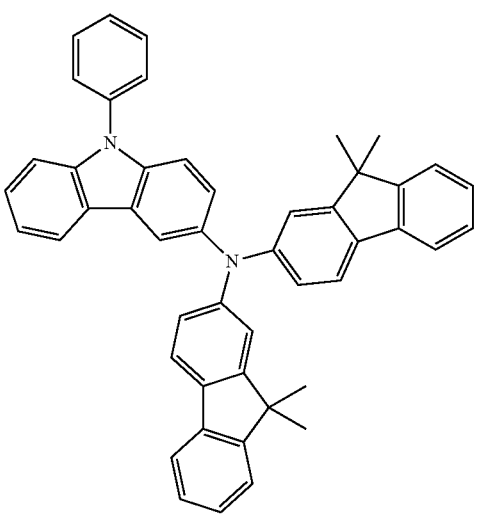

HT10
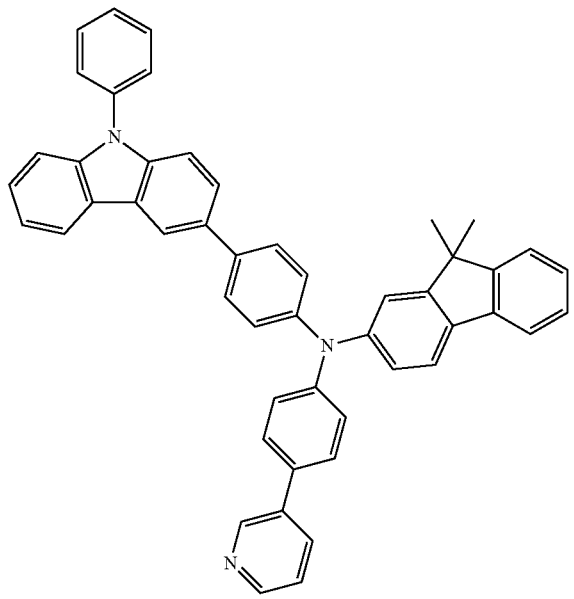
HT11
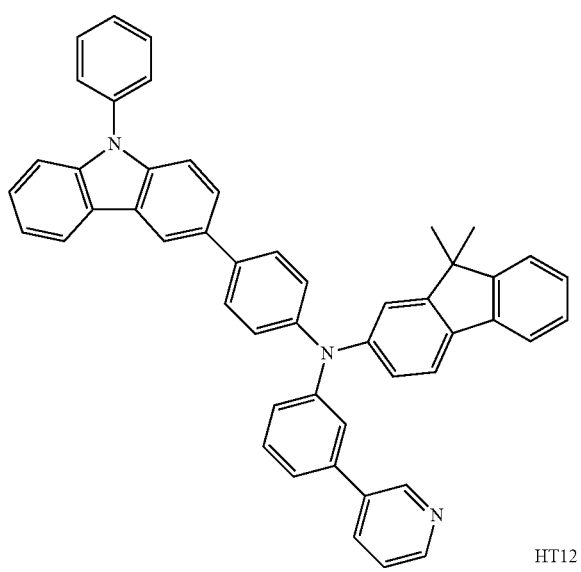
HT12
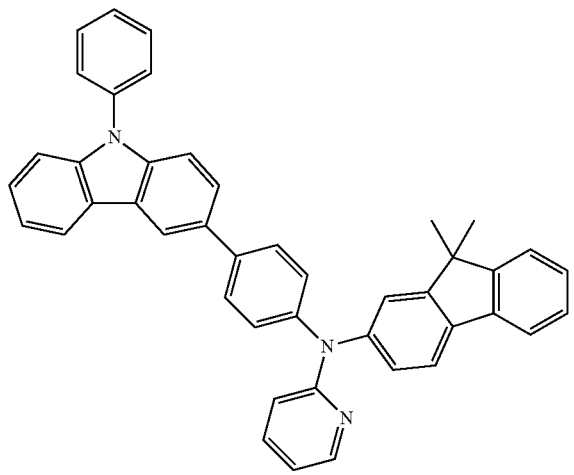
HT13
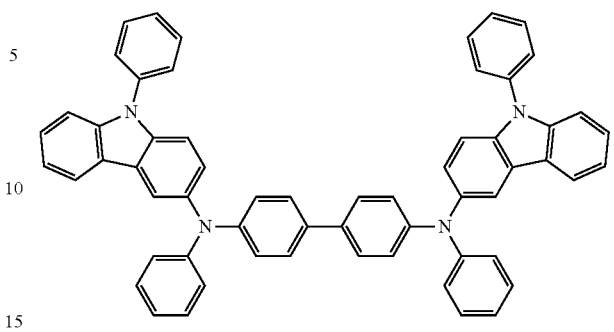
HT14
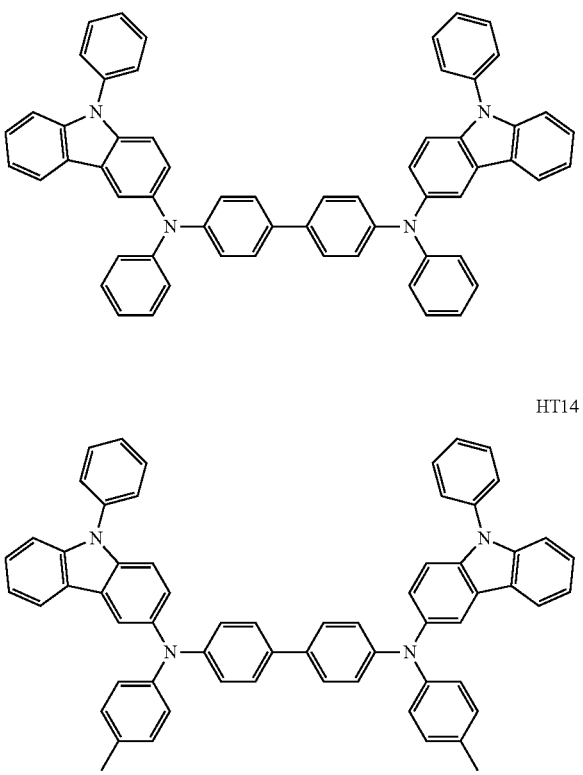
HT15
HT16
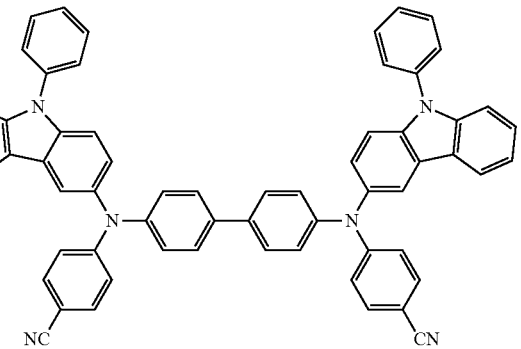

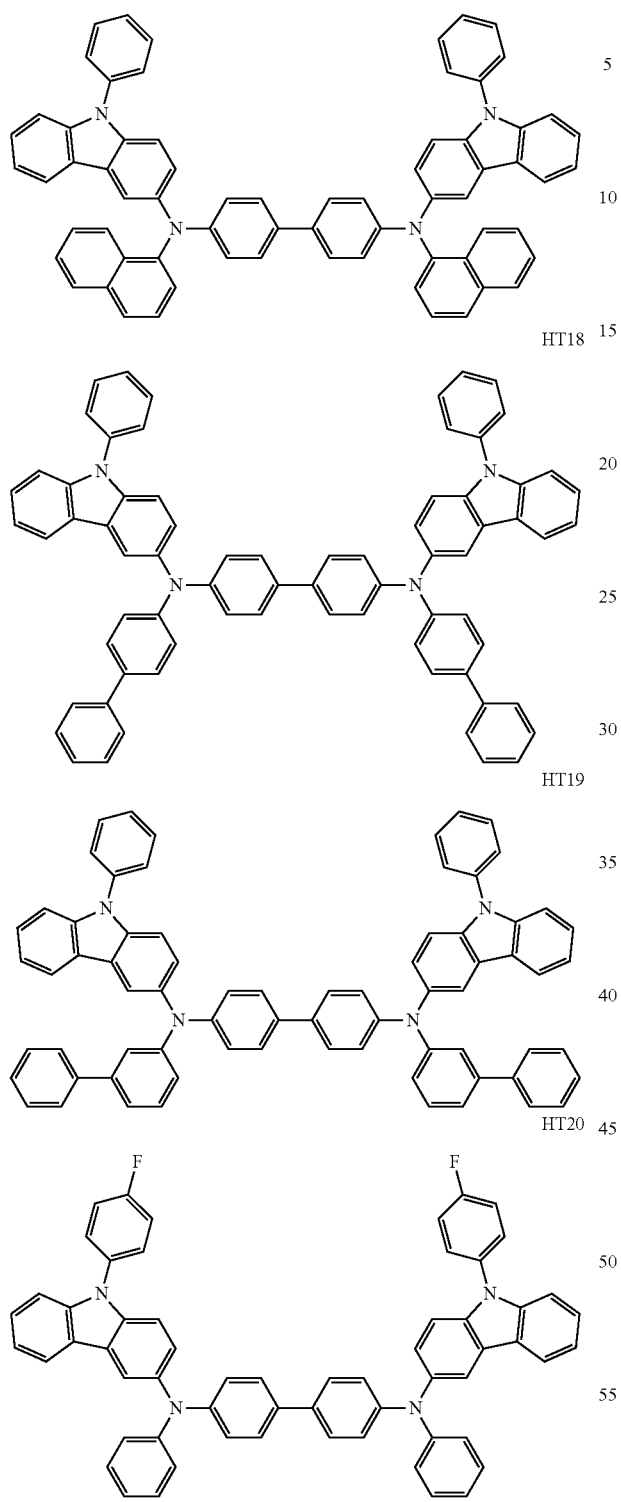

HT17

HT18

HT19

HT20

A thickness of the hole transport region may be in a range of about 100 Angstroms (Å) to about 10,000 Å, for example, about 100 Å to about 1,000 Å. When the hole transport region includes a hole injection layer and a hole transport layer, a thickness of the hole injection layer may be in a range of about 100 Å to about 10,000 Å, for example, about 100 Å to about 1,000 Å, and a thickness of the hole transport layer may be in a range of about 50 Å to about 2,000 Å, for example, about 100 Å to about 1,500 Å. When the thicknesses of the hole transport region, the hole injection layer, and the hole transport layer are within these ranges, the hole transport region may have satisfactory hole transporting properties without a substantial increase in a driving voltage.

The hole transport region may further include, in addition to these materials, a charge-generation material for the improvement of conductive properties. The charge-generation material may be homogeneously or non-homogeneously dispersed in the hole transport region.

The charge-generating material may be, for example, a p-dopant. The p-dopant may be one selected from a quinone derivative, a metal oxide, and a cyano group-containing compound, but it is not limited thereto. For example, non-limiting examples of the p-dopant include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide; and a cyano group-containing compound, such as Compound HT-D1 illustrated below, but they are not limited thereto:

Compound HT-D1

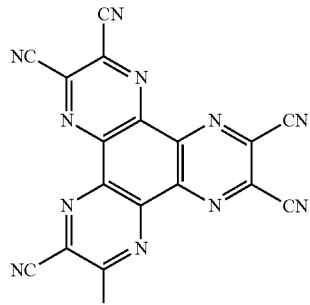

F4-TCNQ

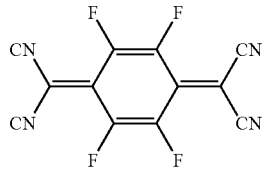

The hole transport region may further include a buffer layer.

The buffer layer compensates an optical resonance distance according to the wavelength of light emitted from an emission layer to increase efficiency of an organic light-emitting device.

An emission layer (EML) may be formed on the hole transport region by using one of various methods, such as vacuum deposition, spin coating, casting, or an LB method. When the EML is formed by vacuum deposition or spin coating, deposition and coating conditions for the emission layer may be generally similar to the conditions for forming a hole injection layer, though the conditions may vary depending on the compound used to form the EML.

When the organic light-emitting device is a full color organic light-emitting device, the emission layer may be patterned into a red emission layer, a green emission layer, and a blue emission layer. Alternatively, the emission layer may have a stacked structure including the red emission layer, the green emission layer, and/or the blue emission layer to emit white light, although other various embodiments are possible.

The EML may include the condensed cyclic compound represented by Formula 1. The EML may further include a dopant. The dopant may include at least one of a phosphorescent dopant and a fluorescent dopant.

For example, in the EML, a host may include the condensed cyclic compound represented by Formula 1.

A dopant in the EML may include a fluorescent dopant that emits light according to a fluorescent emission mechanism or a phosphorescent dopant that emits light according to a phosphorescent emission mechanism.

In an embodiment, the dopant in the EML may be a phosphorescent dopant, and the phosphorescent dopant may include an organic metal compound represented by Formula 81 below:

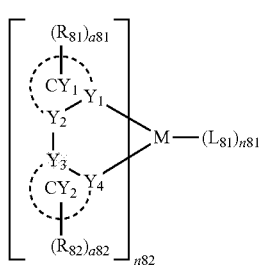

Formula 81

In Formula 81,

M is iridium (Ir), platinum (Pt), osmium (Os), titanium (Ti), zirconium (Zr), hafnium (Hf), europium (Eu), terbium (Tb), or thulium (Tm);

$Y_1$ to $Y_4$ are each independently carbon (C) or nitrogen (N);

$Y_1$ and $Y_2$ are linked via a single bond or a double bond, and $Y_3$ and $Y_4$ are linked via a single bond or a double bond;

$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isooxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzooxazole, an isobenzooxazole, a triazole, a tetrazole, an oxadiazole, a triazine, a dibenzofuran, or a dibenzothiophene, and $CY_1$ and $CY_2$ are optionally linked to each other via a single bond or an organic linking group;

$R_{81}$ to $R_{82}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{13}$ cycloalkenyl group, a substituted or unsubstituted $C_1$-$C_{10}$ heterocycloalkenyl group, a substituted or unsubstituted $C_8$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N($Q_1$)($Q_2$), —Si($Q_3$)($Q_4$)($Q_5$), and —B($Q_6$)($Q_7$);

a81 and a82 are each independently an integer of 1 to 5;

n81 is an integer of 0 to 4;

n82 is 1, 2, or 3; and $L_{81}$ is selected from a monovalent organic ligand, a divalent organic ligand, and a trivalent organic ligand.

The descriptions of $R_{81}$ and $R_{82}$ are the same as defined in connection with $R_2$ in the present specification.

The phosphorescent dopant may include at least one of Compounds PD1 to PD78, but it is not limited thereto:

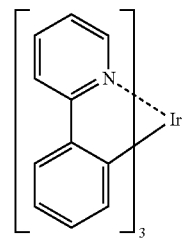

PD1

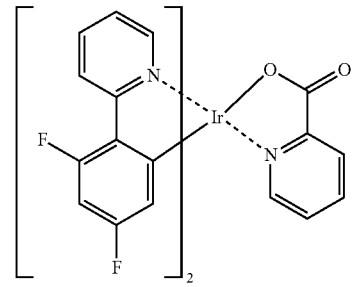

PD2

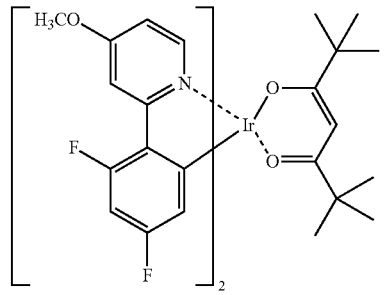

PD3

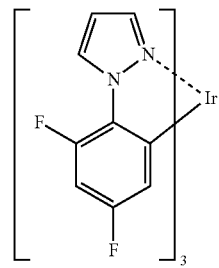

PD4

-continued
PD5 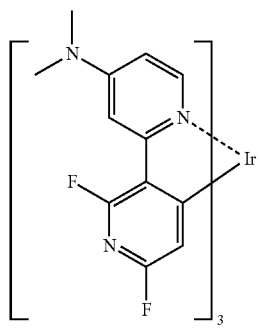
PD6 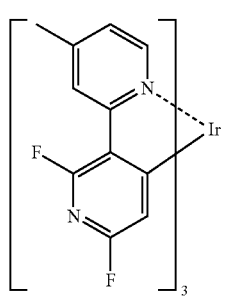
PD7 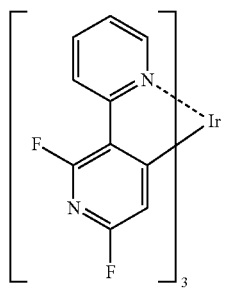
PD8 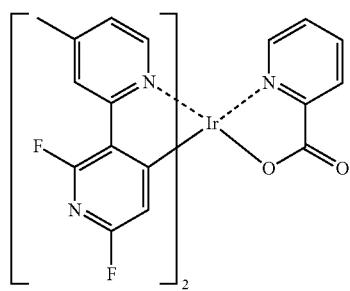
PD9 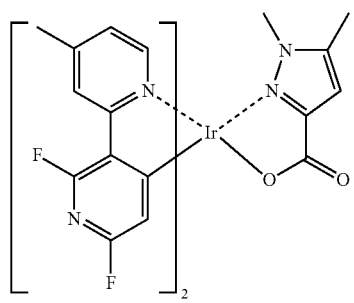
-continued
PD10 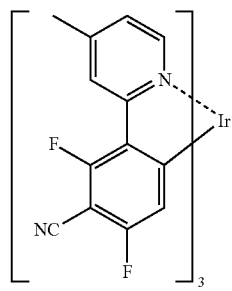
PD11 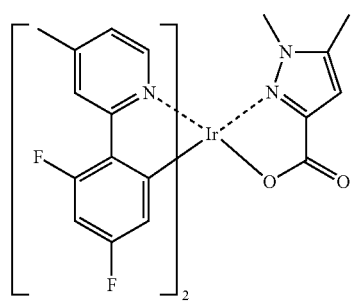
PD12 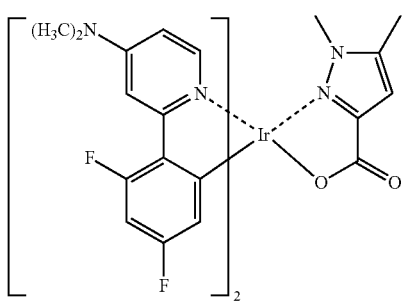
PD13 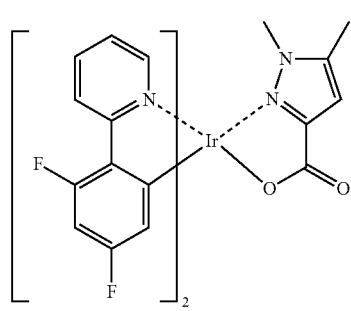
PD14 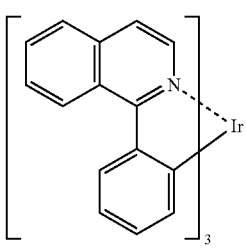

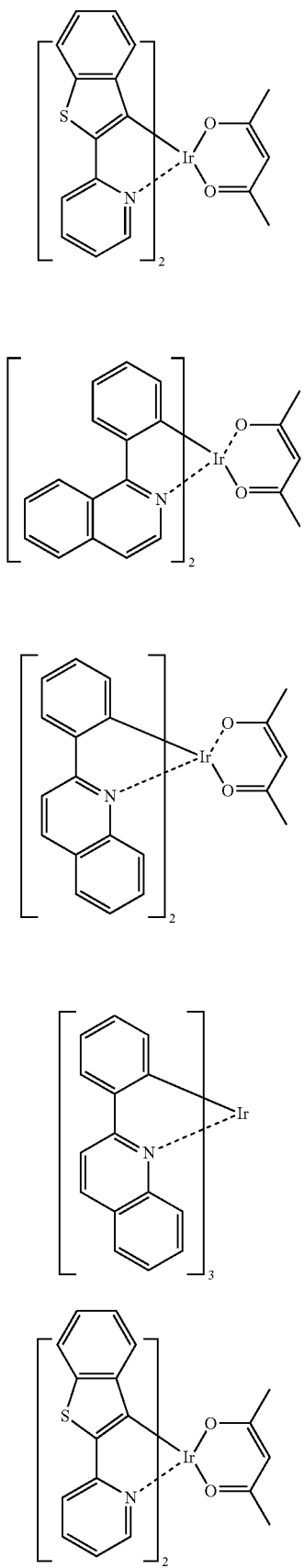

-continued
PD25
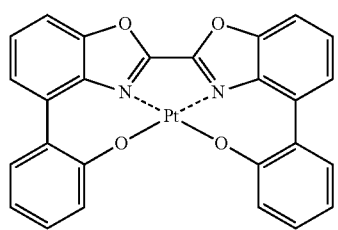
PD26
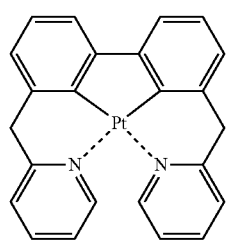
PD27
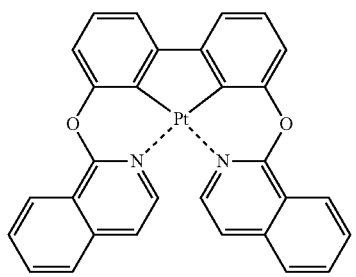
PD28
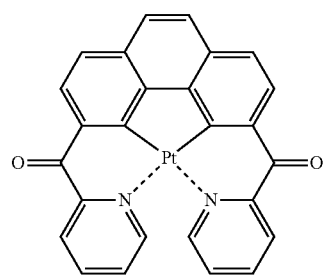
PD29
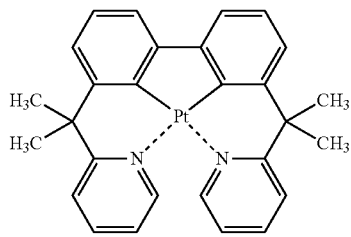
PD30
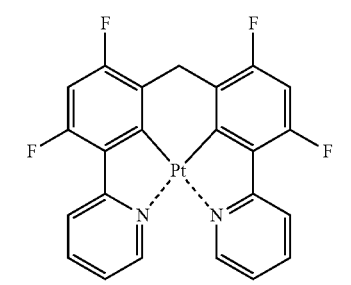
-continued
PD31
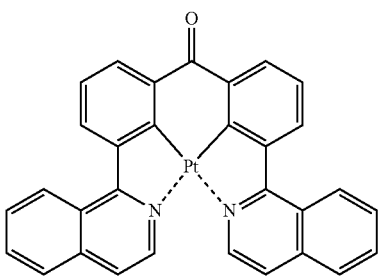
PD32
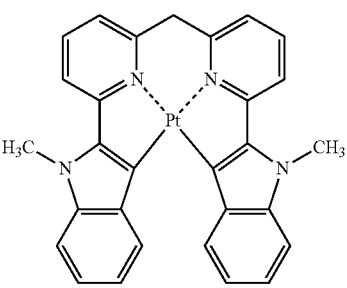
PD33
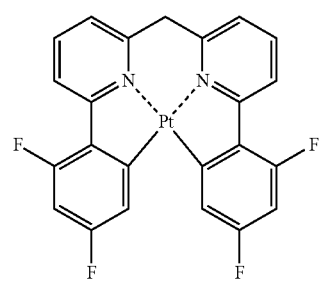
PD34
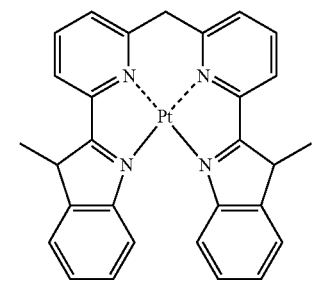
PD35
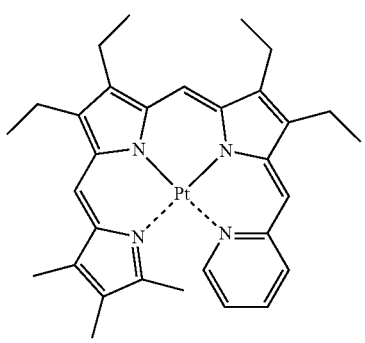

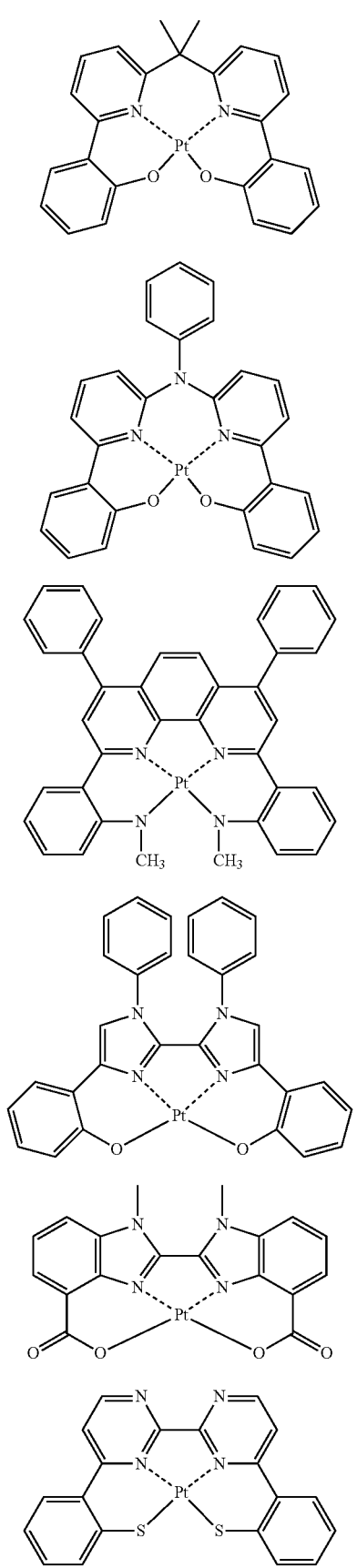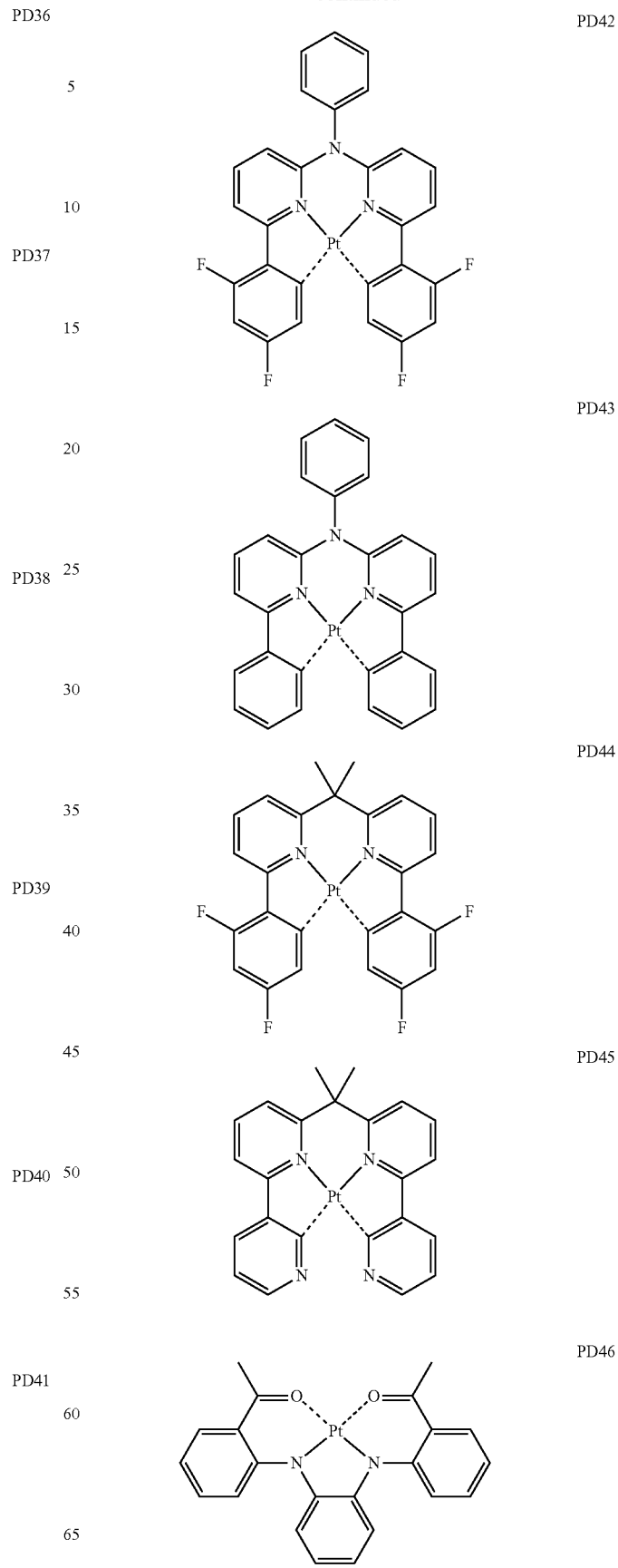

PD47
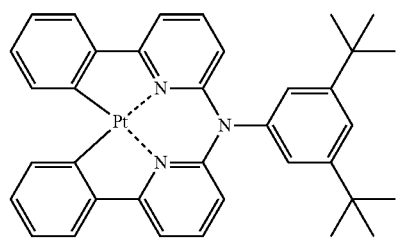
PD48
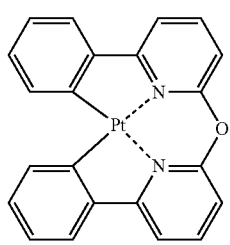
PD49
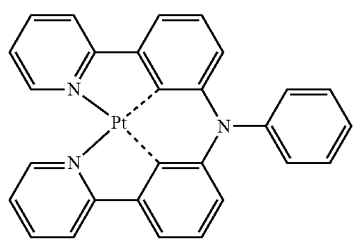
PD50
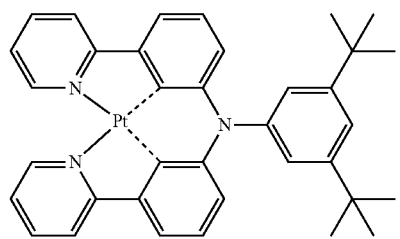
PD51
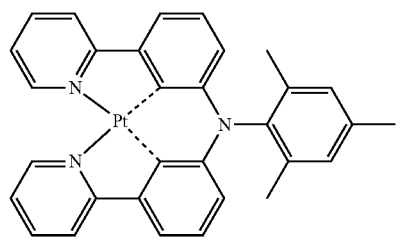
PD52
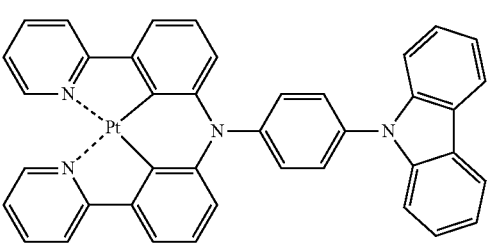
PD53
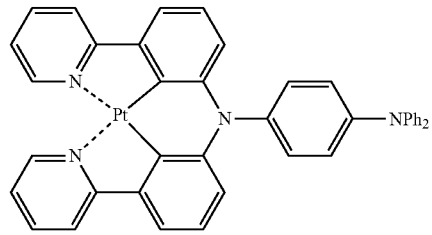
PD54
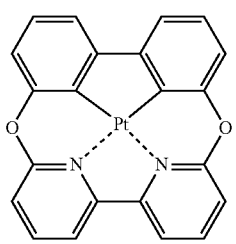
PD55
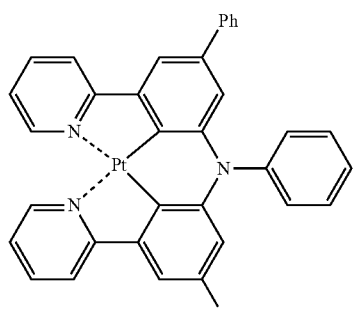
PD56
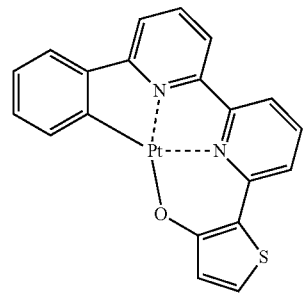
PD57
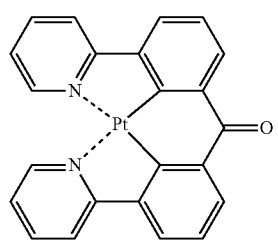

-continued
PD58
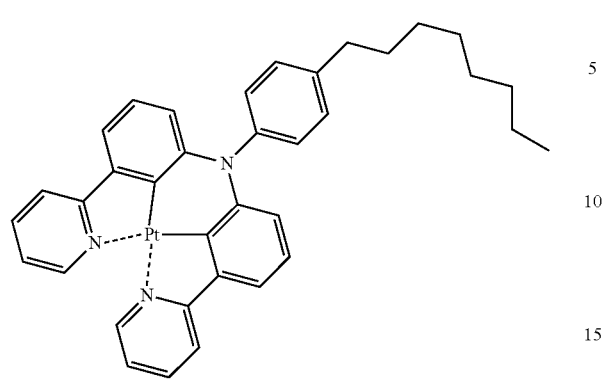
PD59
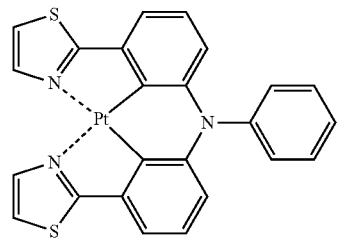
PD60
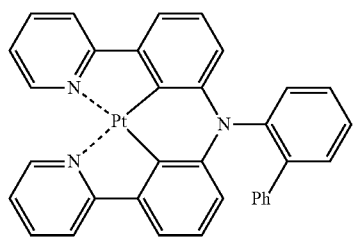
PD61
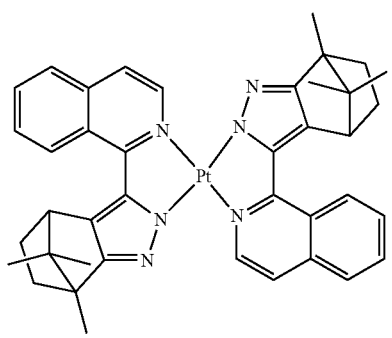
PD62
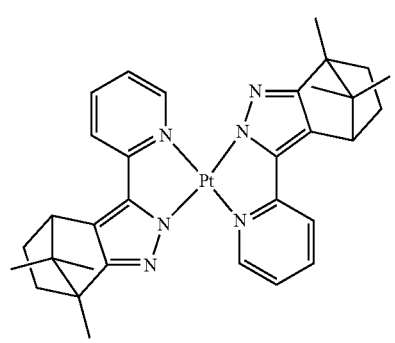
-continued
PD63
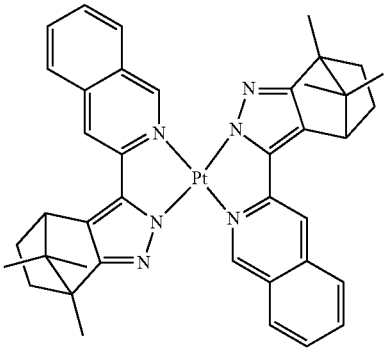
PD64
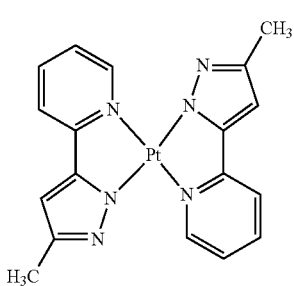
PD65
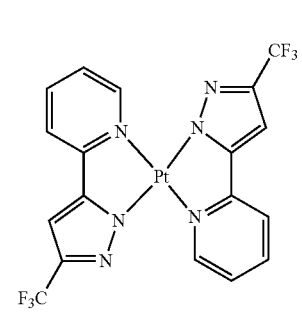
PD66
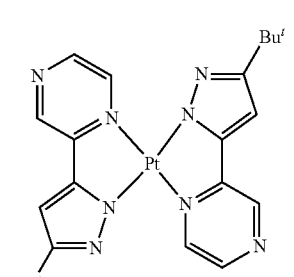
PD67
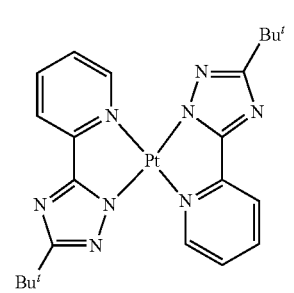

-continued
PD68
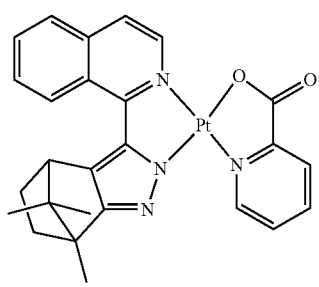
PD69
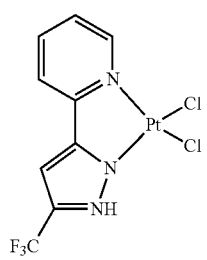
PD70
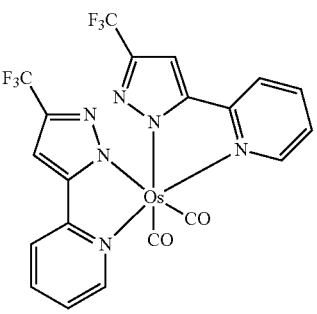
PD71
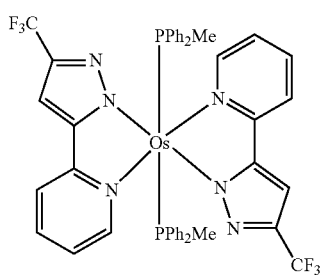
PD72
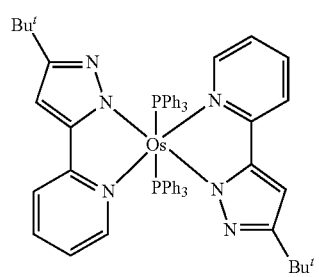
-continued
PD73
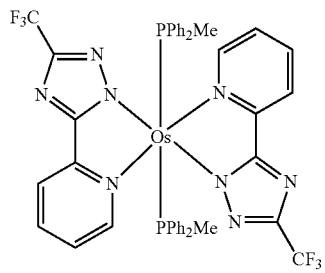
PD74
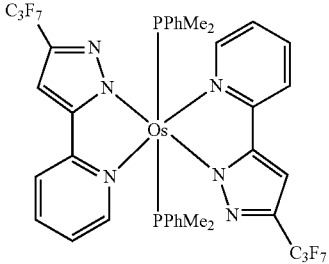
PD75
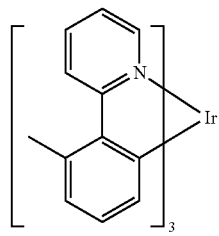
PD76
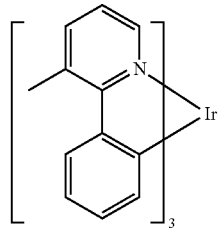
PD77
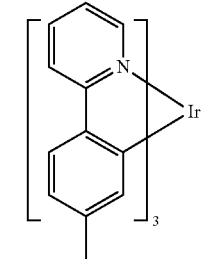
PD78
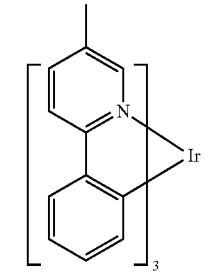
In some embodiments, the phosphorescent dopant may include PtOEP or FIr6:

229
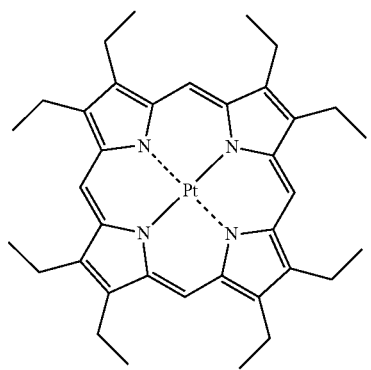
PtOEP
230
-continued
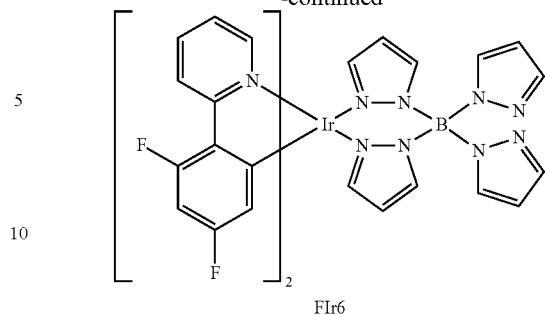
FIr6
The fluorescent dopant may include at least one selected from DPAVBi, BDAVBi, TBPe, DCM, DCJTB, Coumarin 6, and C545T.
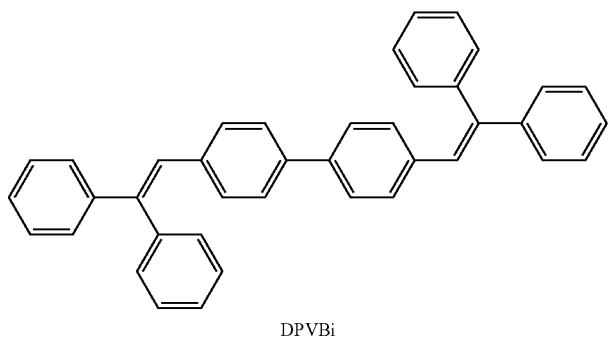
DPVBi
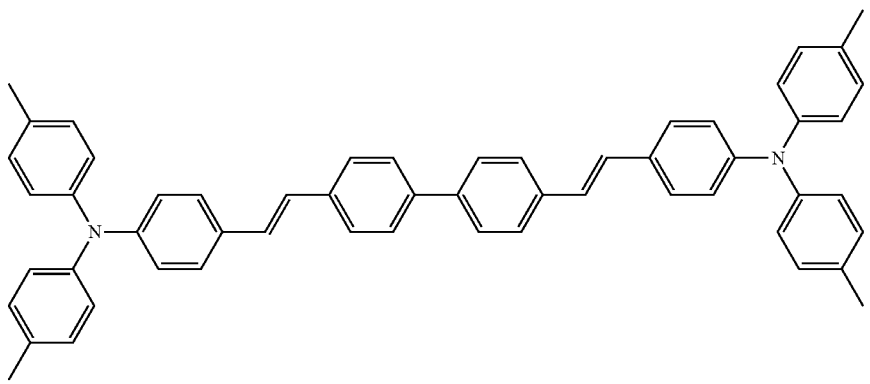
DPAVBi
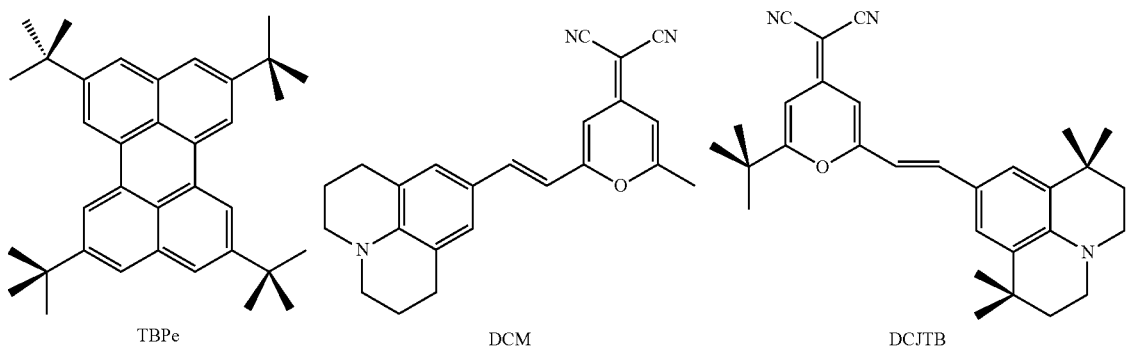
TBPe　　　　DCM　　　　DCJTB When the EML includes a host and a dopant, an amount of the dopant may be in a range of about 0.01 parts to about 20 parts by weight based on 100 parts by weight of the host, but the amount is not limited thereto.

A thickness of the EML may be in a range of about 100 Å to about 1,000 Å, for example, about 200 Å to about 600 Å. When the thickness of the EML is within these ranges, the EML may have excellent light-emission characteristics without a substantial increase in driving voltage.

Then, an electron transport region may be disposed on the EML.

The electron transport region may include at least one of a hole blocking layer, an electron transport layer, and an electron injection layer.

For example, the electron transport region may have a structure of electron transport layer, hole blocking layer/electron transport layer/electron injection layer or electron transport layer/electron injection layer, but the structure is not limited thereto. The electron transport layer may have a single-layered structure or a multi-layer structure including two or more different materials.

Conditions for forming the hole blocking layer, the electron transport layer, and the electron injection layer which constitute the electron transport region may be inferred based on the conditions for forming the hole injection layer.

When the electron transport region includes a hole blocking layer, the hole blocking layer may include, for example, at least one of BCP and Bphen, but it is not limited thereto:

A thickness of the hole blocking layer may be in a range of about 20 Å to about 1,000 Å, for example, about 30 Å to about 300 Å. When the thickness of the hole blocking layer is within these ranges, the hole blocking layer may have excellent hole blocking characteristics without a substantial increase in driving voltage.

The electron transport layer may further include at least one selected from BCP, Bphen, Alq$_3$, Balq, TAZ, and NTAZ:

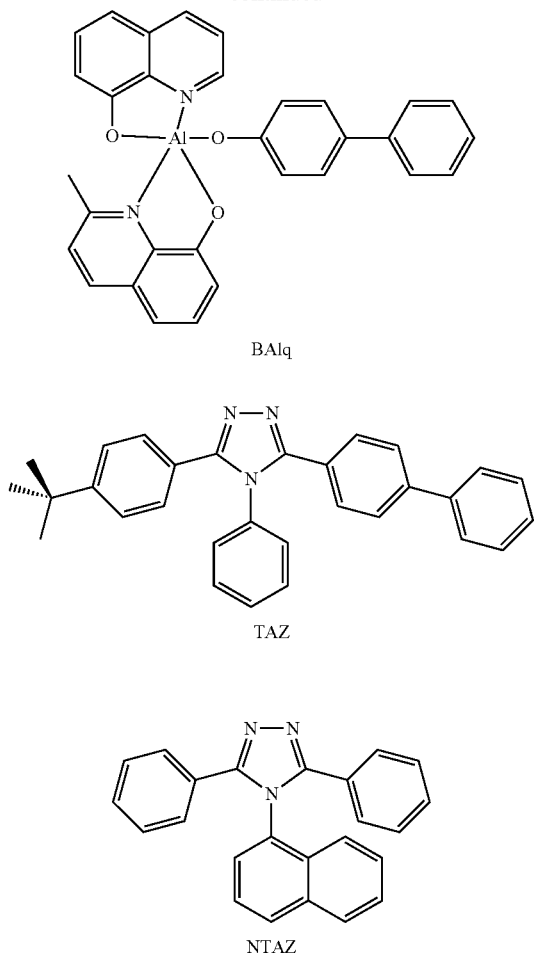

BAlq

TAZ

NTAZ

In some embodiments, the electron transport layer may include at least one of Compounds ET1 and ET2, but it is not limited thereto:

ET1

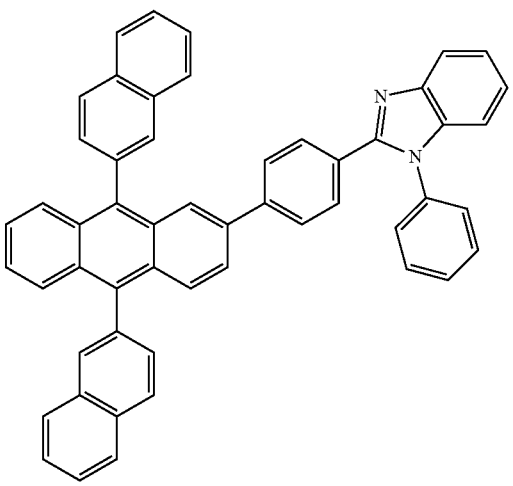

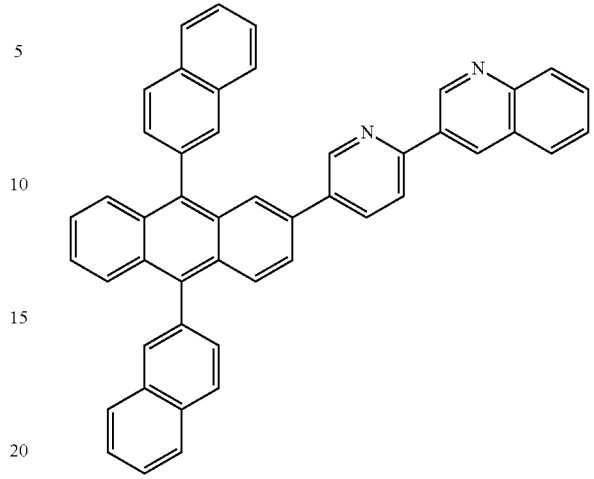

ET2

A thickness of the electron transport layer may be in a range of about 100 Å to about 1,000 Å, for example, about 150 Å to about 500 Å. When the thickness of the electron transport layer is within these ranges, the electron transport layer may have satisfactory electron transport characteristics without a substantial increase in driving voltage.

The electron transport layer may further include a metal-containing material. n addition to the materials described above.

The metal-containing material may include a Li complex. The Li complex may include, for example, Compound ET-D1 (lithium quinolate, LiQ) or ET-D2:

ET-D1

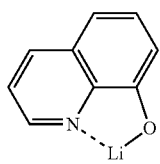

ET-D2

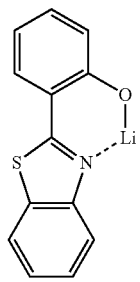

Also, the electron transport region may include an electron injection layer (EIL) that facilitates electron injection from the second electrode 19.

The EIL may include at least one selected from LiF, NaCl, CsF, Li$_2$O, and BaO.

A thickness of the EIL may be in a range of about 1 Å to about 100 Å, for example, about 3 Å to about 90 Å. When the thickness of the EIL is within these ranges, the EIL may have satisfactory electron injection characteristics without a substantial increase in driving voltage.

The second electrode 19 is disposed on the organic layer 15. The second electrode 19 may be a cathode. A material for forming the second electrode 19 may be selected from a metal, an alloy, an electrically conductive compound, and a combination thereof, which have a relatively low work function. For example, lithium (Li), magnesium (Mg), aluminum (Al), aluminum-lithium (Al—Li), calcium (Ca), magnesium-indium (Mg—In), or magnesium-silver (Mg—Ag) may be used as the material for forming the second electrode 19. In some embodiments, a transmissive electrode formed of ITO or IZO may be used as the second electrode 19 to manufacture a top emission type light-emitting device.

Hereinbefore, the organic light-emitting device 10 has been described with reference to the FIGURE, but it is not limited thereto.

As used herein, a $C_1$-$C_{60}$ alkyl group refers to a linear or branched aliphatic hydrocarbon monovalent group having 1 to 60 carbon atoms. Examples thereof include a methyl group, an ethyl group, a propyl group, an isobutyl group, a sec-butyl group, a tert-butyl group, a pentyl group, an iso-amyl group, and a hexyl group. As used herein, a $C_1$-$C_{60}$ alkylene group refers to a divalent group having the same structure as the $C_1$-$C_{60}$ alkyl group.

As used herein, a $C_1$-$C_{60}$ alkoxy group refers to a monovalent group represented by —$OA_{101}$ (wherein, $A_{101}$ is the $C_1$-$C_{60}$ alkyl group). Examples thereof include a methoxy group, an ethoxy group, and an isopropyloxy group.

As used herein, a $C_2$-$C_{60}$ alkenyl group has a structure including at least one carbon double bond in the middle or at the end of the $C_2$-$C_{60}$ alkyl group. Examples thereof include an ethenyl group, a propenyl group, and a butenyl group. As used herein, a $C_2$-$C_{60}$ alkenylene group refers to a divalent group having the same structure as the $C_2$-$C_{60}$ alkenyl group.

As used herein, a $C_2$-$C_{60}$ alkynyl group has a structure including at least one carbon triple bond in the middle or at the end of the $C_2$-$C_{60}$ alkyl group. Examples thereof include an ethynyl group and a propynyl group. As used herein, a $C_2$-$C_{60}$ alkynylene group refers to a divalent group having the same structure as the $C_2$-$C_2$ alkynyl group.

As used herein, a $C_3$-$C_{10}$ cycloalkyl group refers to a monovalent hydrocarbon monocyclic group having 3 to 10 carbon atoms. Examples thereof include a cyclopropyl group, a cyclobutyl group, a cyclopentyl group, a cyclohexyl group, and a cycloheptyl group. As used herein, a $C_3$-$C_{10}$ cycloalkylene group refers to a divalent group having the same structure as the $C_3$-$C_{10}$ cycloalkyl group.

As used herein, a $C_1$-$C_{10}$ heterocycloalkyl group refers to a monovalent monocyclic group having at least one hetero atom selected from N, O, P, and S as a ring-forming atom and 1 to 10 carbon atoms. Examples thereof include a tetrahydrofuranyl group and a tetrahydrothiophenyl group. As used herein, a $C_1$-$C_{10}$ heterocycloalkylene group refers to a divalent group having the same structure as the $C_1$-$C_{10}$ heterocycloalkyl group.

As used herein, a $C_3$-$C_{10}$ cycloalkenyl group used herein refers to a monovalent monocyclic group that has 3 to 10 carbon atoms and at least one double bond in the ring thereof, which is not aromatic. Examples thereof include a cyclopentenyl group, a cyclohexenyl group, and a cycloheptenyl group. As used herein, a $C_3$-$C_{10}$ cycloalkenylene group refers to a divalent group having the same structure as the $C_3$-$C_{10}$ cycloalkenyl group.

As used herein, a $C_1$-$C_{10}$ heterocycloalkenyl group refers to a monovalent monocyclic group that has at least one hetero atom selected from N, O, P, and S as a ring-forming atom, 1 to 10 carbon atoms, and at least one double bond in its ring. Examples of the $C_1$-$C_{10}$ heterocycloalkenyl group include a 2,3-dihydrofuranyl group and a 2,3-dihydrothiophenyl group. As used herein, a $C_1$-$C_{10}$ heterocycloalkenylene group refers to a divalent group having the same structure as the $C_1$-$C_{10}$ heterocycloalkenyl group.

As used herein, a $C_6$-$C_{60}$ aryl group refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Examples of the $C_6$-$C_{60}$ aryl group include a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, the rings may be fused to each other.

As used herein, a $C_1$-$C_{60}$ heteroaryl group refers to a monovalent group having a carbocyclic aromatic system that has at least one hetero atom selected from N, O, P, and S as a ring-forming atom, and 1 to 60 carbon atoms. As used herein, a $C_1$-$C_{60}$ heteroarylene group refers to a divalent group having a carbocyclic aromatic system that has at least one hetero atom selected from N, O, P, and S as a ring-forming atom, and 1 to 60 carbon atoms. Examples of the $C_1$-$C_{60}$ heteroaryl group include a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, the rings may be fused to each other.

As used herein, a $C_6$-$C_{60}$ aryloxy group denotes —$OA_{102}$ (wherein, $A_{102}$ is the $C_6$-$C_{60}$ aryl group), and a $C_6$-$C_{60}$ arylthio group denotes —$SA_{103}$ (wherein, $A_{103}$ is the $C_6$-$C_{60}$ aryl group).

As used herein, a monovalent non-aromatic condensed polycyclic group refers to a monovalent non-aromatic condensed polycyclic group that has two or more rings condensed to each other, only carbon atoms (for example, the number of carbon atoms may be in a range of 8 to 60) as a ring forming atom, which is non-aromatic in the entire molecular structure. Examples of the monovalent non-aromatic condensed polycyclic group include a fluorenyl group. As used herein, a divalent non-aromatic condensed polycyclic group refers to a divalent group having the same structure as the monovalent non-aromatic condensed polycyclic group.

As used herein, a monovalent non-aromatic condensed heteropolycyclic group refers to a monovalent group that has two or more rings condensed to each other, has a heteroatom selected from N, O P, and S, other than carbon atoms (for example, the number of carbon atoms may be in a range of 1 to 60), as a ring forming atom, which is non-aromatic in the entire molecular structure. Examples of the monovalent non-aromatic condensed heteropolycyclic group include a carbazolyl group. As used herein, a divalent non-aromatic condensed heteropolycyclic group refers to a divalent group having the same structure as the monovalent non-aromatic condensed heteropolycyclic group.

As used herein, at least one substituent of the substituted $C_1$-$C_{60}$ alkylene group, substituted $C_2$-$C_{60}$ alkenylene group, substituted $C_2$-$C_{60}$ alkynylene group, substituted $C_3$-$C_{10}$ cycloalkylene group, substituted $C_1$-$C_{10}$ heterocycloalkylene group, substituted $C_3$-$C_{10}$ cycloalkenylene group, substituted $C_1$-$C_{10}$ heterocycloalkenylene group, substituted $C_6$-$C_{60}$ arylene group, substituted $C_1$-$C_{60}$ heteroarylene group, substituted a divalent non-aromatic condensed polycyclic group, substituted a divalent non-aromatic condensed heteropolycyclic group, substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_r$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$).

Also, as used herein, $Q_1$ to $Q_7$, $Q_{11}$ to $Q_{17}$, $Q_{21}$ to $Q_{27}$, and $Q_{31}$ to $Q_{37}$ are each independently selected from a hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

As used herein, the term "a biphenyl group" denotes "a phenyl group substituted with a phenyl group".

Hereinafter, a compound and an organic light-emitting device according to exemplary embodiments are described in detail with reference to Synthesis Example and Examples. However, the organic light-emitting device is not limited thereto. The wording "B was used instead of A" used in describing Synthesis Examples denotes that a molar equivalent of A was identical to a molar equivalent of B.

EXAMPLES

Synthesis Example 1

Synthesis of Compound 5

Compound 5 was synthesized according to Reaction Scheme below:

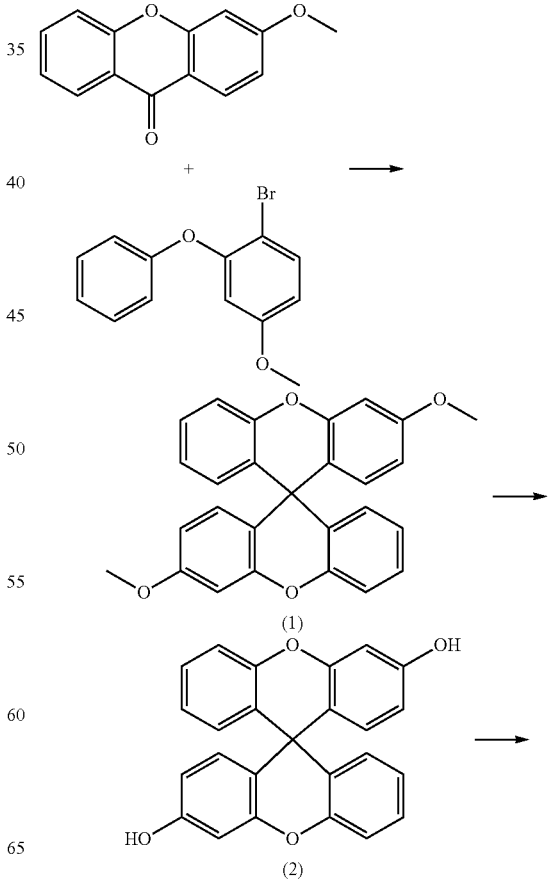

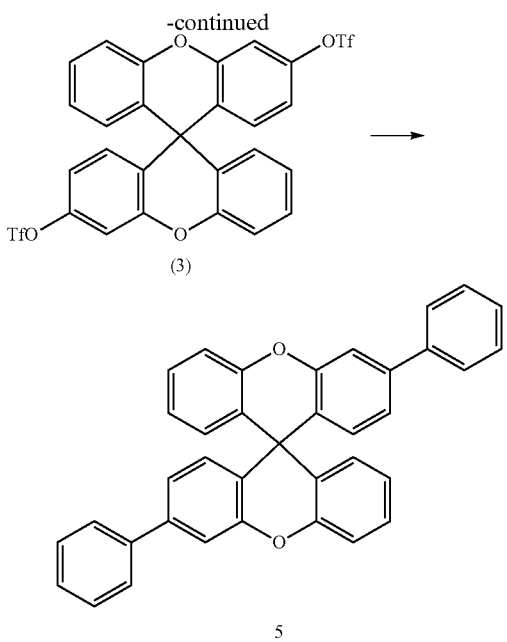

Synthesis of Intermediate (1)

7 g (25 mmol) of 1-bromo-4-methoxy-2-phenoxybenzene was dissolved in 80 ml of tetrahydrofuran, and a temperature of the solution was decreased to −78° C. 20 ml (50 mmol) of n-butyllithium (2.5 M in hexane) was slowly added to the solution, and the solution was stirred for 30 minutes at a low temperature. Next, a temperature of the solution was increased to room temperature, and the solution was stirred for 2 hours. A temperature of the resultant obtained therefrom was decreased to −78° C., and the resultant was slowly added to a mixture (−78° C.) of 5.7 g (25 mmol) of 3-methoxy-9H-xanthen-9-one and 40 ml of tetrahydrofuran by using a cannula and stirred for 19 hours. 20 ml of an ammonium chloride (NH$_4$Cl) saturated aqueous solution was slowly added to the resultant obtained therefrom to complete the reaction, the produced solid was celite-filtered, a solvent was concentrated under reduced pressure, and the filtrate was washed with dichloromethane. An organic layer thus obtained was dried with anhydrous sodium sulfate (Na$_2$SO$_4$), and impurities were washed by using concentrated acetone to obtain 8.6 g (20 mmol) of white solid. The white solid was added to a mixture solution of 80 ml of acetic anhydride and 50 ml of saturated HCl and refluxed for 6 hours. Next, acetic anhydride and acetic acid were removed under reduced pressure, and the resultant was washed with dichloromethane and a saturated sodium hydrogen carbonate (NaHCO$_3$) aqueous solution. The organic layer thus obtained was dried with anhydrous sodium sulfate (Na$_2$SO$_4$) and concentrated, and impurities were washed by using acetone to obtain 5.8 g (14 mmol) of Intermediate (1) (yield: 56%).

Synthesis of Intermediate (2)

5.8 g (14 mmol) of Intermediate (1) was dissolved in 100 ml of dichloromethane. 7 g (28 mmol) of boron tribromide (BBr$_3$) was slowly added thereto, the mixture was stirred at room temperature for 17 hours and extracted with distilled water and dichloromethane. An organic layer obtained therefrom was dried with anhydrous sodium sulfate (Na$_2$SO$_4$), and a solid produced by concentrating the resultant was recrystallized by using dichloromethane/ethanol to obtain 5.2 g (14 mmol) of Intermediate (2) (yield: 98%) as a white solid.

Synthesis of Intermediate (3)

5.2 g (14 mmol) of Intermediate (2) and 5.7 g (56 mmol) of triethylamine were dissolved in 200 ml of dichloromethane, and a temperature of the solution was decreased to 0° C. 7.9 g (28 mmol) of triflic anhydride in a 10% hydrochloric aqueous solution was added thereto to complete the reaction. The resultant was extracted with dichloromethane and washed with a saturated sodium hydrogen carbonate (NaHCO$_3$) aqueous solution. An organic layer obtained therefrom was dried with anhydrous sodium sulfate (Na$_2$SO$_4$), and a solid produced by concentrating the resultant was recrystallized by using dichloromethane/ethanol to obtain 5.9 g (9.2 mmol) of Intermediate (3) (yield: 65%) as a white solid.

Synthesis of Compound 5

5.9 g (9.2 mmol) of Intermediate (3), 2.5 g (20 mmol) of phenylboronic acid, 0.46 g (0.4 mmol) of tetrakis(triphenylphosphine)palladium (Pd(PPh$_3$)$_4$), and 8.3 g (60 mmol) of potassium carbonate (K$_2$CO$_3$) were added to 80 ml of tetrahydrofuran and 40 ml of distilled water, and the mixture was heated and refluxed. After the reaction was completed, the mixture was cooled to room temperature. The organic layer was extracted with ethyl acetate, dried with anhydrous sodium sulfate (Na$_2$SO$_4$), and a solid produced by concentrating the resultant was recrystallized by using dichloromethane/acetone to obtain 4 g (8 mmol) of Compound 5 (yield: 87%) as a white solid.

MALDI-TOF Mass (calculated: 500.18 g/mol, measured: 499.98 g/mol)

Synthesis Example 2

Synthesis of Compound 507

5.2 g of Compound 507 (yield: 54%) was synthesized in the same manner as in Synthesis Example 1, except that dibenzo[b,d]furan-4-ylboronic acid was used instead of phenylboronic acid in the synthesis of Compound 5.

MALDI-TOF Mass (calculated: 600.20 g/mol, measured: 600.01 g/mol)

Synthesis Example 3

Synthesis of Compound 508

7 g of Compound 508 (yield: 66%) was synthesized in the same manner as in Synthesis Example 1, except that benzofuro[3,2-c]pyridin-6-ylboronic acid was used instead of phenylboronic acid in the synthesis of Compound 5.

MALDI-TOF Mass (calculated: 682.19 g/mol, measured: 682.00 g/mol)

Synthesis Example 4

Synthesis of Compound 510

6.3 g of Compound 510 (yield: 88%) was synthesized in the same manner as in Synthesis Example 1, except that biphenyl-3-ylboronic acid was used instead of phenylboronic acid in the synthesis of Compound 5.

MALDI-TOF Mass (calculated: 652.24 g/mol, measured: 652.03 g/mol)

Synthesis Example 5

Synthesis of Compound 64

Synthesis of Intermediate (4)

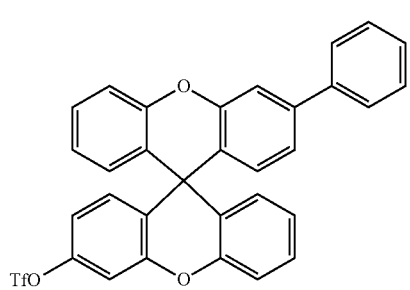

(4)

Intermediate (4) was obtained by sequentially performing synthesis of Intermediates (1), (2), and (3) of Synthesis Example 1, except that 3-phenyl-9H-xanthen-9-one was used instead of 3-methoxy-9H-xanthen-9-one in the synthesis of Intermediate (1).

Synthesis of Compound 64

8 g of Compound 64 (yield: 78%) was synthesized in the same manner as in Synthesis Example 1, except that Intermediate (4) was used instead of Intermediate (3), and 9-phenyl-9H-carbazol-3-ylboronic acid was used instead of phenylboronic acid in the synthesis of Compound 5.

MALDI-TOF Mass (calculated: 665.24 g/mol, measured: 665.11 g/mol)

Synthesis Example 6

Synthesis of Compound 425

5.1 g of Compound 425 (yield: 65%) was synthesized in the same manner as in Synthesis Example 1, except that Intermediate (4) was used instead of Intermediate (3), and (3-(pyridine-3-yl)phenyl)boronic acid was used instead of phenylboronic acid in the synthesis of Compound 5.

MALDI-TOF Mass (calculated: 577.20 g/mol, measured: 577.00 g/mol)

Synthesis Example 7

Synthesis of Compound 465

7.5 g of Compound 465 (yield: 60%) was synthesized in the same manner as in Synthesis Example 1, except that Intermediate (4) was used instead of Intermediate (3), and dibenzo[b,d]furan-1-ylboronic acid was used instead of phenylboronic acid in the synthesis of Compound 5.

MALDI-TOF Mass (calculated: 590.19 g/mol, measured: 589.99 g/mol)

Synthesis Example 8

Synthesis of Compound 304

Synthesis of Intermediate (5)

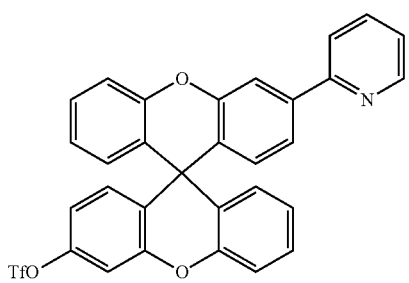

(5)

Intermediate (5) was obtained by sequentially performing synthesis of Intermediates (1), (2), and (3) of Synthesis Example 1, except that 3-(pyridine-2-yl)-9H-xanthen-9-one was used instead of 3-methoxy-9H-xanthen-9-one in the synthesis of Intermediate (1).

Synthesis of Compound 304

4.2 g of Compound 304 (yield: 52%) was synthesized in the same manner as in Synthesis Example 1, except that Intermediate (5) was used instead of Intermediate (3), and 9-phenyl-9H-carbazol-3-ylboronic acid was used instead of phenylboronic acid in the synthesis of Compound 5.

MALDI-TOF Mass (calculated: 666.23 g/mol, measured: 666.05 g/mol)

Synthesis Example 9

Synthesis of Compound 468

3.5 g of Compound 468 (yield: 43%) was synthesized in the same manner as in Synthesis Example 1, except that. Intermediate (5) was used instead of Intermediate (3), and dibenzo[b,d]thiophen-1-ylboronic acid was used instead of phenylboronic acid in the synthesis of Compound 5.

MALDI-TOF Mass (calculated: 607.16 g/mol, measured: 606.98 g/mol)

Synthesis Example 10

Synthesis of Compound 474

2.5 g of Compound 474 (yield: 32%) was synthesized in the same manner as in Synthesis Example 1, except that Intermediate (5) was used instead of Intermediate (3), and benzofuro[2,3-c]pyridin-5-ylboronic acid was used instead of phenylboronic acid in the synthesis of Compound 5.

MALDI-TOF Mass (calculated: 592.18 g/mol, measured: 592.01 g/mol)

Synthesis Example 11

Synthesis of Compound 16

Synthesis of Intermediate (6)

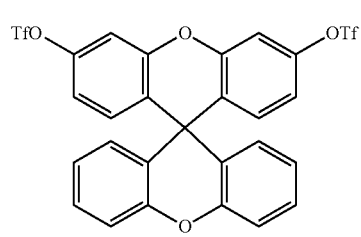

(6)

Intermediate (6) was obtained by sequentially performing synthesis of Intermediates (1), (2), and (3) of Synthesis Example 1, except that 3,6-dimethoxy-9H-xanthen-9-one and 1-bromo-2-phenoxybenzene were used instead of 3-methoxy-9H-xanthen-9-one and 1-bromo-4-methoxy-2-phenoxybenzene, each respectively, in the synthesis of Intermediate (1).

Synthesis of Compound 16

5.2 g of Compound 16 (yield: 52%) was synthesized in the same manner as in Synthesis Example 1, except that Intermediate (6) was used instead of Intermediate (3) in the synthesis of Compound 5.

MALDI-TOF Mass (calculated: 500.18 g/mol, measured: 499.99 g/mol)

Synthesis Example 12

Synthesis of Compound 32

Synthesis of Intermediate (7)

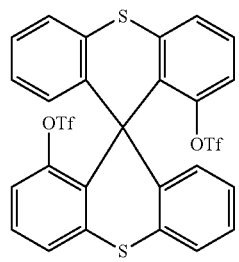

(7)

Intermediate (7) was obtained by sequentially performing synthesis of Intermediates (1), (2), and (3) of Synthesis Example 1, except that 1-methoxy-9H-thioxanthen-9-one and (2-bromo-3-methoxyphenyl)phenylsulfone were used instead of 3-methoxy-9H-xanthen-9-one and 1-bromo-4-methoxy-2-phenoxybenzene, each respectively, in the synthesis of Intermediate (1).

Synthesis of Compound 32

3.1 g of Compound 32 (yield: 34%) was synthesized in the same manner as in Synthesis Example 1, except that Intermediate (7) was used instead of Intermediate (3) in the synthesis of Compound 5.

MALDI-TOF Mass (calculated: 532.13 g/mol, measured: 531.97 g/mol)

Synthesis Example 13

Synthesis of Compound 409

6.9 g of Compound 409 (yield: 82%) was synthesized in the same manner as in Synthesis Example 1, except that Intermediate (4) was used instead of Intermediate (3), and 3-biphenylboronic acid was used instead of phenylboronic acid in the synthesis of Compound 5.

MALDI-TOF Mass (calculated: 576.21 g/mol, measured: 576.01 g/mol)

Synthesis Example 14

Synthesis of Compound 417

4.3 g of Compound 417 (yield: 63%) was synthesized in the same manner as in Synthesis Example 1, except that Intermediate (4) was used instead of Intermediate (3), and 2-phenyl-pyridine-6-boronic acid was used instead of phenylboronic acid in the synthesis of Compound 5.

MALDI-TOF Mass (calculated: 577.20 g/mol, measured: 577.01 g/mol)

Synthesis Example 15

Synthesis of Compound 433

6.0 g (10.5 mmol) of Intermediate (4), 1.68 g (10.5 mmol) of carbazole, 0.1 g (1.1 mmol) of $Pd_2(dba)_3$, 1.0 mL (2.1 mmol) of tri-tert-butylphosphine (ttbp) (50% in toluene), and 2.0 g (21 mmol) of sodium tert-butoxide were added to 100 ml of xylene, and the solution was heat-stirred at a temperature of 145° C. After the reaction was completed, the resultant was cooled to room temperature and filtered under reduced pressure through a silica gel, and the filtrate was concentrated under reduced pressure. The product was purified through recrystallization by using dichloromethane/acetone to synthesize 5.1 g of Compound 433 (yield: 67%).

MALDI-TOF Mass (calculated: 589.20 g/mol, measured: 589.13 g/mol)

Synthesis Example 16

Synthesis of Compound 473

5.1 g of Compound 473 (yield: 67%) was synthesized in the same manner as in Synthesis Example 1, except that Intermediate (4) was used instead of Intermediate (3), and benzofuro[2,3-c]pyridin-5-ylboronic acid was used instead of phenylboronic acid in the synthesis of Compound 5.

MALDI-TOF Mass (calculated: 591.18 g/mol, measured: 591.00 g/mol)

Synthesis Example 17

Synthesis of Compound 475

3.4 g of Compound 475 (yield: 65%) was synthesized in the same manner as in Synthesis Example 1, except that Intermediate (4) was used instead of Intermediate (3), and benzothieno[2,3-c]pyridin-5-ylboronic acid was used instead of phenylboronic acid in the synthesis of Compound 5.

MALDI-TOF Mass (calculated: 607.16 g/mol, measured: 606.98 g/mol)

Synthesis Example 18

Synthesis of Compound 486

Synthesis of Intermediate (8)

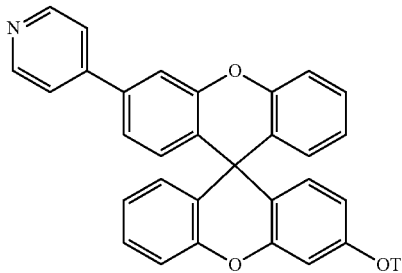

(8)

Intermediate (8) was obtained by sequentially performing synthesis of Intermediates (1), (2), and (3) of Synthesis Example 1, except that 3-(pyridine-2-yl)-9H-xanthen-9-one was used instead of 3-methoxy-9H-xanthen-9-one in the synthesis of Intermediate (1).

Synthesis of Compound 486

2.9 g of Compound 486 (yield: 44%) was synthesized in the same manner as in Synthesis Example 1, except that Intermediate (8) was used instead of Intermediate (3), and 9-phenyl-9H-carbazol-3-ylboronic acid was used instead of phenylboronic acid in the synthesis of Compound 5.

MALDI-TOF Mass (calculated: 666.23 g/mol, measured: 666.05 g/mol)

Synthesis Example 19

Synthesis of Compound 509

Synthesis of Intermediate (9)

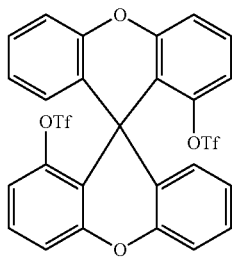

(9)

Intermediate (9) was obtained by sequentially performing synthesis of Intermediates (1), (2), and (3) of Synthesis Example 1, except that 1-methoxy-9H-xanthen-9-one and 2-bromo-1-methoxy-3-phenoxybenzene were used instead of 3-methoxy-9H-xanthen-9-one and 1-bromo-4-methoxy-2-phenoxybenzene, each respectively, in the synthesis of Intermediate (1).

Synthesis of Compound 509

3.3 g of Compound 509 (yield: 45%) was synthesized in the same manner as in Synthesis Example 1, except that Intermediate (9) was used instead of Intermediate (3), and 3-biphenylboronic acid was used instead of phenylboronic acid in the synthesis of Compound 5.

MALDI-TOF Mass (calculated: 680.20 g/mol, measured: 680.02 g/mol)

Synthesis Example 20

Synthesis of Compound 512

Synthesis of Intermediate (10)

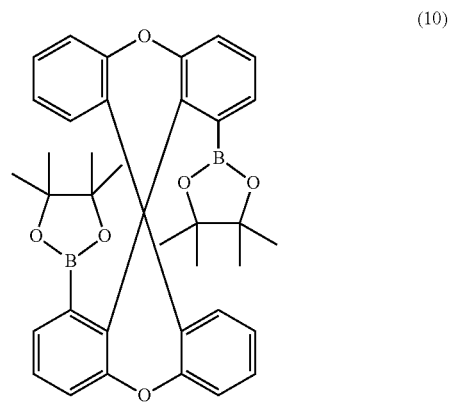

(10)

5.0 g (7.76 mmol) of Intermediate (9), 4.72 g (46.6 mmol) of triethylamine, and 0.34 g (0.47 mmol) of $PdCl_2(dppf)$ were dissolved in 50 ml of anhydrous dioxane. 5.0 g (38.8 mmol) of pinacolborane was added thereto, and heat-stirred for 16 hours. 100 ml of distilled water was added thereto to complete the reaction. The mixture was extracted with dichloromethane, and the resultant was dried with magnesium sulfate and concentrated. The resultant was dissolved in dichloromethane, and the solution was filtered through a short silica filter to remove a catalyst and precipitated by using a combination of dichloromethane/hexane to synthesize 2.56 g of Intermediate (10) (yield: 55%).

Synthesis of Compound 512

2.1 g of Compound 512 (yield: 37%) was synthesized in the same manner as in Synthesis Example 1, except that Intermediate (10) was used instead of Intermediate (3), and 2-chloro-4,6-diphenylpyrimidine was used instead of phenylboronic acid in the synthesis of Compound 5.

MALDI-TOF Mass (calculated: 808.28 g/mol, measured: 808.12 g/mol)

Evaluation Example 1

HOMO, LUMO, and Triplet (T1) Energy Level Evaluation

HOMO, LUMO and T1 energy levels of Compounds 5, 16, 32, 64, 304, 409, 417, 425, 433, 465, 468, 473, 474, 475, 486, 507, 508, 509, 510, and 512 and Compounds A and B were evaluated according to methods described in Table 1, and the results are shown in Table 2.

TABLE 1

| | |
|---|---|
| HOMO energy level evaluation method | Cyclic voltammetry (CV) (electrolyte: 0.1M $Bu_4NClO_4$/solvent: 2-MeTHF/electrode: 3 electrode system (working electrode: GC, reference electrode: Ag/AgCl, auxiliary electrode: Pt)) was used to obtain a voltage (V)-current (A) graph of each of the compounds, and then a HOMO energy level of each of the compounds was calculated from a reduction onset of the graph. |
| LUMO energy level evaluation method | Each of the compounds was diluted in 2-MeTHF to a concentration of $1 \times 10^{-5}$ M, and an UV absorption spectrum was obtained by using Shimadzu UV-350 Spectrometer at room temperature. Then, a LUMO energy level of each of the compounds was calculated by using an optical band gap (Eg) from an edge of the absorption spectrum. |
| T1 energy level evaluation method | A mixture of 2-MeTHFd and each of the compounds (1 mg of the compound in 3 cubic centimeters (cc) of 2-MeTHFd) was placed in a quartz cell, liquid nitrogen (at 77 K) was added thereto, and a photoluminescence spectrum was obtained by using a photoluminescence spectroscopy. Then, the spectrum was compared with a general photoluminescence spectrum obtained at room temperature to analyze peaks that are only observed at a low temperature, and thus a T1 energy level of each of the compounds is calculated. |

TABLE 2

| Compound No. | HOMO (eV) (actual measured value) | LUMO (eV) (actual measured value) | T1 energy level (eV) |
|---|---|---|---|
| Compound 5 | −6.11 | −2.22 | 2.81 |
| Compound 16 | −6.12 | −2.16 | 2.80 |
| Compound 32 | −5.99 | −1.85 | 3.05 |
| Compound 64 | −5.65 | −2.12 | 2.78 |
| Compound 304 | −5.62 | −2.40 | 2.73 |
| Compound 409 | −6.12 | −2.24 | 2.77 |
| Compound 417 | −6.10 | −2.45 | 2.65 |
| Compound 425 | −6.15 | −2.33 | 2.77 |
| Compound 433 | −5.70 | −2.30 | 2.81 |
| Compound 465 | −6.20 | −2.35 | 2.70 |
| Compound 468 | −6.18 | −2.48 | 2.68 |
| Compound 473 | −6.28 | −2.70 | 2.73 |
| Compound 474 | −6.15 | −2.48 | 2.67 |
| Compound 475 | −6.29 | −2.60 | 2.78 |
| Compound 486 | −5.69 | −2.45 | 2.68 |
| Compound 507 | −6.05 | −2.42 | 2.62 |
| Compound 508 | −6.19 | −2.62 | 2.66 |
| Compound 509 | −5.87 | −2.22 | 2.79 |
| Compound 510 | −6.10 | −2.26 | 2.74 |
| Compound 512 | −5.75 | −2.78 | 2.62 |
| Compound A | −5.77 | −2.80 | 2.15 |
| Compound B | −5.95 | −2.61 | 2.34 |

Compound A

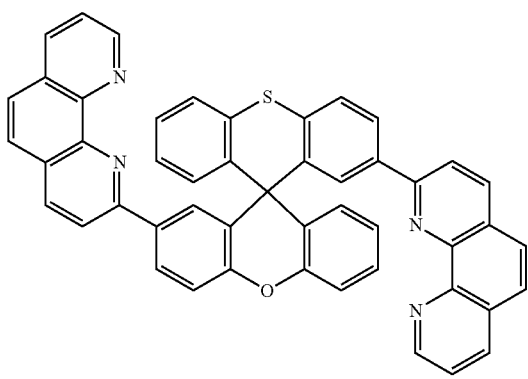

Compound B

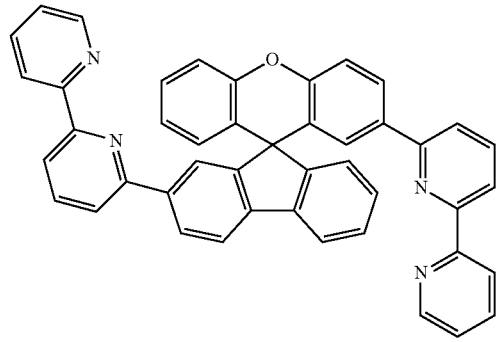

As shown in Table 2, it may be determined that the instant compounds had appropriate electric characteristics for use as a material for an organic light-emitting device. While not wishing to be bound by any particular theory, it is understood that Compounds A and B have relatively low $T_1$ energy levels, and thus, may not be appropriate for use as a material for a blue emission layer.

Evaluation Example 2

Thermal Characteristics Evaluation

Thermal analysis was performed on Compounds 5, 64, and 304 and Compound B by using Thermo Gravimetric Analysis (TGA) and Differential Scanning calorimetry (DSC) ($N_2$ atmosphere, temperature intervals: room temperature to 800° C. (10° C./min)-TGA, room temperature to 400° C.-DSC, Pan Type: a Pt Pan in a disposable Al Pan (TGA), a disposable Al pan (DSC)), and the results are shown in Table 3 in terms of their decomposition temperatures. As shown in Table 3, it was confirmed that Compounds 5, 64, and 304 had excellent thermal stability compared to that of Compound B.

TABLE 3

| Compound No. | Decomposition starting temperature (° C.) |
|---|---|
| 5 | 309 |
| 64 | 380 |
| 304 | 372 |
| B | 281 |

Example 1

As a first electrode (an anode), a glass substrate having indium tin oxide (ITO) electrode deposited thereon at a thickness of 1,500 Å was washed in distilled water using ultrasound waves. When the washing with distilled water was completed, ultrasound wave washing was performed on the substrate by using a solute such as isopropyl alcohol, acetone, or methanol. Then, the substrate was dried, transferred to a plasma washer to wash the substrate for 5 minutes using an oxygen plasma, and then mounted in a vacuum depositor.

Then, 4,4'-bis[N-(1-naphthyl)-N-phenylamino]biphenyl (NPB) was vacuum deposited on the ITO electrode on the glass substrate to form a hole transport layer having a thickness of 1,200 Å, and then mCP was vacuum deposited on the hole transport layer to form an electron blocking layer at a thickness of 100 Å, thereby forming a hole transport region.

Compound 5 (a host) and 10 percent by weight (wt %) Compound FIr6 (a dopant) were co-deposited on the hole transport region to form an emission layer having a thickness of 300 Å.

TmPyPB was vacuum deposited on the emission layer to form a hole blocking layer having a thickness of 100 Å, Alq$_3$ was deposited on the hole blocking layer to form an electron transport layer having a thickness of 250 Å, LiF was deposited on the electron transport layer to form an electron injection layer having a thickness of 5 Å, and then, an Al second electrode (a cathode) having a thickness of 1,000 Å was formed on the electron injection layer, thereby completing manufacturing of an organic light-emitting device.

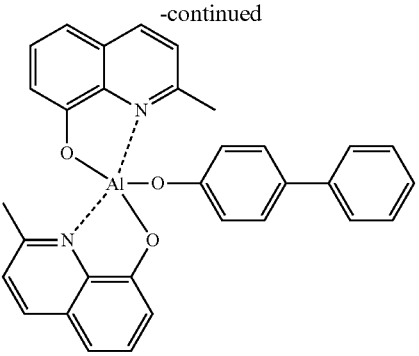

BAlq

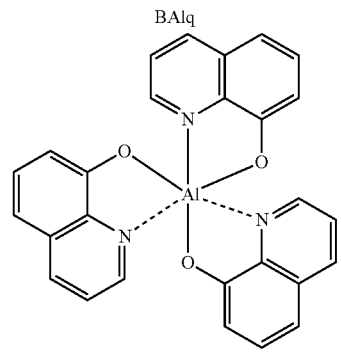

Alq$_3$

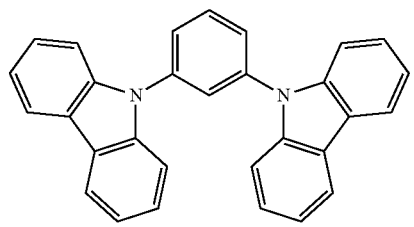

mCP

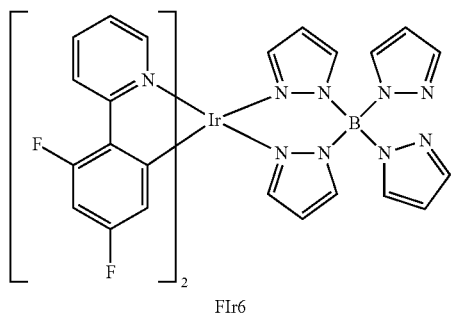

FIr6

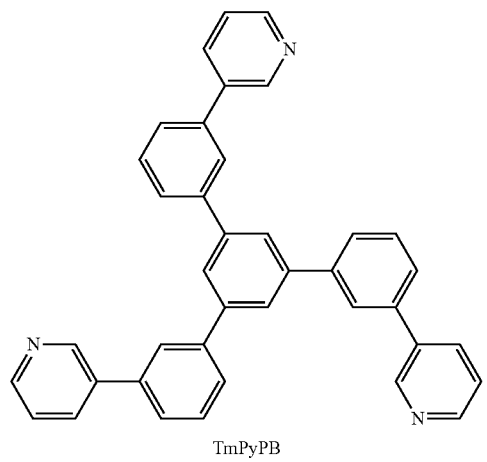

TmPyPB

Example 2

An organic light-emitting device was manufactured in the same manner as in Example 1, except that Compound 16 was used instead of Compound 5 as a host in the formation of the emission layer.

Example 3

An organic light-emitting device was manufactured in the same manner as in Example 1, except that Compound 32 was used instead of Compound 5 as a host in the formation of the emission layer.

Example 4

An organic light-emitting device was manufactured in the same manner as in Example 1, except that Compound 64 was used instead of Compound 5 as a host in the formation of the emission layer.

Example 5

An organic light-emitting device was manufactured in the same manner as in Example 1, except that Compound 304 was used instead of Compound 5 as a host in the formation of the emission layer.

Example 6

An organic light-emitting device was manufactured in the same manner as in Example 1, except that Compound 409 was used instead of Compound 5 as a host in the formation of the emission layer.

Example 7

An organic light-emitting device was manufactured in the same manner as in Example 1, except that Compound 417 was used instead of Compound 5 as a host in the formation of the emission layer.

Example 8

An organic light-emitting device was manufactured in the same manner as in Example 1, except that Compound 425 was used instead of Compound 5 as a host in the formation of the emission layer.

Example 9

An organic light-emitting device was manufactured in the same manner as in Example 1, except that Compound 433 was used instead of Compound 5 as a host in the formation of the emission layer.

Example 10

An organic light-emitting device was manufactured in the same manner as in Example 1, except that Compound 465 was used instead of Compound 5 as a host in the formation of the emission layer.

Example 11

An organic light-emitting device was manufactured in the same manner as in Example 1, except that Compound 468 was used instead of Compound 5 as a host in the formation of the emission layer.

Example 12

An organic light-emitting device was manufactured in the same manner as in Example 1, except that Compound 473 was used instead of Compound 5 as a host in the formation of the emission layer.

Example 13

An organic light-emitting device was manufactured in the same manner as in Example 1, except that Compound 474 was used instead of Compound 5 as a host in the formation of the emission layer.

Example 14

An organic light-emitting device was manufactured in the same manner as in Example 1, except that Compound 475 was used instead of Compound 5 as a host in the formation of the emission layer.

Example 15

An organic light-emitting device was manufactured in the same manner as in Example 1, except that Compound 486 was used instead of Compound 5 as a host in the formation of the emission layer.

Example 16

An organic light-emitting device was manufactured in the same manner as in Example 1, except that Compound 507 was used instead of Compound 5 as a host in the formation of the emission layer.

Example 17

An organic light-emitting device was manufactured in the same manner as in Example 1, except that Compound 508 was used instead of Compound 5 as a host in the formation of the emission layer.

Example 18

An organic light-emitting device was manufactured in the same manner as in Example 1, except that Compound 509 was used instead of Compound 5 as a host in the formation of the emission layer.

Example 19

An organic light-emitting device was manufactured in the same manner as in Example 1, except that Compound 510 was used instead of Compound 5 as a host in the formation of the emission layer.

Example 20

An organic light-emitting device was manufactured in the same manner as in Example 1, except that Compound 512 was used instead of Compound 5 as a host in the formation of the emission layer.

Comparative Example 1

An organic light-emitting device was manufactured in the same manner as in Example 1, except that Compound A was used instead of Compound 5 as a host in the formation of the emission layer.

Comparative Example 2

An organic light-emitting device was manufactured in the same manner as in Example 1, except that Compound B was used instead of Compound 5 as a host in the formation of the emission layer.

Comparative Example 3

An organic light-emitting device was manufactured in the same manner as in Example 1, except that Compound C was used instead of Compound 5 as a host in the formation of the emission layer.

Compound C

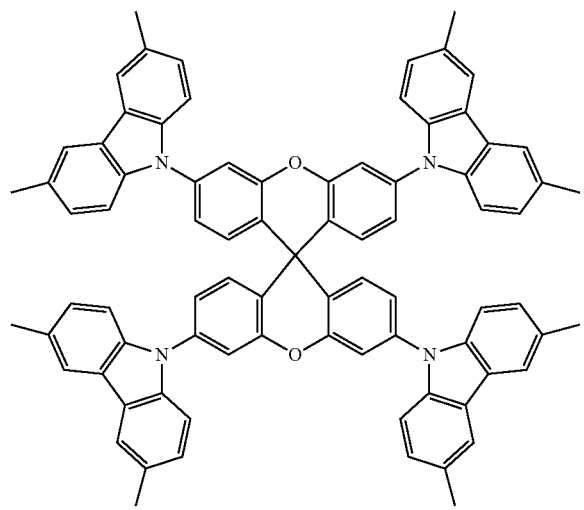

Evaluation Example 3

Evaluation of Characteristics of Organic Light-Emitting Device

Driving voltages, current efficiencies, and brightnesses of the organic light-emitting devices prepared in Examples 1 to 20 and Comparative Examples 1 to 3 were evaluated by using a luminance meter PR650 Spectroscan Source Measurement Unit (PhotoResearch) by applying power from a current-voltmeter (Keithley SMU 236). The driving voltages, current efficiencies, and brightnesses of the organic light-emitting devices prepared in Examples 2 to 20 and Comparative Examples 1 to 3 were converted to relative values based on when the driving voltage, current efficiency, and brightness of the organic light-emitting device prepared in Example 1 were set 100, and the results are shown in Table 4. In Table 4, a life span ($T_{95}$) is a time period (hr) during which an initial brightness under 500 nit set at 100% decreased to 95% after start driving the organic light-emitting devices. In Table 4, life spans ($T_{95}$) of the organic light-emitting devices prepared in Examples 2 to 20 and Comparative Examples 1 to 3 are converted into relative values based on when a life span ($T_{95}$) of the organic light-emitting device prepared in Example 1 was set 100.

TABLE 4

| Host | Dopant | Driving voltage (V) (relative value) | Efficiency (cd/A) (relative value) | $T_{95}$ (hr) (relative value) |
|---|---|---|---|---|
| Example 1 | Compound 5 | Flr6 | 100 | 100 | 100 |
| Example 2 | Compound 16 | Flr6 | 105 | 92 | 97 |
| Example 3 | Compound 32 | Flr6 | 110 | 95 | 88 |
| Example 4 | Compound 64 | Flr6 | 89 | 105 | 121 |
| Example 5 | Compound 304 | Flr6 | 85 | 107 | 110 |
| Example 6 | Compound 409 | Flr6 | 82 | 97 | 105 |
| Example 7 | Compound 417 | Flr6 | 83 | 98 | 99 |
| Example 8 | Compound 425 | Flr6 | 80 | 101 | 96 |
| Example 9 | Compound 433 | Flr6 | 92 | 109 | 93 |
| Example 10 | Compound 465 | Flr6 | 97 | 97 | 94 |
| Example 11 | Compound 468 | Flr6 | 103 | 97 | 90 |
| Example 12 | Compound 473 | Flr6 | 102 | 95 | 92 |

TABLE 4-continued

| Host | Dopant | Driving voltage (V) (relative value) | Efficiency (cd/A) (relative value) | $T_{95}$ (hr) (relative value) |
|---|---|---|---|---|
| Example 13 | Compound 474 | Flr6 | 100 | 93 | 89 |
| Example 14 | Compound 475 | Flr6 | 112 | 93 | 80 |
| Example 15 | Compound 486 | Flr6 | 95 | 101 | 93 |
| Example 16 | Compound 507 | Flr6 | 110 | 99 | 97 |
| Example 17 | Compound 508 | Flr6 | 108 | 102 | 92 |
| Example 18 | Compound 509 | Flr6 | 112 | 92 | 89 |
| Example 19 | Compound 510 | Flr6 | 81 | 105 | 103 |
| Example 20 | Compound 512 | Flr6 | 119 | 89 | 75 |
| Comparative Example 1 | Compound A | Flr6 | 123 | 72 | 67 |
| Comparative Example 2 | Compound B | Flr6 | 120 | 75 | 72 |
| Comparative Example 3 | Compound C | Flr6 | 113 | 78 | 75 |

As shown in Table 4, it was confirmed that the organic light-emitting devices prepared in Examples 1 to 20 had low driving voltages, high efficiencies, and long lifespans compared to those of the organic light-emitting devices prepared in Comparative Examples 1 to 3. While not wishing to be bound by any particular theory, it is understood that Compound C has a high molecular weight (1,121.37 g/mol), and thus a deposition temperature of Compound C is relatively high. Also, Compound C has four C—N bonds between carbazole and a core, so when an organic light-emitting device includes Compound C, the organic light-emitting device may have a relatively high driving voltage and a short life span.

As described above, according to the one or more of the above embodiments, a condensed cyclic compound has excellent electrical characteristics and thermal stability, and thus, when an organic light-emitting device includes the condensed cyclic compound, the organic light-emitting device may have a low driving voltage, a high efficiency, a high brightness, and a long life span.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the FIGURES, it will be understood by those of ordinary skill in the art that various changes in form and details may be made therein without departing from the spirit and scope of the present disclosure as defined by the following claims.

What is claimed is:

1. A condensed cyclic compound represented by Formula 1(4):

Formula 1(4)

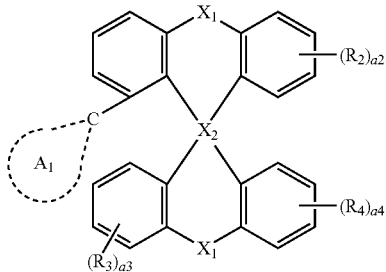

wherein, in Formula 1(4),
each $X_1$ is independently O or S, provided that at least one $X_1$ is S,
$X_2$ is C,
ring $A_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group,
$R_2$ to $R_4$ are each independently selected from a hydrogen, a deuterium, —F, —Cl, —Br, —I, a cyano group, a nitro group, an amidino group, a hydrazine group, a hydrazone group, a sulfonic acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_3$)($Q_4$)($Q_5$), and —B($Q_6$)($Q_7$);
a2, a3, and a4 are each independently an integer selected from 0 to 4; and
when a2 is 2 or greater, groups $R_2$ are identical to or different from each other,
when a3 is 2 or greater, groups $R_3$ are identical to or different from each other, and
when a4 is 2 or greater, groups $R_4$ are identical to or different from each other,
at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from
a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{60}$ alkyl group, $C_2$-$C_{60}$ alkenyl group, $C_2$-$C_{60}$ alkynyl group and $C_1$-$C_{60}$ alkoxy group;
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;
a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and
—N($Q_{31}$)($Q_{32}$), —Si($Q_{33}$)($Q_{34}$)($Q_{35}$), and —B($Q_{36}$)($Q_{37}$), and
$Q_3$ to $Q_7$, $Q_{11}$ to $Q_{17}$, $Q_{21}$ to $Q_{27}$, and $Q_{31}$ to $Q_{37}$ are each independently selected from a hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted heterocycloalkyl group, a substituted or unsubstituted $C_3$-$C_{10}$ cycloalkenyl group, a substituted or unsubstituted heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted heteroaryl group, a substituted or unsubstituted monovalent non-aromatic condensed polycyclic group, and a substituted or unsubstituted monovalent non-aromatic condensed heteropolycyclic group.

2. The condensed cyclic compound of claim 1, wherein ring $A_1$ is selected from
- a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a dibenzofuranyl group, a dibenzothiophenyl group, a triazinyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group; and
- a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$), and
- a phenyl group, a triphenylenyl group, a pyrimidinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$), and $Q_{31}$ to $Q_{35}$ are each independently selected from
- a hydrogen, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group; and
- a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group.

3. The condensed cyclic compound of claim 1, wherein $R_2$ to $R_4$ are each independently selected from:
- a hydrogen, a deuterium, —F, —Cl, —Br, —I, a cyano group, a nitro group, an amidino group, a hydrazine group, a hydrazone group, a sulfonic acid group or a salt thereof, and a $C_1$-$C_{20}$ alkyl group;
- a $C_1$-$C_{20}$ alkyl group and a $C_1$-$C_{20}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a pyridinyl group, a pyrimidinyl group, and a triazinyl group;
- a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group;

a cyclopentyl group, a cyclohexyl group, a cyclopentenyl group, a cyclohexenyl group, a cycloheptenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pyrrolyl group, an imidazolyl group, a pyrazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoxazolyl group, a benzoimidazolyl group, a furanyl group, a benzofuranyl group, a thiophenyl group, a benzothiophenyl group, a thiazolyl group, an isothiazolyl group, a benzothiazolyl group, an isoxazolyl group, an oxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, an imidazopyrimidinyl group, an imidazopyridinyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$); and Si($Q_3$)($Q_4$)($Q_5$), and $Q_3$ to $Q_5$ and $Q_{31}$ to $Q_{35}$ are each independently selected from a hydrogen, a $C_1$-$C_{20}$ alkyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group; and a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group a phthalazinyl group, a quinoxalinyl group, a cinnolinyl group, and a quinazolinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_2$-$C_{20}$ alkenyl group, a $C_2$-$C_{20}$ alkynyl group, a $C_1$-$C_{20}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, and a quinazolinyl group, wherein selection of $R_1$ to $R_4$ is subject to limitations of claim 1.

4. The condensed cyclic compound of claim 1, wherein $R_2$ to $R_4$ are each independently selected from:

a hydrogen, a deuterium, —F, —Cl, —Br, —I, a cyano group, a nitro group, an amidino group, a hydrazine group, a hydrazone group, a sulfonic acid group or a salt thereof, and a $C_1$-$C_{10}$ alkyl group;

a $C_1$-$C_{10}$ alkyl group and a $C_1$-$C_{10}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group;

a phenyl group, a naphthyl group, a fluorenyl group, a spiro-fluorenyl group, a phenanthrenyl group, an anthracenyl group, a triphenylenyl group, a pyrenyl group, a chrysenyl group, a pyridinyl group, a pyrazinyl group, a pyrimidinyl group, a pyridazinyl group, an isoindolyl group, an indolyl group, a quinolinyl group, an isoquinolinyl group, a benzoquinolinyl group, a quinoxalinyl group, a quinazolinyl group, a carbazolyl group, a furanyl group, a benzofuranyl group, a thiophenyl group, a benzothiophenyl group, a triazinyl group, a dibenzofuranyl group, a dibenzothiophenyl group, a benzocarbazolyl group, a dibenzocarbazolyl group, a pyridoindolyl group, a benzofuropyridinyl group, a benzothienopyridinyl group, a pyrimidoindolyl group, a benzofuropyrimidinyl group, a benzothienopyrimidinyl group, a phenoxazinyl group, a pyridobenzooxazinyl group, and a pyridobenzothiazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$); and —Si($Q_3$)($Q_4$)($Q_5$), and $Q_3$ to $Q_5$ and $Q_{31}$ to $Q_{35}$ are each independently selected from a hydrogen, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group; and a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, wherein selection of $R_1$ to $R_4$ is subject to limitations of claim 1.

5. The condensed cyclic compound of claim 1, wherein $R_2$ to $R_4$ are each independently selected from a hydrogen, a deuterium, —F, —Cl, —Br, —I, a cyano group, a nitro group, an amidino group, a hydrazine group, a hydrazone group, a sulfonic acid group or a salt thereof, a $C_1$-$C_{20}$ alkyl group, —Si($Q_3$)($Q_4$)($Q_5$), and groups represented by Formulae 2-1 to 2-59:

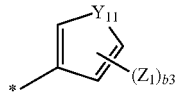

Formula 2-1

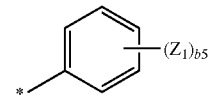

Formula 2-2

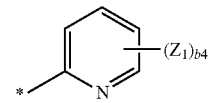

Formula 2-3

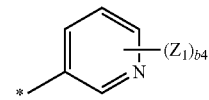

Formula 2-4

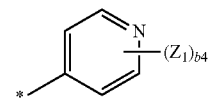

Formula 2-5

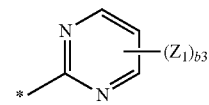

Formula 2-6

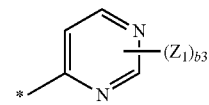

Formula 2-7

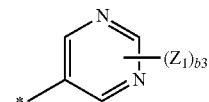

Formula 2-8

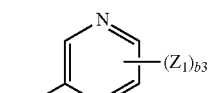

Formula 2-9

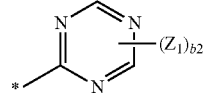

Formula 2-10

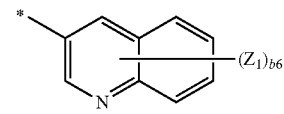

Formula 2-11

-continued
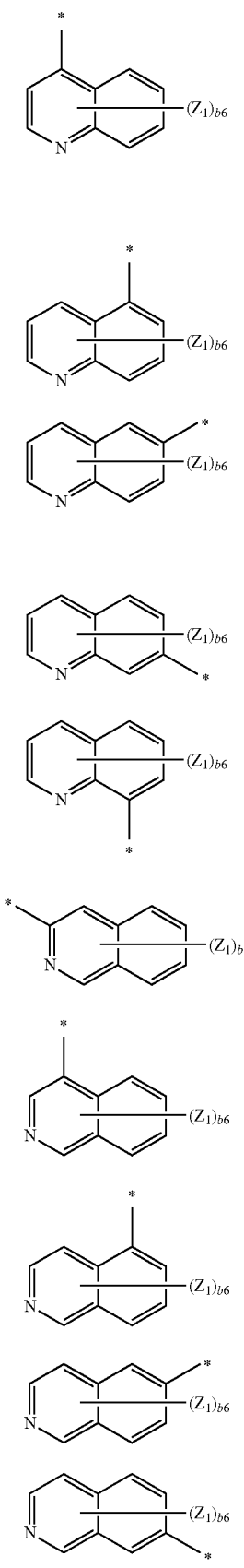
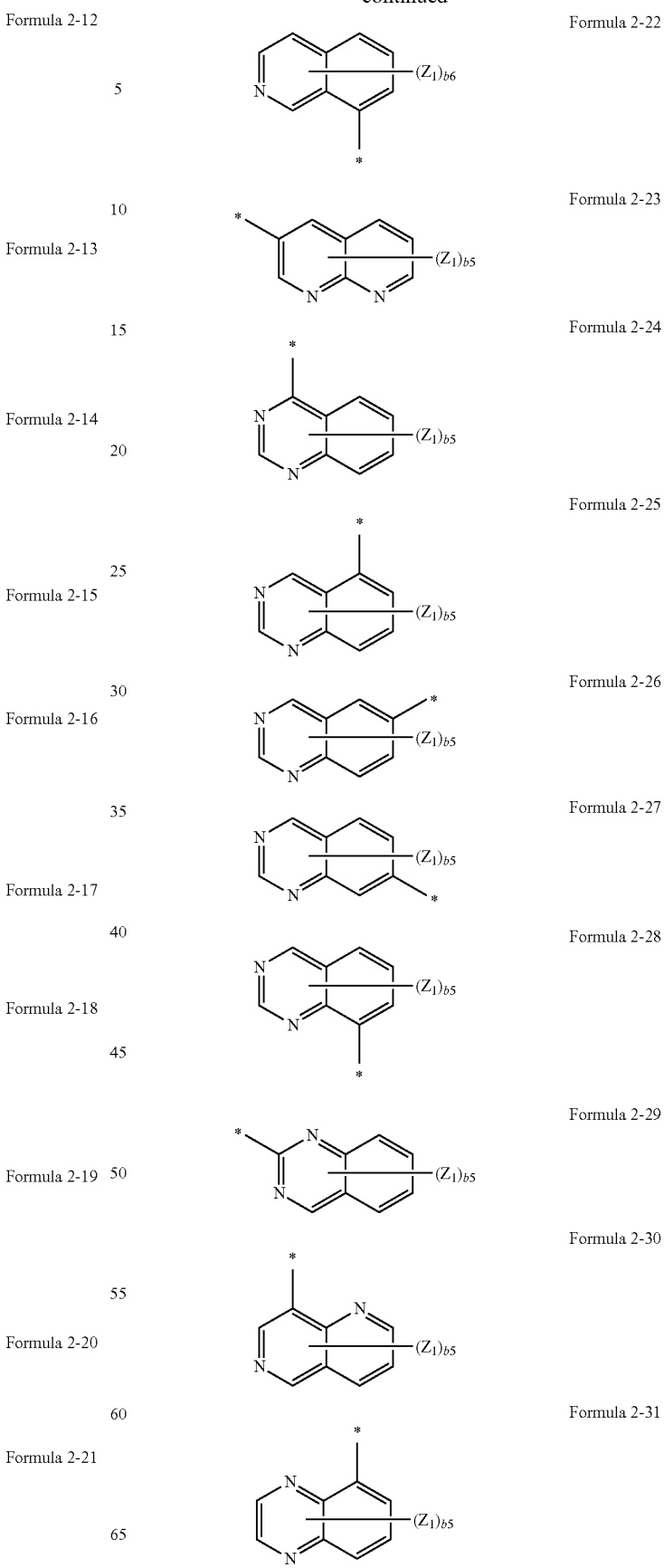

Formula 2-32
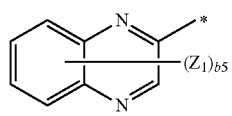
Formula 2-33
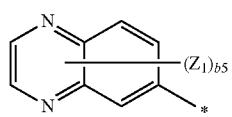
Formula 2-34
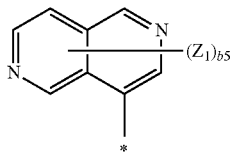
Formula 2-35
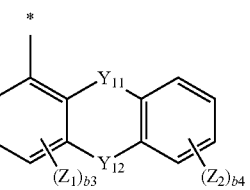
Formula 2-36
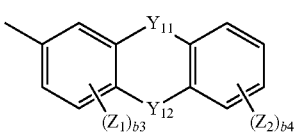
Formula 2-37
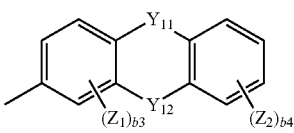
Formula 2-38
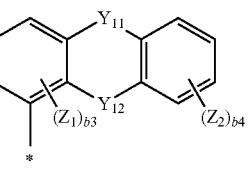
Formula 2-39
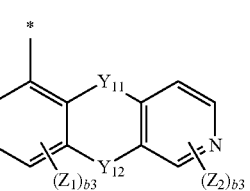
Formula 2-40
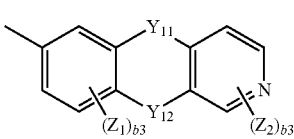
Formula 2-41
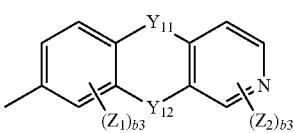
Formula 2-42
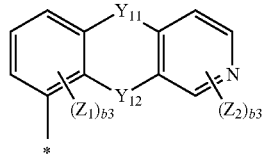
Formula 2-43
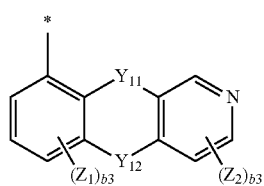
Formula 2-44
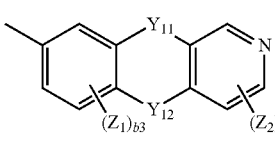
Formula 2-45
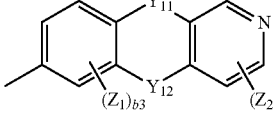
Formula 2-46
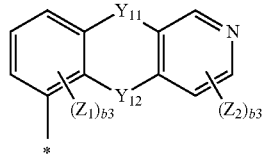
Formula 2-47
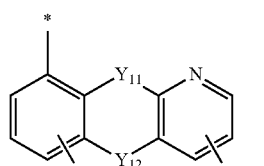
Formula 2-48
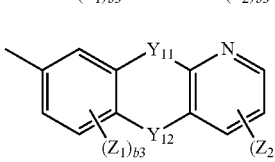
Formula 2-49
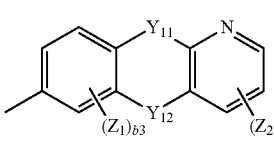
Formula 2-50
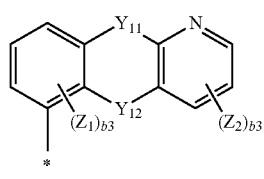

-continued

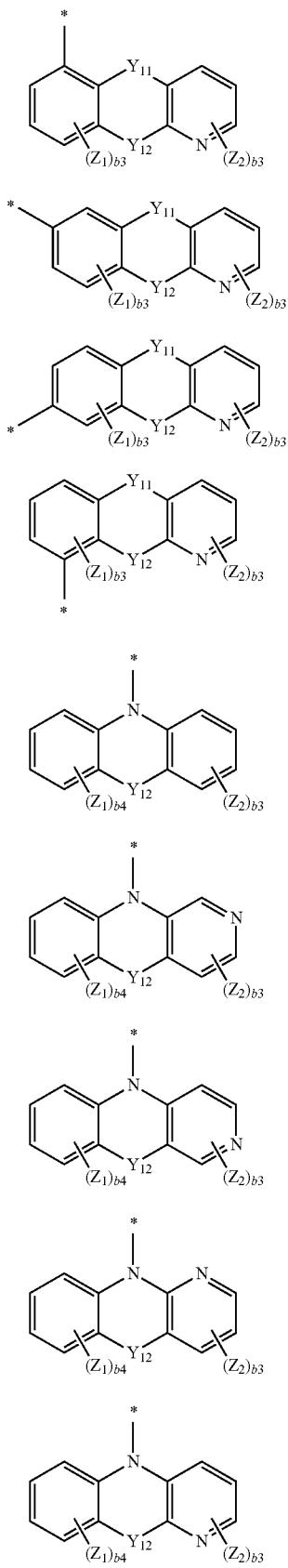

Formula 2-51
Formula 2-52
Formula 2-53
Formula 2-54
Formula 2-55
Formula 2-56
Formula 2-57
Formula 2-58
Formula 2-59 wherein, in Formulae 2-1 to 2-59,
$Y_{11}$ is O, S, N($Z_3$), or C($Z_3$)($Z_4$),
$Y_{12}$ is a single bond, O, S, N($Z_5$), or C($Z_5$)($Z_6$),
$Z_1$ to $Z_6$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a benzocarbazolyl group, a dibenzocarbazolyl group, a pyridinyl group, a pyrimidinyl group, a pyrazinyl group, a pyridazinyl group, a triazinyl group, a quinolinyl group, an isoquinolinyl group, a phthalazinyl group, a quinoxalinyl group, a cinnolinyl group, a quinazolinyl group, —N($Q_{31}$)($Q_{32}$), and —Si($Q_{33}$)($Q_{34}$)($Q_{35}$),
$Q_3$ to $Q_5$ and $Q_{31}$ to $Q_{35}$ are each independently selected from
a hydrogen, $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group; and
a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, an anthracenyl group, a pyrenyl group, a phenanthrenyl group, a fluorenyl group, a carbazolyl group, a pyridinyl group, a pyrimidinyl group, a pyrazinyl group, a pyridazinyl group, and a triazinyl group,
wherein selection of $R_1$ to $R_4$ is subject to limitations of claim 1,
b2 is an integer of 1 or 2,
b3 is an integer selected from 1 to 3,
b4 is an integer selected from 1 to 4,
b5 is an integer selected from 1 to 5, and
b6 is an integer selected from 1 to 6, and
\* is a binding site to a neighboring atom.

6. The condensed cyclic compound of claim 5, wherein, in Formulae 2-34 to 2-39, $Y_{11}$ is O, S, or N($Z_3$), and $Y_{12}$ is a single bond or O.

7. The condensed cyclic compound of claim 5, wherein $R_2$ to $R_4$ are each independently selected from a hydrogen, a deuterium, —F, —Cl, —Br, —I, a cyano group, a nitro group, an amidino group, a hydrazine group, a hydrazone group, a sulfonic acid group or a salt thereof, a $C_1$-$C_{10}$ alkyl group, —Si($Q_3$)($Q_4$)($Q_5$), and groups represented by Formulae 2-1 to 2-10 and 2-35 to 2-54,
wherein, in Formulae 2-1 to 2-10 and 2-35 to 2-54,
$Y_{11}$ is O, S, or N($Z_3$),
$Y_{12}$ is a single bond or O,
$Z_1$ to $Z_8$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a pyridinyl group, a pyrimidinyl group, a pyrazinyl group, a pyridazinyl group, and a triazinyl group, $Q_3$ to $Q_5$ are each independently selected from a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group; and a phenyl group, a naphthyl group, a pyridinyl group, a pyrimidinyl group, a pyrazinyl group, a pyridazinyl group, and a triazinyl group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a phenyl group, a naphthyl group, a pyridinyl group, a pyrimidinyl group, a pyrazinyl group, a pyridazinyl group, and a triazinyl group, wherein selection of $R_1$ to $R_4$ is subject to limitations of claim 1;

b2 to b6 are each independently 1 or 2, and

\* is a binding site to a neighboring atom.

8. The condensed cyclic compound of claim 1, wherein ring $A_1$ is selected from groups represented by Formulae 3-1, 3-20 to 3-26, 3-28 to 3-40, and 3-42 to 3-121, $R_2$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, —Si($Q_3$)($Q_4$)($Q_5$) (wherein, $Q_3$ to $Q_5$ are each independently a phenyl group, a phenyl group substituted with a phenyl group, a naphthyl group, a pyridinyl group, a pyrimidinyl group, a pyrazinyl group, a pyridazinyl group, and a triazinyl group), and groups represented by Formulae 3-1 to 3-131:

Formula 3-1

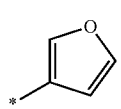

Formula 3-2

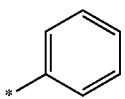

Formula 3-3

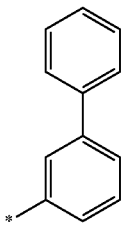

-continued

Formula 3-4

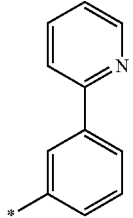

Formula 3-5

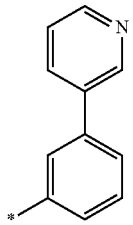

Formula 3-6

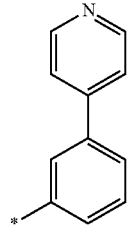

Formula 3-7

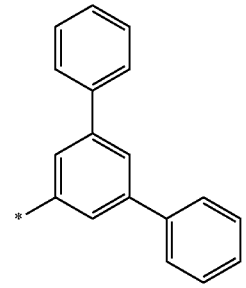

Formula 3-8

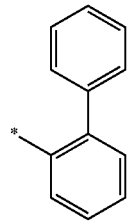

Formula 3-9

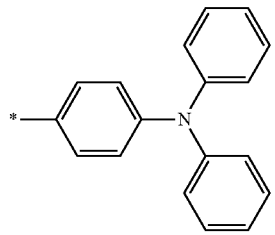

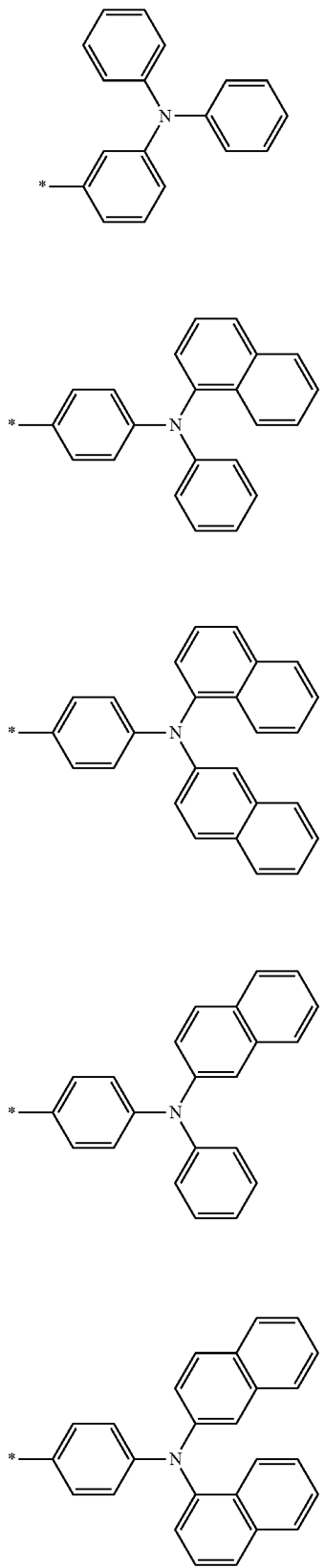
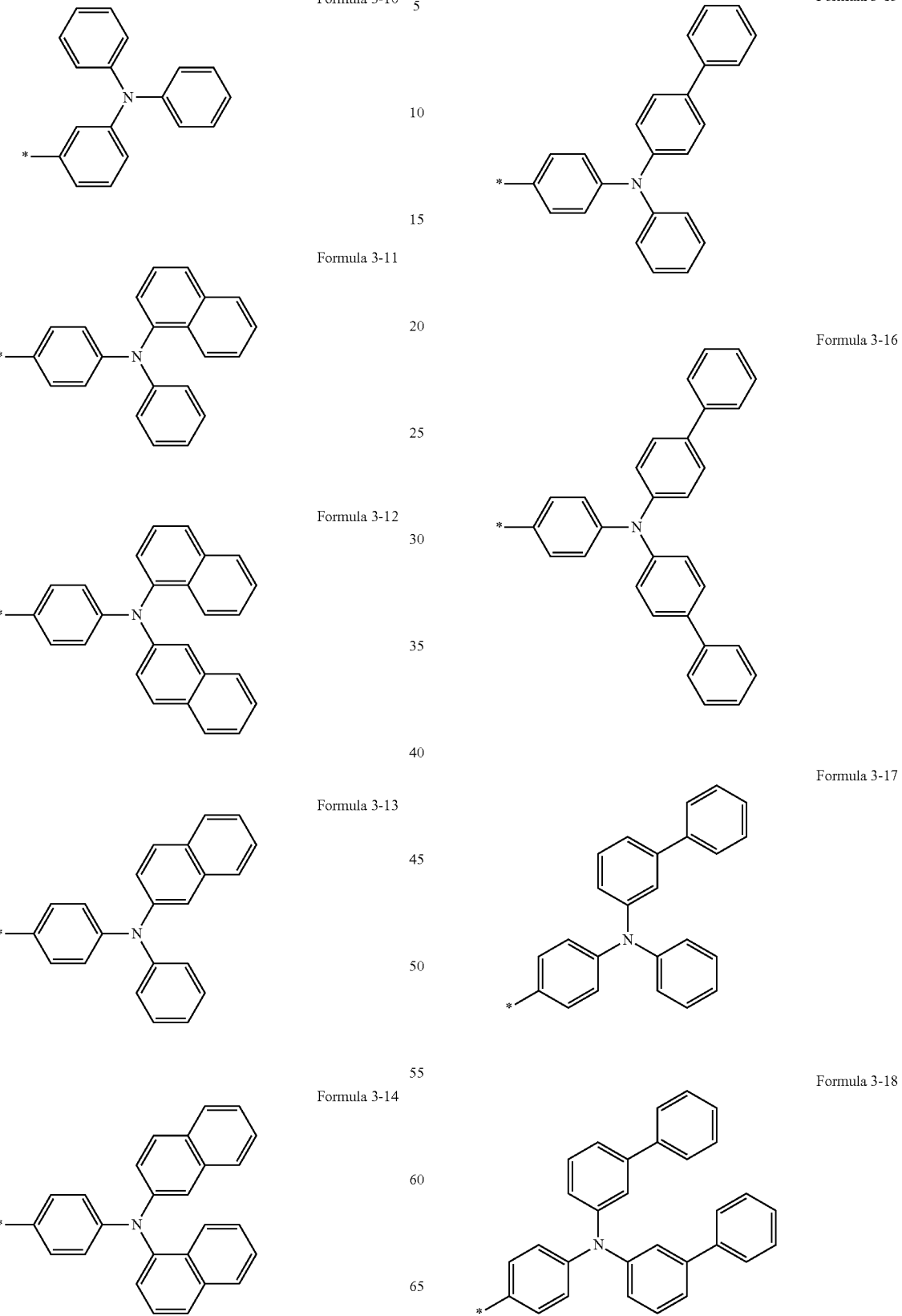

US 10,505,128 B2
273
-continued
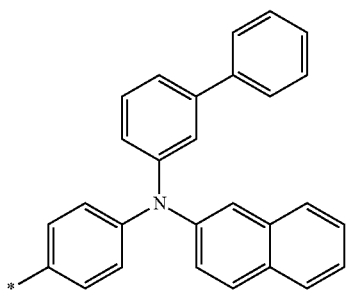
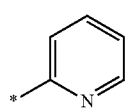
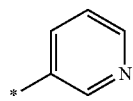
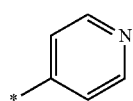
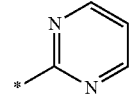
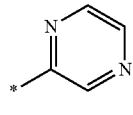
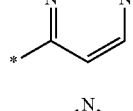
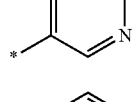
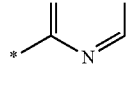
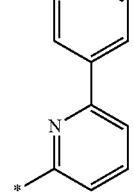
274
-continued
Formula 3-19
Formula 3-20
Formula 3-21
Formula 3-22
Formula 3-23
Formula 3-24
Formula 3-25
Formula 3-26
Formula 3-27
Formula 3-28
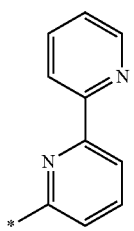
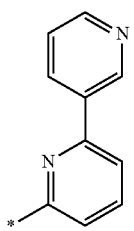
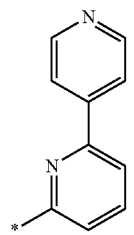
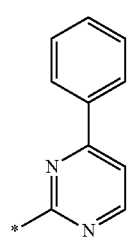
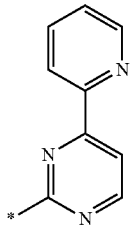
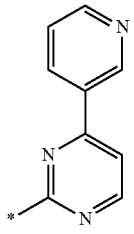
Formula 3-29
Formula 3-30
Formula 3-31
Formula 3-32
Formula 3-33
Formula 3-34

Formula 3-35
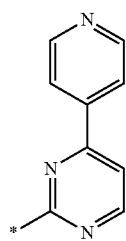
Formula 3-36
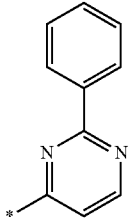
Formula 3-37
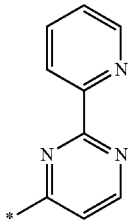
Formula 3-38
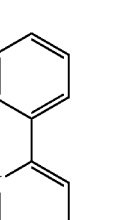
Formula 3-39
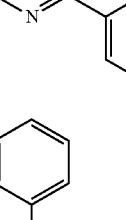
Formula 3-40
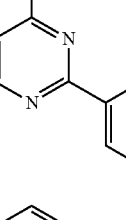
Formula 3-41
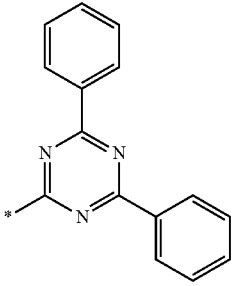
Formula 3-42
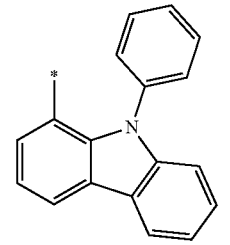
Formula 3-43
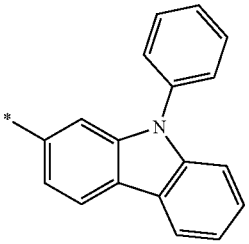
Formula 3-44
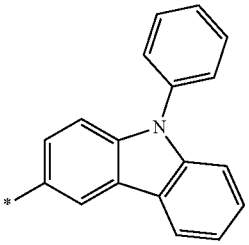
Formula 3-45
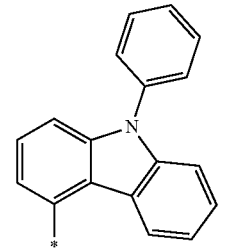
Formula 3-46
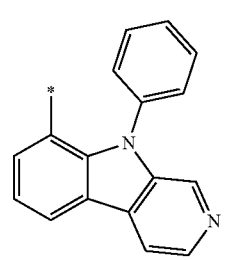

| | |
|---|---|
| -continued | -continued |
| 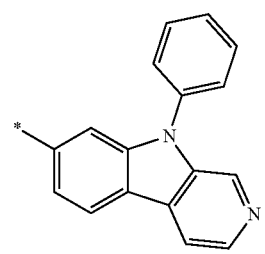   Formula 3-47 | 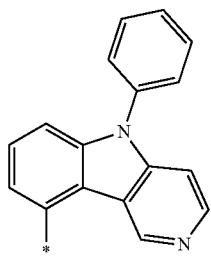   Formula 3-53 |
| 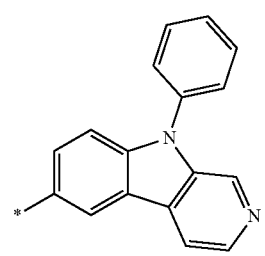   Formula 3-48 | 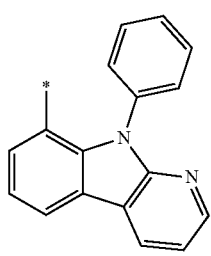   Formula 3-54 |
| 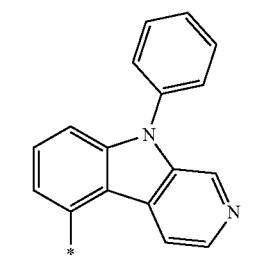   Formula 3-49 | 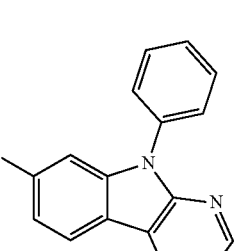   Formula 3-55 |
| 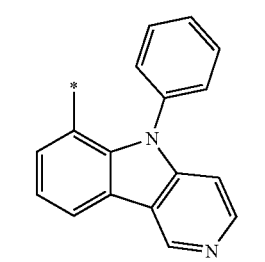   Formula 3-50 | 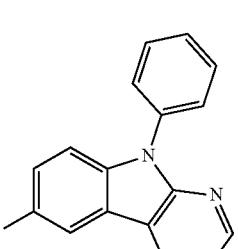   Formula 3-56 |
| 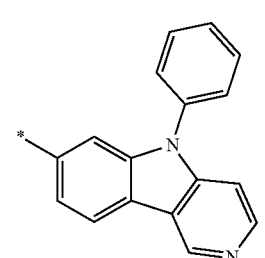   Formula 3-51 | 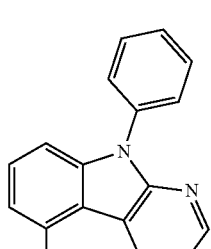   Formula 3-57 |
| 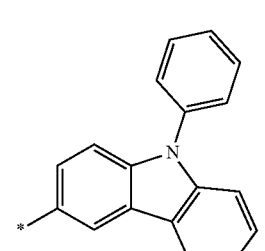   Formula 3-52 | 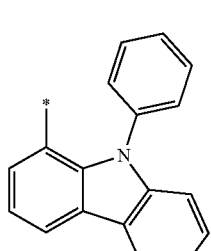   Formula 3-58 |

Formula 3-59
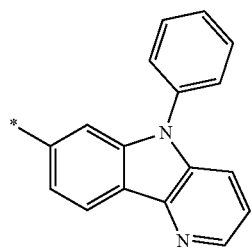
Formula 3-60
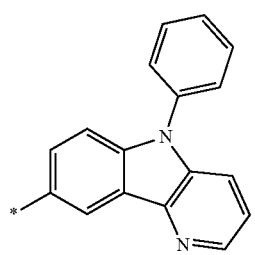
Formula 3-61
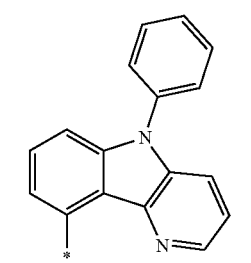
Formula 3-62
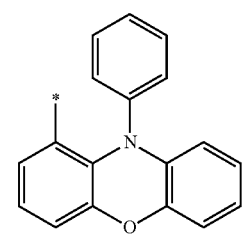
Formula 3-63
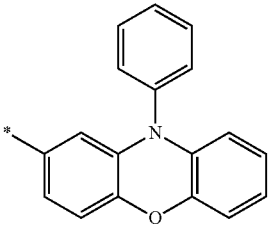
Formula 3-64
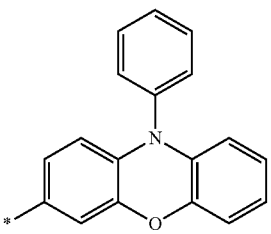
Formula 3-65
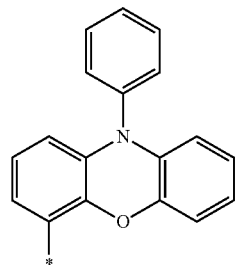
Formula 3-66
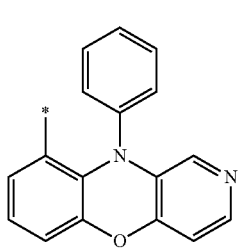
Formula 3-67
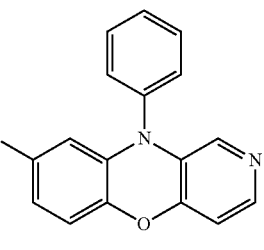
Formula 3-68
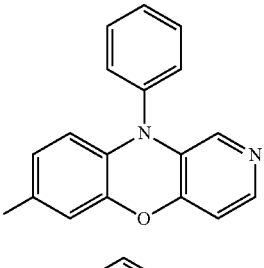
Formula 3-69
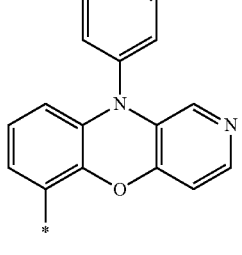
Formula 3-70
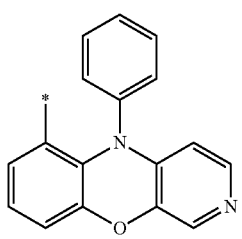

281
-continued
Formula 3-71
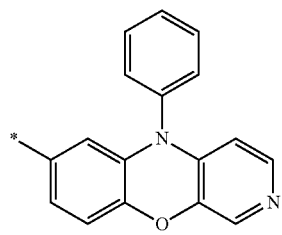
Formula 3-72
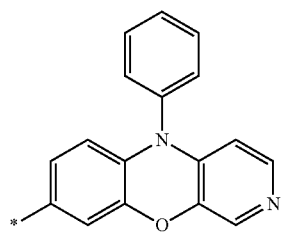
Formula 3-73
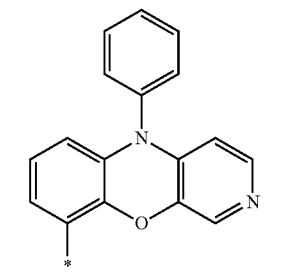
Formula 3-74
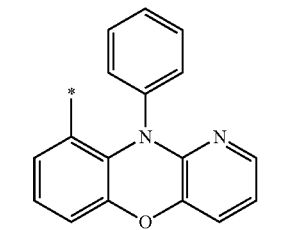
Formula 3-75
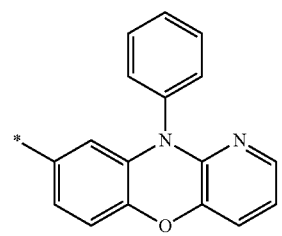
Formula 3-76
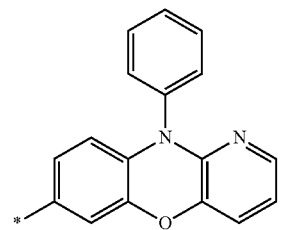
282
-continued
Formula 3-77
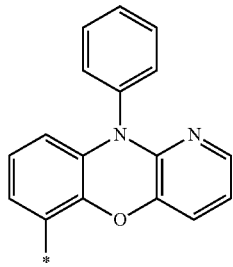
Formula 3-78
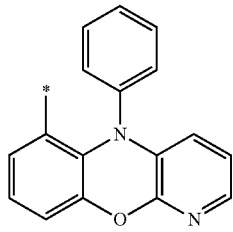
Formula 3-79
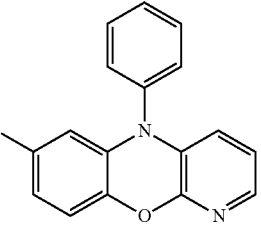
Formula 3-80
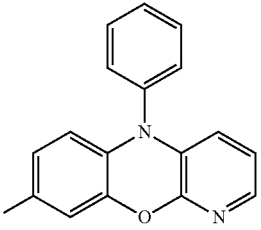
Formula 3-81
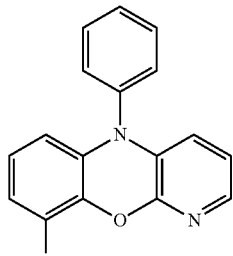
Formula 3-82
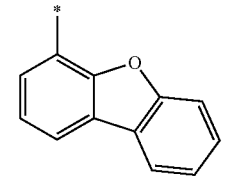
Formula 3-83
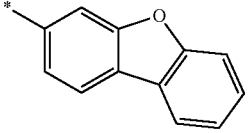

Formula 3-84
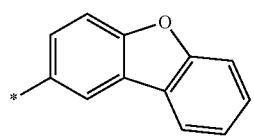
Formula 3-85
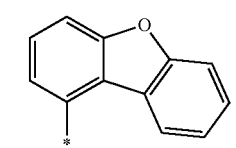
Formula 3-86
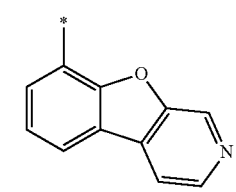
Formula 3-87
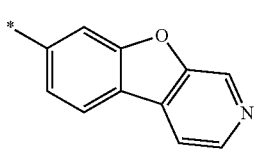
Formula 3-88
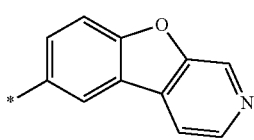
Formula 3-89
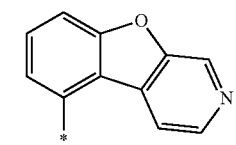
Formula 3-90
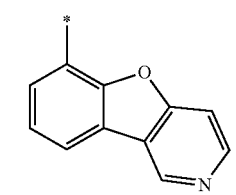
Formula 3-91
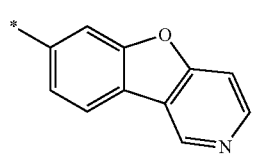
Formula 3-92
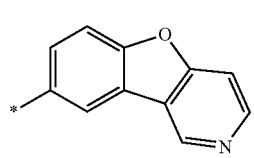
Formula 3-93
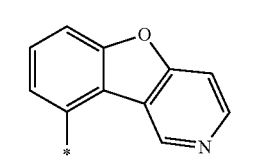
Formula 3-94
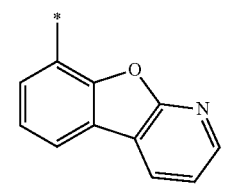
Formula 3-95
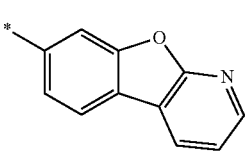
Formula 3-96
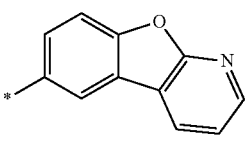
Formula 3-97
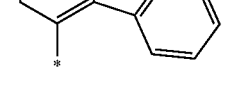
Fiormula 3-98
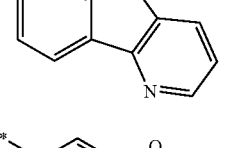
Formula 3-99
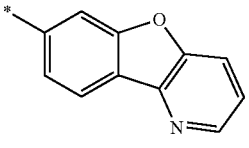
Formula 3-100
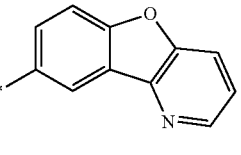
Formula 3-101
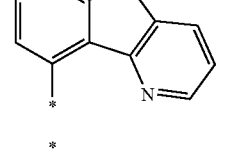
Formula 3-102
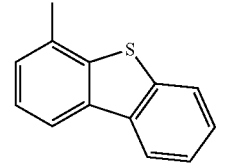
Formula 3-103
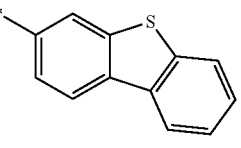
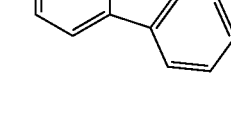

-continued
Formula 3-104
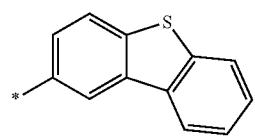
Formula 3-105
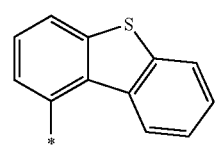
Formula 3-106
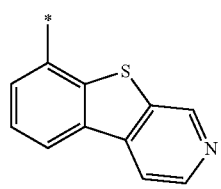
Formula 3-107
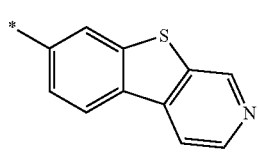
Formula 3-108
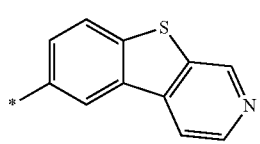
Formula 3-109
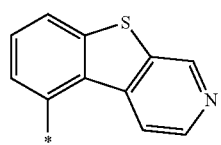
Formula 3-110
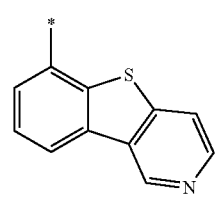
Formula 3-111
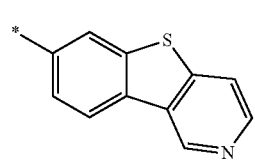
Formula 3-112
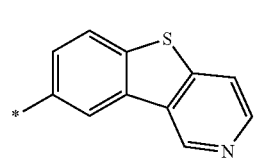
Formula 3-113
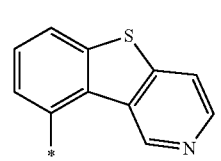
-continued
Formula 3-114
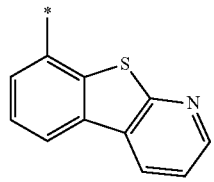
Formula 3-115
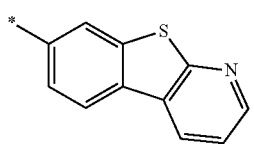
Formula 3-116
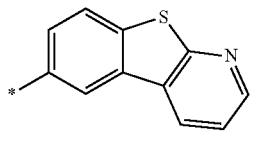
Formula 3-117
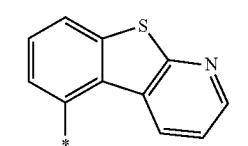
Formula 3-118
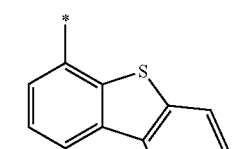
Formula 3-119
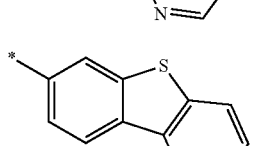
Formula 3-120
Formula 3-121
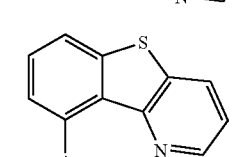
Formula 3-122
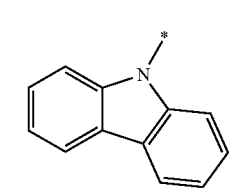

-continued

Formula 3-123
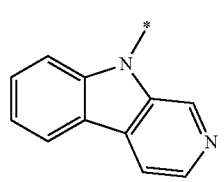

Formula 3-124
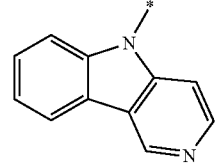

Formula 3-125
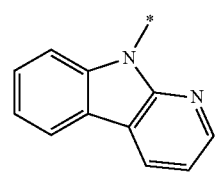

Formula 3-126
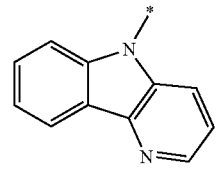

Formula 3-127
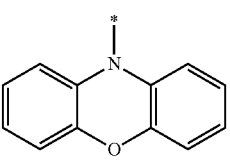

Formula 3-128
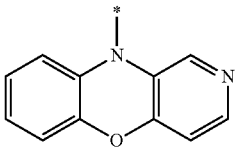

Formula 3-129
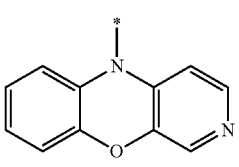

Formula 3-130
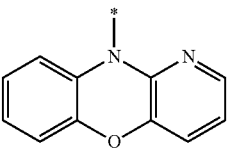

Formula 3-131
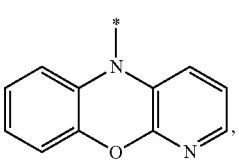

wherein selection of $R_1$ to $R_4$ is subject to limitations of claim 1.

9. A condensed cyclic compound represented by one of Formulae 1(1) to 1(3):

Formula 1(1)
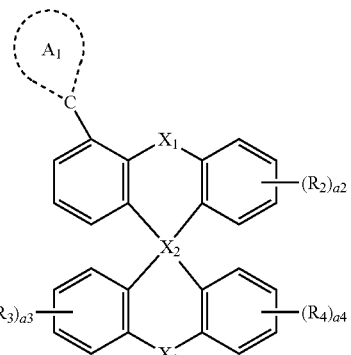

Formula 1(2)
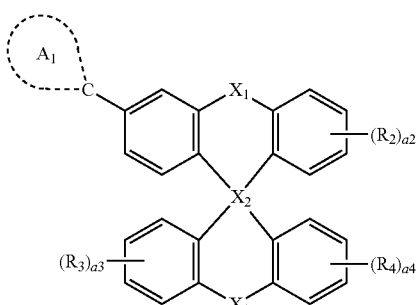

Formula 1(3)
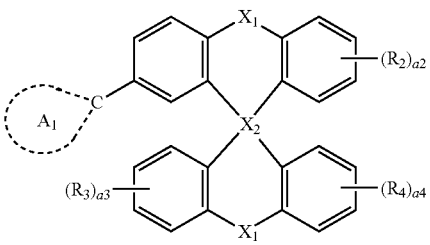

wherein, in Formulae 1(1) to 1(3), $X_1$ is O or S, provided that at least one $X_1$ is S, $X_2$ is C, Si, or Ge, ring $A_1$ is selected from groups represented by Formulae 3-1, 3-20 to 3-26, 3-28 to 3-40 and 3-42 to 3-121, a2, a3, and a4 are each independently an integer selected from 1 to 4, and $R_2$ to $R_4$ are each independently selected from a hydrogen, a deuterium, —F, —Cl, —Br, —I, a cyano group, a nitro group, an amidino group, a hydrazine group, a hydrazone group, a sulfonic acid group or a salt thereof, a $C_1$-$C_{20}$ alkyl group, —Si($Q_3$)($Q_4$)($Q_5$) (wherein, $Q_3$ to $Q_5$ are each independently a phenyl group, a phenyl group substituted with a phenyl group, a naphthyl group, a pyridinyl group, a pyrimidinyl group, a pyrazinyl group, a pyridazinyl group, and a triazinyl group), and groups represented by Formulae 3-1 to 3-131, provided that when each $X_1$ is O and $X_2$ is C, at least one of $R_2$ to $R_4$ is selected from groups represented by Formulae 3-3 to 3-19, 3-28 to 3-81, 3-86 to 3-101, 3-106 to 3-121, and 3-127 to 3-131:

Formula 3-1
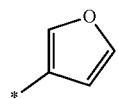

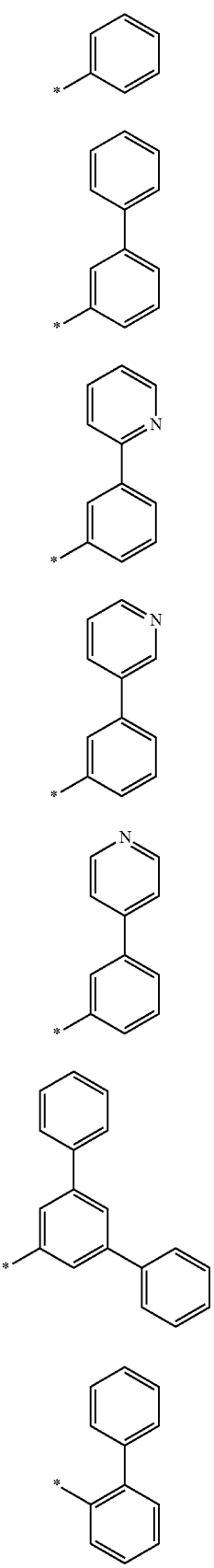
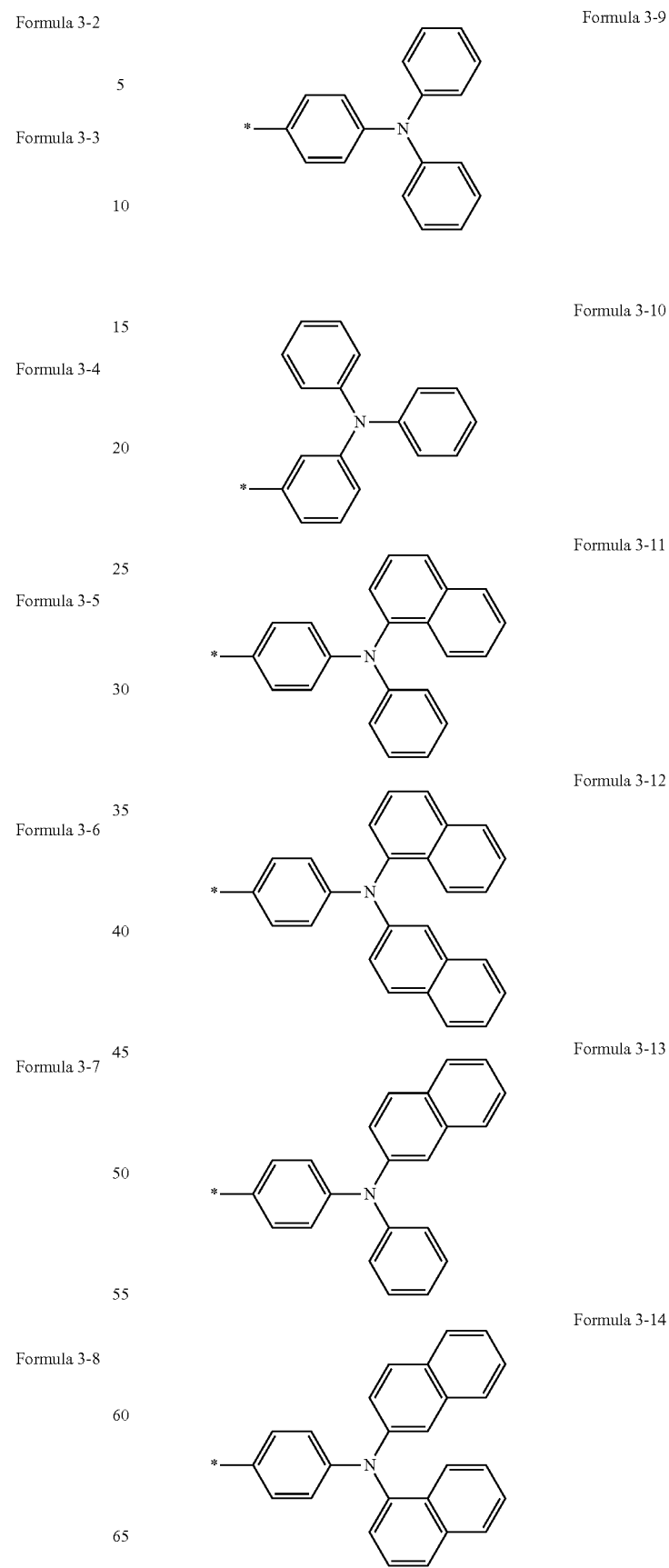

Formula 3-15
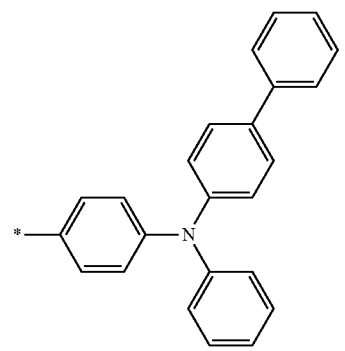
Formula 3-16
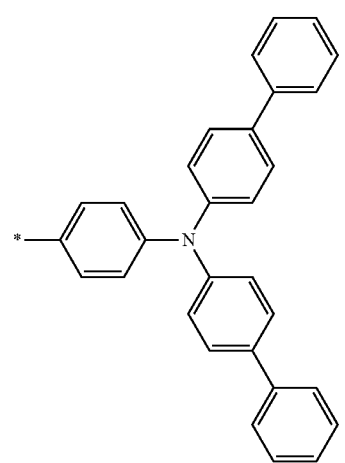
Formula 3-17
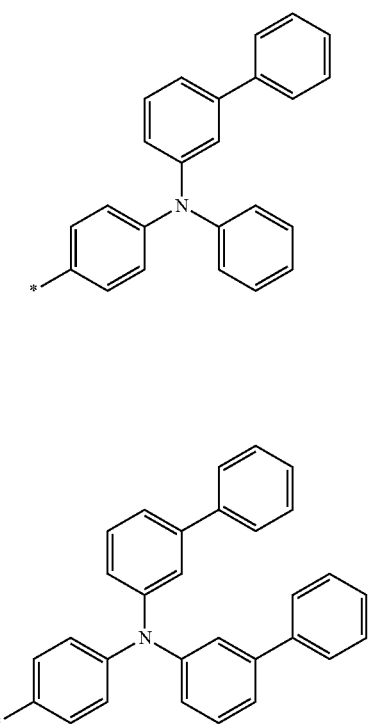
Formula 3-18
Formula 3-19
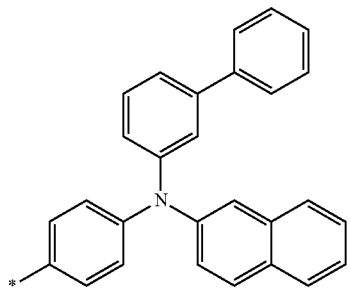
Formula 3-20
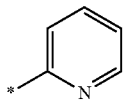
Formula 3-21
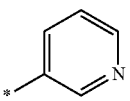
Formula 3-22
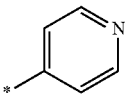
Formula 3-23
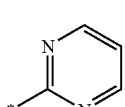
Formula 3-24
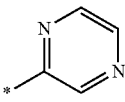
Formula 3-25
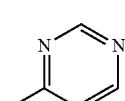
Formula 3-26
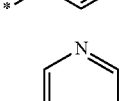
Formula 3-27
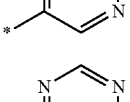
Formula 3-28
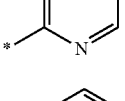

Formula 3-29

Formula 3-30

Formula 3-31

Formula 3-32

Formula 3-33

Formula 3-34

Formula 3-35

Formula 3-36

Formula 3-7

Formula 3-38

Formula 3-39

Formula 3-40

Formula 3-41

Formula 3-42

Formula 3-43

Formula 3-44

Formula 3-45

Formula 3-46

Formula 3-47

Formula 3-48

Formula 3-49

Formula 3-50

Formula 3-51

Formula 3-52

Formula 3-53
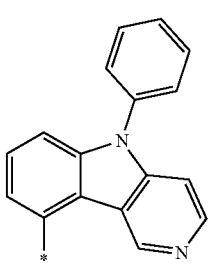
Formula 3-54
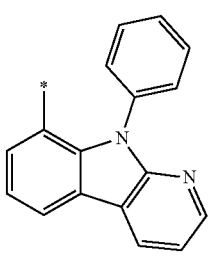
Formula 3-55
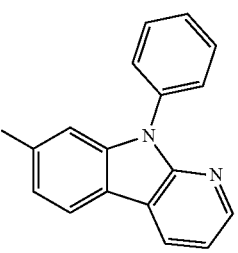
Formula 3-56
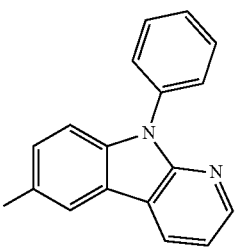
Formula 3-57
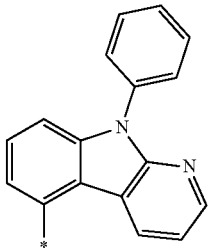
Formula 3-58
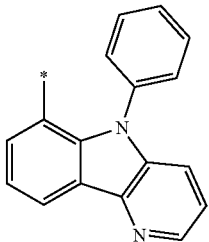
Formula 3-59
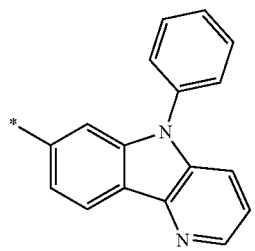
Formula 3-60
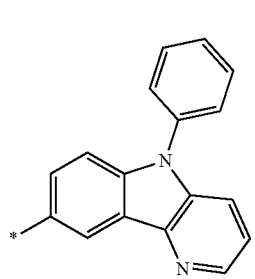
Formula 3-61
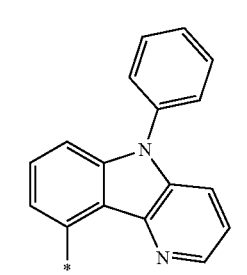
Formula 3-62
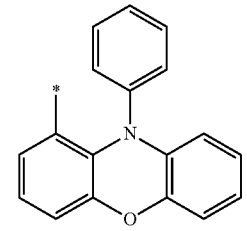
Formula 3-63
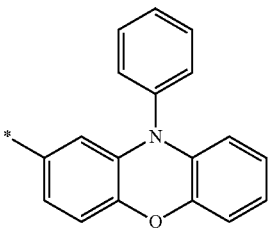
Formula 3-64
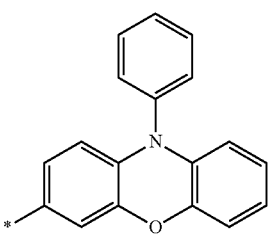

Formula 3-65

Formula 3-66

Formula 3-67

Formula 3-68

Formula 3-69

Formula 3-70

Formula 3-71

Formula 3-72

Formula 3-73

Formula 3-74

Formula 3-75

Formula 3-76

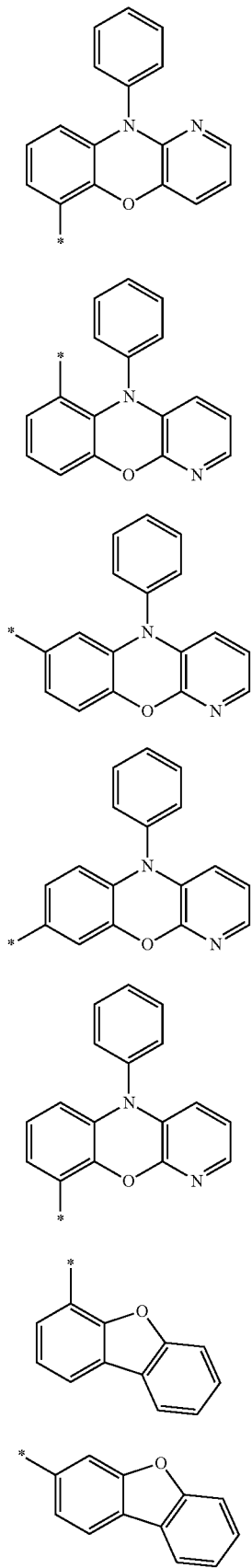
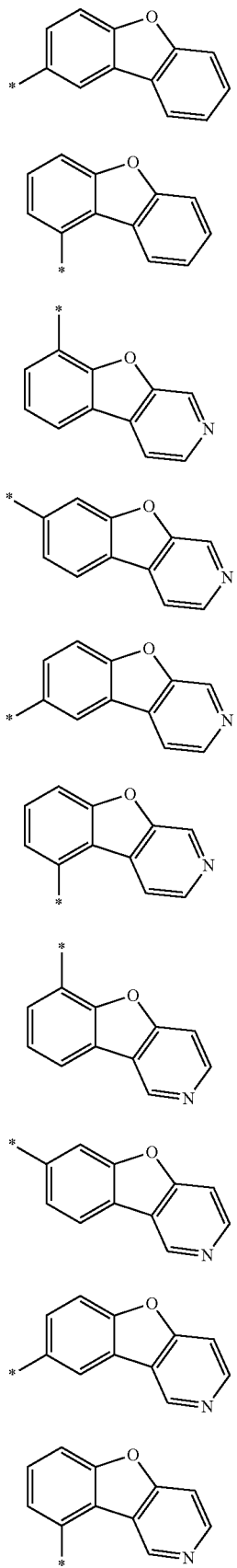

303
-continued
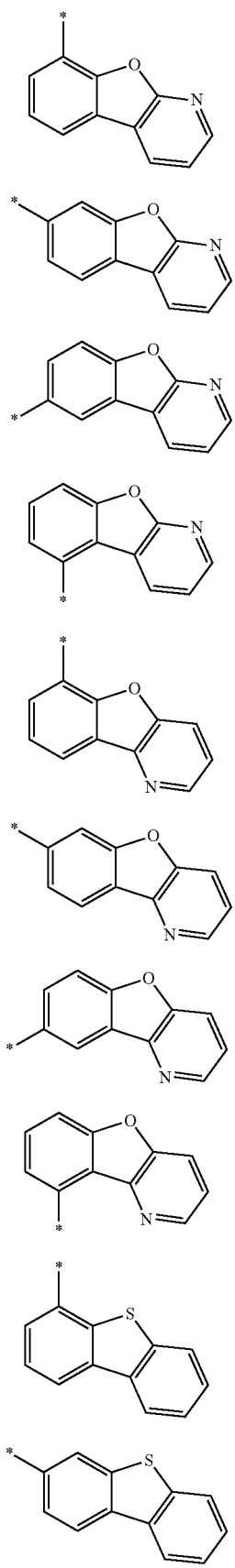
Formula 3-94
Formula 3-95
Formula 3-96
Formula 3-97
Formula 3-98
Formula 3-99
Formula 3-100
Formula 3-101
Formula 3-102
Formula 3-103
304
-continued
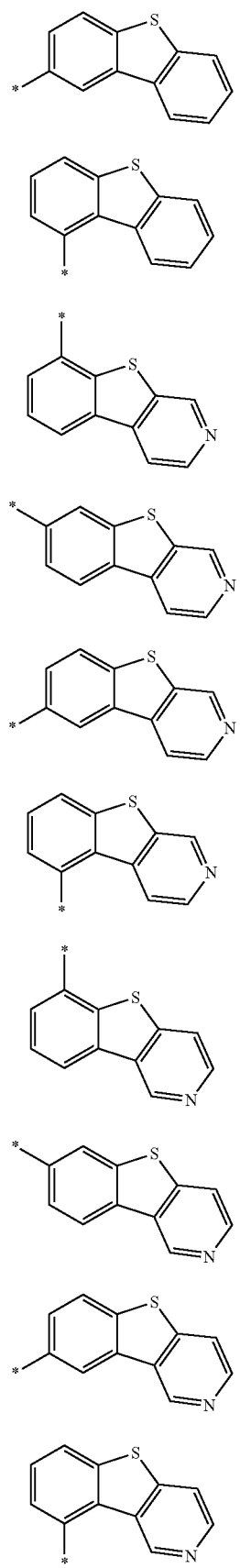
Formula 3-104
Formula 3-105
Formula 3-106
Formula 3-107
Formula 3-108
Formula 3-109
Formula 3-110
Formula 3-111
Formula 3-112
Formula 3-113

-continued
Formula 3-114
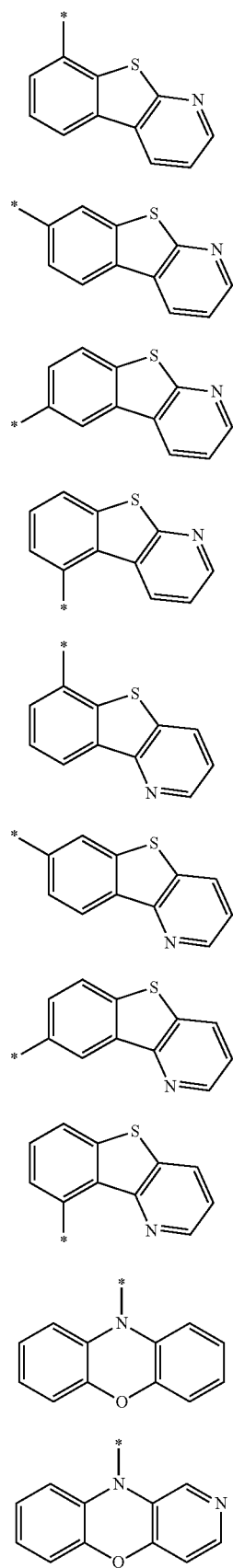
Formula 3-115
Formula 3-116
Formula 3-117
Formula 3-118
Formula 3-119
Formula 3-120
Formula 3-121
Formula 3-127
Formula 3-128
-continued
Formula 3-129
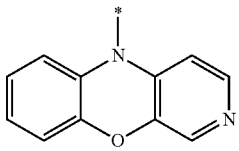
Formula 3-130
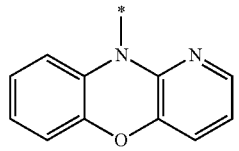
Formula 3-131
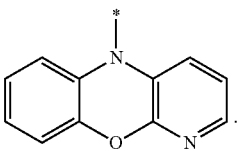
10. A condensed cyclic compound, wherein the condensed cyclic compound is one of Compounds 22 to 42, 171-288, 331-362, 383-400, 405 to 408, 411, 412, 415, 416, 419, 420, 423, 424, 427, 428, 431, and 432:
22
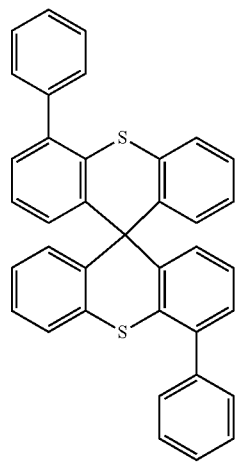
23
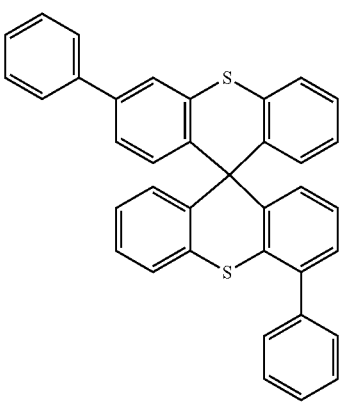

24
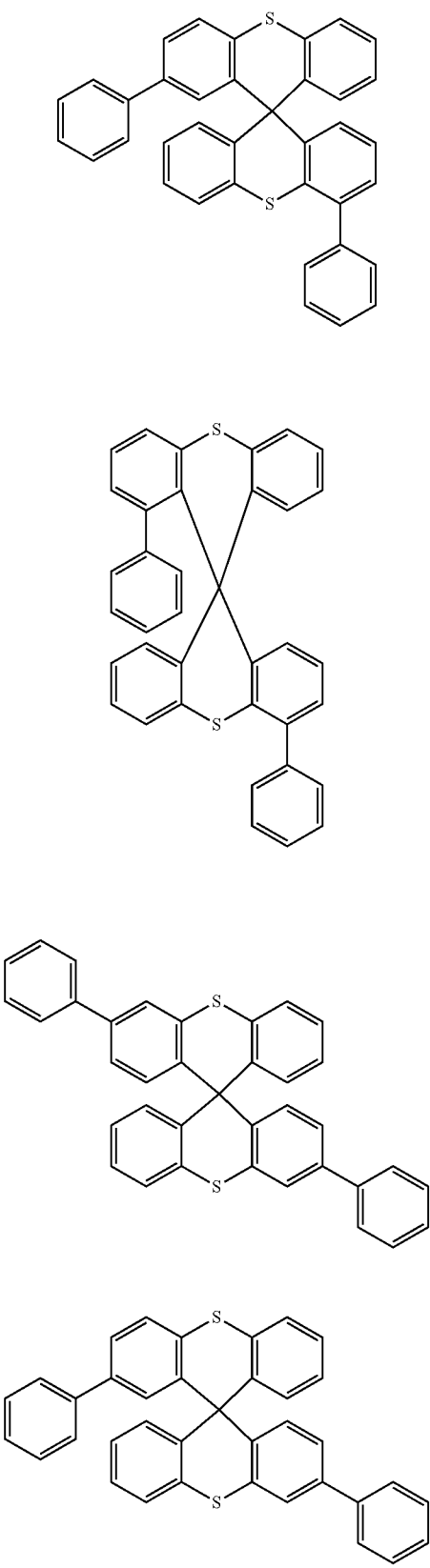
25
26
27
28
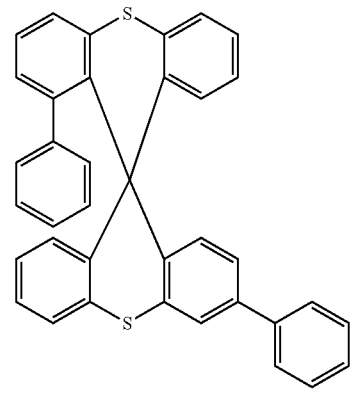
29
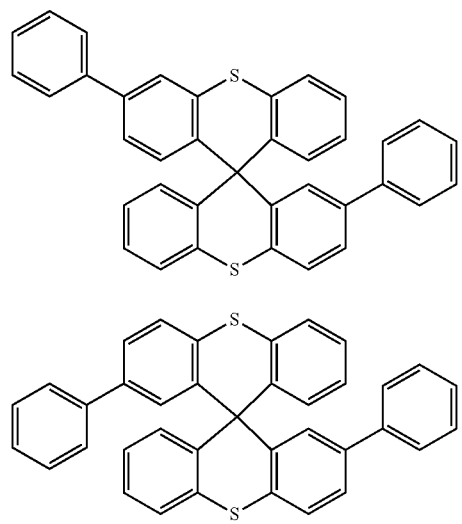
30
31
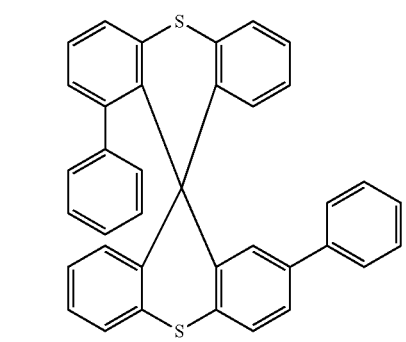
32
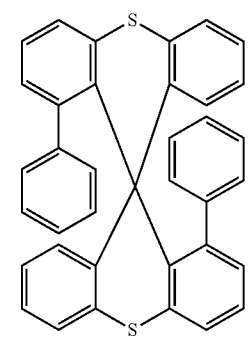

33
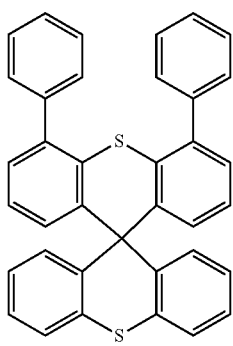
34
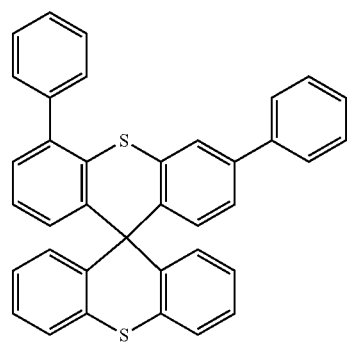
35
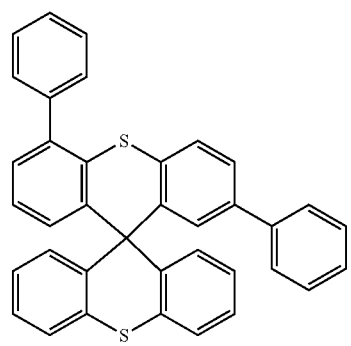
36
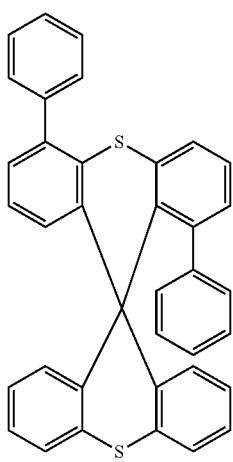
37
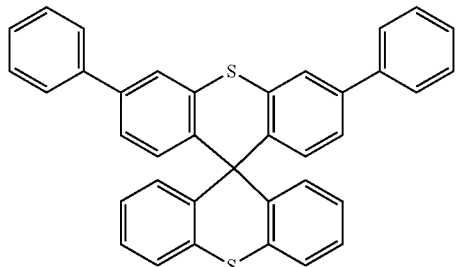
38
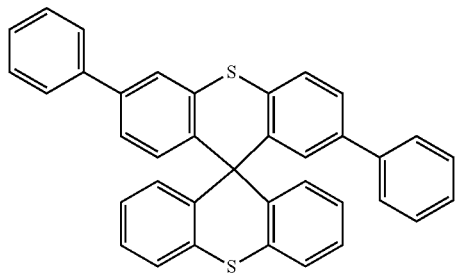
39
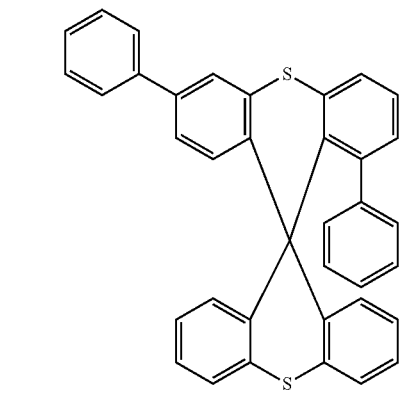
40
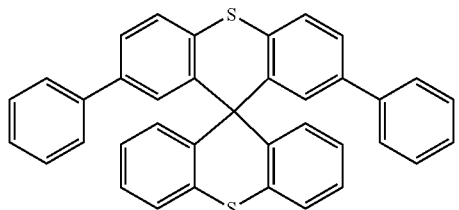
41
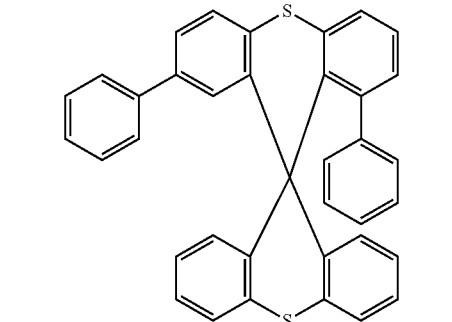

311
-continued
42
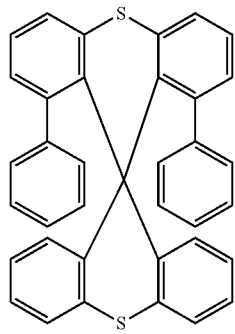
171
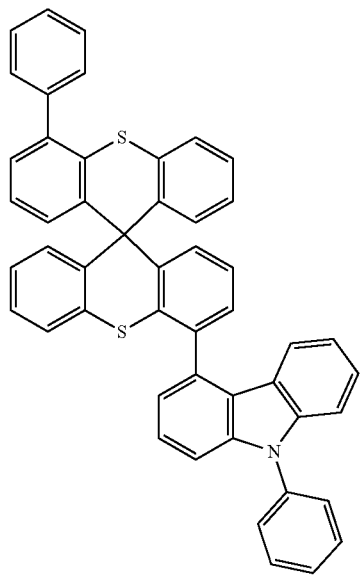
172
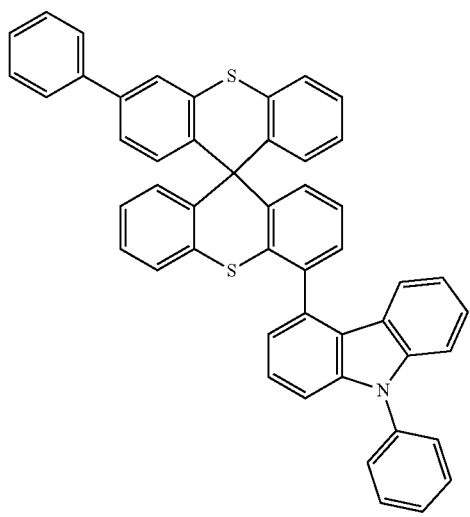
312
-continued
173
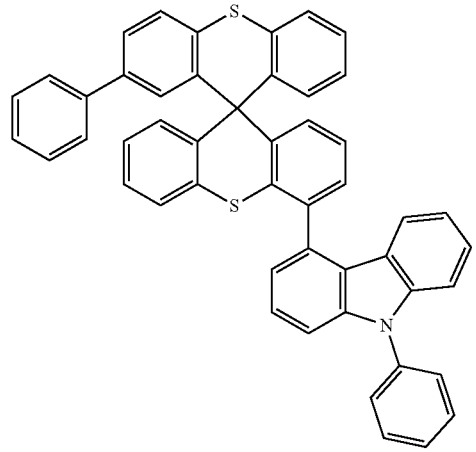
174
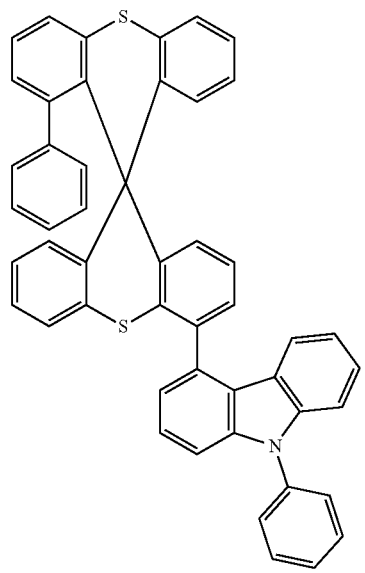
175
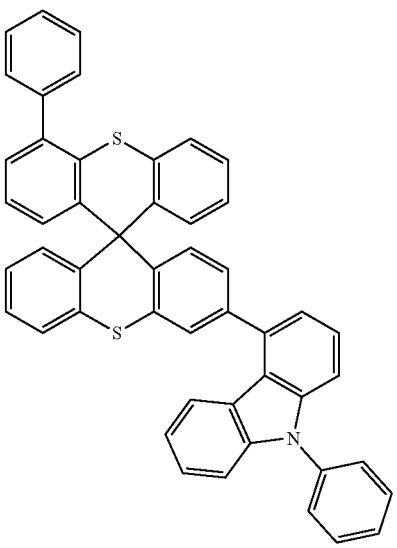

-continued
176
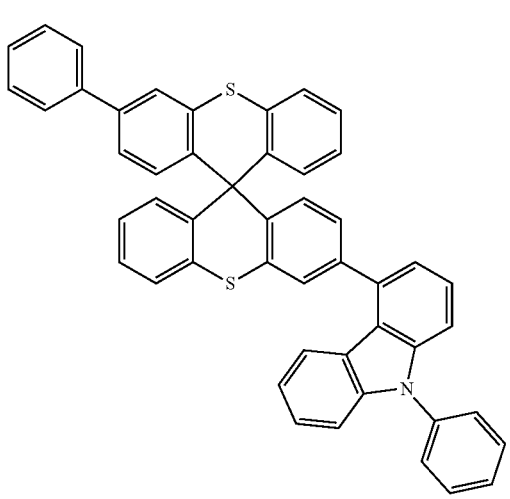
177
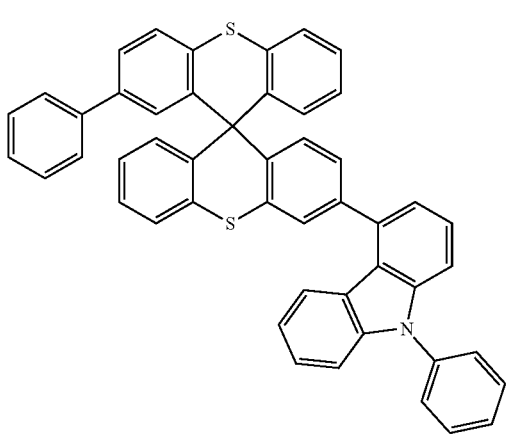
178
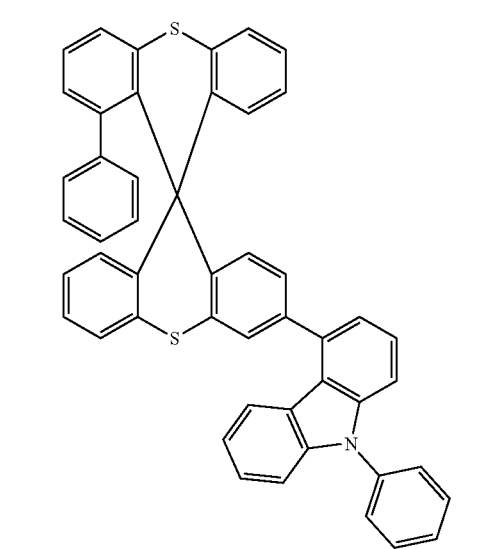
-continued
179
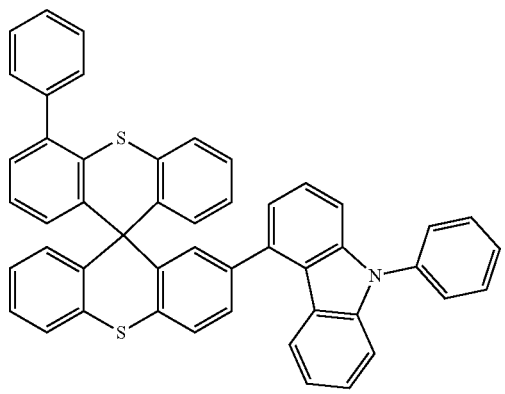
180
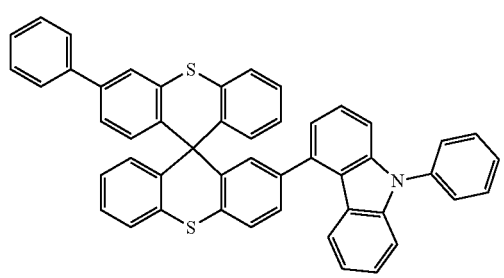
181
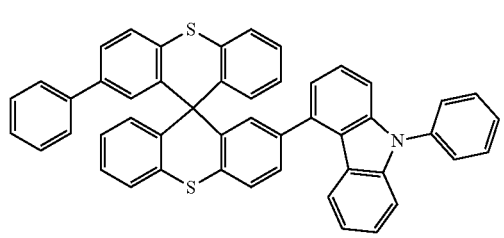
182
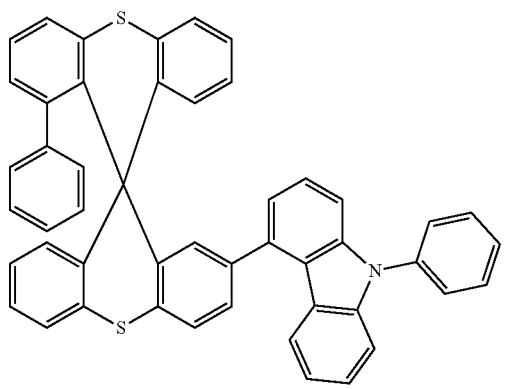

183
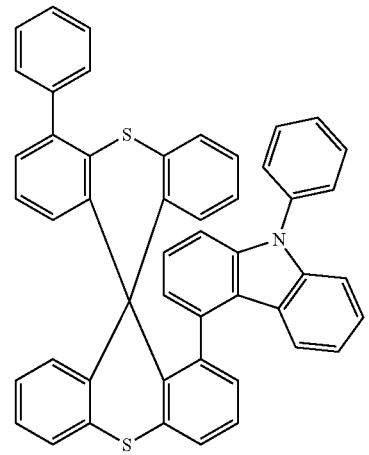
184
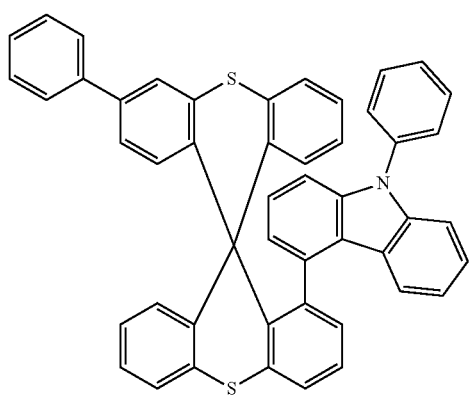
185
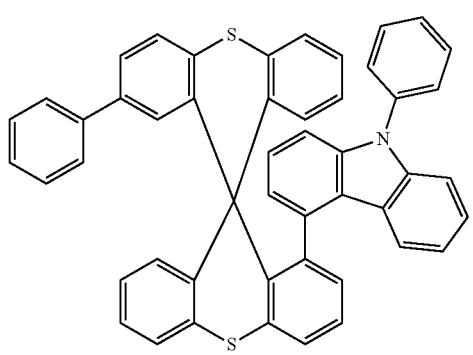
186
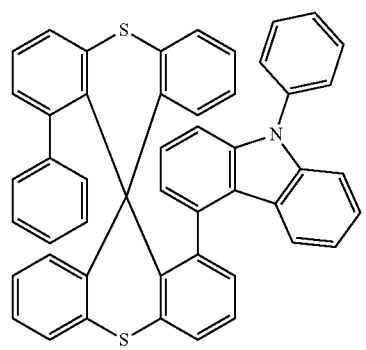
187
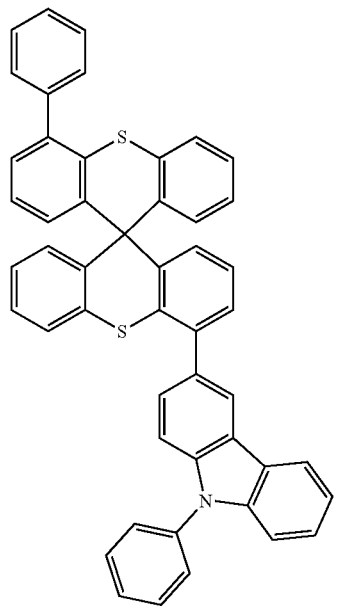
188
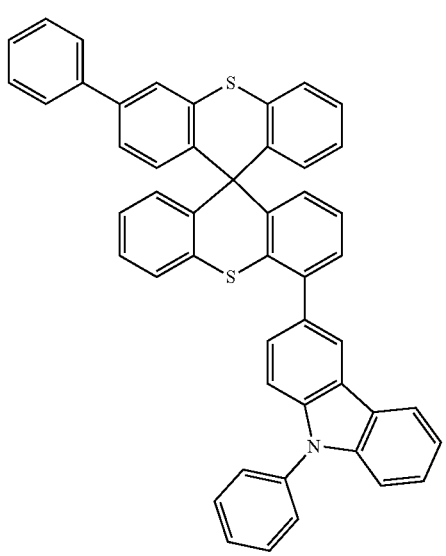
189
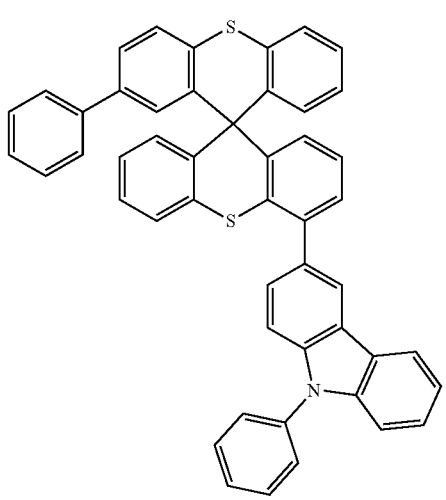

317
-continued
318
-continued
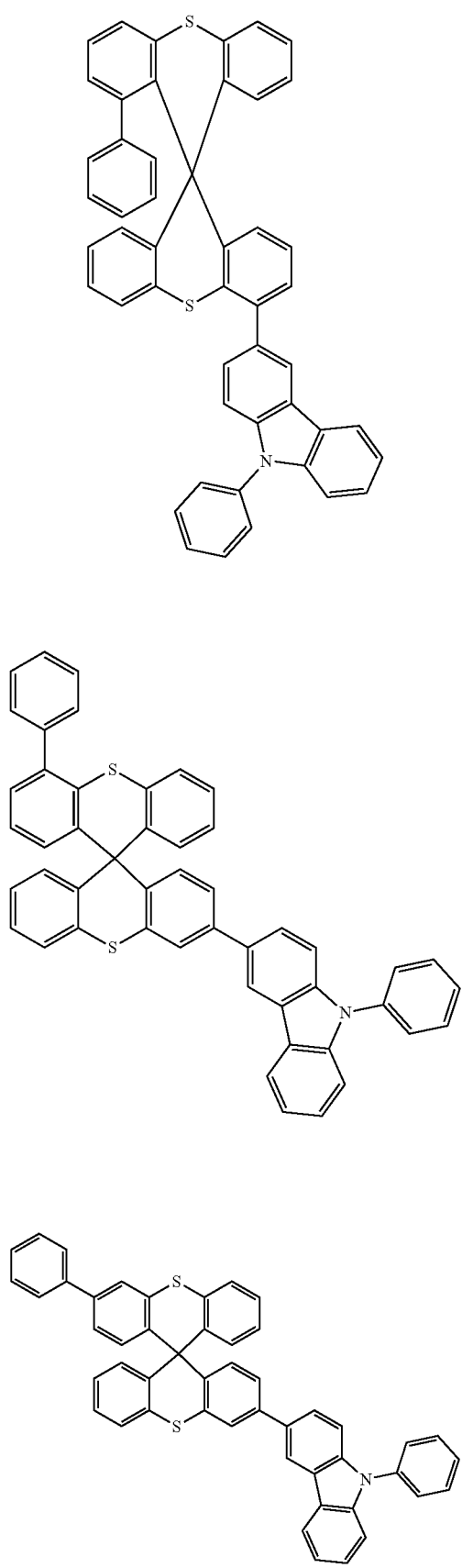
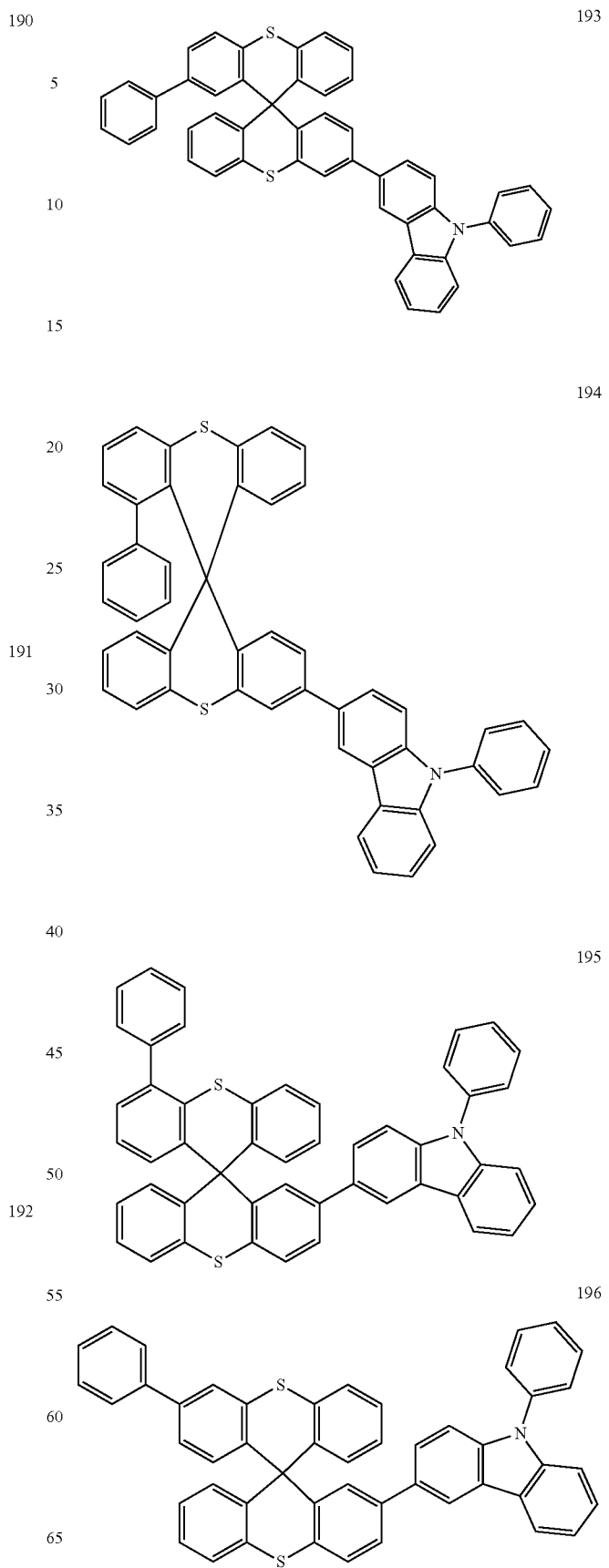

319
-continued
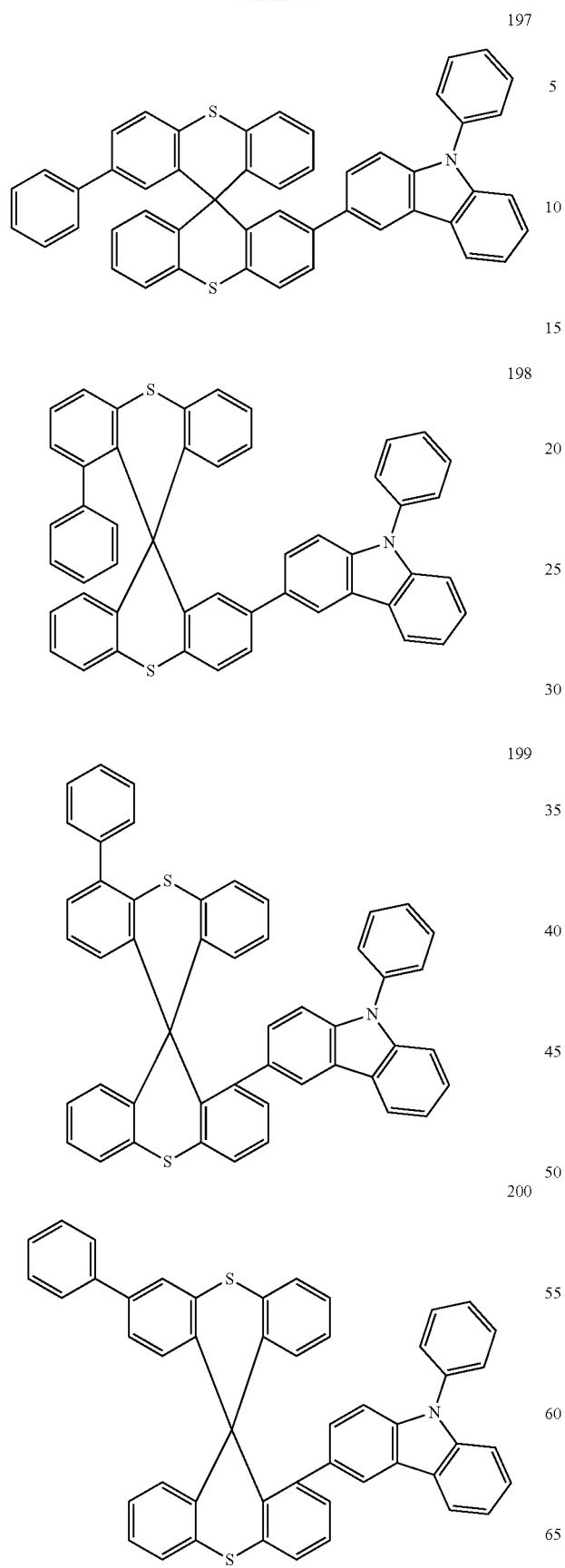
320
-continued
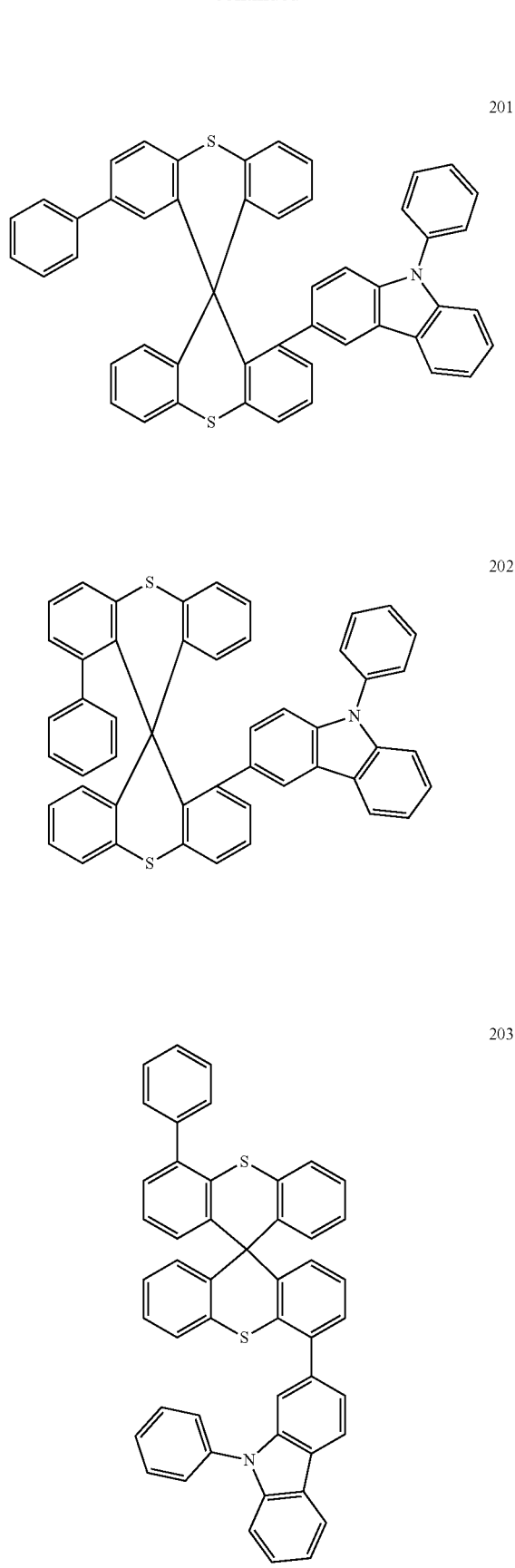

321
-continued
204
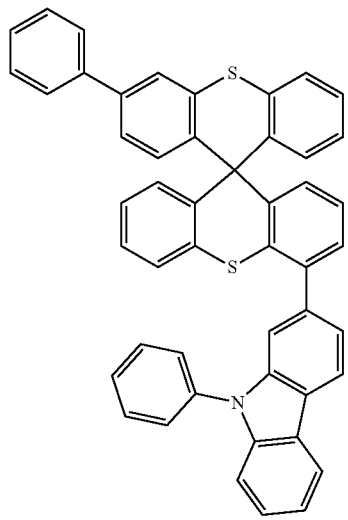
205
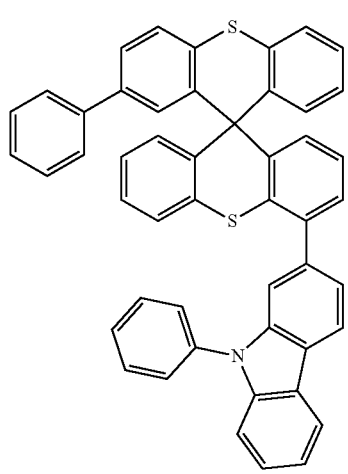
206
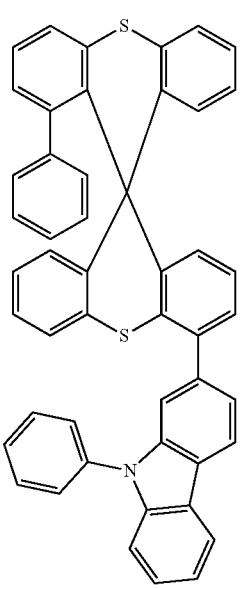
322
-continued
207
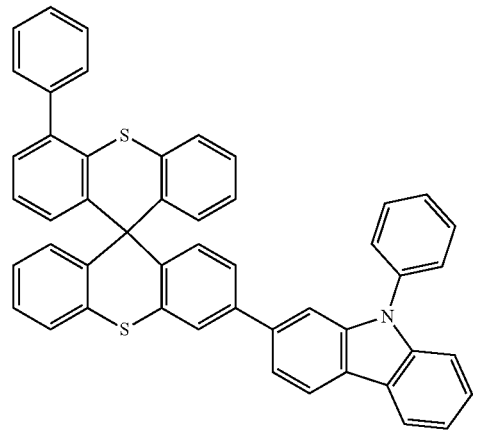
208
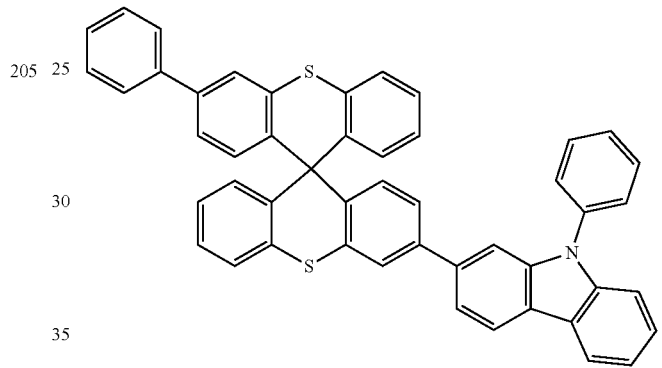
209
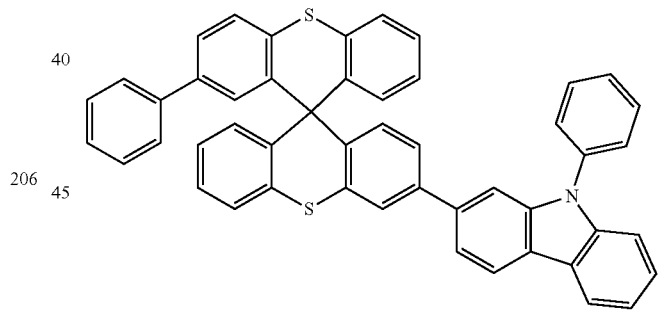
210
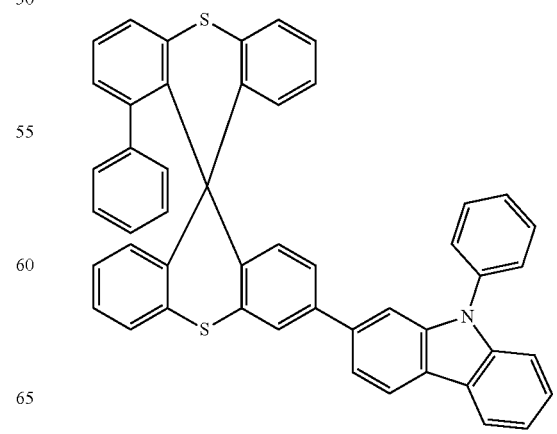

323
-continued
211
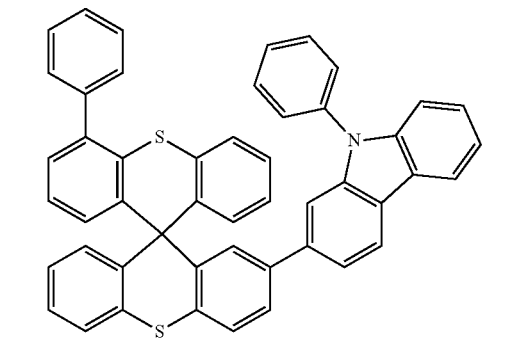
212
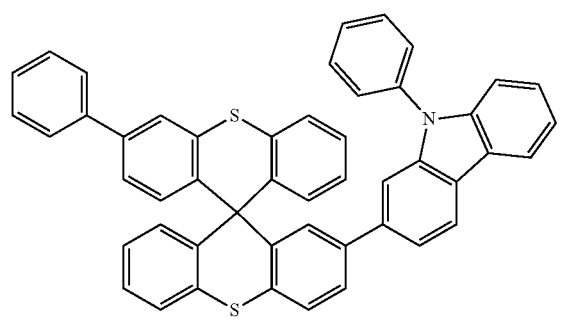
213
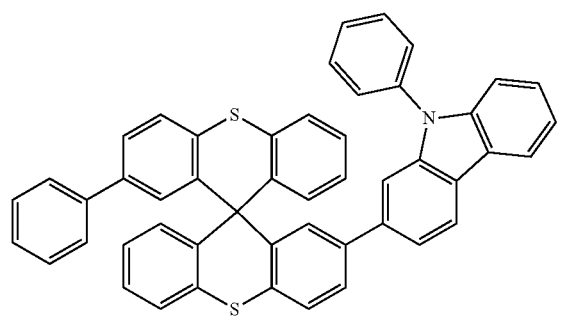
214
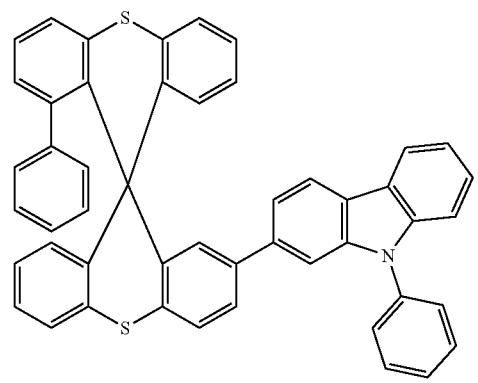
324
-continued
215
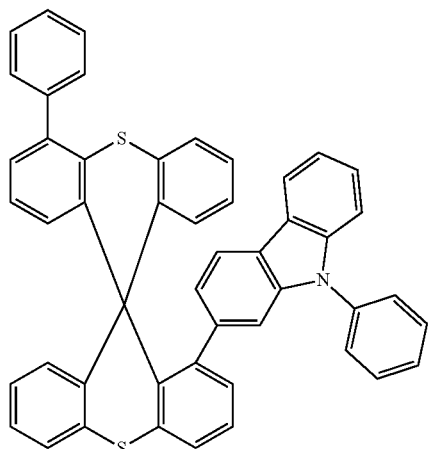
216
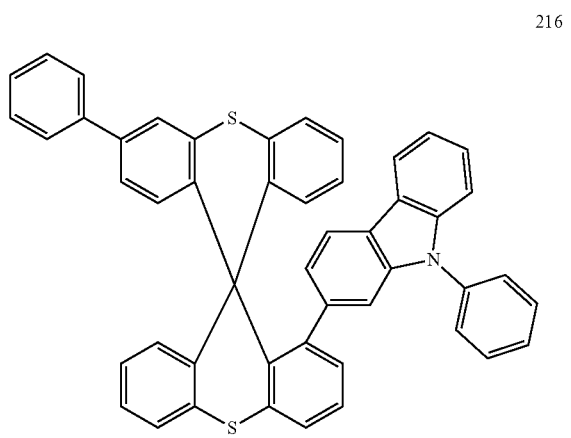
217
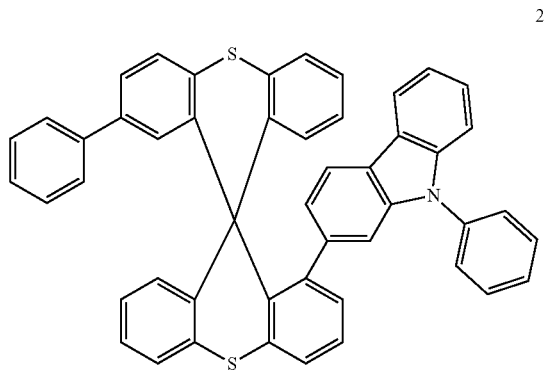
218
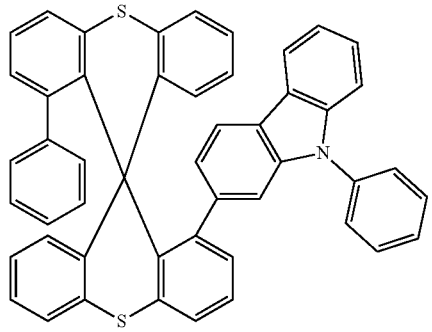

325
-continued
219
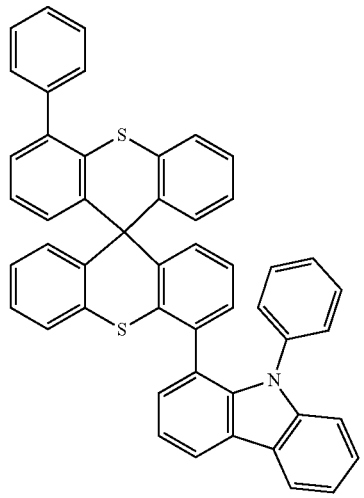
220
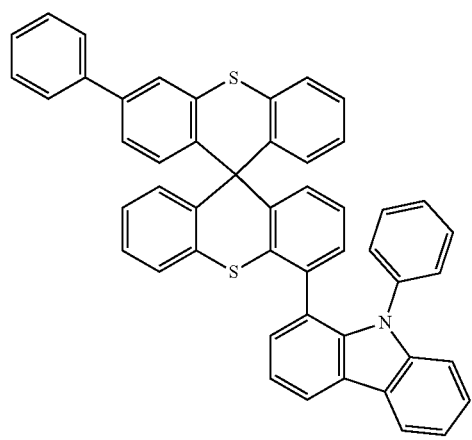
221
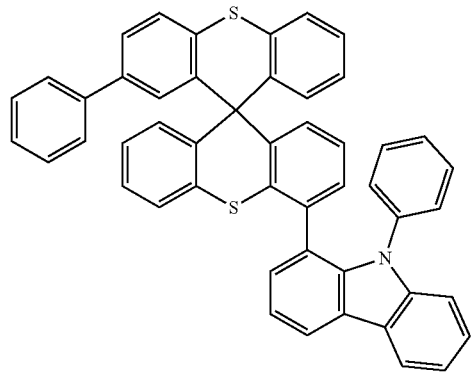
326
-continued
222
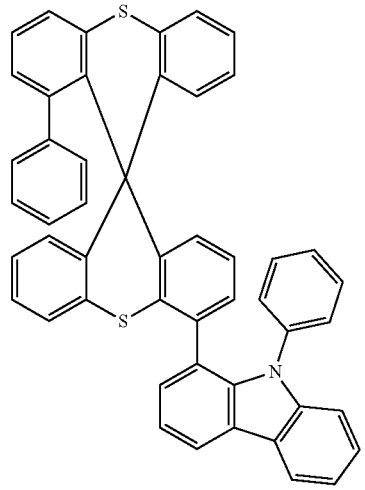
223
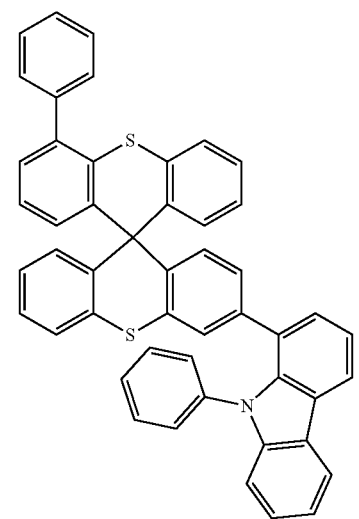
224
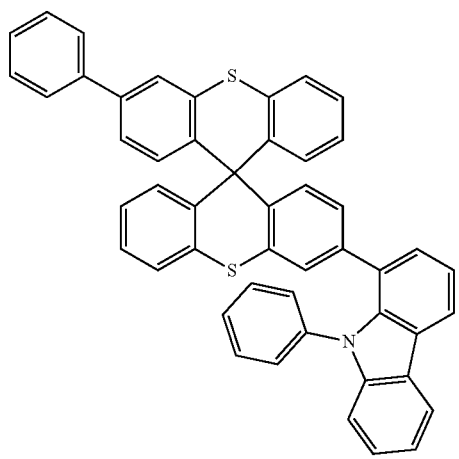

225
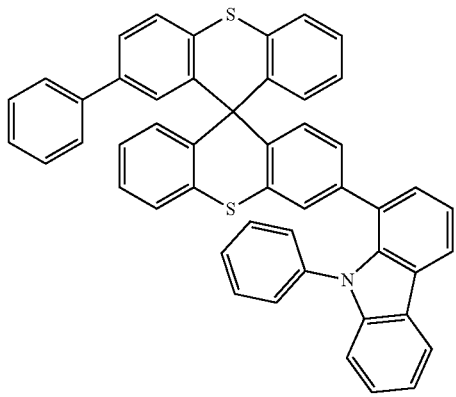
226
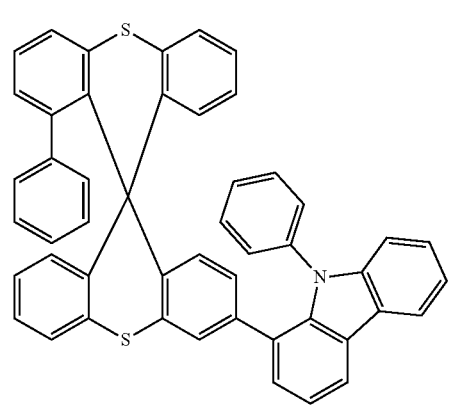
227
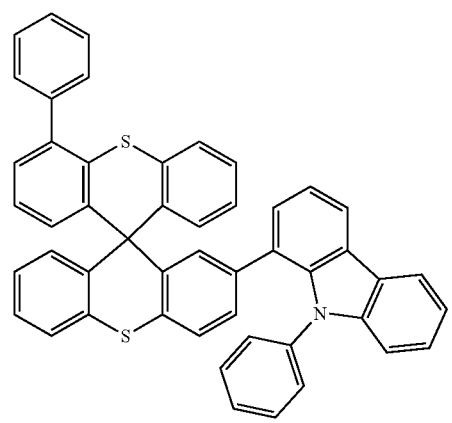
228
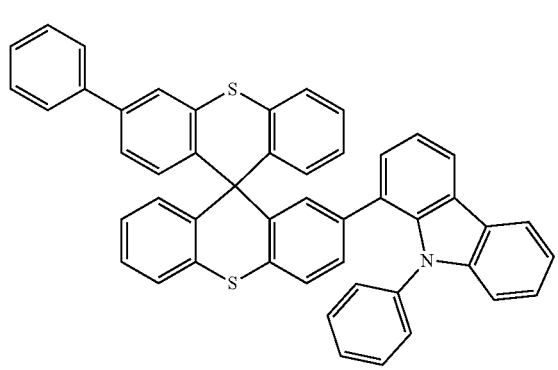
229
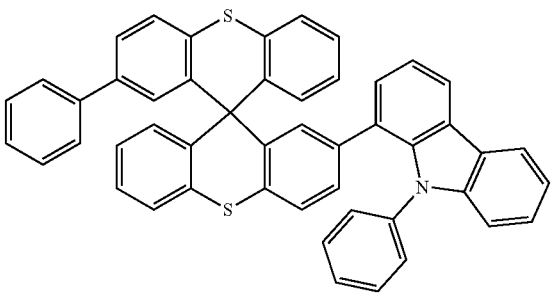
230
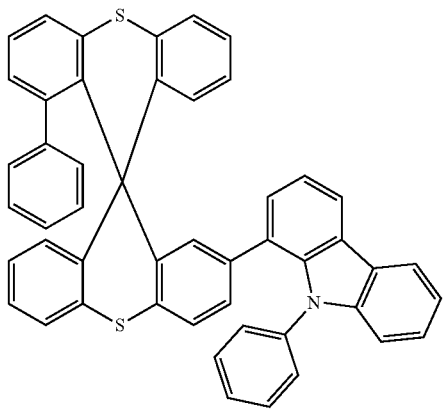
231
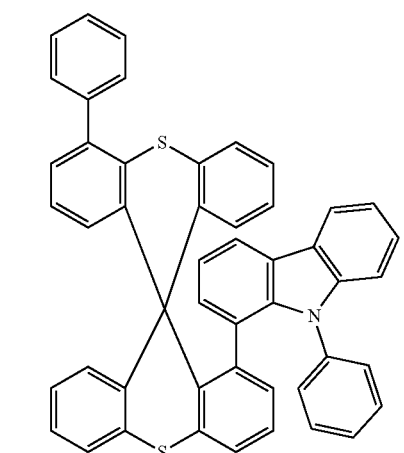
232
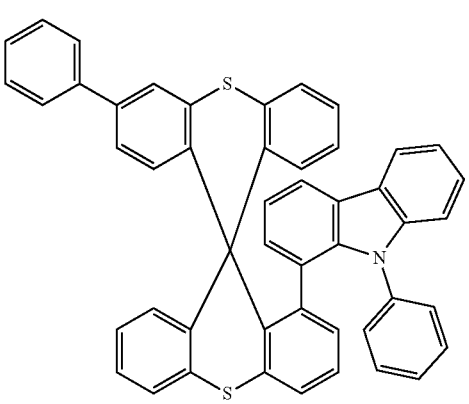

329
-continued
233
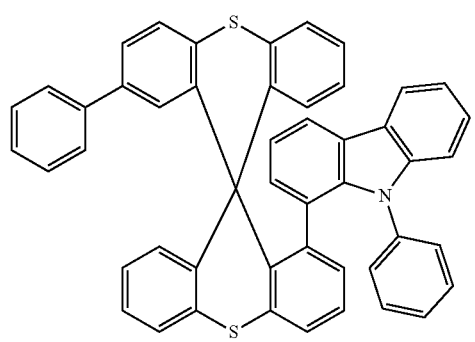
234
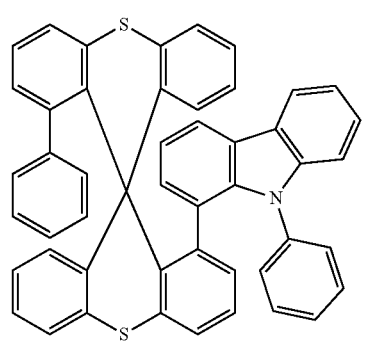
235
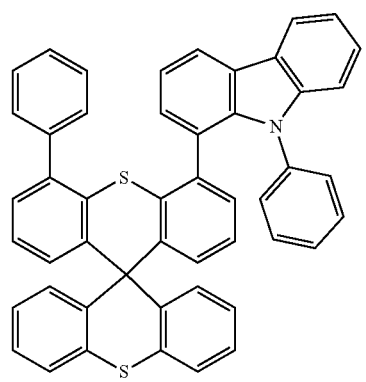
236
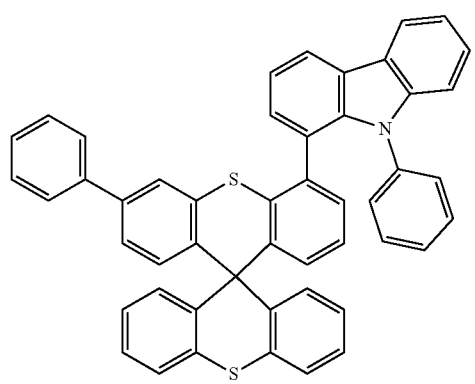
330
-continued
237
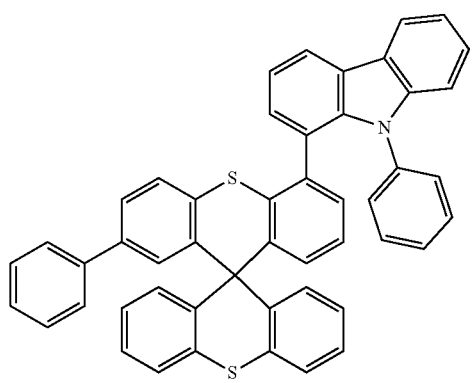
238
239
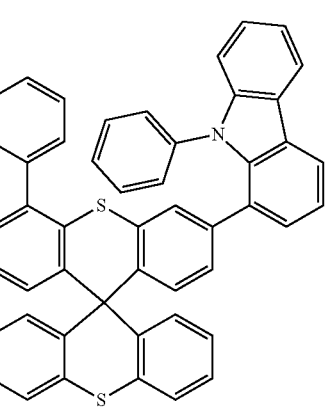

240
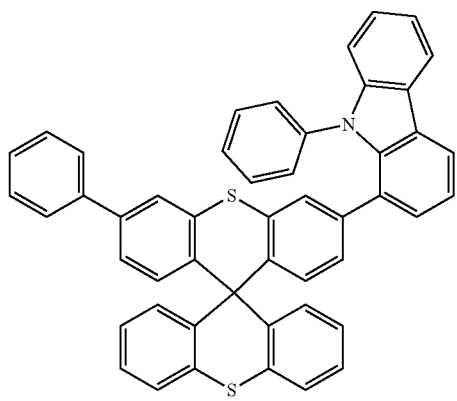
241
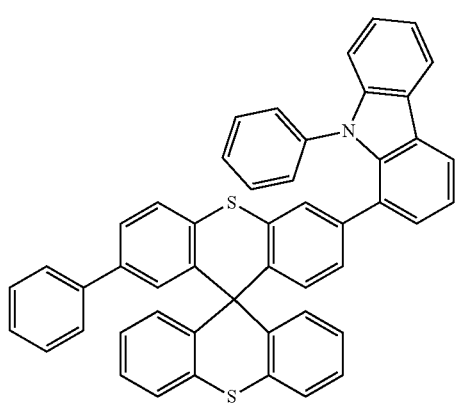
242
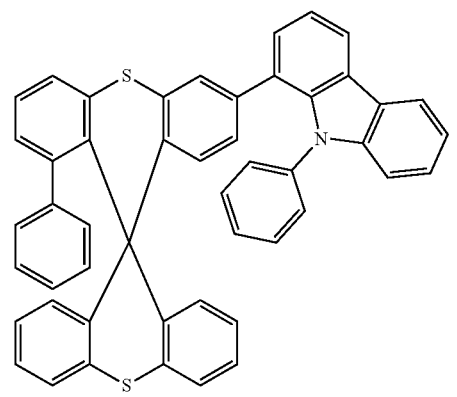
243
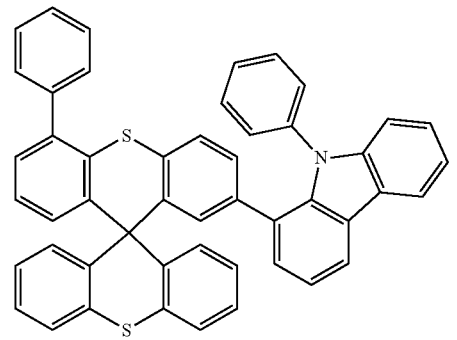
244
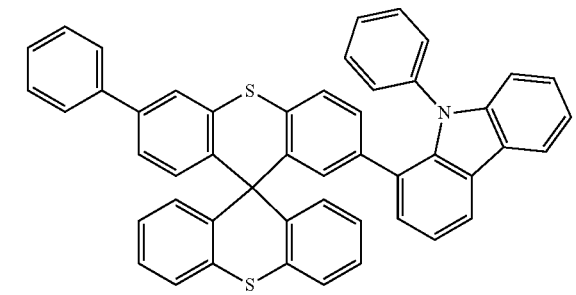
245
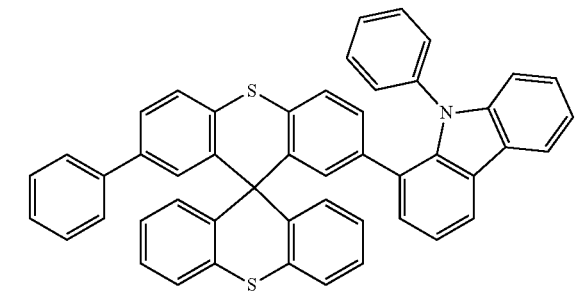
246
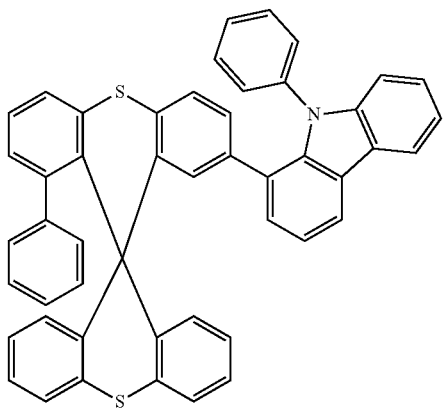
247
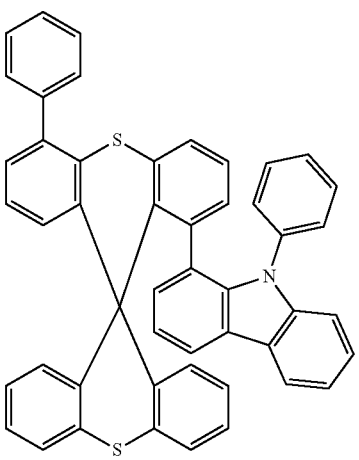

333
-continued
248
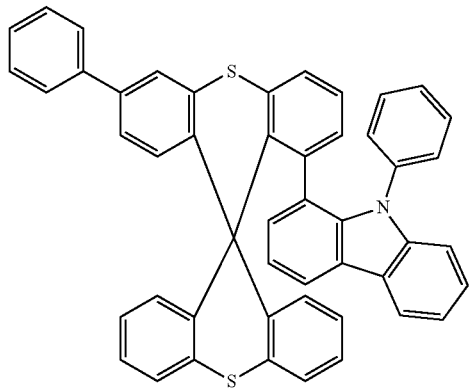
249
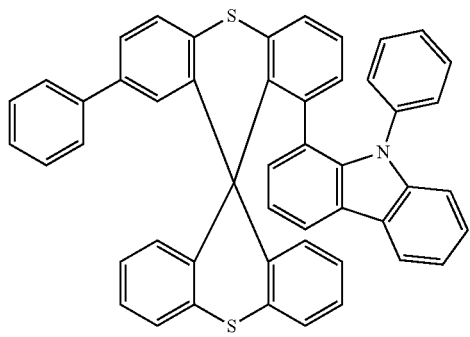
250
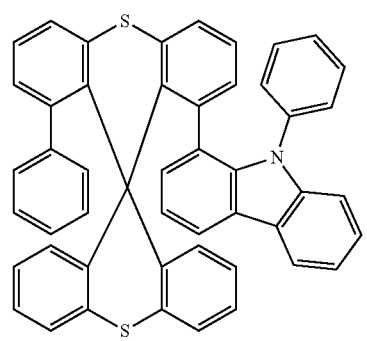
251
334
-continued
252
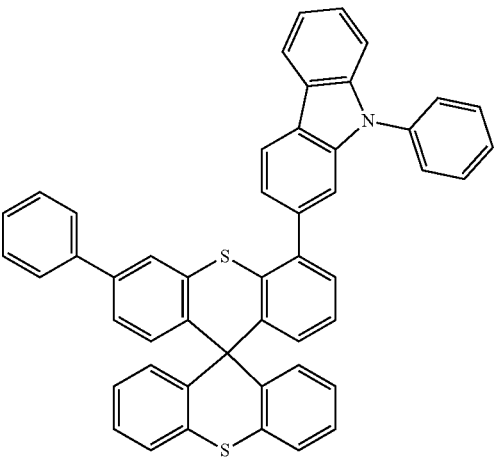
253
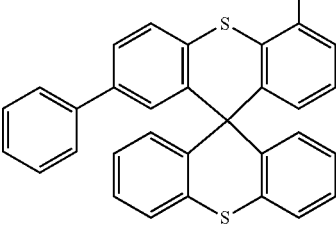
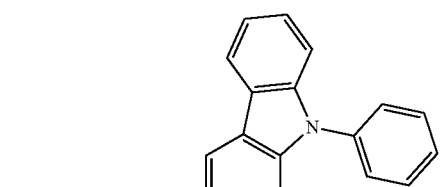
254
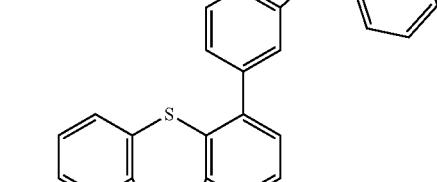
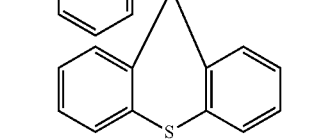
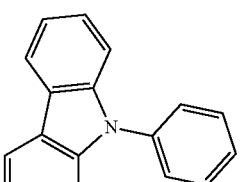

335
-continued
336
-continued
255
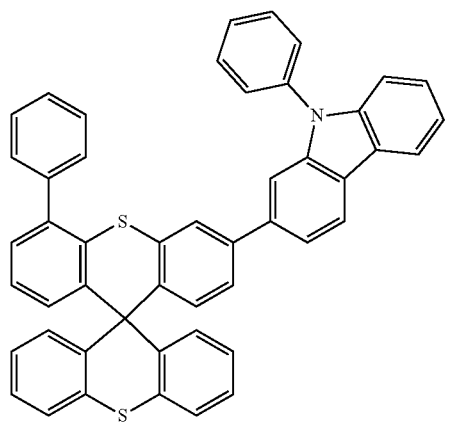
258
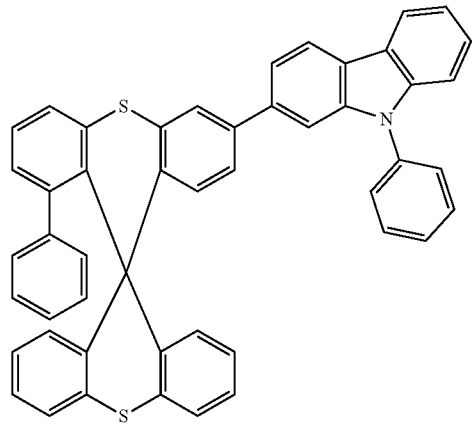
256
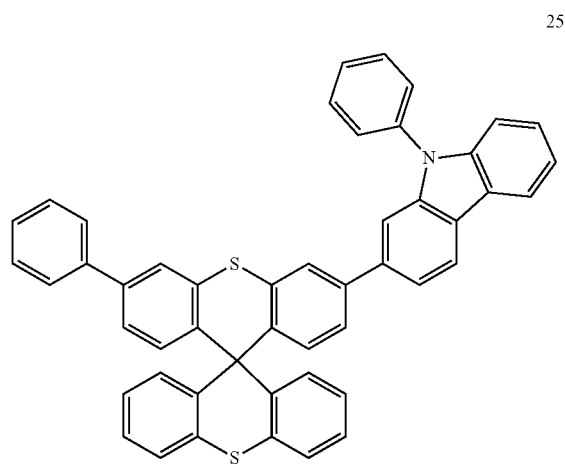
259
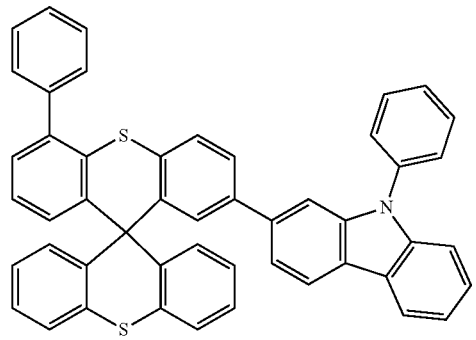
260
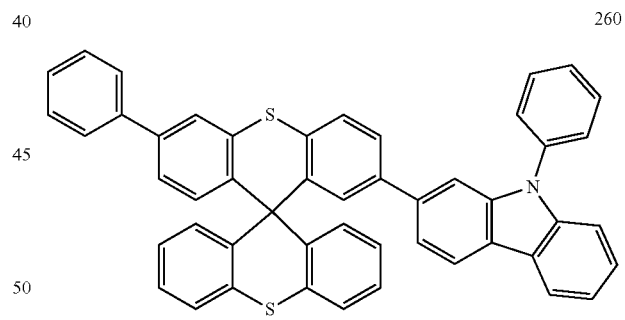
257
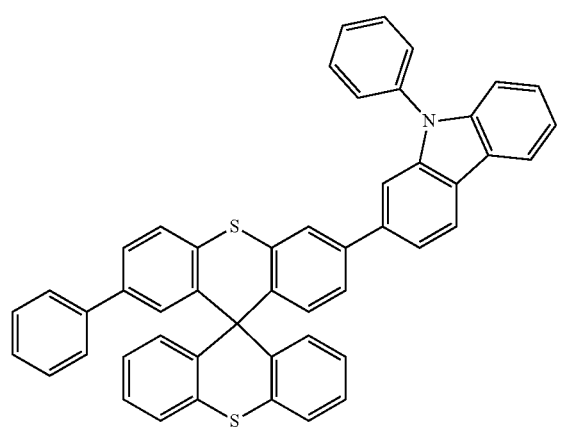
261
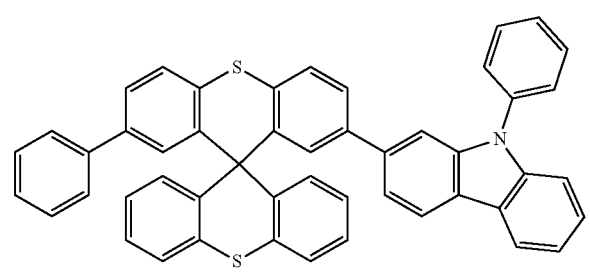

337
-continued
338
-continued
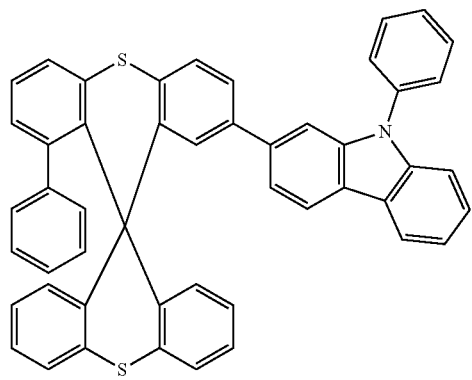
262
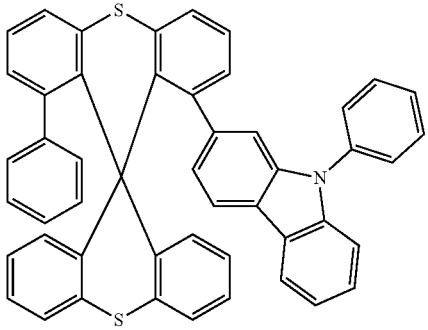
266
263
267
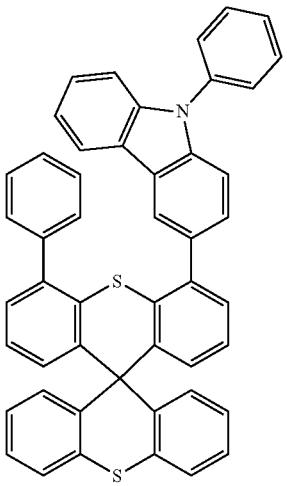
264
265
268
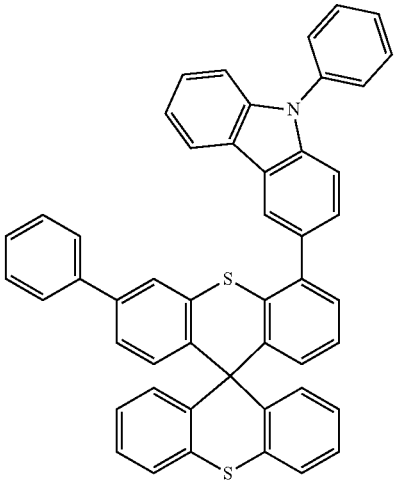

-continued
269
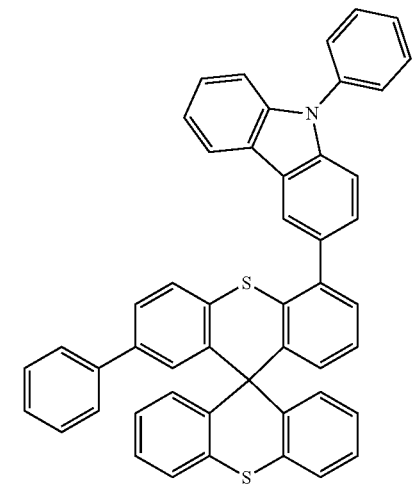
270
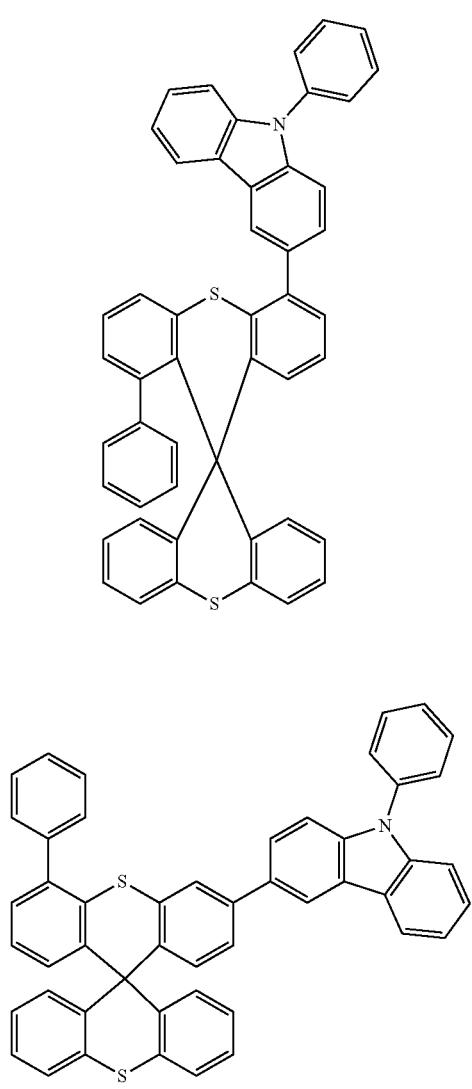
271
-continued
272
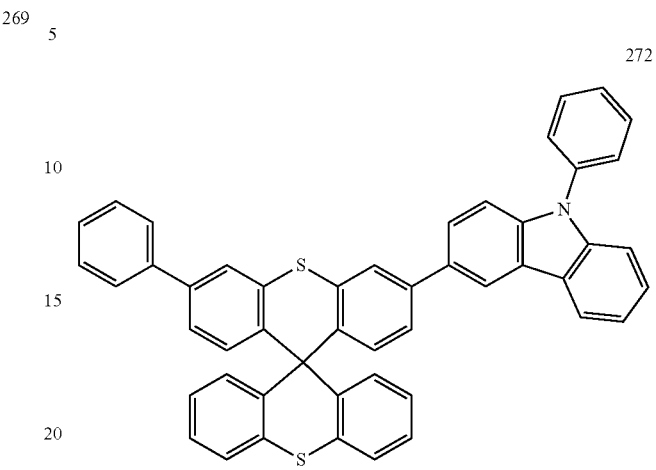
273
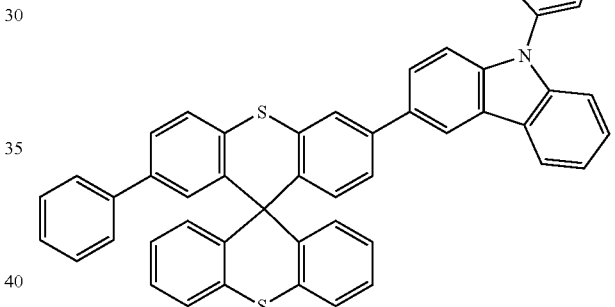
274
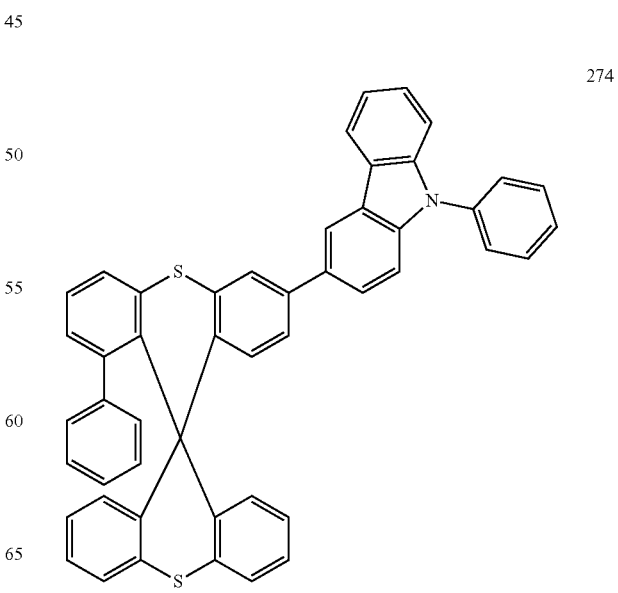

275
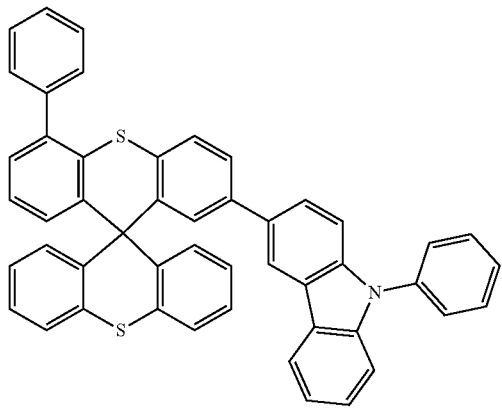
276
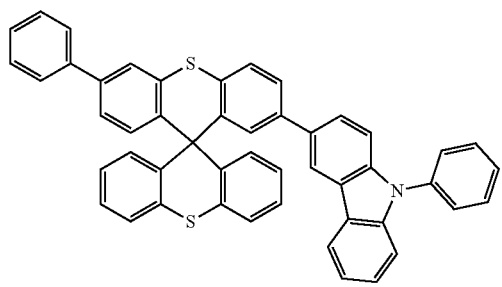
277
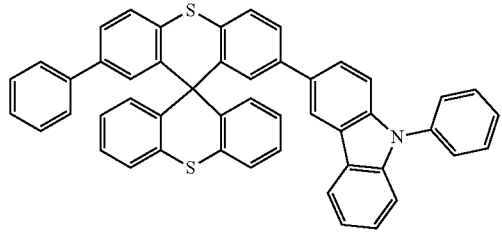
278
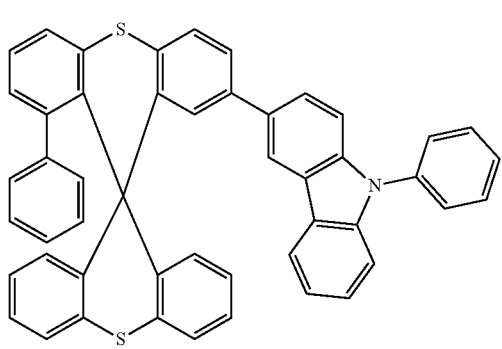
279
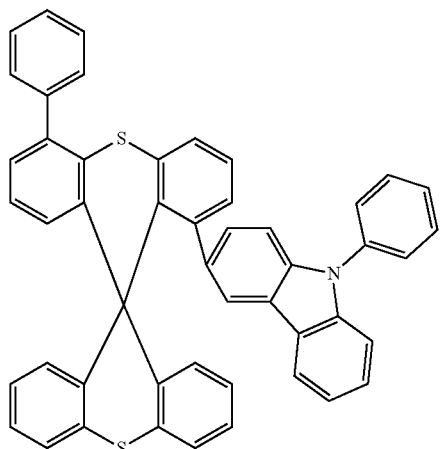
280
281
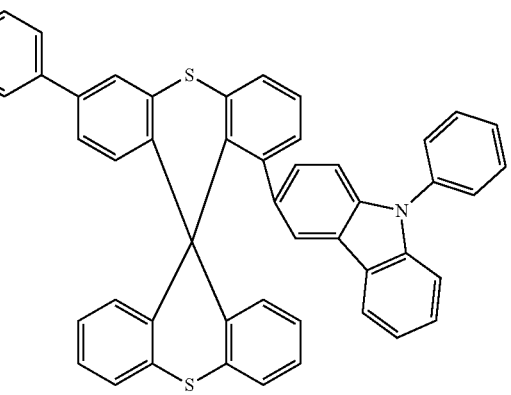
282
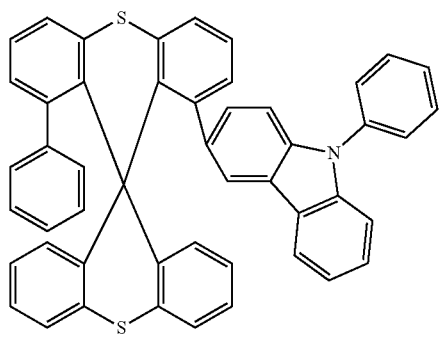

283
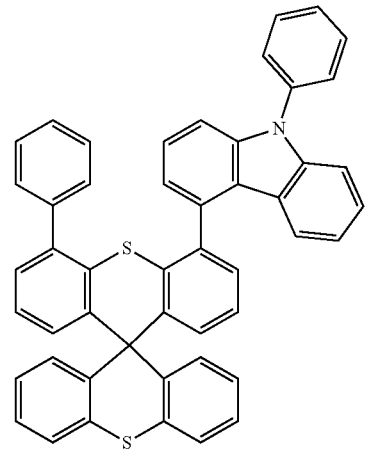
284
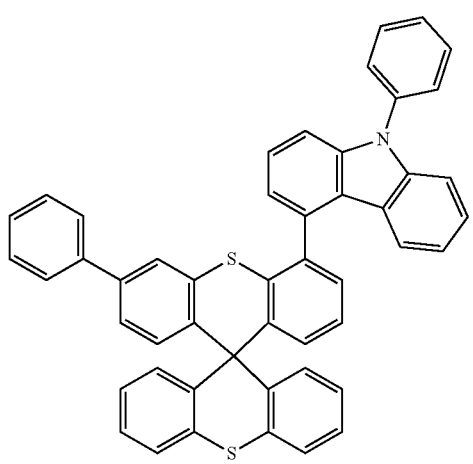
285
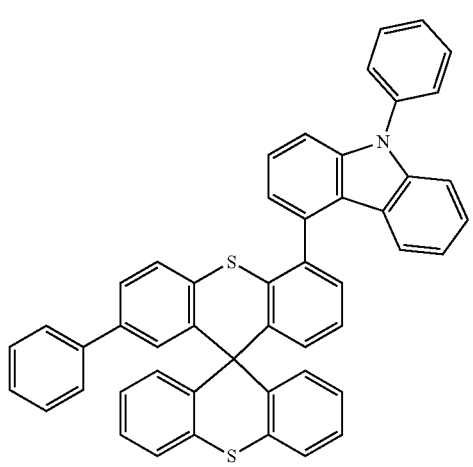
286
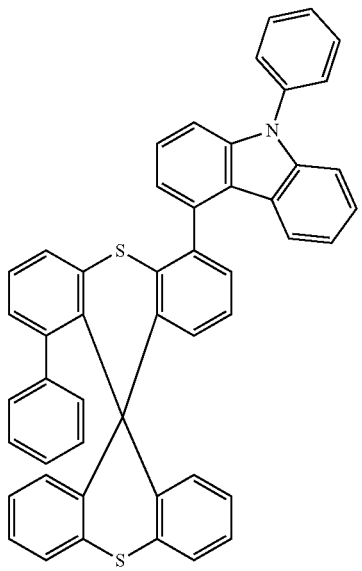
287
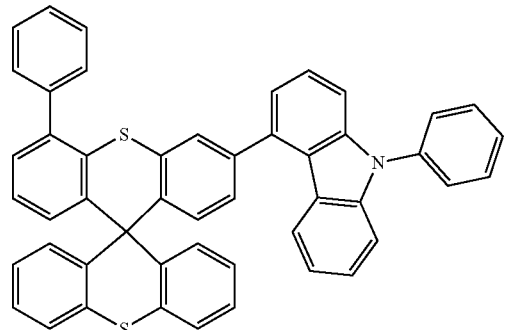
288
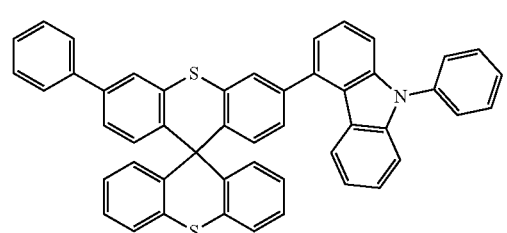
331
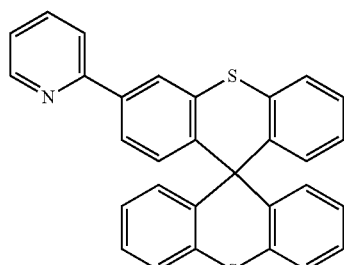

-continued
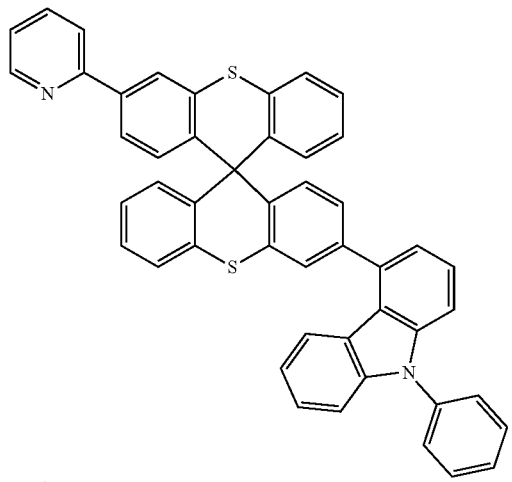
332
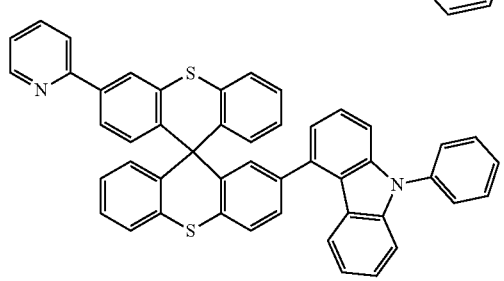
333
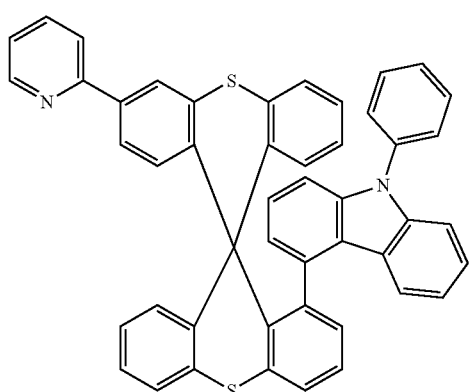
334
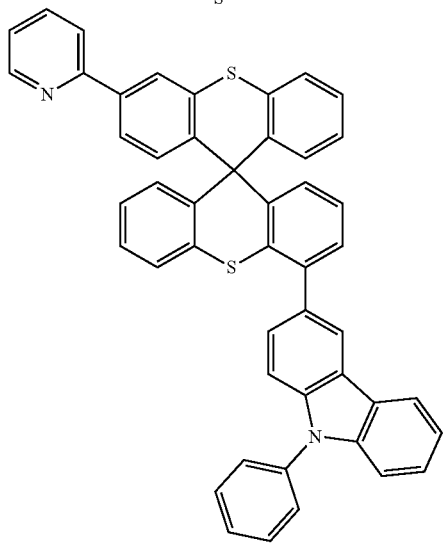
335
-continued
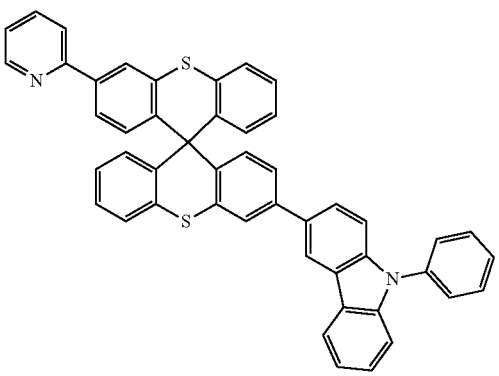
336
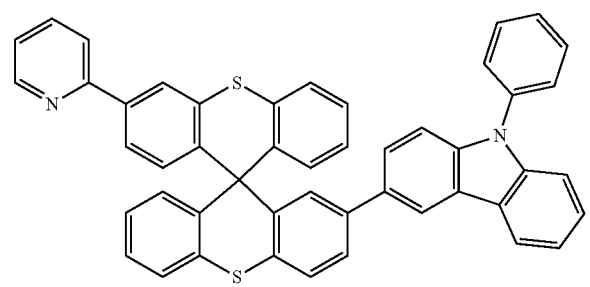
337
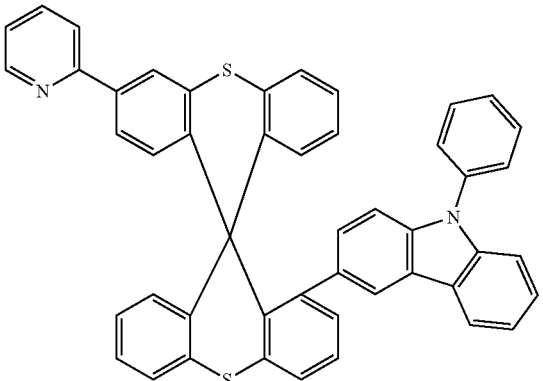
338
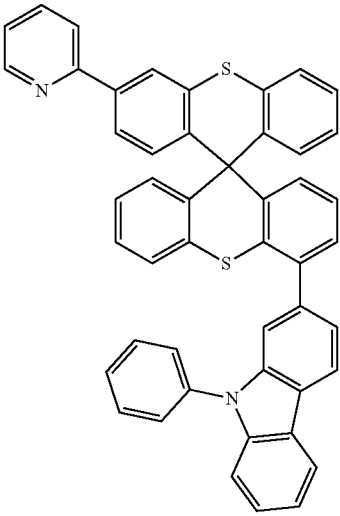
339

340
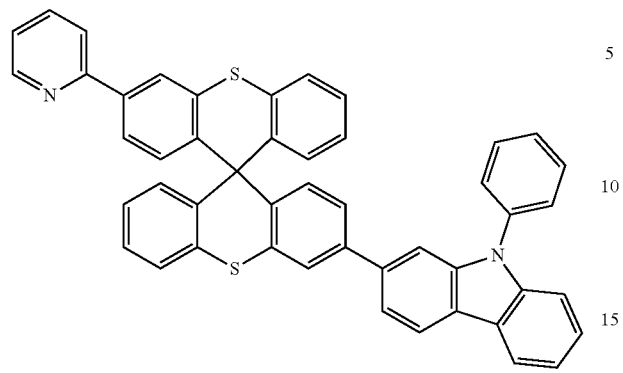
341
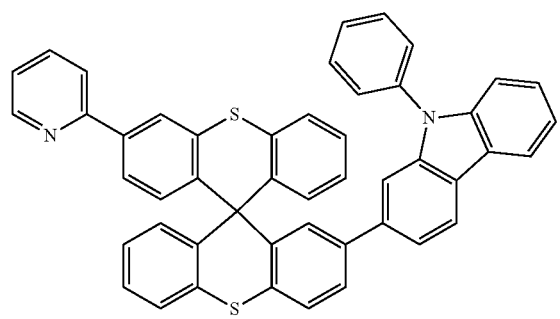
342
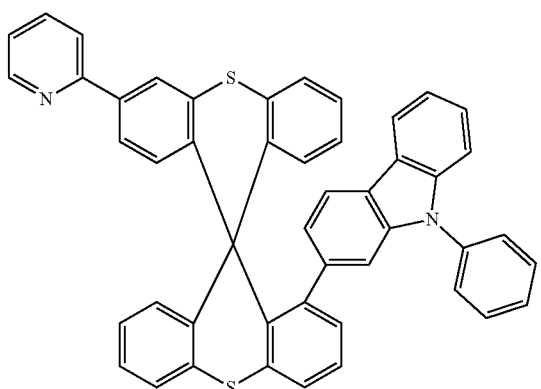
343
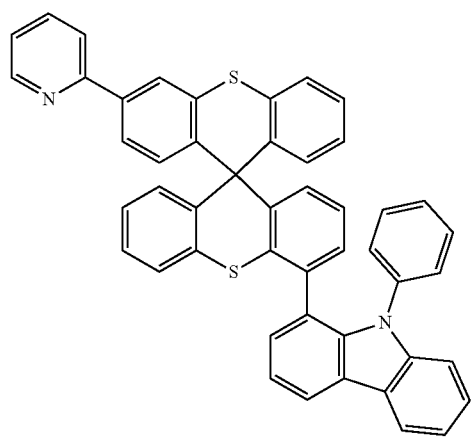
344
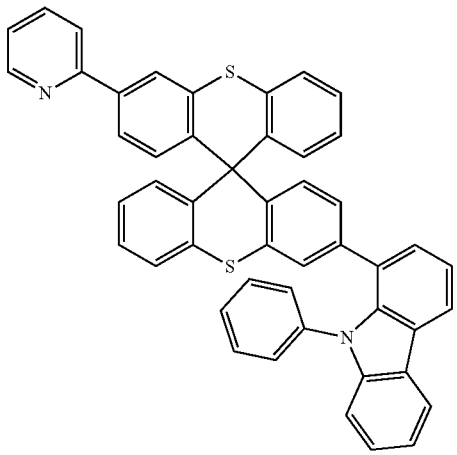
345
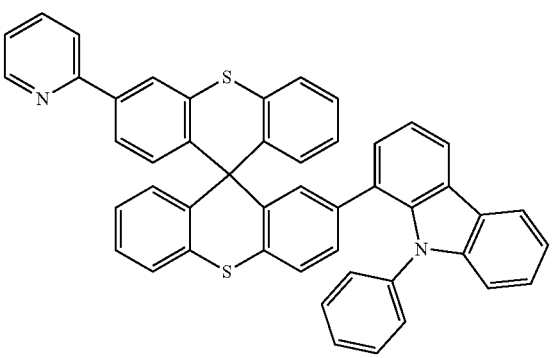
346
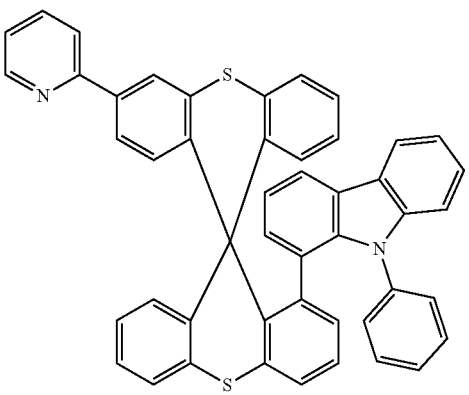
347
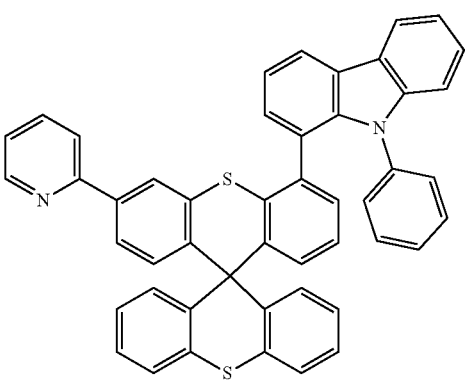

348
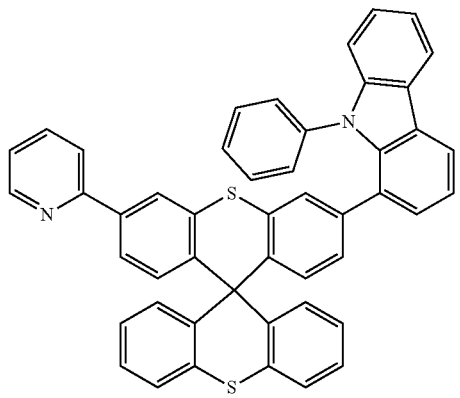
349
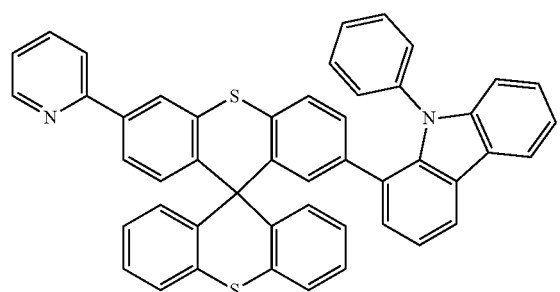
350
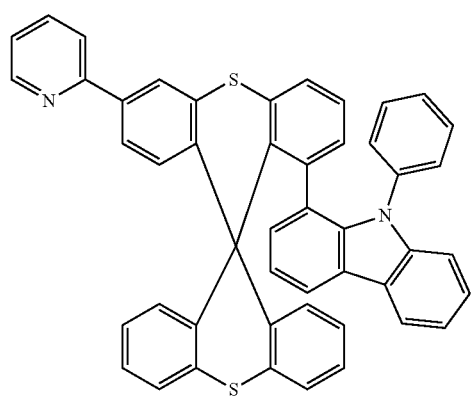
351
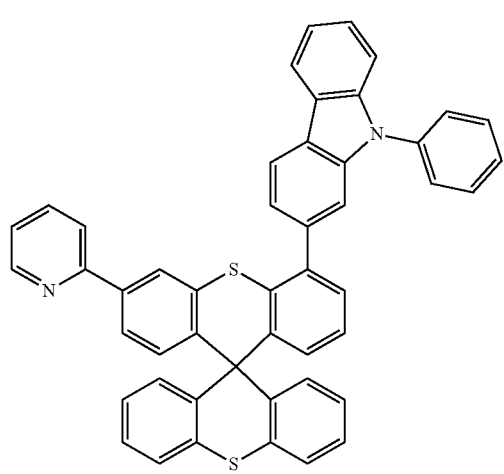
352
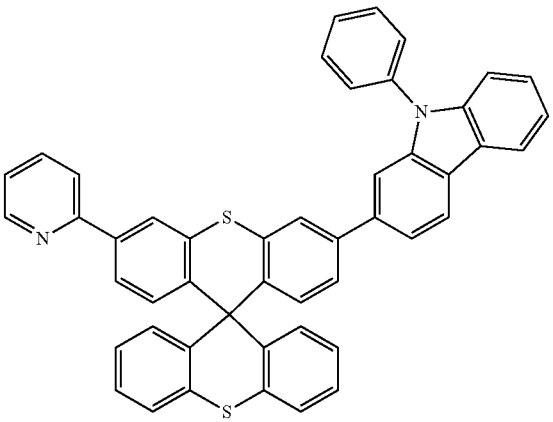
353
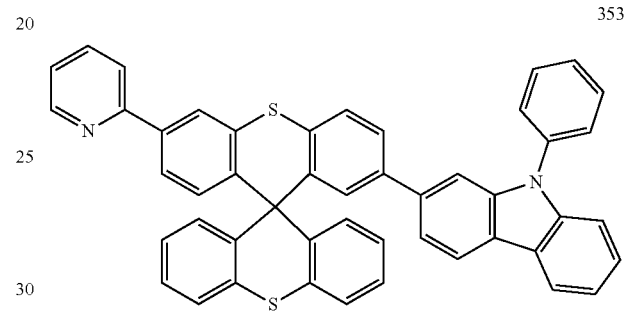
354
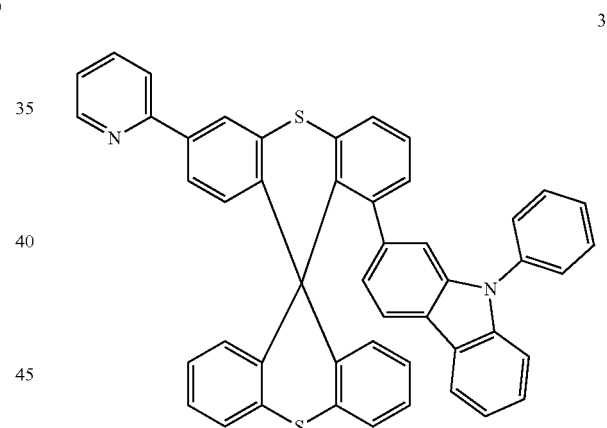
355
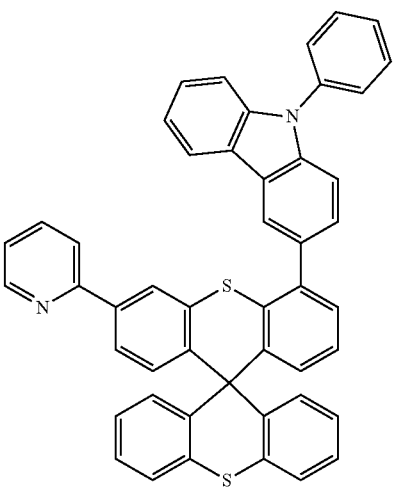

356
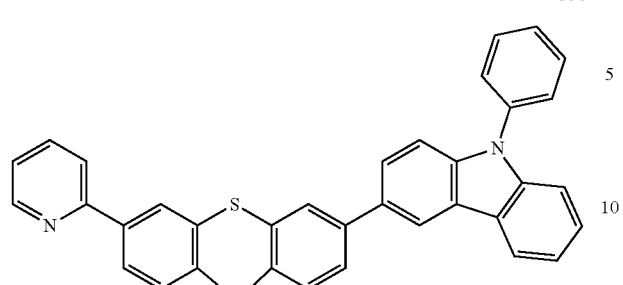
357
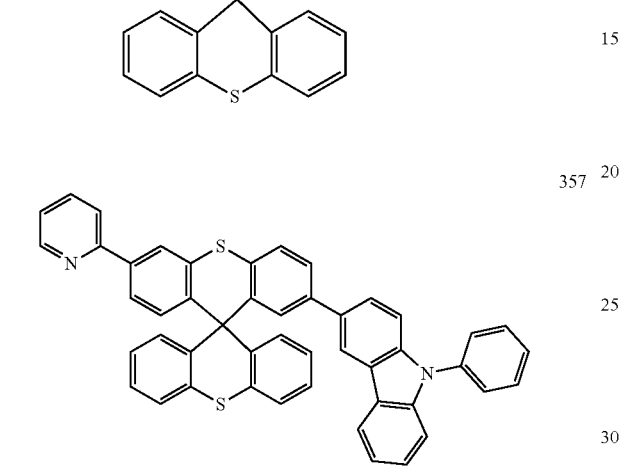
358
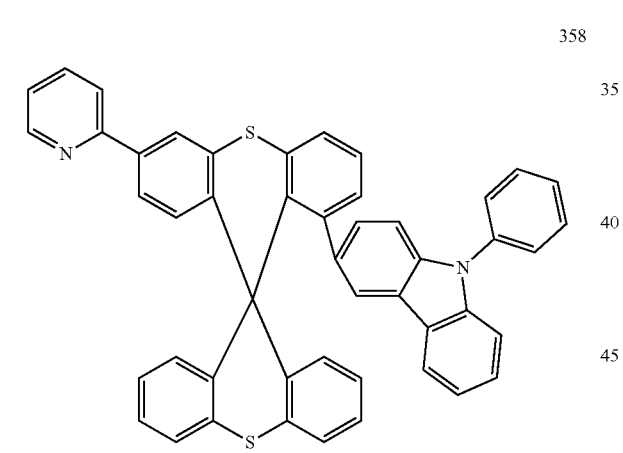
359
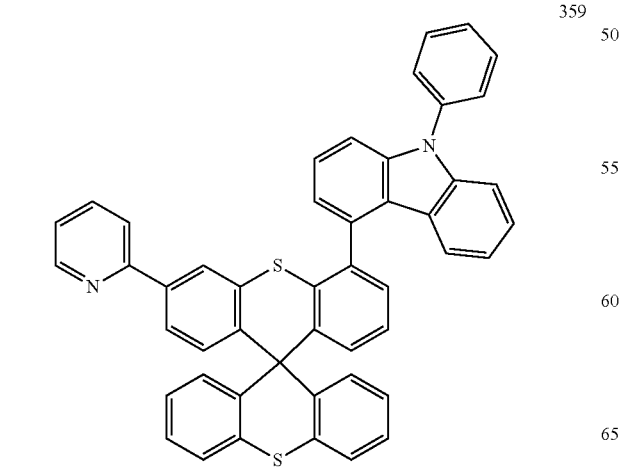
360
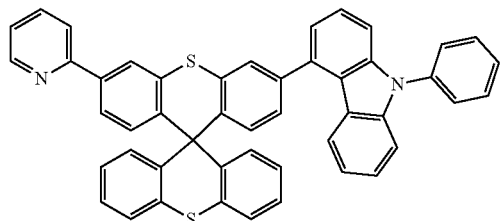
361
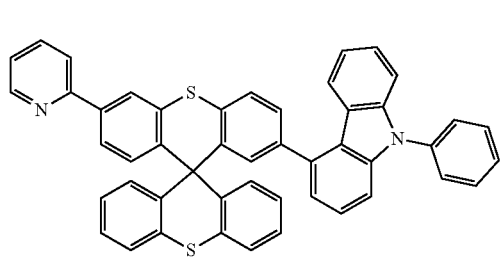
362
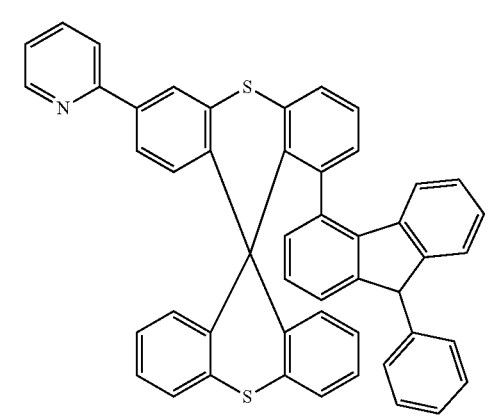
383
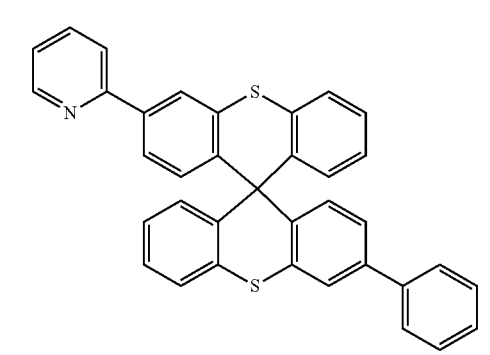
384
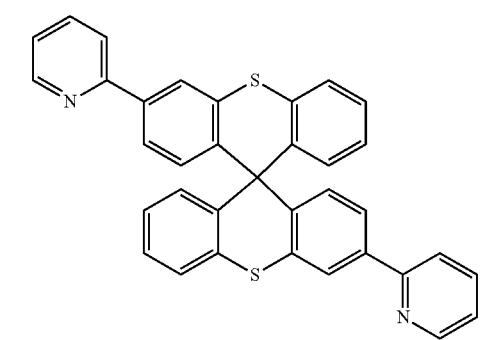

385
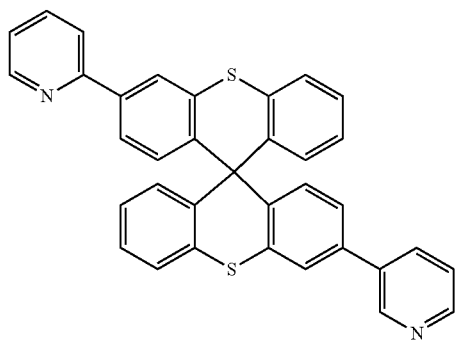
386
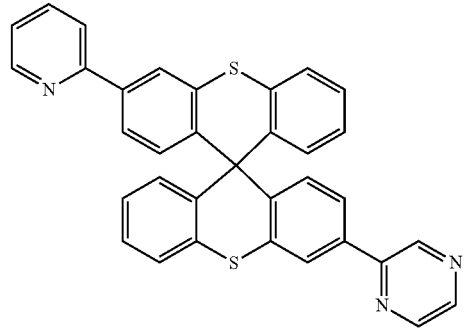
387
388
389
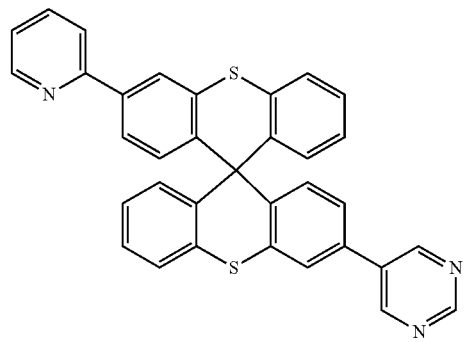
390
391
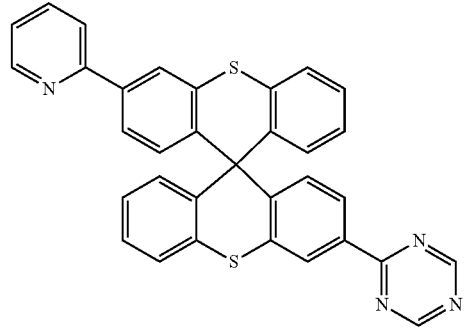
392
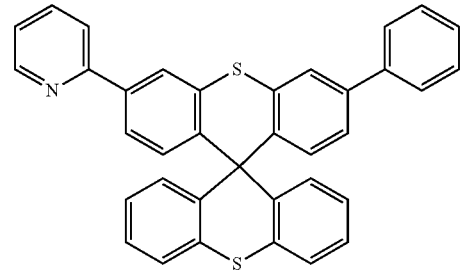
393
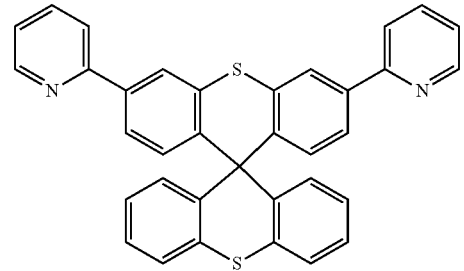

| 394 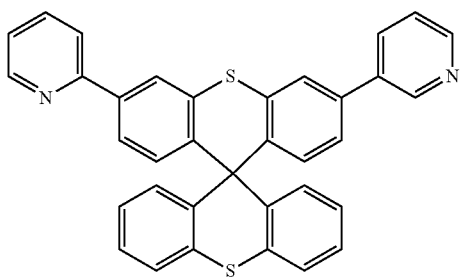 | 399 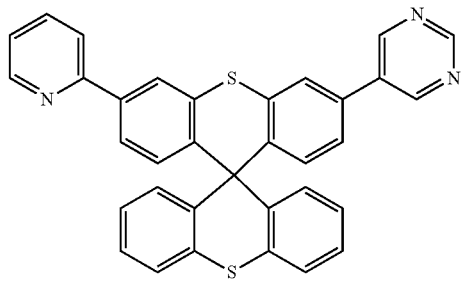 |
| --- | --- |
| 395 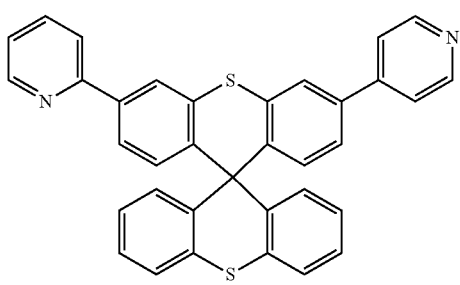 | 400 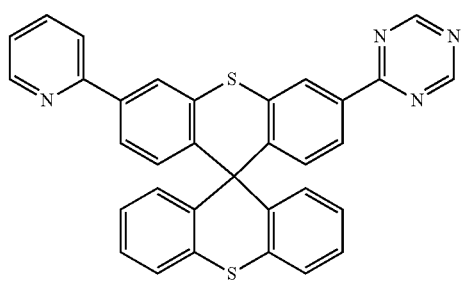 |
| 396 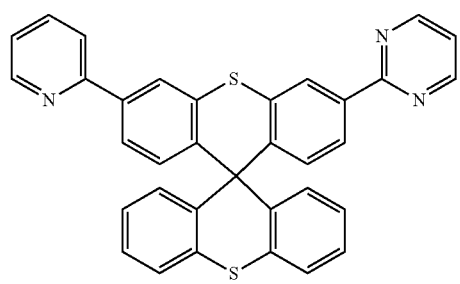 | 405 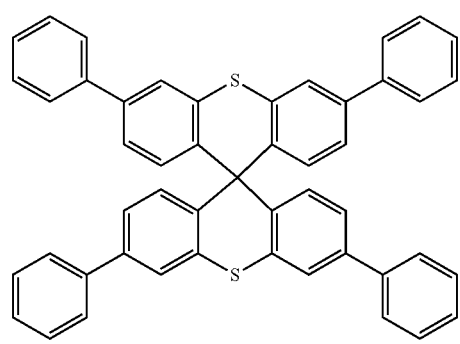 |
| 397 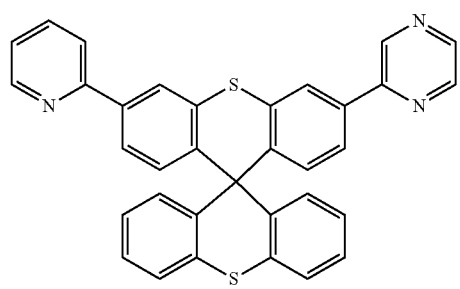 | 406 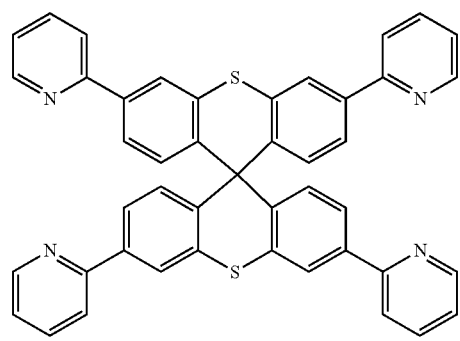 |
| 398 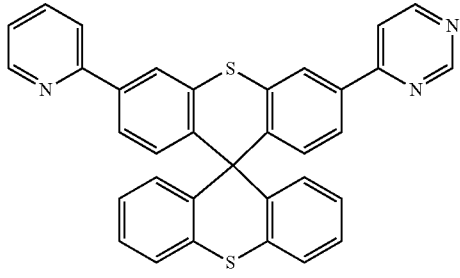 | 407 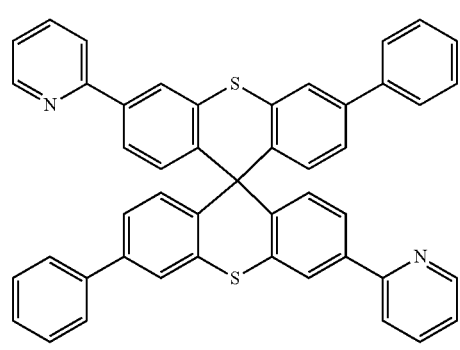 |

-continued
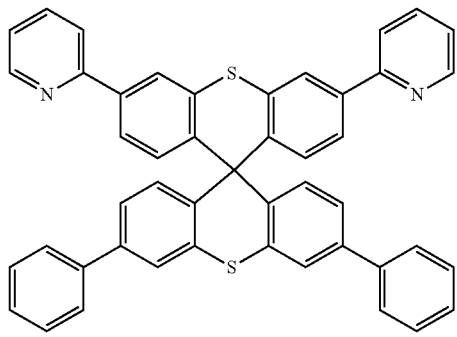
408
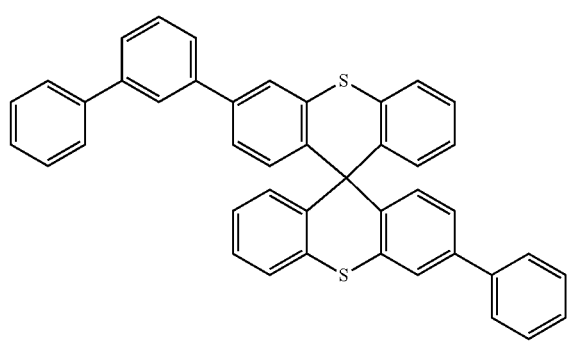
411
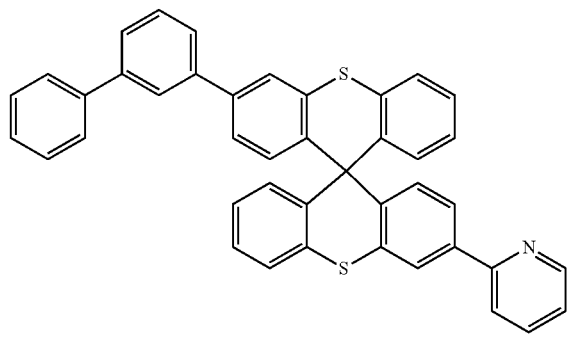
412
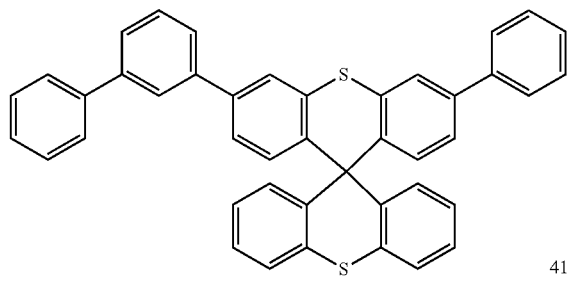
415
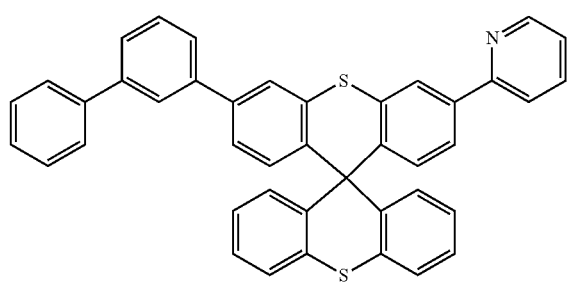
416
-continued
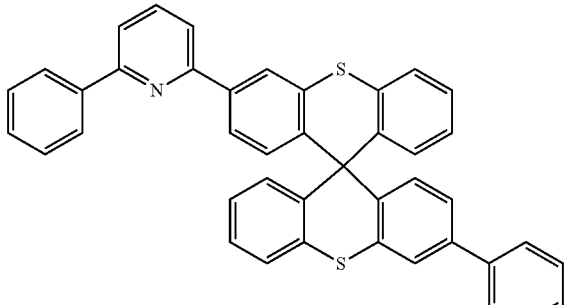
419
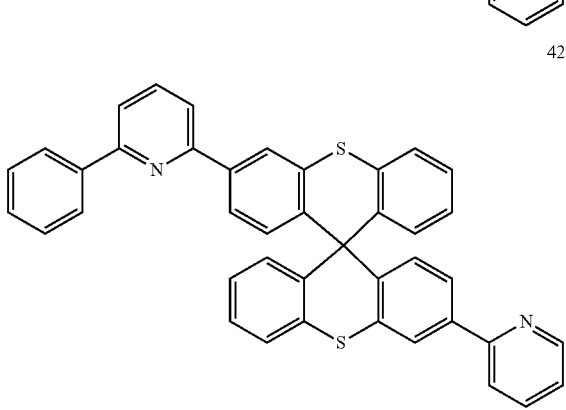
420
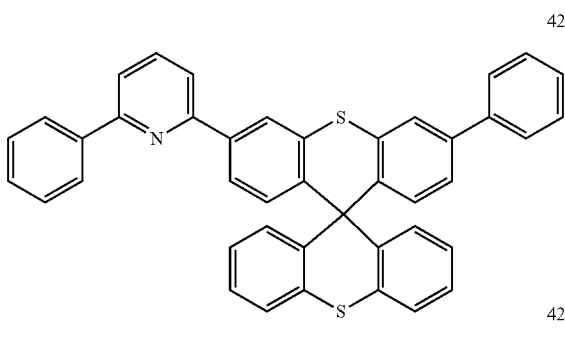
423
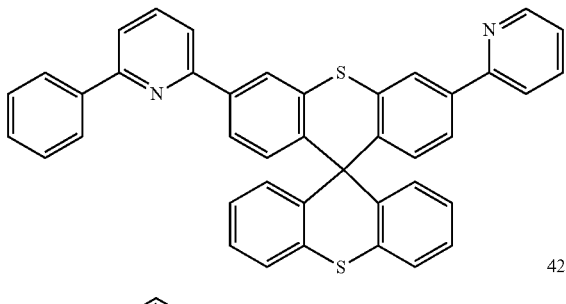
424
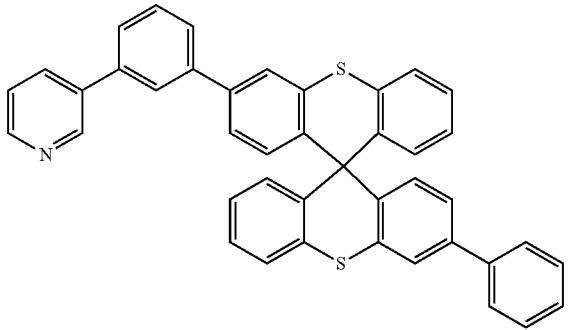
427

-continued

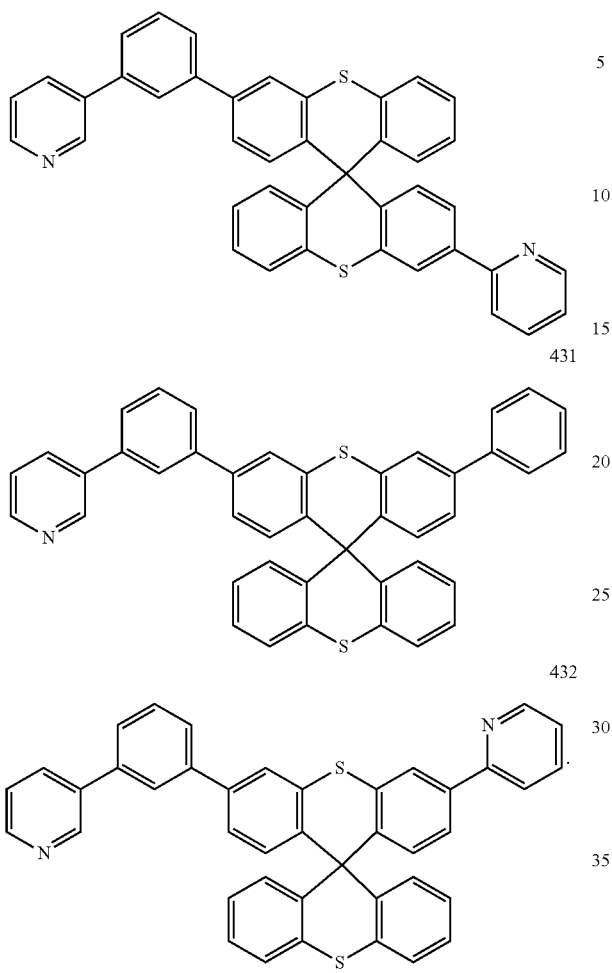

428

431

432

11. An organic light-emitting device comprising:
a first electrode;
a second electrode; and
an organic layer disposed between the first electrode and the second electrode,
wherein the organic layer comprises an emission layer and further comprises the condensed cyclic compound represented by Formula 1 of claim 1.

12. The organic light-emitting device of claim 11, wherein the first electrode is an anode,
the second electrode is a cathode, and
the organic layer comprises:
i) a hole transport region disposed between the first electrode and the emission layer, wherein the hole transport layer comprises at least one of a hole injection layer, a hole transport layer, and an electron blocking layer; and
ii) an electron transport region disposed between the emission layer and the second electrode, wherein the electron transport layer comprises at least one of a hole blocking layer, an electron transport layer, and an electron injection layer.

13. The organic light-emitting device of claim 11, wherein the emission layer comprises the condensed cyclic compound.

14. The organic light-emitting device of claim 13, wherein the emission layer further comprises a phosphorescent dopant, and wherein the condensed cyclic compound in the emission layer serves as a host.

15. The organic light-emitting device of claim 14, wherein the phosphorescent dopant comprises an organometallic compound that is represented by Formula 81:

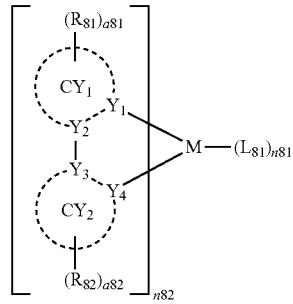

Formula 81 wherein, in Formula 81,
M is Ir, Pt, Os, Ti, Zr, Hf, Eu, Tb, or Tm;
$Y_1$ to $Y_4$ are each independently C or N;
$Y_1$ and $Y_2$ are linked by a single bond or a double bond, and $Y_3$ and $Y_4$ are linked by a single bond or a double bond;
$CY_1$ and $CY_2$ are each independently selected from a benzene, a naphthalene, a fluorene, a spiro-fluorene, an indene, a pyrrole, a thiophene, a furan, an imidazole, a pyrazole, a thiazole, an isothiazole, an oxazole, an isoxazole, a pyridine, a pyrazine, a pyrimidine, a pyridazine, a quinoline, an isoquinoline, a benzoquinoline, a quinoxaline, a quinazoline, a carbazole, a benzoimidazole, a benzofuran, a benzothiophene, an isobenzothiophene, a benzoxazole, an isobenzoxazole, a triazole, a tetrazole, oxadiazole, a triazine, a dibenzofuran, and a dibenzothiophene, and $CY_1$ and $CY_2$ are optionally linked to each other by a single bond or an organic linking group;
$R_{81}$ and $R_{82}$ are each independently selected from a hydrogen, a deuterium, —F, —Br, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, —SF$_5$, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —N(Q$_1$)(Q$_2$), —Si(Q$_3$)(Q$_4$)(Q$_5$), and —B(Q$_6$)(Q$_7$);
a81 and a82 are each independently an integer selected from 1 to 5;
n81 is an integer selected from 0 to 4;
n82 is 1, 2, or 3; and $L_{81}$ is a monovalent organic ligand, a divalent organic ligand, or a trivalent organic ligand.

16. A condensed cyclic compound represented by Formula 1:

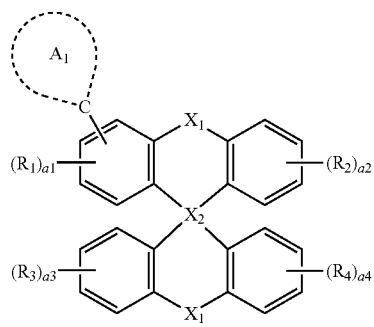

Formula 1 wherein, in Formula 1,
$X_1$ is S,
$X_2$ is C,
ring $A_1$ is selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_1$ to $R_4$ are each independently selected from a hydrogen, a deuterium, —F, —Cl, —Br, —I, a cyano group, a nitro group, an amidino group, a hydrazine group, a hydrazone group, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, —Si($Q_3$)($Q_4$)($Q_5$), and —B($Q_6$)($Q_7$), provided that at least one of $R_1$ to $R_4$ is selected from a substituted or unsubstituted $C_1$-$C_{60}$ heteroaryl group or a substituted or unsubstituted monovalent non-aromatic condensed heteropolycyclic group;

a1 is an integer selected from 0 to 3;
a2, a3, and a4 are each independently an integer selected from 0 to 4; and
when a1 is 2 or greater, groups $R_1$ are identical to or different from each other,
when a2 is 2 or greater, groups $R_2$ are identical to or different from each other,
when a3 is 2 or greater, groups $R_3$ are identical to or different from each other, and
when a4 is 2 or greater, groups $R_4$ are identical to or different from each other, at least one of substituents of the substituted $C_1$-$C_{60}$ alkyl group, substituted $C_2$-$C_{60}$ alkenyl group, substituted $C_2$-$C_{60}$ alkynyl group, substituted $C_1$-$C_{60}$ alkoxy group, substituted $C_3$-$C_{10}$ cycloalkyl group, substituted $C_1$-$C_{10}$ heterocycloalkyl group, substituted $C_3$-$C_{10}$ cycloalkenyl group, substituted $C_1$-$C_{10}$ heterocycloalkenyl group, substituted $C_6$-$C_{60}$ aryl group, substituted $C_6$-$C_{60}$ aryloxy group, substituted $C_6$-$C_{60}$ arylthio group, substituted $C_1$-$C_{60}$ heteroaryl group, substituted monovalent non-aromatic condensed polycyclic group, and substituted monovalent non-aromatic condensed heteropolycyclic group is selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, $C_1$-$C_{60}$ alkyl group, $C_2$-$C_{60}$ alkenyl group, $C_2$-$C_{60}$ alkynyl group and $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group and a monovalent non-aromatic condensed heteropolycyclic group, each substituted with at least one selected from a deuterium, —F, —Cl, —Br, —I, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —N($Q_{21}$)($Q_{22}$), —Si($Q_{23}$)($Q_{24}$)($Q_{25}$), and —B($Q_{26}$)($Q_{27}$); and —N($Q_{31}$)($Q_{32}$), —Si($Q_{33}$)($Q_{34}$)($Q_{35}$), and —B($Q_{36}$)($Q_{37}$), and $Q_3$ to $Q_7$, $Q_{11}$ to $Q_{17}$, $Q_{21}$ to $Q_{27}$, and $Q_{31}$ to $Q_{37}$ are each independently selected from a hydrogen, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

\* \* \* \* \*